United States Patent
Metz et al.

(10) Patent No.: US 10,793,837 B2
(45) Date of Patent: Oct. 6, 2020

(54) PRODUCTION OF POLYUNSATURATED FATTY ACIDS (PUFAS) USING A NOVEL MODULAR DOCOSAHEXAENOIC ACID (DHA) SYNTHASE

(71) Applicant: DSM IP Assets B.V., Heerlen (NL)

(72) Inventors: James G. Metz, Longmont, CO (US); Jun Wang, Cooksville, MD (US); Bastien Chevreux, Rheinfelden (DE); Ross E. Zirkle, Mount Airy, MD (US); Anne-Cecile Bayne, Ellicott City, MD (US); James Casey Lippmeier, Columbia, MD (US)

(73) Assignee: DSM IP Assets B.V, Heerlen (NL)

( * ) Notice: Subject to any disclaimer, the term of this patent is extended or adjusted under 35 U.S.C. 154(b) by 66 days.

(21) Appl. No.: 15/579,751

(22) PCT Filed: Jun. 6, 2016

(86) PCT No.: PCT/US2016/035974
§ 371 (c)(1),
(2) Date: Dec. 5, 2017

(87) PCT Pub. No.: WO2016/200720
PCT Pub. Date: Dec. 15, 2016

(65) Prior Publication Data
US 2018/0171310 A1    Jun. 21, 2018

Related U.S. Application Data

(60) Provisional application No. 62/172,049, filed on Jun. 6, 2015.

(51) Int. Cl.
| | | |
|---|---|---|
| *C12N 15/82* | (2006.01) | |
| *C12N 9/10* | (2006.01) | |
| *C12N 9/00* | (2006.01) | |
| *A23K 20/158* | (2016.01) | |
| *A23L 33/115* | (2016.01) | |
| *C12P 7/64* | (2006.01) | |

(52) U.S. Cl.
CPC .......... *C12N 9/1029* (2013.01); *A23K 20/158* (2016.05); *A23L 33/115* (2016.08); *C12N 9/00* (2013.01); *C12N 15/8247* (2013.01); *C12P 7/6427* (2013.01); *C12Y 203/01085* (2013.01); *A23V 2002/00* (2013.01); *C12N 2510/02* (2013.01)

(58) Field of Classification Search
None
See application file for complete search history.

(56) References Cited

U.S. PATENT DOCUMENTS

| | | |
|---|---|---|
| 7,001,772 B2 | 2/2006 | Roessler et al. |
| 7,585,659 B2 | 9/2009 | Weaver et al. |
| 7,759,548 B2 | 7/2010 | Metz et al. |
| 8,940,884 B2 | 1/2015 | Apt et al. |
| 2006/0024806 A1 | 2/2006 | Stinear et al. |
| 2011/0277190 A1 | 11/2011 | Abad |

OTHER PUBLICATIONS

Read et al., NCBI, GenBank Sequence Accession No. KB868684.1, Published May 2, 2013.*
Beach et al, Biosynthesis of Oleic Acid and Docosahexaenoic Acid by a Heterotrophic Marine Dinoflagellate Crypthecodinium Cohnii, Biochimica et Biophysica Acta, 1974, 16-24, 369.
Beld et al, The phosphopantetheinyl transferases: catalysis of a post-translational modification cruical for life, Royal Society of chemistry, 2014, 61-108, 31.
Broadwater et al, Desaturation and Hydroxylation, The Journal of Biomedical Chemistry, 2002, 15613-15620, 277.
Cheng et al, Type I polyketide synthase requiring a discrete acyltransferase for polyketide biosynthesis, PNAS, 2003, 3149-3154, 100.
Choi et al, Isolation of the biosynthetic gene cluster for tautomycetain, a linear polyketide T cell-specific immunomodulator from *Streptomyces* sp. CK4412, Microbiology, 2007, 1095-1102, 153.
GenBank Accession, FX532503, FX532503, 2014, entire doc, entire doc.
GenBank Accession, FX532631, FX532631, 2014, entire doc, entire doc.
GenBank Accession, FX535234, FX535234, 2014, entire doc, entire doc.
J. Sambrook, Molcular Cloning, A Laboratory Manual, 1989, Table of contents, Second.
Jiang et al, The role of Tandem Acyl Carrier Protein Domains in Polyunsaturated Fatty Acid Biosynthesis, JACS, 2008, 6336-6337, 130.
Kellmann et al, Biosynthesis and Molecular Genetics of Polyketides in Marine Dinoflagellates, Marine Drugs, 2010, 1011-1048, 8.
Lambalot et al, A New Enzyme Superfamily—the phosphopantetheinyl transferases, Chemistry & Biology, 1996, 923-936, vol. 3 No. 11.
Lippmeier, Fatty Acid Metabolism of Marine Microalgae, The University of Hull / Thesis, 2007, n/a, n/a.
Metz et al., Production of Polyunsaturated Fatty Acids by Polyketide Synthasese in Both Prokaryotes and Eukaryotes, Science, 2001, 290-293, 293.
Morrison and Smith, Preparation of fatty acid methyl esters and dimethylacetals from lipids with boron fluoride-methanol, Journal of Lipid Research, 1964, 600-608, 5.

(Continued)

*Primary Examiner* — Vinod Kumar
(74) *Attorney, Agent, or Firm* — Xi Chen; Shannon McGarrah

(57) ABSTRACT

This disclosure concerns a novel modular docosahexaenoic acid (DHA) synthase and recombinant host organisms genetically modified with such synthase and one or more accessory proteins that allow for and/or improve the production of PUFAs in the host organism. The disclosure also concerns methods of making and using such organisms as well as products obtained from such organisms.

15 Claims, 6 Drawing Sheets
Specification includes a Sequence Listing.

(56) References Cited

OTHER PUBLICATIONS

Nikolova, Silver Ion Chromatography and Lipids, Institute of Organic Chemistry, Centr of Phytochemistry, 1992, Ed. W.W. Christie, Oily Press, Ayr, 1992 pp. 181-237, n/a.
Sanchez et al, Chemistry & Biology, Cloning and characterization of a photsphopantetheinyk transferase from Streptomyces verticillus . . . , 2001, 725-738, 8.
Schwecke et al., The biosynthetic gene cluster for the polyketide immunosuppressant rapamycin, Proc. Natl. Acad. Sci., 1995, 7839-7843, 92.
Shanklin et al, Desaturases: Emerging Models for Understanding Functional Diversification of Diiron-containing Enzymes, Journal of Biological Chemistry, 2009, 18559-18563, 284.
Shoguchi et al, Draft Assembly of the Symbiodinium minutum Nuclear Genome Reveals Dinoflagellate Gene Structure, Current Biology, 2013, 1399-1408, 23.
uniprot.org, Q1JTE1, Q1JTE1, 2014, entire doc, entire doc, US.
UniProtKB Accession, F0WK91, F0WK91, 2014, entire doc, entire doc.
UniProtKB Accession, G4ZRU8, G4ZRU8, 2014, entire doc, entire doc.
UniProtKB Accession, K3X3T9, K3X3T9, 2014, entire doc, entire doc.
Zhang et al, Spliced leader RNA trans-splicing in dinoflagellates, PNAS, 2007, 4618-4623, vol. 104, No. 11.
Ana Mendes, et al., Crypthecodinium cohnii with emphasis on DHA production: a review,, J Appl Phycol, Aug. 2008, pp. 199-214, vol. 21.
Hongseok Tae et al., ASMPKS: an analysis system forlar polyketide synthases,, BMC bioinformatics, Sep. 2007, p. 1-9, vol. 8.
Pfeifer et al, Biosynthesisof polyketides in heterologous hosts, Microbiology and molecular biology reviews, 2001, 106-118, 65.
Robert Bunet et al., A single sfp-type phosphopantetheinyl transferase plays a major role in the biosynthesis of PKS and NRPS derived metabolites in streptomyces ambofaciens ATCC23877, PLOS One, Jan. 2014, pp. 1-12, vol. 9, No. 1, e87607.
Smith et al, Architecture of the polyketide synthase module: surprises from electron cryo-microscopy, HHS Public Access, Apr. 1, 2016, 9-19, 31, Curr. Opin Struct Biol.
Somnath Dutta et al, Structure of a molecular plyketide synthase, HHS Public Access, 2014, 512-517, 510, Nature.
Udwary et al, a method for prediction of the locations of linker . . . , J. Mol. Biol., 2002, 585-598, 323.

\* cited by examiner

SEQUENCE LISTING

```
<160> NUMBER OF SEQ ID NOS: 22

<210> SEQ ID NO 1
<211> LENGTH: 15896
<212> TYPE: PRT
<213> ORGANISM: Crypthecodinium cohnii

<400> SEQUENCE: 1

Met Arg Arg Ser Gly Glu Met Lys Gly Ala Ser Gly Ser Ser Gly Ser
1               5                   10                  15

Ser Gly Pro Ser Lys Arg Ser Gly Leu Lys Arg Ser Gly Gly Asn Thr
            20                  25                  30

Gly Ser Gln Ser Gln Leu Ala Asp Met Val Asp Gln Leu Ser Val Thr
        35                  40                  45

Thr Ser Thr Gly Ser Ile Arg Met Leu Ala Arg Ala Gly Leu Cys Leu
    50                  55                  60

Ser Met Gly Ile Val Leu Ala Met Gly Arg His Thr Pro Trp Trp Leu
65                  70                  75                  80

Ile Pro Phe Gly Val Val Phe Glu Gly Val Ser Leu Ala Trp Phe His
                85                  90                  95

Leu Ile Gln Lys Glu Cys Glu Gln Gly Lys Phe Leu Pro Ser Pro Glu
            100                 105                 110

Leu Asn Arg Val Leu Ala Ala Leu Leu Arg Trp Glu Val Cys Ser Ala
        115                 120                 125

Leu Val Ile Val Leu Phe Leu Ser Gly Ala Trp Asp Ile Tyr Ser Ile
    130                 135                 140

Phe Lys Tyr Trp Leu Leu Pro Leu Leu Val Thr Gln Ala Thr Phe Ser
145                 150                 155                 160

Thr Ser Ser Ala Thr Glu Lys Pro Lys Ser Glu Ser Ala Glu Gly Ser
                165                 170                 175

Gly Arg Leu Ser Lys Thr Pro Ser Met Ser Ser Leu Asp Leu Leu Phe
            180                 185                 190

Pro Glu Leu Glu Ser Ala Ala Ser Gln Ile Ser Glu Leu Leu Glu Ala
```

```
            195                 200                 205
Ala Gln His Ala Asp Gln Ser Asn Met Phe Thr His His Val Gly Ala
            210                 215                 220

Asp Asp Ala Ser Ser Gly Asp Asp Trp His Phe Gly Val Ala Leu His
225                 230                 235                 240

Gln Ile Pro Met Tyr His Leu Gln Ser Leu Ser Arg Asn Leu Asn Lys
            245                 250                 255

Glu Leu Lys Arg Ala Arg Pro Phe Gly Ser Ser Ala Asn Leu Ala Ala
            260                 265                 270

Leu Met Gly Gly Gly Ser Gln Asp Ala Glu Pro Gly Gly Glu Gln Asp
            275                 280                 285

Glu Gly Leu Arg Gln Arg Arg Ser Lys Pro Ala Ala Arg Lys Lys Glu
            290                 295                 300

Glu Lys Gly Lys Lys Asp Ala Val Gln Gln Thr Pro Trp Ala Gln Val
305                 310                 315                 320

Met Asn Leu Ile Gly Trp Pro Ala Arg Tyr Leu Phe Arg Glu Met Trp
            325                 330                 335

Leu Trp Thr Glu Lys Asp Leu Thr Leu Tyr Ala Val Ala Ile Phe
            340                 345                 350

Leu Leu Glu Val Tyr Ile Gly Thr Lys Tyr Phe Ser Phe Ala Pro Ile
            355                 360                 365

Cys Leu Leu Tyr Pro Leu Leu Ser Ser Ser Gly Ala Arg Met Ala
            370                 375                 380

Ser Glu Leu Gln Glu Glu Ile Val Met Val Met Gly Leu Glu His Arg
385                 390                 395                 400

Phe Trp Arg Arg Leu His Ile Pro Val Ala Leu Gln Val Leu Val Cys
            405                 410                 415

His Asn Met Val Val Tyr Phe Ile Phe Ser Gln Ile Ile Phe Gly Gly
            420                 425                 430

Val Asp Pro Tyr Val Gly Val Ala Pro Lys Trp Gln Thr Phe Leu Phe
            435                 440                 445

Gly Val Val Leu Tyr Val Leu Ser Met Val Gly Met Ile Gly Met Asn
            450                 455                 460

Leu Val Trp Ala Cys Gly Ala Val Val Leu Asp Leu Pro Gln Lys Val
465                 470                 475                 480

Phe Leu Met Ile Cys Ala Ser Thr Ala Asn Gln Gly Ser Ile Phe Arg
            485                 490                 495

Trp Cys Arg Asp His Arg Ala His Leu Met Asn Lys Gly Thr Val Ala
            500                 505                 510

Asp Pro Tyr Asp Tyr Asn Arg Gly Ala Thr Phe Ala Tyr Ile Gly Trp
            515                 520                 525

Phe Val Gln Gln Lys Thr Arg Arg Ala Ile Glu Ala Ser Arg Ser Val
            530                 535                 540

Asp Met Ser Asp Leu Leu Ala Asp Gln Val Val Met Phe Gln Ala Asp
545                 550                 555                 560

Val Asp Thr Trp Trp Asn Leu Ser Trp Cys His Ala Ile Pro Ala Phe
            565                 570                 575

Leu Thr Leu Met Trp Gly Glu Asp Leu Phe Leu Gly Val Ile Cys
            580                 585                 590

Gly Cys Phe Arg Tyr Val Leu Ala Leu His Ser Asn Leu Leu Leu Val
            595                 600                 605

Tyr His Gln His Ala Trp Gly Pro Met Glu Val Lys Ala Gln Pro Val
            610                 615                 620
```

```
Leu Thr Gly Glu Val Thr Ala Ala Thr Gly Arg Thr Gly Gly
625                 630                 635                 640

Ser Gln Met Leu Arg Ser Ala Ser Ile Ala Glu Gln Leu Gln Ser Val
                645                 650                 655

Pro Glu Thr Glu Val Ala Pro Asn Arg Pro Ala Pro Leu Asp Thr Ala
            660                 665                 670

Ala Ala Ile Ala Gln Gln Ala Arg Asn Ala Glu Asp Gly Gly Val Phe
                675                 680                 685

Val Lys Tyr Lys Val Gly Gln Ala Ser Ala Gly Gly Glu Pro Ser Leu
        690                 695                 700

Glu Val Arg Leu Glu Pro Leu Trp Arg Arg Ser Thr Leu Ile Asp Leu
705                 710                 715                 720

Ala Lys Asp Ala Val Ala Asp Ile Leu Lys Val Gln Ser Ser Gln Val
                725                 730                 735

Arg Pro Asp Arg Pro Leu Met Asp Leu Gly Phe Asp Ser Ala Ser Ala
            740                 745                 750

Leu Arg Leu Arg Asp Lys Leu Ser Arg Arg Leu Asn Val Glu Leu Pro
        755                 760                 765

Pro Thr Leu Leu Phe Asp His Pro Thr Ile Asn Asp Met Val Asp Asn
770                 775                 780

Gly Leu Thr Lys Phe Ala Gln Arg Pro Met Thr Pro Ser Gly Ile Thr
785                 790                 795                 800

Pro Asp Gln Lys Ala Ala Ala Met Pro Asp Leu Val Val Thr Ser Thr
                805                 810                 815

Ala Cys Asn Met Pro Lys Ala Gly Ser Pro Gly Glu Leu Trp Asn Met
            820                 825                 830

Leu Val Thr Lys Thr Asp Ala Val Val Glu Val Pro Leu Ala Arg Trp
        835                 840                 845

Asp His Cys Glu Tyr Tyr Ser Pro Glu Pro Gln Glu Gly Gln Thr Tyr
850                 855                 860

Ala Arg His Gly Gly Phe Ile Asp Asn Ala Asp Leu Phe Asp Val Pro
865                 870                 875                 880

Phe Phe Gly Leu Thr Ala Ala Glu Ala Lys Ala Thr Asp Pro Gln Gln
                885                 890                 895

Arg Leu Ile Leu Thr Thr Ala Tyr Asn Cys Phe Tyr Gly Asp Gly Tyr
            900                 905                 910

Asp Lys Ala Ala Leu Ala Gly Asp Asn Ile Gly Val Phe Val Gly Leu
        915                 920                 925

Ser Asn Leu Asp Trp Tyr His Leu Ser Leu Ser Lys Pro Ser Val Tyr
930                 935                 940

Thr Gly Thr Gly Val Ala Ser Ala Ile Ala Ser Asn Arg Ile Ser Tyr
945                 950                 955                 960

Val Phe Gly Leu Lys Gly Pro Ser Met Thr Val Asp Thr Ala Cys Ser
                965                 970                 975

Ser Ser Ile Ser Ala Leu Thr Ser Gly Ile Ala Ser Ile Asn Lys Ser
            980                 985                 990

His Ala Val Arg Glu Ala Leu Val Ala Gly Ala Glu Leu Ile His Gly
        995                 1000                1005

Pro Asn Ser Phe Ile Leu Arg Ser Val Ala Gly Met Leu Ser Pro
        1010                1015                1020

Glu Gly Arg Cys Lys Thr Phe Asn Ala Thr Ala Asp Gly Tyr Ile
        1025                1030                1035
```

```
Arg Gly Glu Gly Ala Ala Ala Ile Ile Lys Leu Ala Ser Asp
    1040            1045            1050

Ala Glu Glu Lys Arg Cys Ala Val Val Ala Asp Val Lys Ser Ala
    1055            1060            1065

Val Met Asn Gln Asp Gly Lys Ser Ala Thr Leu Thr Ala Pro Asn
    1070            1075            1080

Gly Pro Ser Gln Glu Glu Val Leu Ala Thr Ala Leu Arg Glu Ala
    1085            1090            1095

Ala Met Gln Pro Asn Gln Val Lys Ala Ile Glu Cys His Gly Thr
    1100            1105            1110

Gly Thr Ala Leu Gly Asp Pro Ile Glu Val Ser Ala Ile Lys Ala
    1115            1120            1125

Val Leu Gly Ala Glu Ser Lys Glu Ala Pro Lys Leu Met Leu Cys
    1130            1135            1140

Ala Gly Lys Ser Asn His Gly His Leu Glu Gly Ser Ala Gly Phe
    1145            1150            1155

Ala Gly Leu Met Lys Val Phe Gly Cys Leu Thr Gln Ser Glu Val
    1160            1165            1170

Pro Pro Asn Ile His Phe Glu Arg Leu Asn Pro His Met Ser Leu
    1175            1180            1185

Glu Gly Ser Arg Leu Thr Val Ala Glu Ala Gln Thr Thr Ile Pro
    1190            1195            1200

Lys Gly Asn Thr Val Met Gly Val Ser Ser Phe Gly Phe Gly Gly
    1205            1210            1215

Thr Asn Ala His Ala Leu Leu Ala His Ser Ile Arg Lys Lys Pro
    1220            1225            1230

Lys Lys Leu Ser Glu His Arg Val Ala Phe Leu Phe Thr Gly Gln
    1235            1240            1245

Gly Ser Gln Arg Gln Ala Met Gly Lys Arg Leu Tyr Lys Val Asp
    1250            1255            1260

Glu Ala Phe Lys Val Ala Leu Asp Glu Ala Ala Val Ile Cys Lys
    1265            1270            1275

Asp Leu Ile Asp Gln Asp Leu Leu Asp Leu Met Phe Ser Glu Asp
    1280            1285            1290

Arg Glu Met Leu Glu Lys Leu Asn Thr Thr Tyr Tyr Ser Gln Ile
    1295            1300            1305

Ala Ile Phe Ser Ile Glu Tyr Ala Leu Ser Lys Met Trp Ala Ala
    1310            1315            1320

Lys Gly Ile Thr Pro Phe Ala Val Leu Gly His Ser Val Gly Glu
    1325            1330            1335

Tyr Thr Ala Ala Val Val Ala Gly Ser Leu Ser Leu Lys Asp Ala
    1340            1345            1350

Leu Lys Ala Leu Ala Thr Arg Gly Arg Leu Ile Gln Glu Lys Cys
    1355            1360            1365

Asp Pro Ala Ile Gly Asn Met Cys Ser Ile Phe Ala Ser Ala Ala
    1370            1375            1380

Asp Val Glu Ser Ala Ile Arg Ser Val Asp Leu Gln Gly Glu Thr
    1385            1390            1395

Val Asn Ile Ala Ala Ile Asn Gly Pro Ser Ala Thr Val Val Ser
    1400            1405            1410

Gly His Lys Lys Ala Val Glu Lys Val Cys Lys Gln Val Asn Ala
    1415            1420            1425

Gly Asn Lys Glu Leu Ala Ile Gln His Ala Met His Ser Lys Leu
```

-continued

```
              1430                 1435                 1440

Thr Glu Cys Ile Leu Pro Asp Leu Lys Lys Val Leu Asp Thr Cys
    1445                 1450                 1455

Glu Leu Lys Lys Pro Ser Ser Asp Ile His Phe Val Ser Thr Leu
    1460                 1465                 1470

Thr Gly Thr Glu Ile Ser Asn Glu Leu Thr Lys Ala Ala His Trp
    1475                 1480                 1485

Val Gly His Asp Glu Asp Lys Pro Met Leu Phe Leu Gln Gly Met
    1490                 1495                 1500

Glu Thr Leu Glu Lys Leu Gly Cys Thr Ala Phe Val Glu Leu Gly
    1505                 1510                 1515

Pro Gln Pro Val Leu Met Lys Met Gly Arg Arg Cys Val Gln Thr
    1520                 1525                 1530

Ala Ala Thr Asn Phe Glu Trp Leu Ser Ser Leu Thr Pro Gly Arg
    1535                 1540                 1545

Asp Glu Val Glu Asn Ile Leu Leu Ile Ser Arg Ala Leu Gly Ala
    1550                 1555                 1560

Ala Tyr Asp Arg Val Ser Glu Leu Lys Pro Thr Pro Leu Pro Trp
    1565                 1570                 1575

Arg Ala Pro Leu Leu His Pro Leu Leu Gly Lys Lys Gln Gln Asp
    1580                 1585                 1590

Ala Ser Gly Ala Thr Val Phe Glu Ser Gly Ala Ile Lys Ser Gly
    1595                 1600                 1605

Ala Ala Met Glu Leu Phe Glu Gln His Cys Val Phe Gly Gln Val
    1610                 1615                 1620

Val Leu Pro Gly Ala Ser His Ile Leu Leu Ala Ala Ala Ala Gln
    1625                 1630                 1635

Leu Glu Ser Ala Thr Thr Arg Val Gly Ala Gly Ala Ala Val Glu
    1640                 1645                 1650

Leu Asn Asp Ala Val Phe Glu Arg Pro Phe Val Val Pro Glu Asp
    1655                 1660                 1665

Ser Asp Leu Thr Val Arg Cys Arg Ala Thr Val Asp Thr Thr Glu
    1670                 1675                 1680

Val Ala Ser Ser Thr Asp Gly Ala Ala Pro Val Val His Ala Arg
    1685                 1690                 1695

Phe Gly Ser Ala Arg Val Val Gly Ala Pro Ala Leu Ala Thr Pro
    1700                 1705                 1710

Val Gln Glu Arg Leu Ser Ala Leu Glu Thr Pro Pro Ser Ala Glu
    1715                 1720                 1725

Gly Val Lys Asp Leu Tyr Lys Ala Phe Glu Asp Lys Gly Leu Gly
    1730                 1735                 1740

Tyr Gly Pro Ser Phe Gln Pro Leu Gln Glu Phe Ser Phe Gln Ser
    1745                 1750                 1755

Ser Gly Ala Leu Ala Arg Leu Gly Ile Thr Leu Lys Thr Trp Glu
    1760                 1765                 1770

Gln Ser Leu Gln Met Leu His Pro Ala Leu Leu Asp Gly Ala Leu
    1775                 1780                 1785

Gln Leu Leu Val Glu Ser Ala Thr Arg Arg Val Glu Glu Lys Cys
    1790                 1795                 1800

Thr Phe Leu Pro Phe Ala Val Lys Lys Ala Ile Val Ala Ala Gln
    1805                 1810                 1815

Cys Pro Thr Gly Glu Leu Trp Ala Ser Val Lys Val Leu Asp Ser
    1820                 1825                 1830
```

```
Thr Ala Thr Ser Leu Asn Ala Asp Val Glu Val Phe Asn Ala Glu
    1835            1840                1845

Gly Lys Leu Ala Ile Arg Leu Glu Gly Ala Ser Cys Arg Arg Val
    1850            1855                1860

Glu Glu Gly Ala Ala Ala Glu Lys Asp Asn Gly Asp Gln Cys Leu
    1865            1870                1875

Tyr Ser Ile Ser Trp Val Gly Ala Glu Glu Asp Ser Arg Gly Ile
    1880            1885                1890

Leu Val Thr Gly Thr Thr Leu Val Val Ala Pro Glu Ser Glu Ile
    1895            1900                1905

Pro Ala Ile Ala Lys Ala Ile Gly Val Ser Glu Ser Arg Cys Ser
    1910            1915                1920

Ala Val Ser Thr Ala Glu Glu Ala Val Lys Thr Ala Ala Asp Arg
    1925            1930                1935

Pro Cys Asn Thr Ile Val Tyr Gln Ala Ala Gly Ser Glu Ile Asp
    1940            1945                1950

Ala Leu Glu Val Ala Leu Lys Leu Thr Gln Gly Val Ala Lys Phe
    1955            1960                1965

Asp Gly Asp Val Pro Arg Ile Val Leu Val Thr Thr Ala Ala Gln
    1970            1975                1980

Gln Pro Asp Leu Lys Asp Lys Glu His Asp Pro Lys His Ser Gly
    1985            1990                1995

Leu Trp Gly Phe Ala Arg Ala Ala Arg Leu Glu Tyr Pro His Met
    2000            2005                2010

Gln Val Ser Cys Val Asp Leu Glu Gly Ser Ser Glu Val Ala Ala
    2015            2020                2025

Pro Thr Pro Ser Ala Ala Leu Ser Ala Ala Glu Val Glu Val Ser
    2030            2035                2040

Val Arg Asn Gly Ala Ser Leu Gly Ala Arg Leu Ala Arg Ser Ser
    2045            2050                2055

Met Ala Pro Lys Arg Pro Leu Arg Leu Asn Met Ala Arg Arg Gly
    2060            2065                2070

Ser Leu Met Asn Leu Arg Pro Val Pro Gln Thr Lys Arg Lys Ala
    2075            2080                2085

Pro Glu Ala Gly Glu Ile Glu Val Arg Val Gly Ala Ile Gly Leu
    2090            2095                2100

Asn Phe Arg Asp Val Leu Asn Val Met Gly Leu Tyr Pro Gly Asp
    2105            2110                2115

Pro Gly Glu Pro Gly Met Asp Cys Ser Gly Thr Val Val Asn Val
    2120            2125                2130

Gly Glu Gly Cys Pro Lys Glu Leu Arg Cys Gly Asp Asp Ala Phe
    2135            2140                2145

Gly Ile Ile Trp Gly Cys Leu Cys Thr Tyr Gly Lys Thr Lys His
    2150            2155                2160

Gln Leu Met Ala Pro Arg Pro Asn Asp Trp Asp Ala Ala Ser Ala
    2165            2170                2175

Ala Ala Leu Pro Thr Val Tyr Thr Thr Val Asp Val Ala Phe Ala
    2180            2185                2190

Glu Leu Ala Lys Leu Lys Lys Gly Glu Lys Val Leu Ile His Gly
    2195            2200                2205

Ala Thr Gly Gly Val Gly Leu Ile Ala Val Gln Tyr Ala Gln Lys
    2210            2215                2220
```

```
Leu Gly Ala Val Val Tyr Ala Thr Ala Gly Lys Glu Glu Lys Arg
    2225            2230            2235

Gln His Leu Arg Asp Leu Gly Val Lys Phe Ile Thr Ser Ser Arg
    2240            2245            2250

Ser Gly Asp Glu Phe Glu Ala Asp Met Lys Lys Phe Leu Gly Lys
    2255            2260            2265

Glu Lys Ile Asp Val Val Leu Asn Ser Met Ser His Asp Asp Tyr
    2270            2275            2280

Ile Pro Arg Ser Leu Arg Leu Leu Gly Lys Gly Gly Arg Phe Val
    2285            2290            2295

Glu Ile Gly Lys Arg Asp Ala Trp Thr Pro Glu Gln Val Ala Lys
    2300            2305            2310

Glu Phe Pro Asp Val His Tyr Tyr Pro Leu Ala Ile Asp His Val
    2315            2320            2325

Cys Glu Phe Glu Pro Asp Arg Tyr Gln Gly Leu Leu Lys Arg Leu
    2330            2335            2340

Glu Gly Ala Met Arg Glu Gly Trp Lys Pro Leu Pro Met Lys Thr
    2345            2350            2355

Phe Glu Gly Leu Glu Gln Gly Val Ala Ala Phe Gln Phe Leu Gln
    2360            2365            2370

Arg Ala Gln His Ile Gly Lys Val Val Leu Thr Val Pro Gln Arg
    2375            2380            2385

Met Gly Leu Gln Lys Asp Ala Ser Tyr Met Leu Ser Gly Gly Met
    2390            2395            2400

Gly Ala Leu Gly Ile Val Thr Ala Gln Thr Met Val Glu Glu Gly
    2405            2410            2415

Ala Lys Glu Leu Ile Leu Leu Ser Arg Ser Gly Lys Val Pro Ala
    2420            2425            2430

Glu Val Gln Glu Gln Trp Ala Trp Leu Glu Asn Ser Ala Ala Glu
    2435            2440            2445

Val Ile Ser Trp Lys Cys Asp Val Gly Lys Gly Ser Asp Asp Ile
    2450            2455            2460

Leu Lys Lys Leu Lys Gly Lys Lys Gly Asn Gly Leu Lys Gly Leu
    2465            2470            2475

Leu His Leu Ala Gly Val Leu Asp Asp Gly Met Ile Pro Asp Leu
    2480            2485            2490

Ala Arg Ser Asn Phe Glu Asn Ala Tyr Gly Pro Lys Val Phe Gly
    2495            2500            2505

Ala His His Leu Arg Glu Ala Ala Lys Lys Asn Gly Ser Thr Leu
    2510            2515            2520

Asp Phe Phe Ala Leu Tyr Ser Ser Thr Ala Ser Leu Leu Gly Ala
    2525            2530            2535

Ala Gly Gln Ala Asn Tyr Cys Ala Ala Asn Ser Ala Leu Asp Ala
    2540            2545            2550

Leu Ala Asn Ala Trp Arg Cys Gln Gly Glu Ser Val Gln Ser Val
    2555            2560            2565

Gln Trp Gly Pro Trp Leu Ser Val Gly Met Ala Ala Gln Asn Asn
    2570            2575            2580

Ser Phe Ala Arg Leu Lys Leu Gly Gly Ile Ser Asn Glu Leu Gly
    2585            2590            2595

Leu Ser Val Leu Ser Ser Ala Ile Thr Ser Gly Ala Cys Val Val
    2600            2605            2610

Gly Cys Ala Ile Val Gln Trp Pro Gly Phe Leu Lys Gln Phe Pro
```

```
                2615                2620                2625

Lys Thr Pro Leu Tyr Leu Glu Ser Phe Lys Asp Thr Ala Ala Gly
            2630                2635                2640

Ala Gly Gly Ala Gly Arg Ala Gly Gly Ser Glu Met Glu Met Thr
    2645                2650                2655

Pro Glu Gly Ile Leu Ala Trp Val Ser Ser Val Ala Ala Asp Val
    2660                2665                2670

Val Gly Thr Glu Val Ser Pro Asp Glu Pro Leu Met Ala Ala Gly
    2675                2680                2685

Met Asp Ser Leu Ser Ser Val Glu Phe Arg Asn Arg Leu Thr Ala
    2690                2695                2700

Glu Cys Ser Phe Ala Lys Phe Pro Asn Thr Leu Met Phe Asp His
    2705                2710                2715

Pro Thr Leu Arg Ala Val Thr Glu Leu Val Thr Ser Gln Leu Ser
    2720                2725                2730

Pro Glu Leu Val Ala Ser Ala Thr Ser Ala Val Ala Thr Ala Gly
    2735                2740                2745

Pro Ala Ser Asp Ile Gln Val Val Ala Arg Gly Leu Phe Ser Arg
    2750                2755                2760

Phe Pro Ser Gly Asp Gly Leu Gln Ala Asn Trp Glu Asn Trp Gln
    2765                2770                2775

Lys Lys Met Asp Ser Ile Ile Glu Val Pro Phe Ala Arg Trp Asp
    2780                2785                2790

Leu Leu Glu Phe Trp Asn Pro Asp Met Glu Ala Ser Gly Asn Val
    2795                2800                2805

Thr Tyr Ser Arg His Gly Ser Phe Ile Ala Asp Ala Glu Met Phe
    2810                2815                2820

Asp Pro Gly Phe Phe Gly Met Ser Ala Val Glu Ala Lys Thr Ile
    2825                2830                2835

Asp Pro Gln Gln Arg His Leu Leu Glu Val Ser Tyr Ala Ala Cys
    2840                2845                2850

His His Ala Gly Met Ser Lys Glu Lys Leu Leu Ala Thr Asp Thr
    2855                2860                2865

Gly Val Phe Val Gly Gln Cys Asn Asn Asp Trp Ala Lys Phe Ser
    2870                2875                2880

Ser Asp Arg Pro Ala Asn Pro Tyr Thr Gly Pro Gly Thr His Ala
    2885                2890                2895

Ser Ile Ser Ser Asn Arg Ile Ser Tyr Asn Leu Gly Leu Arg Gly
    2900                2905                2910

Pro Ser Ala Ser Ile Asp Thr Ala Cys Ser Ser Ser Leu Val Ala
    2915                2920                2925

Leu Asp Ile Ala Cys Asn Lys Leu Lys Gly Ser Leu Ile Gly Ser
    2930                2935                2940

Ala Ile Gly Ala Gly Cys Gln Leu Asn Leu Ile Ala Glu Pro Phe
    2945                2950                2955

Val Ala Phe Gly Lys Ala Arg Met Leu Ala Pro Asp Gly Arg Cys
    2960                2965                2970

Lys Thr Phe Asp Ala Ser Ala Asn Gly Tyr Val Arg Gly Glu Gly
    2975                2980                2985

Cys Gly Ala Val Tyr Leu Val Gly Ala Ala Ala Ser Lys Gln Asp
    2990                2995                3000

Glu Leu Ala Ile Leu Pro Gly Ile Ala Ala Thr Ala Thr Asn Gln
    3005                3010                3015
```

```
Asp Gly Arg Ser Ser Thr Leu Thr Ala Pro Asn Gly Pro Ser Gln
    3020              3025                3030

Gln Asp Val Ile Arg Lys Ala Leu Ala Gln Ala Gln Val Leu Ala
    3035              3040                3045

Tyr Ala Leu Gly Phe Val Glu Cys His Gly Thr Gly Thr Ala Leu
    3050              3055                3060

Gly Asp Pro Ile Glu Val Gly Ala Leu Lys Ala Val Leu Ala Pro
    3065              3070                3075

Asn Arg Thr Thr Pro Leu Ile Leu Gly Thr Val Lys Thr Asn Ile
    3080              3085                3090

Gly His Leu Glu Gly Ala Ala Gly Ile Ala Gly Met Val Lys Ala
    3095              3100                3105

Met Leu Ser Val Gln Asn Ser Glu Val Pro Pro Asn Leu His Phe
    3110              3115                3120

Asn Thr Leu Asn Pro Asn Ile Asp Leu Glu Asp Phe Pro Thr Thr
    3125              3130                3135

Ile Pro Thr Ser Ile Glu Asn Leu Thr Gly Asp Gln Pro Thr Ala
    3140              3145                3150

Gly Leu Ser Ser Phe Gly Phe Gly Gly Thr Asn Ala His Leu Thr
    3155              3160                3165

Phe Arg Ala Ala Pro Lys Pro Leu Glu Asn Ala Gln Asp Ser Glu
    3170              3175                3180

Gly Gly Ala Lys Arg Arg Val Ala Phe Leu Phe Thr Gly Gln Gly
    3185              3190                3195

Ser Gln Tyr Ile Asn Met Gly Lys Gln Leu Tyr Glu Ala Glu Pro
    3200              3205                3210

Val Phe Lys Ser Val Leu Glu Lys Cys Ala Glu Leu Leu Asn Pro
    3215              3220                3225

Leu Leu Glu Gln Pro Leu Leu Glu Val Ile Phe Asp Ala Gly Gly
    3230              3235                3240

Lys Phe Gly Lys Leu Leu Asp Gln Thr His Met Ser Gln Pro Ala
    3245              3250                3255

Ile Phe Ala Ile Glu Val Ala Leu Ala Ser Met Trp Lys Ala Lys
    3260              3265                3270

Gly Phe Glu Pro Glu Val Val Met Gly His Ser Val Gly Glu Tyr
    3275              3280                3285

Ala Ala Ala Val Thr Cys Gly Val Met Ser Leu Glu Asp Gly Cys
    3290              3295                3300

Lys Met Ile Ala Ala Arg Gly Lys Leu Ile Ala Asp Lys Cys Glu
    3305              3310                3315

Ala Gly Val Gly Ala Met Val Ala Thr Phe Ala Pro Glu Ala Ala
    3320              3325                3330

Ile Ile Ala Ala Ile Asp Ser Leu Ser Asp Asn Glu Lys Lys Glu
    3335              3340                3345

Val Ala Ile Ala Gly Val Asn Gly Pro Lys Met Cys Val Val Ser
    3350              3355                3360

Gly Arg Lys Asp Val Val Glu Lys Val Val Ala Ala Thr Gly Ala
    3365              3370                3375

Gly Asn Lys Ala Leu Asn Val Ser His Ala Phe His Ser Pro Leu
    3380              3385                3390

Met Ala Pro Met Leu Asp Ser Phe Arg Gln Thr Ala Arg Ala Ala
    3395              3400                3405
```

```
Asp Leu Lys Thr Pro Ser Ser Gly Arg Phe Val Ser Thr Val Thr
    3410                3415                3420

Gly Lys Ala Val Thr Thr Glu Leu Gln Asp Ala Glu Tyr Trp Val
    3425                3430                3435

Lys His Val Ala Gln Thr Val Arg Phe Ala Asp Ala Met Ser Thr
    3440                3445                3450

Leu Glu Lys Glu Gly Val Asp Ala Phe Leu Glu Ile Gly Pro Glu
    3455                3460                3465

Pro Thr Leu Val Lys Met Gly Arg Arg Cys Val Ser Gly Thr Gly
    3470                3475                3480

Tyr Gln Trp Leu Thr Ser Ile Glu Gly Lys Gly Ala Pro Val Ser
    3485                3490                3495

Glu Val Asp Ala Val Lys Gln Ala Ala Ala Val Met Arg Gly Gly
    3500                3505                3510

Leu Pro Pro Leu Thr Tyr Lys Lys Gln Ala Phe Pro Trp Arg Asp
    3515                3520                3525

Ala Gly Pro Arg Met Leu Arg Arg Arg Ala Thr Thr Asp Lys Glu
    3530                3535                3540

Ala His Phe Asp Val Pro Val Arg Ser Asp Leu Phe Ala Val Ala
    3545                3550                3555

Ala Glu His Val Val Tyr Gly Glu Ile Val Pro Gly Val Ile
    3560                3565                3570

Phe Val Glu Met Ala Leu Glu Ser Val Arg Ala His Leu Gly Glu
    3575                3580                3585

His Val Gln Leu Arg Asp Val Ser Met Val Trp Pro Leu Val Val
    3590                3595                3600

Pro Lys Asn Ala Asp Cys Glu Glu Lys Gln Val Trp Met Arg Leu
    3605                3610                3615

Ala Ile Ile Gln Asn Lys Arg Phe Glu Leu Arg Ser Gln Thr Pro
    3620                3625                3630

Gly Asp Asp Lys Trp Thr Thr His Cys Glu Gly Lys Leu Asp Leu
    3635                3640                3645

Asn Gly Pro Ala Ala Pro Val Val Glu Glu Ser Phe Asp Glu Ile
    3650                3655                3660

Arg Glu Arg Cys Pro Glu Asp Val Asp Glu Thr Lys Leu Tyr Pro
    3665                3670                3675

Leu Val Asp Ser Val Gly Leu Trp Leu Gly Pro Lys Phe Gln Val
    3680                3685                3690

Val Ser Glu Met Lys Arg Ser Lys Glu Glu Ile Ser Cys Lys Met
    3695                3700                3705

Met Leu His Pro Asp Val Ile Asn Asn Gly Tyr Ile Ile His Pro
    3710                3715                3720

Ser Leu Met Asp Gly Thr Ile His Ala Val Cys Ala Thr Met Leu
    3725                3730                3735

Asp Gln Asp Pro Pro Phe Leu Lys Ile Phe Ala Gly Val Gly Arg
    3740                3745                3750

Ile Ala Met His Ala Lys Ala Ala Pro Lys Asn Val Lys Val Asn
    3755                3760                3765

Leu His Leu Lys Ile Ser Glu Leu Ser Asp Gln Gln Ile Phe
    3770                3775                3780

Gln Cys Val Val Thr Asp Asp Lys Lys Val Leu Trp Val Met
    3785                3790                3795

Glu Asp Val Leu Phe Arg Lys Val Leu Pro Glu Gln Ile Gln Lys
```

```
                    3800            3805             3810

Ala Leu Ala Ala Thr Lys Glu Lys Asp Ala Val Asn Tyr Phe Glu
        3815            3820            3825

Ala Gln Trp Gln Pro Ala Thr Val Asp Asn Leu Ser Gly Gly Phe
        3830            3835            3840

Ile Glu Lys Gly Pro Met Leu Val Ile Cys Glu Asp Ala Asp Val
        3845            3850            3855

Leu Glu Gly Met Gln Ala Glu Leu Ser Glu Glu His Ser Leu Gly
        3860            3865            3870

Thr Phe Ala Glu Gly Tyr Pro Glu Ala Leu Glu Glu Phe Ser Gln
        3875            3880            3885

Val Leu Cys Val Ala Ser Pro Val Ala Gly Pro Val Asp Phe Leu
        3890            3895            3900

Gly Gly Ala Leu Glu Leu Leu Gln Lys Val Ile Lys Lys Lys Met
        3905            3910            3915

Asp Gly Lys Asp Val Pro Glu Val Trp Phe Val Leu Asn Ser Thr
        3920            3925            3930

Thr Ala Val Asn Leu Ser Glu Leu Lys Gly Lys Ala Val Pro Lys
        3935            3940            3945

His Ala Gly Leu Trp Gly Leu Ser Arg Cys Leu Arg Leu Glu His
        3950            3955            3960

Pro Asp Ile Ala Cys Gly Val Ile Asp Leu Gly Ser Lys Val His
        3965            3970            3975

Val Asp Asp Ala Ala Gly Ile Leu Glu Arg Leu Ala Ser Ala Lys
        3980            3985            3990

Thr Leu Gln Asp Asp Ala Phe Glu Ala Glu Val Leu Met Glu Asp
        3995            4000            4005

Ser Gln Gln Tyr Val Ala Arg Leu Val Glu Thr Thr Ser Gln Leu
        4010            4015            4020

Gln Asn Leu Pro Ser Glu Gln Ser Phe Ser Lys Asp Ala Ser Tyr
        4025            4030            4035

Val Val Thr Gly Gly Thr Gly Gly Leu Gly Leu Leu Phe Ala Gln
        4040            4045            4050

Trp Met Ala Asp Gln Gly Ala Gly His Leu Gly Leu Leu Ser Arg
        4055            4060            4065

Thr Gly Lys Ala Pro Ala Gly Pro Ala Tyr Lys Lys Leu Ala Ser
        4070            4075            4080

Thr Pro Gly Val Glu Val Ala Val Arg Ser Cys Asp Val His Ser
        4085            4090            4095

Glu Glu Ser Val Arg Ser Ile Ile Gly Glu Leu Ser Lys Thr Ala
        4100            4105            4110

Ala Val Lys Gly Val Leu His Ala Ala Gly Val Leu Glu Asp His
        4115            4120            4125

Leu Ile Val Asp Leu Lys Lys Glu His Leu Asp Pro Val Leu Arg
        4130            4135            4140

Pro Lys Ile Asp Gly Thr Leu Asn Leu His Gly Ala Thr Ser Asp
        4145            4150            4155

Leu Asp Phe Phe Val Met Phe Ser Ser Ile Ala Ala Met Leu Gly
        4160            4165            4170

Ser Pro Gly Gln Ala Asn Tyr Cys Ser Gly Asn Ala Phe Met Asp
        4175            4180            4185

Ala Phe Thr Leu His Arg Arg Ala Gln Gly Gln Ser Ala Val Ser
        4190            4195            4200
```

-continued

Val Gln Trp Gly Pro Trp Ala Glu Val Gly Met Ala Ala Arg Ala
4205                4210                4215

Gly Thr Ser Glu Thr Ser Tyr Gln Arg Leu Asp Pro Thr Ala Ser
4220                4225                4230

Leu Ala Ala Met Gly Ala Ile Leu Gly Ala Gly Ser Glu Ala Val
4235                4240                4245

Thr Asn Gly Ile Val Gly Val Ala Arg Val Asn Trp Ser Asn Phe
4250                4255                4260

Leu Ala Gly Phe Pro Thr Leu Pro Pro Tyr Leu Gln Asn Phe Lys
4265                4270                4275

Asn Phe Arg Ser Ala Gly Val Lys Met Thr Asp Gly Val Ser Lys
4280                4285                4290

Thr Val Val Arg Asp Thr Ile Glu Ala Val Leu Cys Asp Val Leu
4295                4300                4305

Gly Asp Pro Asp Leu Ala Asp Phe Ser Val Pro Leu Met Asp Met
4310                4315                4320

Gly Leu Asp Ser Leu Ser Ala Val Glu Phe Arg Asn Arg Val Gln
4325                4330                4335

Ala Ala Phe Glu Gly Leu His Leu Thr Ala Thr Val Met Phe Asp
4340                4345                4350

Tyr Pro Thr Val Ala Asp Leu Thr Asp Phe Val Cys Ser Gln Phe
4355                4360                4365

Ser Glu Gly Glu Glu Glu Glu Ala Ala Gly Gly Ala Ala Arg Gly
4370                4375                4380

Glu Val Asn Ala Gln Glu Pro Leu Ala Met Leu Gly Val Ala Ala
4385                4390                4395

Arg Phe Pro Gly Cys Arg Thr Asn Asn Pro Glu Glu Tyr Trp Asn
4400                4405                4410

Met Leu Leu Leu Gly Arg Asp Met Ile Gln Glu Val Pro Ile Glu
4415                4420                4425

Arg Trp Asp Val Asp Leu Tyr Tyr Asp Glu Asp His Ser Ala Pro
4430                4435                4440

Gly Lys Met Tyr Ala Arg Asn Gly Gly Phe Ile Leu Gly Leu Glu
4445                4450                4455

Gly Phe Asp Ala Lys Met Phe Gly Ile Ala Asp Ser Glu Ala His
4460                4465                4470

Ala Met Asp Pro His Gln Arg Ile Leu Leu Glu Val Ala Tyr Glu
4475                4480                4485

Ser Phe Trp Asn Ala Gly Phe Asn Lys Asp Asp Leu Met Asn Ser
4490                4495                4500

Asp Thr Gly Cys Phe Ile Gly Cys Ala Thr Leu Gly Gly Ile Ser
4505                4510                4515

Val Glu Asp Asp Ile Gly Pro Phe Thr Asn Ile Gly Ser Phe
4520                4525                4530

Pro Ser Gly Asn Ser Gly Arg Val Ser His Ala Leu Gly Leu Arg
4535                4540                4545

Gly Pro Cys Phe Thr Leu Asp Thr Ala Cys Ser Ala Thr Ile Val
4550                4555                4560

Ala Leu Asp Cys Ala Ala Gln Ala Met Arg Leu Asn Lys Gly Glu
4565                4570                4575

Arg Ser Cys Val Ala Gly Ser Asn Leu Gln Leu Gln Ala Asn Thr
4580                4585                4590

```
Trp Ile Gly Phe Cys Lys Met Gly Ala Leu Ser Val Asp Gly Arg
4595                4600                4605

Cys Lys Thr Phe Asp Ala Ser Ala Asn Gly Phe Thr Arg Ser Glu
4610                4615                4620

Gly Ala Gly Ser Met Ile Leu Glu Leu Gln Asp Ala Ala Leu Arg
4625                4630                4635

Lys Gly Arg Thr Glu Ile Ala Thr Val Leu Gly Ala Cys Val Asn
4640                4645                4650

Gln Asp Gly Arg Ser Ala Thr Ile Thr Ala Pro Ser Gly Pro Ala
4655                4660                4665

Gln Gln Arg Cys Ile Gln Ser Ala Leu Ala Asp Gly Ser Val Asp
4670                4675                4680

Pro Leu Asp Val Thr Met Ile Glu Val His Gly Thr Gly Thr Ala
4685                4690                4695

Leu Gly Asp Pro Ile Glu Ile Gly Gly Leu Lys Ser Thr Val Gly
4700                4705                4710

Lys Gly Arg Ser Ala Asp Ser Pro Leu Ile Leu Gly Ala Val Lys
4715                4720                4725

Ser Ile Ile Gly His Glu Glu Gly Ala Ala Gly Val Ala Gly Val
4730                4735                4740

Ile Lys Met Val Cys Glu Phe Lys Tyr Arg Gln Ile Pro Lys Asn
4745                4750                4755

Leu His Leu His Lys Leu Asn Pro Asn Ile Asp Leu Ser Asp Phe
4760                4765                4770

Ala Ser Val Val Met Pro Asp Ser Ile Ile Asp Trp Lys Ser Thr
4775                4780                4785

Ser Thr Lys Ser Gly Thr Ser Ser Phe Gly Phe Ser Gly Thr Asn
4790                4795                4800

Ser His Ala Ile Leu Glu Ala Val Asp Gly Asp Glu Ile Gly Gly
4805                4810                4815

Val Ala Leu Gln Asn Ser Thr Pro Leu Lys Trp Ala Arg Val Pro
4820                4825                4830

His Arg Met Ser Thr Glu Trp Ser Ser Gly Leu Trp Trp Ser Leu
4835                4840                4845

Glu Trp Lys Asn Thr Pro Leu Ala Thr Gly Ser Leu Asp Asp Leu
4850                4855                4860

Pro Cys Leu Leu Val Gly Gly Gly Glu Ile Ala Lys Ala Val Ala
4865                4870                4875

Lys Val Ile Ser Asp Val Thr Val Val Asp Ile Lys Asn Ala Ala
4880                4885                4890

Lys Ala Ile Glu Glu Lys Glu Trp Ala Thr Ile Leu Ile Thr Glu
4895                4900                4905

Pro Ile Thr Ser Thr Asp Asp Cys Leu Glu Gly Ala Ala Ile Met
4910                4915                4920

Gln Leu Ile Glu Val Thr Lys Ala Val Val Ala Ser Gly Arg Ala
4925                4930                4935

Leu Arg Phe Val Val Ala Thr Ala Gly Ala Gln Ser Ala Ser Thr
4940                4945                4950

Glu Asp Ser Lys Leu Ser Gln Gly Cys Leu Gly Ala Ala Ala Trp
4955                4960                4965

Gly Leu Met Arg Thr Ile Ile Trp Glu Ala Pro Ser Leu Lys Leu
4970                4975                4980

Gln Thr Ile Asp Leu Pro Ser Gln Ala Ser Ala Glu Glu Met Ala
```

```
                4985                4990                4995
         Thr Leu Leu Lys Asp Glu Leu Ser Ala Glu Gly Asp Ile Glu Pro
             5000                5005                5010
         Glu Ile Ala Tyr Met Ser Gly Gln Arg Ser Val Pro Arg Leu Ser
             5015                5020                5025
         Ser Thr Arg Leu Gln Gln Thr Ser Trp Ser Leu Lys Lys Pro Glu
             5030                5035                5040
         Gly Thr Gln Leu Leu Thr Gly Gly Phe Gly Gly Leu Gly Leu Leu
             5045                5050                5055
         Cys Ala Gln Thr Leu Val Gln Leu Gly Ser Lys Ser Ile Leu Leu
             5060                5065                5070
         Val Ser Arg Lys Gly Lys Ile Ala Asp Gly Asp Asp Val Ile Ala
             5075                5080                5085
         Asp His Met Lys Lys Leu Gln Glu Thr Asp Ala Glu Ile His Ala
             5090                5095                5100
         Trp Ser Cys Asp Val Ser Ser Arg Thr Asn Val Lys Lys Leu Val
             5105                5110                5115
         Asp Arg Val Gln Gln Glu Leu Pro Glu Asn Pro Leu Ser Gly Val
             5120                5125                5130
         Val His Ala Ala Gly Ile Leu Asp Tyr Ala Glu Ile Pro Ser Gln
             5135                5140                5145
         Thr Ser Glu Arg Leu Ser Ser Val Tyr Lys Ala Lys Val Ala Gly
             5150                5155                5160
         Ala Trp Asn Leu His Ser Glu Ser Gln Asn Thr Glu Leu Glu Asn
             5165                5170                5175
         Phe Ile Val Phe Ser Ser Val Ser Ala Leu Ile Gly Leu Thr Arg
             5180                5185                5190
         Gly Ala Ser Tyr Ser Ser Ser Asn Ala Tyr Leu Asp Gly Leu Val
             5195                5200                5205
         Leu Trp Arg Arg Ala Arg Gly Leu Ala Ala Ser Ser Leu Gln Trp
             5210                5215                5220
         Gly Pro Val Ala Glu Val Gly Met Ala Ala Lys Asp Asp Leu Ala
             5225                5230                5235
         Thr Ala Asp Ser Pro Leu Lys Tyr Leu Lys Pro Ser Gln Val Gln
             5240                5245                5250
         Ala Ala Phe Lys Gln Ser Ile Leu Ser Ala Ser Gln Pro Ser Ser
             5255                5260                5265
         Leu Leu Phe Ala Lys Cys Asp Trp Pro Arg Phe Val Gln Ser Leu
             5270                5275                5280
         Gly Thr Glu Val Pro Val Leu Lys Asp Phe Val Gly Ala Glu Glu
             5285                5290                5295
         Glu Val Ser Ser Gly Ala Lys Thr Ala Val Ser Ser Ala Phe Gln
             5300                5305                5310
         Gly Met Ser Lys Ser Glu Val Glu Ser Arg Val Gly Asp Met Val
             5315                5320                5325
         Leu Ser Val Ala Cys Thr Val Leu Gly Ile Asp Asp Leu Ser Pro
             5330                5335                5340
         Glu Ala Pro Leu Met Glu Ser Gly Leu Asp Ser Leu Ser Ala Val
             5345                5350                5355
         Asp Phe Arg Asn Gln Val Ala Lys Thr Leu Pro Gly Leu Lys Leu
             5360                5365                5370
         Pro Ser Thr Leu Met Phe Asp Tyr Pro Thr Thr Ser Ala Ile Ala
             5375                5380                5385
```

```
Asn Phe Ala Ala Ser Gln Leu Ala Pro Ala Glu Ser Ser Arg Gln
    5390            5395                5400
Ala Val Val Ala Ala Pro Ala Gly Ser Ala Leu Glu Thr Thr Glu
    5405            5410                5415
Pro Ile Ala Leu Arg Ala Gly Ala Tyr Arg Phe Pro Ile Glu Gly
    5420            5425                5430
Glu Asn Leu Gln Gln Tyr Trp Asp Ala Leu Val Asn Lys Val Asn
    5435            5440                5445
Gly Val Thr Glu Ile Pro Leu Glu Arg Trp Asp Val Asp Ala Tyr
    5450            5455                5460
Phe Asp Ala Asn Pro Glu Thr Pro Gly Lys Met Tyr Val Arg His
    5465            5470                5475
Gly Ser Phe Val Lys Asn Ala Asp Gln Phe Asp Cys Gly Phe Phe
    5480            5485                5490
Gly Leu Ser Pro Ala Glu Ser Lys Val Met Asp Pro Gln Gln Arg
    5495            5500                5505
Leu Leu Leu Glu Val Ile Tyr Arg Gly Phe His Glu His Gly Leu
    5510            5515                5520
Arg Gln Asp Thr Leu Lys Gly Met Asp Gly Cys Ile Ala Val Gly
    5525            5530                5535
Gln Cys Asn Asn Asp Trp Gly His Met Gly Phe Ser Pro Asp Glu
    5540            5545                5550
Ala Asp Val Ile Gly Pro Tyr Thr Gly Leu Ala Val Ser Thr Ser
    5555            5560                5565
Ile Ser Ser Asn Arg Val Ser Tyr Ile Leu Gly Leu Lys Gly Pro
    5570            5575                5580
Ser Leu Thr Val Asp Thr Ala Cys Ser Ser Ser Leu Thr Ala Ala
    5585            5590                5595
Asp Ile Ala Ile Ser Asn Leu Arg Arg Arg Arg Cys Glu Ile Ser
    5600            5605                5610
Ala Ala Ala Gly Val Asn Leu Asn Leu Ile Pro Gly Pro Phe Ile
    5615            5620                5625
Ala Cys Ser Lys Ala His Met Leu Ser Glu Asp Gly Phe Cys Lys
    5630            5635                5640
Thr Phe Asp Ala Ser Ala Asn Gly Tyr Val Arg Gly Glu Gly Cys
    5645            5650                5655
Gly Val Ala Ile Leu Gln Arg Leu Ala Asp Leu Gly Thr Gly Lys
    5660            5665                5670
Ser Ala Leu Val Val Val His Gly Ser Ala Val Asn Gln Asp Gly
    5675            5680                5685
Arg Ser Ser Gln Thr Ala Pro His Gly Pro Ser Gln Gln Asp
    5690            5695                5700
Val Ile Met Thr Ala Val Asn Glu Ala Gly Leu Leu Ala Ser Lys
    5705            5710                5715
Val Asn Ile Ile Glu Cys His Gly Thr Gly Thr Ala Leu Gly Asp
    5720            5725                5730
Pro Ile Glu Val Gly Ala Leu Lys Asn Thr Leu Gly Glu Gly Arg
    5735            5740                5745
Glu Glu Ser Asn Pro Leu Ala Leu Ala Ala Val Lys Ser Asn Ile
    5750            5755                5760
Gly His Leu Glu Gly Ala Ala Gly Val Ala Gly Leu Leu Lys Val
    5765            5770                5775
```

```
Ala Cys Met Leu Pro Arg Lys Gln Val Pro Ser Asn Leu His Phe
    5780            5785            5790

Lys Glu Leu Asn Pro His Ile Asp Leu Asp Asp Phe Pro Ser Thr
    5795            5800            5805

Ile Pro Thr Asp Val Val Ser Ile Lys Gln Ala Gly Val Leu Ser
    5810            5815            5820

Ala Gly Leu Ser Ser Phe Gly Phe Gly Gly Thr Asn Ala His Ile
    5825            5830            5835

Val Ser Lys Gln Phe Glu Gly Glu Pro Glu Ser Gln Pro Gln Glu
    5840            5845            5850

Leu Thr Tyr Thr Arg Gln Ser Phe Ala Trp Gln Gln Thr Arg His
    5855            5860            5865

Thr Leu Leu Ala Lys Arg Phe Lys Thr Ala Glu Asn Val Gln Val
    5870            5875            5880

Phe Ser Ala Pro Phe Gln Gly Arg Leu Leu Gln Leu Val Ser His
    5885            5890            5895

His Ile Ile Phe Gly Glu Ile Val Val Pro Gly Ala Thr Tyr Leu
    5900            5905            5910

Glu Met Val Leu Ala Ala Gly Glu Phe His Leu Gly Gly Lys Gly
    5915            5920            5925

Thr Glu Trp Tyr Ile Lys Asn Val Gly Phe Gln Ala Pro Leu Val
    5930            5935            5940

Leu Lys Thr Ser Asp Thr Gly Lys Leu Ser Arg Glu Ile Asp Leu
    5945            5950            5955

Tyr Leu Glu Val Phe Pro Asp Gly His Trp Ala Met Ser Ser Trp
    5960            5965            5970

Asp Val Ala Gln Gln Arg Lys Ala Ala Thr His Ser Glu Gly Glu
    5975            5980            5985

Val Glu Phe Thr Gly Arg Ala Val Ala Asp Lys Gln Thr Ile Asp
    5990            5995            6000

Ile Glu Ala Val Lys Ala Arg Cys Asp Glu Asp Val Val Leu Glu
    6005            6010            6015

Arg Leu Tyr Leu Pro Phe Ser Lys Ile Gly Leu Pro Leu Gln Pro
    6020            6025            6030

Arg Phe Arg Thr Val Arg His Ile Leu Arg Gly Asp Asp Glu Val
    6035            6040            6045

Ile Cys Lys Val Glu Ala Glu Asn Asp Ser Thr Asn Gln Gly Phe
    6050            6055            6060

Leu Phe Asn Pro Ala Val Leu Asp Gly Thr Phe Gln Gly Ser Met
    6065            6070            6075

Ala Leu Met Leu Ala Arg Arg Ala Thr Glu Val Asp Asp Leu Thr
    6080            6085            6090

Ser Leu Arg Ile Pro Leu Leu Cys Gln Lys Ile Thr Asn Tyr Ser
    6095            6100            6105

Gln Gly His Ser Thr Ser Ile Trp Val Asn His Ser Leu Arg Glu
    6110            6115            6120

Ile Thr Asp Lys Glu Asn Cys Val Asp Ala Lys Ile Cys Lys Asp
    6125            6130            6135

Asp Gly Thr Val Leu Leu Ala Met Asp Thr Leu Lys Phe Arg Glu
    6140            6145            6150

Val Arg Pro Glu His Ile Gln Lys Met Leu Gln Gln Ala Thr Glu
    6155            6160            6165

Asp Asn Glu Gln Asp Val Leu Glu Gln Glu Trp Thr Thr Leu Glu
```

```
            6170              6175              6180
Gly Lys Leu Gly Thr Ala Gly Pro Leu Ser Gly Lys Val Ile Phe
            6185              6190              6195
Val Gly Ala Ser Ala Ala Met Glu Lys Ala Leu Arg Val Lys Tyr
            6200              6205              6210
Ser Ser Ala Ser Phe Val Arg Gly Gly Glu Asp Leu Gly Asp Cys
            6215              6220              6225
Ala Lys Ala Lys Ile Val Phe Val Glu Ala Leu Cys Glu Glu Ala
            6230              6235              6240
Gly Glu Met Glu Ile Ile His His Ala Met Leu Leu Val Gln Val
            6245              6250              6255
Val Met Lys Met Ala Asp Lys Asp Ser Asp Thr Ala Pro Ala Leu
            6260              6265              6270
Trp Trp Ile Thr Arg Gly Thr Gln Ala Val Gly Ala Cys Ser Ser
            6275              6280              6285
Tyr Ala Thr Ala Gly Leu Trp Gly Met Ala Arg Thr Ala Arg Leu
            6290              6295              6300
Glu Glu Arg Ser Leu Lys Leu Arg Cys Leu Asp Leu Asp Thr Thr
            6305              6310              6315
Gln Gly Thr Glu Glu Ala Ala Glu Ala Leu Ser Thr Trp Leu Gly
            6320              6325              6330
Thr Leu Ser Gly Asn Ala Asn Val Asp Ala Glu Ala Glu Val Ala
            6335              6340              6345
Leu Arg Ile Ala Asp Gly Glu Thr Lys Ala Tyr Ile Ala Arg Leu
            6350              6355              6360
Ala Arg Ser Asn Thr Glu Val Lys Lys Pro Met Gln Leu Lys Met
            6365              6370              6375
Ser Ser Arg Gly Ser Leu Ala Asn Leu Arg Pro Val Pro Gln Thr
            6380              6385              6390
Asn Arg Arg Ala Pro Gly Ala Gly Glu Cys Glu Leu Arg Val Arg
            6395              6400              6405
Ala Ile Gly Leu Asn Phe Arg Asp Val Leu Asn Val Met Gly Met
            6410              6415              6420
Tyr Pro Gly Asp Pro Gly Asn Pro Gly Gly Asp Cys Ala Gly Thr
            6425              6430              6435
Val Thr Ala Ile Gly Glu Gly Val Glu His Leu Arg Pro Gly Met
            6440              6445              6450
Asp Val Phe Gly Ile Ala Trp Gly Ser Leu Gln Thr Tyr Val Thr
            6455              6460              6465
Thr Asn Ala Leu Leu Met Val Glu Lys Phe Lys Asp Trp Ser Phe
            6470              6475              6480
Glu Gln Met Ala Ala Trp Ser Val Thr Phe Ala Thr Thr Glu Glu
            6485              6490              6495
Ala Phe Gln Glu Leu Ala Pro Leu Val Lys Gly Glu Arg Val Leu
            6500              6505              6510
Ile His Ala Ala Thr Gly Gly Val Gly Leu Val Ala Val Gln Phe
            6515              6520              6525
Ala Gln Arg Val Gly Ala Thr Ile Phe Ala Thr Cys Ser Ala Ser
            6530              6535              6540
Lys Val Glu His Leu Lys Gly Met Gly Val Lys Tyr Ile Thr Thr
            6545              6550              6555
Thr Arg Asp Gly Ala Ala Phe Glu Ala Asp Met Gln Lys Phe Leu
            6560              6565              6570
```

-continued

```
Lys Glu Asp Gly Ala Asp Gly Ile Asp Cys Val Met Asn Ser Leu
        6575            6580                6585

Ser His Asp Asp Tyr Ile Pro Arg Ser Leu Lys Leu Leu Lys Lys
        6590            6595                6600

Gly Gly Arg Phe Met Glu Ile Gly Lys Arg Gly Ile Trp Thr His
        6605            6610                6615

Glu Gln Met Ala Gln Glu Arg Pro Asp Val Met Tyr Glu Lys Ile
        6620            6625                6630

Ala Met Asp Trp Val Met Glu His Gln Pro Glu Arg Tyr Asn Ser
        6635            6640                6645

Leu Met Lys Arg Leu Val Glu Gln Ile Gly Lys Gly Trp Trp Ala
        6650            6655                6660

Pro Met Pro Thr Thr Pro Phe Val Gly Leu Glu Asn Gly Val Asp
        6665            6670                6675

Ala Leu Arg Tyr Leu Gln Arg Ala Gln Gln Ile Gly Lys Val Val
        6680            6685                6690

Leu Thr Gln Pro Ser Arg Met Ser Cys Glu Gln Asp Gly Cys Tyr
        6695            6700                6705

Leu Leu Ser Gly Gly Val Gly Ala Leu Gly Leu Val Thr Ala Gln
        6710            6715                6720

Thr Met Ala Glu Glu Gly Ala Lys Ser Leu Val Leu Met Ser Arg
        6725            6730                6735

Arg Gly Ala Ile Pro Ser Asp Leu Glu Ala Gln Trp Ala Lys Leu
        6740            6745                6750

Gln Gln Phe Lys Val Asp Leu His Leu Lys Ser Cys Asp Val Ala
        6755            6760                6765

Asn Met Asp Ser Val Gln Leu Met Leu Asn Gly Leu Lys Lys Glu
        6770            6775                6780

Leu Pro Thr Lys Thr Val Ile Arg Gly Leu Leu His Leu Ala Ala
        6785            6790                6795

Val Leu Asp Asp Ala Thr Leu Pro Lys Leu Thr Arg Ser His Leu
        6800            6805                6810

Glu Lys Ala Tyr Gly Ala Lys Val Tyr Gly Ala Lys His Leu His
        6815            6820                6825

Thr Ala Leu Ala Ser Ala Lys Thr Pro Leu Asp Phe Leu Val Leu
        6830            6835                6840

Phe Ser Ser Thr Ala Gly Leu Leu Gly Ser Pro Gly Gln Ala Asn
        6845            6850                6855

Tyr Ser Ala Ala Asn Val Thr Leu Asp Ala Ala Ala Asn Cys Trp
        6860            6865                6870

Gln Gly Arg Gly Glu Lys Ala Val Ala Val Gln Trp Gly Pro Trp
        6875            6880                6885

Arg Glu Ala Gly Met Ala Ala Gln Lys Gly Thr Val Glu Arg Leu
        6890            6895                6900

Lys Ala Gln Gly Leu Gly Ser Leu Gly Asn Val Val Gly Met Ser
        6905            6910                6915

Val Leu Ala Gly Ser Leu Gly Ala Thr Ala Gly Val Val Ala Ala
        6920            6925                6930

Cys Pro Val Tyr Trp Gly Val Tyr Leu Lys Gln Phe Gly Ser Ser
        6935            6940                6945

Val Pro Arg Phe Leu Ser Arg Phe Gln Lys Glu Ala Gly Ala Gly
        6950            6955                6960
```

-continued

```
Ser Ser Gly Pro Arg Pro Ile Thr Gly Gln Gln Asp Arg Gly Leu
    6965                6970                6975

Ser Ile Ala Pro Ala Asp Val Lys Asn Leu Val His Thr Ile Ala
    6980                6985                6990

Val Glu Val Met Gly Ser Thr Ser Val Asp Asp Thr Glu Pro Leu
    6995                7000                7005

Met Glu Ala Gly Met Asp Ser Leu Ala Ala Val Glu Phe Arg Asn
    7010                7015                7020

Arg Leu Ser Ser Gln Leu Pro Gly Ile Lys Leu Pro Asn Thr Leu
    7025                7030                7035

Ile Phe Asp Tyr Pro Thr Val Asn Ala Ile Gly Asp Tyr Ala Ala
    7040                7045                7050

Ala Gln Val Val Pro Val Ser Gly Gly Ala Glu Pro Ala Gly Ile
    7055                7060                7065

Ser Phe Ser Arg Ser Asp Val Glu Gln Leu Val Leu Ser Thr Ala
    7070                7075                7080

Ile Glu Val Met Gly Ser Ser Thr Val Asp Val Ser Glu Pro Leu
    7085                7090                7095

Met Glu Ala Gly Met Asp Ser Leu Ala Ala Val Glu Leu Arg Asn
    7100                7105                7110

Arg Leu Ser Ser Gln Leu Pro Gly Val Lys Leu Pro Asn Thr Leu
    7115                7120                7125

Ile Phe Asp His Pro Thr Val Ser Ala Ile Thr Asp Phe Ala Ala
    7130                7135                7140

Ser Gln Ile Ala Pro Ser Ala Gly Ser Arg Gly Ala Ser Ala Ala
    7145                7150                7155

Leu Gly Gly Ala Thr Gln Glu Lys Lys Leu Leu Asp Val Arg Gly
    7160                7165                7170

Met Ser Ser Ile Phe Pro Gly Ser Arg Asp Ala Ala Tyr Trp Lys
    7175                7180                7185

Asp Phe Val Asp Lys Lys Asp Ser Val Ile Glu Ile Pro Tyr Thr
    7190                7195                7200

Arg Trp Asp Val Asp Ala Tyr Phe Asp Lys Asp Gln Asp Ala Pro
    7205                7210                7215

Gly Lys Met Tyr Thr Arg His Gly Gly Phe Ile Asp Gly Ala Glu
    7220                7225                7230

Met Phe Asp Ala Gly Met Phe Ser Leu Ser Ala Ala Glu Ala Ala
    7235                7240                7245

Met Met Asp Pro Gln Gln Arg Leu Ile Leu Glu Val Thr Asn Thr
    7250                7255                7260

Ala Phe Asn Leu Ala Gly Arg Asp Lys Ala Ser Leu Met Gly Ala
    7265                7270                7275

Asp Val Gly Val Phe Ile Gly Gln Cys Gln Tyr Asp Trp Phe Val
    7280                7285                7290

Met Lys Ser Ala Gly Asp His Phe Asn Thr Tyr Thr Gly Thr Gly
    7295                7300                7305

Ile Ser Ala Ser Ile Ser Ser Asn Arg Thr Ser Tyr Ile Phe Gly
    7310                7315                7320

Phe Lys Gly Pro Ser Leu Thr Cys Asp Thr Ala Cys Ser Ser Ser
    7325                7330                7335

Leu Val Ala Met Asp Ala Gly Tyr Ser Ser Ile Gln Arg Gly Val
    7340                7345                7350

Ser Glu Met Ala Leu Ile Gly Gly Thr Asn Leu Met Leu Gln Pro
```

```
            7355                7360                7365
Ser Pro Tyr Ile Ser Phe Ser Lys Ala Arg Met Leu Ser Glu Asp
            7370                7375            7380
Gly Arg Cys Phe Thr Phe Asn Ala Thr Ala Asn Gly Tyr Ala Arg
        7385                7390                7395
Gly Glu Gly Val Gly Gly Ile Val Val Gly Val Ala Gly Asp Ala
    7400                7405                7410
Ser Ala Asp Val Ser Ala Met Leu Arg Ala Thr Ala Ala Asn Gln
    7415                7420                7425
Asp Gly Arg Ser Ala Ser Leu Thr Ala Pro Asn Gly Pro Ser Gln
    7430                7435                7440
Gln Ala Val Ile Ala Arg Ala Leu Met Glu Gly Ser Ile Ala Ala
    7445                7450                7455
Lys Asp Val Asn Val Val Glu Cys His Gly Thr Gly Thr Ala Leu
    7460                7465                7470
Gly Asp Pro Ile Glu Val Asp Ala Leu Lys Asn Thr Leu Asn Val
    7475                7480                7485
Asp Arg Ser Gln Thr Leu Met Leu Thr Ser Ala Lys Thr Asn Ile
    7490                7495                7500
Ala His Leu Glu Gly Ser Ala Gly Ile Ala Gly Phe Val Lys Ala
    7505                7510                7515
Ala Tyr Met Met Arg Tyr Gly Gln Cys Pro Ser Asn Leu His Phe
    7520                7525                7530
Lys Glu Leu Asn Pro His Ile Asp Leu Glu Asp Phe Asp Cys Glu
    7535                7540                7545
Ile Ala Thr Glu Leu Lys Pro Leu Ala Gly Lys Pro Val Ala Gly
    7550                7555                7560
Leu Ser Ser Phe Gly Phe Gly Gly Thr Asn Thr His Val Val Leu
    7565                7570                7575
Ser Ser Ser Glu Thr Leu Gly Thr Gln Ala Ala Glu Glu Ala Pro
    7580                7585                7590
Lys Gln Ile Thr Phe Thr Arg Gln Ser Phe Pro Trp Lys Asp Arg
    7595                7600                7605
Ile Tyr Arg Leu Leu Pro Lys Arg Leu Gln Glu Gly Arg Asp Thr
    7610                7615                7620
His Phe Glu Val Ala Ile Lys Thr Asp Val Phe Asn Ile Cys Ala
    7625                7630                7635
Glu His Val Val Phe Asn Glu Ile Val Val Pro Gly Val Val Tyr
    7640                7645                7650
Thr Glu Met Ala Ile Glu Ala Thr Arg Val Ile Ile Gly Lys Glu
    7655                7660                7665
Ala Thr Leu Lys Asp Leu Thr Met Thr Trp Pro Leu Val Val Pro
    7670                7675                7680
Lys Asn Ala Asp Gly Pro Asn Ala Thr Thr Val Trp Leu Arg Phe
    7685                7690                7695
Ala Gln Met Gly Ser Glu Lys Phe Glu Val Arg Ser Arg Arg Gly
    7700                7705                7710
Asp Ser Asp Glu Met Ile Thr His Cys Glu Gly Arg Ile Gly Arg
    7715                7720                7725
Ser Leu Ser Glu Pro Gly Val Met Asp Ile Ala Gly Leu Gln Ser
    7730                7735                7740
Arg Cys Asp Arg Asn Val Asp Pro Lys Asp Val Tyr Ala Ala Ile
    7745                7750                7755
```

-continued

His Lys Gly Gly Leu Tyr Leu Gly Pro Lys Phe Gln Val Cys Arg
    7760              7765              7770

His Met Ile Arg Asn Asp Asp His Val Leu Cys Lys Leu Val His
    7775              7780              7785

Ser Asp Glu Cys Gly Pro Asn Gln Gly Tyr Phe Met His Pro Gly
    7790              7795              7800

Met Leu Asp Gly Thr Ile His Thr Leu Gly Cys Thr Met Val Gly
    7805              7810              7815

Trp Asp Ala Pro Leu Lys Val Phe Ala Gly Ile Gly Lys Leu Val
    7820              7825              7830

Ile Lys Asp His Thr Asp Phe Ser Arg Asn Glu Ser Tyr Trp Cys
    7835              7840              7845

His Leu His Leu Lys Thr Phe Ser Glu Gln Glu Gln Ile Phe Thr
    7850              7855              7860

Ser Thr Val Ala Asn Glu Glu Gly Asn Ile Leu Phe Val Gly Glu
    7865              7870              7875

Asp Val Ser Phe Arg Lys Val Thr Pro Glu Gln Ile Arg Lys Ala
    7880              7885              7890

Met Glu Ser Gln Ala Ala Glu Asp Asp Gln Lys Leu Tyr Glu Val
    7895              7900              7905

Glu Trp Thr Ser Leu Ser Thr Ala Ala Ser Ser Glu Glu Asp Glu
    7910              7915              7920

Asp Ala Lys Trp Leu Val Ile Ala Glu Thr Asp Ser Val Leu Ala
    7925              7930              7935

Asp Leu Lys Lys Glu Phe Gly Glu Ala His Thr Tyr Thr Lys Leu
    7940              7945              7950

Ala Gly Ala Asp Leu Gly Glu Met Glu Asn Tyr Ser Lys Val Val
    7955              7960              7965

Ser Ala Ile Gly Leu Glu Thr Ser Val Asn Cys Leu Asp Gly Leu
    7970              7975              7980

Asp His Ala Leu Gln Leu Met Lys Ala Leu Pro Lys Ser Ala Ser
    7985              7990              7995

Thr Ala Pro Glu Met Trp Phe Leu Thr His Gln Ala Val Gln Ala
    8000              8005              8010

Val Lys Gly Asp Met Lys Asp Ala Ala Ile Pro Val His Ala Gly
    8015              8020              8025

Leu Trp Gly Leu Ser Lys Ala Phe Arg Ala Glu Phe Pro Glu Leu
    8030              8035              8040

Lys Val Ala Cys Phe Asp Leu Glu Gly Gly Lys Ile Thr Ser Leu
    8045              8050              8055

Lys Glu Lys Phe Gln Gln Ala Leu Asp Gln Ala Ala Ala Ser Phe
    8060              8065              8070

Glu Pro Glu Leu Ala Leu Arg Ala Gly Ser Leu Tyr Ala Pro Arg
    8075              8080              8085

Leu Val Asp Ser Thr Thr Asn Leu Glu Ala Lys Ala Leu Asp Ile
    8090              8095              8100

Phe Asp Ala Asp Ala Ser His Val Ile Ser Gly Gly Thr Gly Ala
    8105              8110              8115

Leu Gly Leu Leu Thr Ala Lys Trp Met Ala Glu Lys Gly Ala Lys
    8120              8125              8130

Asn Phe Val Leu Ala Ser Arg Ser Gly Lys Val Gln Glu Asp Ala
    8135              8140              8145

-continued

```
Gln Ala Met Phe Asp Glu Val Ser Ser Val Ala Thr Val Lys Lys
    8150                8155                8160
Leu Asn Met Ser Ser Leu Asp Asp Val Lys Arg Leu Phe Thr Glu
    8165                8170                8175
Val Ala Lys Ser Met Pro Ala Ile Gly Gly Ile Thr His Ala Ala
    8180                8185                8190
Gly Ile Leu Asp Asp His Leu Ile Ala Asp Leu Gln Arg Ser His
    8195                8200                8205
Leu Glu Ala Val Leu Gly Ala Lys Val Asp Gly Thr Leu Asn Leu
    8210                8215                8220
His Glu Gly Ser Lys Asp Met Lys Leu Lys Tyr Phe Ser Met Phe
    8225                8230                8235
Ser Ser Leu Ala Ser Leu Ile Gly Thr Ala Gly Gln Ala Asn Tyr
    8240                8245                8250
Cys Ala Ala Asn Gly Phe Met Asp Ser Phe Ala Ala Tyr Arg Ile
    8255                8260                8265
Asp Ser Gly Lys Pro Ala Val Ala Ile Gln Trp Gly Pro Trp Ala
    8270                8275                8280
Asp Ile Gly Met Ala Ala Arg Ala Gly Thr Ser Glu Ser Val Val
    8285                8290                8295
Leu Arg Ile Asp Ile Glu Glu Gly Leu Arg Ala Met Glu Val Ile
    8300                8305                8310
Leu Ser Asn Ser Gly Asp Leu Met Thr Gly Ala Ile Gly Val Ala
    8315                8320                8325
Arg Ile Lys Trp Lys Ser Phe Leu Ala Gln Met Pro Ala Leu Pro
    8330                8335                8340
Pro Phe Leu Asp Asn Phe Lys Gln Phe Lys Lys Asp Ala Gly Lys
    8345                8350                8355
Lys Ser Ala Val Ala Leu Gly Ala Ala Pro Ser Lys Asp Val Val
    8360                8365                8370
Arg Gly Gly Ile Glu Asn Ile Leu Lys Glu Val Leu Gly Asp Asp
    8375                8380                8385
Thr Leu Asp Asp Phe Ser Ser Pro Leu Met Asp Leu Gly Leu Asp
    8390                8395                8400
Ser Leu Ala Ala Val Glu Phe Arg Asn Arg Val Gln Ser Ala Phe
    8405                8410                8415
Asp Gly Val Arg Leu Ala Ser Thr Val Met Phe Asp Tyr Pro Thr
    8420                8425                8430
Val Ala Asp Leu Thr Asp Phe Ile Leu Ser Gln Phe Ala Pro Glu
    8435                8440                8445
Glu Asp Glu Val Ala Gly Gly Gly Leu Gly Asp Pro Ala Ala Ser
    8450                8455                8460
Leu Arg Asp Ser Met Ala Val Ile Gly Val Ser Gly Arg Tyr Pro
    8465                8470                8475
Gly Met Ser Phe Ser Asn Asp Leu Glu Glu Tyr Trp Thr Ala Leu
    8480                8485                8490
Cys Ser Gly Asn Asp Pro Ile Gln Glu Ile Pro Ile Glu Arg Phe
    8495                8500                8505
Asp Val Asp Glu Ile Tyr Asp Glu Asp Arg Ser Ala Pro Gly Lys
    8510                8515                8520
Val Tyr Val Arg Asn Gly Gly Phe Ile Gln Gly Val Gln Glu Phe
    8525                8530                8535
Asp Asn Gly Phe Phe Gly Ile Ala Asp Thr Glu Ala Lys Ala Met
```

-continued

```
            8540                8545                8550
Asp Ala His Gln Arg Leu Gln Leu Glu Val Ala Tyr Asp Ser Phe
            8555                8560                8565
His Leu Ala Gly Phe Asn Lys Glu Ser Leu Ser Gly Met Glu Val
            8570                8575                8580
Gly Val Tyr Val Gly Cys Cys Thr Leu Thr Gly Ile Asp Val Glu
            8585                8590                8595
Ser Asp Asp Ile Gly Pro Phe Thr Asn Ile Gly Ala Gly Ile Ser
            8600                8605                8610
Gly Leu Ser Gly Arg Ile Ser His Ala Leu Gly Leu Arg Gly Pro
            8615                8620                8625
Cys Phe Ala Ile Asp Thr Ala Cys Ser Ser Thr Leu Val Ala Leu
            8630                8635                8640
Asp Cys Ala Ala Gln Ala Ser Arg Leu Gly Arg Gln Glu Met Ala
            8645                8650                8655
Cys Val Ala Gly Thr Asn Leu Gln Leu Arg Thr Asp Met Trp Ile
            8660                8665                8670
Gly Phe Cys Lys Met Thr Gly Leu Ala Ala Asp Gly Arg Cys Lys
            8675                8680                8685
Thr Phe Asp Val Ser Ala Asp Gly Phe Ala Arg Ser Glu Gly Ser
            8690                8695                8700
Gly Ser Met Ile Leu Arg Met Arg Ala His Ala Glu Ala Lys Gly
            8705                8710                8715
Glu Ala Ser Val Met Met Val Arg Gly Thr Cys Val Asn Gln Asp
            8720                8725                8730
Gly Arg Ser Ala Thr Ile Thr Ala Pro Ser Gly Pro Ala Gln Gln
            8735                8740                8745
Arg Ala Leu Ala Ala Ser Leu Arg Asp Gly Asp Leu Lys Ala Leu
            8750                8755                8760
Glu Val Ser Leu Ile Glu Cys His Gly Thr Gly Thr Ser Leu Gly
            8765                8770                8775
Asp Pro Ile Glu Val Gly Ala Gln Glu Lys Ile Tyr Gly Lys Glu
            8780                8785                8790
Arg Met Glu Gln Asp Thr Ile Val Leu Ala Ala Val Lys Ser Cys
            8795                8800                8805
Ile Gly His Leu Glu Gly Ala Ala Gly Val Ala Gly Leu Ala Lys
            8810                8815                8820
Leu Val Lys Met Ile Glu His Lys Lys Val Pro Pro Asn Leu His
            8825                8830                8835
Leu Lys Ser Met Asn Pro Asn Ile Asp Ile Ser Asn Phe Pro Val
            8840                8845                8850
Asn Ile Pro Thr Ser Gly Ala Ile Asp Trp Ser Asn Pro Gly Pro
            8855                8860                8865
Val Lys Ala Gly Ile Ser Ser Phe Gly Phe Ser Gly Thr Asn Ser
            8870                8875                8880
His Val Asn Thr Glu Glu Pro Ser Asn Ala Glu Gly Val Glu Pro
            8885                8890                8895
Pro Lys Val Gln Pro Leu Val Trp Gln Arg Arg Asp Leu Ser Tyr
            8900                8905                8910
Arg Asp Trp Thr Lys Gly Leu Phe Thr Ser Ile Glu Trp Lys Pro
            8915                8920                8925
Ala Ala Ile Lys Ala Thr Gly Lys Ile Asp Ala Ala Ala Thr Leu
            8930                8935                8940
```

-continued

```
Ile Ile Gly Gly Gly Asp Ile Ala Lys Ala Leu Ala Glu Ile Ile
    8945                8950                    8955

Pro Gly Cys Ile Val Val Ala Pro Gly Lys Ala Ala Lys Thr Ser
    8960                8965                    8970

Gly Asp Val Tyr Ser Met Asp Phe Thr Lys Leu Ala Asp Gln Val Ser
    8975                8980                    8985

Glu Val Leu Asp Asn Lys Glu Trp Ser Thr Val Val Phe Ala Glu
    8990                8995                    9000

Ser Leu Val Ala Asp Glu Pro Thr Leu Glu Gly Gln Ala Val Ser
    9005                9010                    9015

Gly Leu Leu Leu Thr Leu Gln Ala Met Ser Gln Trp Lys Arg Ser
    9020                9025                    9030

Ala Thr Leu Val Ala Leu Thr Ala Gly Ala Gln Thr Ala Glu Ala
    9035                9040                    9045

Gly Gly Lys Met Gly Val Gly Val Val Gly Ala Ala Val Trp Gly
    9050                9055                    9060

Phe Met Arg Ser Val Arg Leu Glu Ala Ala Asn Val Glu Pro Arg
    9065                9070                    9075

Val Ile Asp Phe Ser Ala Asp Ala Thr Ser Asp Ala Ser Ala Leu
    9080                9085                    9090

Ala Thr Val Ile Ser Glu Glu Leu Ala Ala Ser Asp Ala Glu Ile
    9095                9100                    9105

Ala Tyr Val Asn Gly Asn Arg Ser Thr Pro Arg Leu Val Ala Thr
    9110                9115                    9120

Asn Val Lys Asn Gly Gly Lys Pro Glu Gly Ile Glu Gly Thr Tyr
    9125                9130                    9135

Leu Ile Thr Gly Gly Phe Gly Gly Leu Gly Leu Val Ile Ala Gln
    9140                9145                    9150

Gln Leu Val Asp Met Gly Ala Thr Ser Val Ala Leu Val Ser Arg
    9155                9160                    9165

Ser Gly Lys Thr Pro Ala Gly Asp Glu Lys Leu Ala Glu Met Leu
    9170                9175                    9180

Glu Gln Val Gln Ser Ser Ser Ala Thr Val His Ala Trp Ala Cys
    9185                9190                    9195

Asp Val Ser Asp Ser Lys Arg Val Ala Asp Leu Val Lys Lys Ser
    9200                9205                    9210

Lys Lys Glu Leu Ser Ala Asp His Pro Leu Ser Thr Val Val His
    9215                9220                    9225

Ala Ala Gly Ile Ile Asp His Cys Ala Leu Ala Asp Leu Thr Val
    9230                9235                    9240

Asp Ser Ile Ala Asn Val Phe Lys Pro Lys Val Gly Gly Ala Trp
    9245                9250                    9255

His Leu His Ser Ala Thr Lys Asp Asp Gly Leu Lys Asp Phe Val
    9260                9265                    9270

Leu Phe Ser Ser Val Ser Ala Leu Ile Gly Leu Ser Arg Gly Val
    9275                9280                    9285

Thr Tyr Ser Thr Ser Asn Ala Ala Leu Asp Gly Leu Ala Leu Trp
    9290                9295                    9300

Arg Arg Ala Glu Ser Leu Ala Ala Thr Ser Ile Gln Trp Gly Pro
    9305                9310                    9315

Val Ser Glu Val Gly Met Ser Thr Lys Ala Asp His Ala Ala Ser
    9320                9325                    9330
```

```
Ala Asp Phe Ala Leu Lys Met Val Thr Pro Lys Gln Val Gln Ala
9335                9340                9345

Ala Phe Gln Arg Leu Leu Ser Ala Pro Pro Lys Ala Thr Ser Val
9350                9355                9360

Leu Phe Ala Arg Ala Asp Trp Gly Lys Tyr Leu Glu Gln Met Gly
9365                9370                9375

Val Asp Val Pro Val Leu Ala Asp Tyr Ala Ser Thr Gly Gly Ala
9380                9385                9390

Ala Ala Gly Gly Ala Thr Ala Ser Ser Ala Phe Ser Gly Met Ser
9395                9400                9405

Ile Asp Glu Ile Glu Ser Lys Val Thr Glu Met Val Val Asp Cys
9410                9415                9420

Val Arg Thr Val Leu Gly Asp Asp Ser Val Glu Ala Glu Ser Pro
9425                9430                9435

Leu Met Glu Ser Gly Leu Asp Ser Leu Ser Ala Val Asp Phe Arg
9440                9445                9450

Asn Gln Val Ser Lys Gln Leu Pro Gly Leu Lys Leu Pro Asn Thr
9455                9460                9465

Leu Met Phe Asp Tyr Pro Thr Ala Gly Ala Ile Ala Gly Tyr Ala
9470                9475                9480

Ala Ser Gln Leu Ala Pro Ala Thr Ser Ser Gly Gly Ala Ala Arg
9485                9490                9495

Ala Thr Thr Gln Ile Val Ser Ala Ala Glu Ala Arg Gly Pro Val
9500                9505                9510

Ser Ile Leu Gly Met Ala Cys Gln Phe Pro Gly Asp Ala Asp Ser
9515                9520                9525

Leu Asp Asn Phe Trp Asn Val Val Asn Lys Val Asp Cys Val
9530                9535                9540

Gly Asn Ile Pro Pro Glu Arg Trp Asp Ala Asp Glu Tyr Phe Gln
9545                9550                9555

Glu Gly Gly Gly Val Gly Lys Met Tyr Val Lys Gln Ala Ala Phe
9560                9565                9570

Val Arg Asp Val Glu Ser Phe Asp Ala Ser Leu Phe Ala Ile Ser
9575                9580                9585

Ser Ala Glu Ala Tyr Thr Met Asp Pro Gln Gln Arg Met Leu Leu
9590                9595                9600

Glu Thr Val His Thr Ala Trp Gln Leu Gly Thr Gly Gly Lys Lys
9605                9610                9615

Val Ser Leu Asp Val Gly Ser Phe Val Gly Glu Cys Asn Asn Asp
9620                9625                9630

Trp Gly His Phe Lys Asn Leu Glu Val Glu Lys Met Asn Pro Phe
9635                9640                9645

Ser Gly Thr Gly Gly Ser Met Ser Ile Ser Ala Asn Arg Leu Ala
9650                9655                9660

Tyr Val Phe Gly Phe Lys Gly Pro Ser Val Thr Ser Asp Thr Ala
9665                9670                9675

Cys Ser Ser Ser Leu Val Ala Val Asp Gln Ala Val Ser Asn Leu
9680                9685                9690

Trp Arg Gly Arg Cys Ser Ala Ser Val Ala Ala Gly Val Asn Leu
9695                9700                9705

Asn Leu Ile Pro Gly Pro Phe Val Ala Cys Cys Gln Ala Arg Met
9710                9715                9720

Leu Ala Glu Asp Gly Arg Cys Lys Thr Phe Asp Ala Ala Ala Asp
```

-continued

```
            9725                9730                9735
Gly Tyr Ser Arg Gly Glu Gly Cys Gly Ala Ile Ala Ile Arg Gly
            9740                9745                9750
Gln Ser Ser Thr Glu Asn Ala Ala Ser Phe Val Ala Val Val Gly
            9755                9760                9765
Thr Gly Val Asn Gln Asp Gly Arg Ser Ser Ser Leu Thr Ala Pro
            9770                9775                9780
Asn Gly Pro Ser Gln Gln Glu Val Ile Asn Met Ala Trp Gln Glu
            9785                9790                9795
Ala Gly Ile Ala Pro Ser Ala Ala Asp Phe Ile Glu Thr His Gly
            9800                9805                9810
Thr Gly Thr Gly Leu Gly Asp Pro Ile Glu Ile Gly Ala Leu Asn
            9815                9820                9825
Asn Thr Met Ala Glu Gly Arg Thr Ser Glu Val Val Ile Gly Ala
            9830                9835                9840
Val Lys Thr Asn Ile Ser His Leu Glu Gly Ala Ala Gly Ile Ala
            9845                9850                9855
Gly Leu Leu Lys Gly Ala Met Val Leu Glu Asn Cys Lys Val Pro
            9860                9865                9870
Pro Asn Leu His Leu Lys Lys Leu Asn Pro His Leu Asp Val Glu
            9875                9880                9885
Asp Phe Asp Val Ser Phe Pro Thr Glu Leu Val Glu Lys Ser Arg
            9890                9895                9900
Glu Gln Leu Lys Ser Ser Gly Leu Ser Ser Phe Gly Phe Gly Gly
            9905                9910                9915
Thr Asn Thr His Cys Val Thr Thr Ala Pro Thr Glu Gly Lys Val
            9920                9925                9930
Asp Gln Gln Gln Glu Ala Val Val Phe Asn Lys Gln Arg Phe Ala
            9935                9940                9945
Trp Ser Gln Val Lys His Pro Leu Ser Val Val Gly Arg Lys Gly
            9950                9955                9960
Ala Asp Pro Asn Leu Thr Val Phe Thr Ala Pro Ile Arg Gly Lys
            9965                9970                9975
Val Val Gln Leu Leu Ser His His Ile Ile Tyr Gly Glu Ile Val
            9980                9985                9990
Val Pro Gly Ala Thr Tyr Leu Glu Met Val Ile Ala Thr Thr Ala
            9995               10000               10005
Phe Arg Leu Gly Lys Asp Gly Thr Lys Phe Ser Val Glu Gly Val
           10010               10015               10020
Gly Phe Gln Asn Pro Leu Val Leu Arg Thr Ala Thr Pro Thr Glu
           10025               10030               10035
Leu Glu Arg Pro Ile Glu Leu Thr Leu His Met Tyr Asp Asn Gly
           10040               10045               10050
Lys Trp Ser Met Asn Ser Ser Glu Ala Gly Glu Val Leu Ala Thr
           10055               10060               10065
His Ala Glu Gly Ser Val Ser Phe Ala Asn Pro Thr Pro Glu Lys
           10070               10075               10080
Lys Met Leu Glu Leu Glu Glu Ile Lys Ser Arg Cys Pro Glu Val
           10085               10090               10095
Val Gln Asp Glu Arg Met Tyr Val Pro Phe Ala Asn Ile Gly Leu
           10100               10105               10110
Pro Leu Gln Pro Arg Phe Arg Thr Val Arg Thr Ile Asp Arg Ser
           10115               10120               10125
```

```
Ser Asp Glu Ile Ile Ala Trp  Val Ala Glu Glu  Asp Gly Thr
    10130           10135             10140

Asn Ala Gly Phe Ile Phe Gly  Pro Ala Val Ile  Asp Gly Ser Phe
    10145           10150             10155

Gln Ala Ser Cys Ala Phe Gln  Asn Leu Glu Ala  Leu Pro Ser Leu
    10160           10165             10170

Arg Ile Pro Leu Ser Ile Asp  Lys Val Thr Ile  Tyr Gly Gln Gly
    10175           10180             10185

Tyr Ser Gln Lys Val Trp Val  His His Lys Leu  Leu Glu Asn Thr
    10190           10195             10200

Glu Lys Thr Met Ala Thr Asn  Val Gln Leu Ala  Arg Asp Asp Lys
    10205           10210             10215

Thr Ile Ile Leu Thr Met Asp  Arg Met Arg Leu  Arg Glu Val Arg
    10220           10225             10230

Pro Glu His Ile Ala Lys Met  Leu Ala Gln Ala  Ala Gly Asp Glu
    10235           10240             10245

Asp Glu Asp Leu Leu Glu Val  Glu Trp Ala Ala  Met Asp Thr Lys
    10250           10255             10260

Asn Ala Lys Ala Val Glu Leu  Gly Lys Thr Leu  Val Ile Gly Ala
    10265           10270             10275

Asn Asp Ala Leu Lys Glu Ala  Leu Ser Lys Glu  Ile Lys Thr Ala
    10280           10285             10290

Thr Phe Ala Asp Ser Ala Glu  Ala Leu Ala Glu  Ala Thr Gly Val
    10295           10300             10305

Lys Glu Val Leu Phe Val Gly  Ala Leu Val Asp  Ser Ala Pro Glu
    10310           10315             10320

Met Glu Val Leu His Thr Ala  Leu Ser Leu Ala  Gln Glu Ala Ile
    10325           10330             10335

Lys Phe Ala Ala Ser Lys Lys  Lys Glu Ser Pro  Pro Thr Val Trp
    10340           10345             10350

Trp Ala Thr Lys Gly Thr Gln  Ala Ala Gly Leu  Gly Asp Ser Tyr
    10355           10360             10365

Tyr His Ala Gly Leu Trp Gly  Leu Ala Arg Thr  Phe Arg Met Glu
    10370           10375             10380

Glu Arg Ser Val Asn Leu Arg  Cys Leu Asp Leu  Asp Ile Ser Met
    10385           10390             10395

Gly Ser Ala Glu Ala Ala Ala  Ala Ala Leu Lys  Glu Trp Leu Pro
    10400           10405             10410

Leu Leu Ser Ala Ala Asn Leu  Val Gly Glu Thr  Glu Val Thr Leu
    10415           10420             10425

Arg Pro Lys Glu Asp Ser Lys  Glu Met Ala Pro  Leu Val Ser Arg
    10430           10435             10440

Leu Ala Thr Ser Thr Ala Lys  Ser Gln Lys Ala  Gly Met Leu Met
    10445           10450             10455

Met Ser Ser Arg Gly Ser Leu  Ser Asn Leu Arg  Pro Val Leu Gln
    10460           10465             10470

Glu Ser Arg Pro Lys Cys Gly  Pro Asn Asp Ala  Glu Leu Arg Ile
    10475           10480             10485

Arg Ala Val Gly Leu Asn Phe  Arg Asp Val Leu  Asn Val Met Gly
    10490           10495             10500

Leu Tyr Pro Gly Asp Pro Gly  Pro Pro Gly Ala  Asp Thr Ser Gly
    10505           10510             10515
```

```
Thr Val  Leu Thr Val Gly Gly      Glu Val Ser His Ile  Arg Pro Gly
    10520            10525                10530
Asp Asp  Val Phe Gly Glu Ser      Pro Gly Cys Leu Arg  Thr Tyr Asn
    10535            10540                10545
Ala Gly  Pro Ala Pro Leu Leu      Thr Gln Lys Pro Pro  Thr Trp Ser
    10550            10555                10560
Phe Glu  Asp Ala Ser Thr Met      Pro Val Ile Phe Val  Thr Val Glu
    10565            10570                10575
Glu Ser  Leu Gly Asp Leu Ala      Lys Leu Lys Lys Gly  Glu Ile Val
    10580            10585                10590
Leu Ile  His Ala Ala Ala Gly      Gly Val Gly Leu Val  Ala Ile Gln
    10595            10600                10605
Tyr Ala  Gln Phe Val Gly Ala      Thr Ile Ile Gly Thr  Ala Gly Ser
    10610            10615                10620
Glu Glu  Lys His Glu Phe Leu      Arg Asn Leu Gly Val  Lys His Ile
    10625            10630                10635
Thr Ser  Thr Arg Asn Gly Gln      Lys Phe Glu Asp Asp  Met Lys Thr
    10640            10645                10650
Ile Leu  Lys Glu Leu Lys Val      Asp Gly Ile Asp Val  Val Leu Asn
    10655            10660                10665
Ser Leu  Ser His Asp Asp Tyr      Ile Pro Arg Ser Leu  Ala Leu Leu
    10670            10675                10680
Lys Lys  Gly Gly Arg Phe Met      Glu Ile Gly Lys Arg  Gly Ile Trp
    10685            10690                10695
Ser His  Glu Gln Met Phe Glu      Ala Arg Pro Asp Val  Met Tyr Glu
    10700            10705                10710
Lys Ile  Ala Ala Asp Thr Met      Met Asp Leu Glu Ser  Trp Lys Tyr
    10715            10720                10725
Asn Ala  Tyr Met Lys Arg Leu      Leu Thr Arg Val Glu  Glu Gly Gly
    10730            10735                10740
Leu Val  Pro Ile Asn Lys His      Val Phe Thr Asp Ile  Glu Lys Gly
    10745            10750                10755
Val Thr  Ala Met Gln Phe Leu      Gln Arg Ala Gln Asn  Ile Gly Lys
    10760            10765                10770
Val Val  Ile Ala Leu Pro Ser      Arg Met Asp Cys Lys  Pro Asp Ser
    10775            10780                10785
Glu Tyr  Leu Leu Ser Gly Gly      Met Gly Ala Leu Gly  Met Val Thr
    10790            10795                10800
Ala Gln  Tyr Leu Val Glu Glu      Gly Ala Lys His Ile  Thr Leu Leu
    10805            10810                10815
Ser Arg  Ser Gly Lys Pro Ser      Asn Asp Val Leu Asp  Leu Trp Glu
    10820            10825                10830
Trp Leu  Gln Lys Ser Ser Ile      Asn Val Ser Ala Lys  Ala Cys Asp
    10835            10840                10845
Ile Ala  Gln Met Asp Ser Val      Thr Glu Leu Ala Val  Thr Leu Ser
    10850            10855                10860
Lys Asp  Gly Gln Lys Arg Ser      Pro Lys Thr His Val  Gly Gly Val
    10865            10870                10875
Ile His  Leu Ala Ala Val Leu      Asp Asp Ala Thr Leu  Pro Lys Leu
    10880            10885                10890
Thr Arg  Gly His Leu Glu Arg      Ser Phe Ala Ala Lys  Val Trp Gly
    10895            10900                10905
Ala Arg  His Leu His Cys Ala      Tyr Ala Lys Glu Leu  Asp Phe Met
```

-continued

```
            10910                10915                10920
Leu Leu Phe Ser Ser Thr Ser  Ala Leu Leu Gly Ser  Pro Gly Gln
        10925                10930                10935
Ala Asn Tyr Ser Ala Ser Asn  Ser Ser Leu Asp Ala  His Ala Arg
        10940                10945                10950
Tyr Trp Arg Gln Ser Gly Met  Gln Ala Thr Ser Val  Gln Trp Gly
        10955                10960                10965
Pro Trp Arg Glu Val Gly Met  Ala Ala Gln Lys Gly  Thr Val Glu
        10970                10975                10980
Arg Leu Arg Gln Ser Gly Val  Gly Ser Leu Thr Asn  Ala Ala Gly
        10985                10990                10995
Met Ala Ala Leu Ala Gly Ala  Leu Thr Ala Ser Cys  Pro Thr Ile
        11000                11005                11010
Val Ala Gln Pro Met Arg Trp  Ala Asn Tyr Leu Lys  Gln Tyr Pro
        11015                11020                11025
Lys Ile Pro Pro Phe Leu Ser  Arg Phe Ser Ala Glu  Leu Lys Thr
        11030                11035                11040
Lys Lys Pro Ala Ala Pro Ala  Arg Pro Ala Gln Gly  Met Met Met
        11045                11050                11055
Met Gln Gln Ala Ala Pro Ser  Ala Pro Ala Ile Ser  Val Thr Asp
        11060                11065                11070
Leu Lys Ser Met Leu Gln Gln  Ile Ala Ser Asp Val  Ala Gly Gly
        11075                11080                11085
Gly Val Val Asp Glu Asp Ser  Pro Leu Met Glu Ser  Gly Met Asp
        11090                11095                11100
Ser Leu Ser Ala Val Glu Phe  Arg Asn Arg Phe Thr  Ala Lys Val
        11105                11110                11115
Pro Gln Ile Asn Leu Pro Asn  Thr Leu Ile Phe Asp  Tyr Pro Thr
        11120                11125                11130
Ile Ser Ala Ile Ala Asp Phe  Ala Val Gly Gln Met  Gly Pro Ala
        11135                11140                11145
Thr Ala Ala Pro Ala Gly Tyr  Ala Met Gln Ala Ala  Pro Ala Ala
        11150                11155                11160
Pro Gly Met Thr Ala Asp Ala  Ile Met Glu Leu Leu  Asn Arg Ile
        11165                11170                11175
Ala Thr Asp Thr Thr Gly Gly  Ala Val Glu Val Asp  Lys Pro Leu
        11180                11185                11190
Met Glu Ser Gly Met Asp Ser  Leu Ser Ala Val Glu  Phe Arg Asn
        11195                11200                11205
Arg Leu Ser Ser Glu Leu Pro  Ser Leu Gln Leu Pro  Asn Thr Leu
        11210                11215                11220
Ile Phe Asp Tyr Pro Thr Ile  Ser Ala Val Ala Asp  Tyr Ala Val
        11225                11230                11235
Glu Gln Leu Gly Ala Ser Thr  Val Ala Val Pro Thr  Gly Gly Ala
        11240                11245                11250
Met Val Pro Met Ala Ala Gly  Ala Ser Ser Gly Ala  Phe Asp Glu
        11255                11260                11265
Pro Leu Ala Ile Ser Gly Thr  Ala Cys His Phe Pro  Ala Gly Ser
        11270                11275                11280
Thr Gly Pro Asn Val Phe Tyr  Lys Gln Leu Ala Gln  Gly Ala Asp
        11285                11290                11295
Gly Ile Val Glu Val Pro Phe  Thr Arg Trp Glu Leu  Glu Glu Val
        11300                11305                11310
```

```
Tyr Asp Pro Asn Pro Asp Ala Pro Gly Lys Met Tyr Pro Arg His
    11315           11320               11325

Gly Ala Phe Ile Gln Gly Ala Glu Gln Phe Asp Ala Ser Phe Phe
    11330           11335               11340

Gly Ile Ser Ala Pro Glu Ala Arg Ala Met Asp Pro Gln Gln Arg
    11345           11350               11355

Leu Leu Leu Glu Val Ala Tyr Asp Ser Leu Val Asp Ser Gly Phe
    11360           11365               11370

Thr Lys Ser Ser Leu Leu Ser Ser Asn Ile Ala Val Leu Val Gly
    11375           11380               11385

Gln Ala Asn Asn Asp Trp Ile Gln Met Gln Ser Trp Asp Leu Lys
    11390           11395               11400

Lys Val Asn Pro Tyr Thr Ala Thr Gly Met Ser Ala Ser Ile Ser
    11405           11410               11415

Ala Ala Arg Ile Ser Tyr Ser Leu Gly Met Lys Gly Ala Ser Tyr
    11420           11425               11430

Ile Ile Asp Thr Ala Cys Ser Ser Ala Leu Val Ala Leu Asp Ala
    11435           11440               11445

Ala Ala Val Thr Leu Arg Arg Thr Arg Cys Thr Ala Ala Val Asn
    11450           11455               11460

Ala Ala Ala Asn Val Met Val Ser Pro Ser Thr Tyr Ile Ser Phe
    11465           11470               11475

Ser Lys Pro Arg Met Leu Ser Glu Ser Gly Arg Cys Leu Thr Phe
    11480           11485               11490

Asp Gln Ser Ala Asn Gly Tyr Val Arg Gly Glu Gly Gly Gly Ser
    11495           11500               11505

Ala Ala Leu Arg Leu Val Ala Asp Ala Gly Asp Phe Ala Arg Ser
    11510           11515               11520

Ile Val Arg Gly Val Ser Val Asn Gln Asp Gly Arg Ser Ser Thr
    11525           11530               11535

Leu Thr Ala Pro Asn Gly Pro Ser Gln Gln Met Val Met Met Ala
    11540           11545               11550

Ala Leu Asn Glu Ala Lys Leu Ser Pro Gln Ser Val Gly His Leu
    11555           11560               11565

Glu Cys His Gly Thr Gly Thr Pro Leu Gly Asp Pro Ile Glu Leu
    11570           11575               11580

Gly Ala Leu Gln Ala Val Asn Ala Gly Arg Ser Glu Asn Val Pro
    11585           11590               11595

Leu Val Leu Ala Ala Val Lys Thr Asn Val Gly His Leu Glu Gly
    11600           11605               11610

Ala Ala Ala Ser Thr Gly Leu Ile Lys Ile Ala Ser Val Leu Gln
    11615           11620               11625

His Gly Ala Ala Lys Pro Gly Ile His Leu Lys Thr Leu Asn Pro
    11630           11635               11640

Asn Ile Ala Ala Leu Ser Ala Leu Pro Ala Val Phe Ala Ser Glu
    11645           11650               11655

Ser Leu Pro Leu Pro Ser Gly Gly Ala Tyr Arg Thr Ser Gly Leu
    11660           11665               11670

Ser Ser Phe Gly Phe Gly Gly Thr Asn Ala His Ser Val Thr Ser
    11675           11680               11685

Glu Ala Glu Val Pro Ala Glu Pro Val Arg Thr Val Ile Pro Gly
    11690           11695               11700
```

```
Lys Glu Tyr Lys Arg Lys Ala  Phe Pro Trp Arg  Glu Val Gly Phe
    11705            11710                11715
Arg Leu Leu Arg Ser Ser Pro  Ser Asp Asn Val  Phe Glu Val Val
    11720            11725                11730
Met Ile Ser Asp Val Tyr Asp  Val Val Ser His  His Val Val Phe
    11735            11740                11745
Ser Ser Ile Val Val Pro Gly  Val Val Tyr Val  Glu Met Ala Leu
    11750            11755                11760
Glu Ala Thr Arg Lys Ile Phe  Gly His Gly Ala  Lys Leu Thr Asp
    11765            11770                11775
Phe Gly Met Val Phe Pro Phe  Val Ile Pro Phe  Arg Thr Thr Gly
    11780            11785                11790
Val Glu Pro Ala Ala Thr Met  Arg Phe Val Leu  Arg Gly Glu Ser
    11795            11800                11805
Arg Phe Glu Ile Gln Ser Thr  Ser Ala Thr Gly  Ala Val Thr Val
    11810            11815                11820
His Ala Glu Gly Gly Ile Asp  Arg Ser Pro Met  Lys Asp Pro Ser
    11825            11830                11835
Arg Ala Glu Pro Val Asp Leu  Asp Met Val Arg  Lys Arg Val Thr
    11840            11845                11850
Glu Glu Ile Pro Ala Ser Val  Val Tyr Gly Ala  Ile Asp Gly Val
    11855            11860                11865
Gly Leu Trp Leu Gly Pro Met  Phe Gln Val Ala  Lys Gln Leu Trp
    11870            11875                11880
Arg Tyr Glu Glu Gly Asp Ser  Ile Glu Val Leu  Gly Arg Leu Glu
    11885            11890                11895
Leu Asp Lys Thr Ile Pro Asn  Glu Gly Tyr Val  Val His Pro Ala
    11900            11905                11910
Leu Leu Asp Gly Thr Ile His  Thr Leu Gly Thr  Ala Ser Ile Gly
    11915            11920                11925
Lys Asn Val Asn Asp Leu Lys  Ile Phe Gly Gly  Val Gly Arg Val
    11930            11935                11940
Thr Ile Val Glu Glu Ser Asn  Phe Ser Lys Ala  Asp Glu Tyr Trp
    11945            11950                11955
Ile Trp Met Asp Ile Lys Glu  Lys Leu Glu Ala  Ser Glu Thr Phe
    11960            11965                11970
Asp Val Arg Val Met Asn Ser  Ser Gly Lys Val  Leu Met Phe Met
    11975            11980                11985
Asp Asp Val Val Phe Arg Lys  Val Leu Pro Glu  Gln Ile Gln Met
    11990            11995                12000
Ala Ile Ala Ala Gln Ser Ala  Ser Glu Asp Ala  Gln Lys Leu Tyr
    12005            12010                12015
Glu Val Asp Trp Thr Ala Ala  Glu Glu Leu Glu  Glu Val Ala Glu
    12020            12025                12030
Glu Asp Asp Gly Gln Trp Leu  Val Leu Ala Pro  Glu Glu Ala Ala
    12035            12040                12045
Ala Lys Glu Leu Lys Lys Glu  Leu Gly Asp Lys  His Asp Tyr Lys
    12050            12055                12060
Lys Leu Ser Glu Ala Pro Thr  Glu Gly Leu Glu  Lys Tyr Ser Lys
    12065            12070                12075
Ile Val Leu Ala Ala Glu Ser  Glu Arg Gly Thr  Pro Val Asp Val
    12080            12085                12090
Leu Asp Gly Ala Leu Lys Leu  Phe Gln Ser Leu  Ala His Ala Gln
```

```
      12095                12100                12105
Glu Gly Thr Pro Glu Thr Trp Phe Leu Thr Ala Ala Thr Gln Ala
      12110                12115                12120
Ala Ala Ser Asn Glu Asp Leu Lys Gly Ala Ala Ile Pro Thr Thr
      12125                12130                12135
Ala Gly Leu Trp Gly Leu Ser Lys Ala Phe Arg Asn Glu His His
      12140                12145                12150
Asp Val Glu Met Gly Ile Leu Asp Leu Ala Ser Ser Gly Asp Leu
      12155                12160                12165
Lys Lys Pro Leu Thr Glu Lys Leu Thr Asn Ala Ser Ala Leu Met
      12170                12175                12180
Lys Ala Lys Lys Asp Ala Glu Val Ala Ala Arg Ala Asp Gly Leu
      12185                12190                12195
Met Val Pro Arg Leu Val Glu Cys Thr Ser Arg Met Pro Val Gln
      12200                12205                12210
Asp Val Ser Phe Pro Glu Asp Gly Thr Phe Val Ile Ser Gly Gly
      12215                12220                12225
Val Gly Ala Leu Gly Leu Val Phe Ala Glu Trp Met Ala Ala Asn
      12230                12235                12240
Gly Ala Lys His Phe Ala Leu Met Ser Arg Ser Gly Lys Pro Pro
      12245                12250                12255
Ala Asp Gln Lys Ser Thr Leu Arg Lys Leu Ser Ser Val Ala Thr
      12260                12265                12270
Val Lys Lys Cys Asp Ile Ala Ser Lys Asp Ser Val Leu Ala Leu
      12275                12280                12285
Met Lys Glu Ile Ala Lys Glu Met Pro Pro Val Lys Gly Ala Ile
      12290                12295                12300
His Ala Ala Gly Thr Leu Ala Asp Gly Leu Leu Val Asp Leu Asp
      12305                12310                12315
Arg Glu Lys Leu Glu Ala Val Cys Gly Ala Lys Ile Asp Gly Thr
      12320                12325                12330
Leu Asn Leu His Glu Ala Leu Lys Ser Ala Pro Leu Glu His Phe
      12335                12340                12345
Trp Leu Phe Ser Ser Val Ala Ala Met Ile Gly Ser Val Gly Gln
      12350                12355                12360
Gly Asn Tyr Cys Ala Ala Asn Ala Phe Met Asp Ser Phe Ala Ala
      12365                12370                12375
Tyr Arg Ser Ala Gln Gly Leu Pro Ala Ile Ser Val Gln Trp Gly
      12380                12385                12390
Pro Trp Ala Asp Val Gly Met Ala Ala Arg Ala Gly Thr Ser Glu
      12395                12400                12405
Gly Ser Ile Ala Arg Ile Glu Ile Ala Lys Gly Leu Glu Ala Met
      12410                12415                12420
Gln Ser Ile Leu Gly Ala Ser Ser Asn Leu His Gly Gly Val Val
      12425                12430                12435
Gly Val Ala Arg Ile Lys Trp Lys Met Leu Leu Gly Gln Met Pro
      12440                12445                12450
Lys Val Pro Pro Leu Leu Thr Lys Phe Ser Ala Glu Ala Gly Gly
      12455                12460                12465
Lys Lys Ala Ser Ala Val Ser Met Ala Gly Ile Thr Gln Asp Asp
      12470                12475                12480
Val Gln Asn Leu Val Val Gly Val Leu Lys Asp Val Met Ser Gly
      12485                12490                12495
```

```
Asp Asp Met Glu Leu Asp Leu   Ser Ser Pro Leu Met   Glu Met Gly
    12500           12505               12510

Leu Asp Ser Leu Ala Gly Val   Glu Phe Arg Asn Arg   Leu Gln Ala
    12515           12520               12525

Ser Phe Glu Gly Leu Ser Leu   Ser Ser Thr Leu Met   Phe Asp Tyr
    12530           12535               12540

Pro Thr Val Pro Asp Leu Val   Asp Phe Ile Trp Ser   Gln Val Gly
    12545           12550               12555

Pro Ala Glu Asp Glu Glu Val   Gly Gly Ala Val Ala   Gly Gly Asp
    12560           12565               12570

Ala Gly Gly Met Leu Cys Leu   Ser Gly Tyr Ala Gly   Arg Phe Pro
    12575           12580               12585

Gly Ser His Thr Asn Asp Ile   Glu Glu Tyr Trp His   Thr Leu Ser
    12590           12595               12600

His Gly Phe Asp Thr Thr Thr   Glu Leu Pro Pro Glu   Arg Trp Asp
    12605           12610               12615

Ile Asn Ala Tyr Phe Asp Ser   Asp Ile Asp Ala Pro   Gly Lys Thr
    12620           12625               12630

Tyr Val Lys Leu Gly His Phe   Ile Pro Gly Ile Asp   His Phe Asp
    12635           12640               12645

Gly Glu Phe Phe Gly Val Ser   Asp Ala Glu Gln Arg   Ala Met Asp
    12650           12655               12660

Pro His Gln Trp Leu Ala Leu   Glu Ile Ser Tyr Glu   Gly Leu Tyr
    12665           12670               12675

Ala Ala Gly Leu Thr Lys Glu   Thr Met Ser Gly Met   Glu Cys Gly
    12680           12685               12690

Val Tyr Val Gly Ala Cys Asn   Leu Gly Gly Asn Asp   Val Asp Leu
    12695           12700               12705

Glu Ala Leu Gly Pro Phe Ser   Asn Ile Gly Ala Ala   Tyr Ser Gly
    12710           12715               12720

Cys Ser Gly Arg Val Ser His   Val Leu Ser Leu Arg   Gly Pro Cys
    12725           12730               12735

Phe Thr Val Asp Thr Ala Cys   Ser Ser Thr Ile Val   Ala Leu Asp
    12740           12745               12750

Ser Gly Cys Gln Ala Val Arg   Leu Gly Lys Cys Lys   Ser Ala Leu
    12755           12760               12765

Ala Ser Gly Val Asn Val Gln   Ile Ala Ala Ser Ile   Trp Ile Gly
    12770           12775               12780

Phe Ser Lys Met Arg Gly Leu   Ala Met Asp Gly Arg   Cys Lys Thr
    12785           12790               12795

Phe Asp Ala Arg Ala Asp Gly   Phe Ala Arg Gly Glu   Gly Leu Gly
    12800           12805               12810

Ala Val Tyr Ile Gln Ala Ala   Ala Asn Cys Thr Asp   Ala Asn Pro
    12815           12820               12825

Ala Ile Ala Met Ile Thr Gly   Cys Ser Thr Asn His   Asp Gly Arg
    12830           12835               12840

Ala Ala Thr Ile Thr Ala Pro   Asn Gly Thr Ala Gln   Gln Arg Val
    12845           12850               12855

Leu Arg Ser Ala Leu Ala Glu   Arg Gly Thr Leu Ala   Glu Asp Val
    12860           12865               12870

Ala Cys Ile Glu Cys His Gly   Thr Gly Thr Ala Leu   Gly Asp Pro
    12875           12880               12885
```

```
Ile Glu Val Gly Ala Gln Lys Ala Val Tyr Asn Lys Gly Arg Ser
12890               12895               12900

Ala Ala Arg Pro Leu Val Leu Ala Ala Gly Lys Ser Ala Met Gly
12905               12910               12915

His Leu Glu Gly Ser Ala Gly Val Ala Gly Ile Cys Lys Val Ile
12920               12925               12930

Cys Thr Phe Lys His Ser Ala Ile Pro Pro Asn Leu Met Leu Glu
12935               12940               12945

Lys Leu Asn Pro Asn Ile Asp Leu Ser Gly Phe Asp Val Leu Met
12950               12955               12960

Pro Asp Ser Leu Val Asp Trp Lys Ala Val Pro Arg Ala Gly Val
12965               12970               12975

Ser Ser Phe Gly Phe Ser Gly Thr Asn Gly His Ala Ile Leu Glu
12980               12985               12990

Ala Pro Pro Thr Pro Gly Asp Gln Leu Pro Glu Arg Lys Ile Gln
12995               13000               13005

Lys Phe Asn Arg Ser Val Lys Pro Trp His Gln Trp Leu Glu Asn
13010               13015               13020

Val Leu Tyr Glu Glu Ala Trp Asn Thr Cys Glu Leu Val Pro Val
13025               13030               13035

Thr Ala Phe Asp Ala Ser Cys Ile Val Val Gly Ser Gly Ser Ile
13040               13045               13050

Ala Glu Lys Ile Arg Lys Leu Ala Lys Ala Ser Thr Val Val Pro
13055               13060               13065

Ala Gly Thr Ser Ala Lys Asp Val Ser Ala Ala Met Asp Lys Ala
13070               13075               13080

Asn Ala Gln Val Ala Ile Phe Ala Thr Ser Ala Asp Glu Pro Asp
13085               13090               13095

Gly Glu Ile Pro Gly Ala Arg Leu Val Glu Leu Leu Ser Phe Leu
13100               13105               13110

Gln Gly Ala Gln Ser Ala Ser Glu Thr Pro Lys Met Val Val Val
13115               13120               13125

Val Thr Lys Gly Ala Gln Asp Ala Ser Arg Pro Lys Phe Asp Ala
13130               13135               13140

Gly Ala Thr Leu Trp Gly Leu Val Arg Ser Ala Arg Ile Glu Met
13145               13150               13155

Pro Arg Thr Thr Ile Lys Ala Ile Asp Val Pro Val Asp Ala Ala
13160               13165               13170

Ala Asp Ala Ala Ala Lys Ile Val Val Glu Glu Leu Ala Ala Ala
13175               13180               13185

Glu Ala Glu Val Glu Val Ala His Ile Ala Gly Lys Gly Arg Cys
13190               13195               13200

Val Pro Val Val Thr Glu Ala Pro Gln Thr Ala Lys Ser Leu Gln
13205               13210               13215

Arg Gln Asp Ala Met Leu Asp Lys Lys Ile Leu Ser Glu Gly Leu
13220               13225               13230

Gln Ile Val Thr Gly Gly Leu Gly Gly Leu Gly Leu Val Ser Ala
13235               13240               13245

Arg Gln Leu Ala Glu Leu Gly Ala Thr Thr Val Met Leu Thr Ser
13250               13255               13260

Arg Ser Gly Lys Val Pro Ala Gly Gln Gly Leu Glu Glu His Leu
13265               13270               13275

Arg Trp Leu Glu Ala Ile Pro Thr Thr Glu Val Val Ile Lys Lys
```

-continued

```
                13280               13285               13290
Cys Asp Val Ser Ser Ser Ser Val Ser Glu Leu Met Lys Glu
        13295               13300               13305
Ala Thr Asp Ser Lys Gly Pro Val Ala Gly Ile Ile His Ala Ala
        13310               13315               13320
Gly Val Leu Asp Arg Cys Pro Leu Ala Glu Met Ala Lys Glu Asn
        13325               13330               13335
Leu Asp Lys Val Cys Glu Pro Lys Ala Ser Gly Ala Trp Tyr Leu
        13340               13345               13350
His Ser Ser Ser Glu Gln Ser Asp Leu Lys Leu Phe Val Leu Phe
        13355               13360               13365
Ser Ser Val Ser Ala Thr Val Gly Leu Ala Gly Gly Ala Ser Tyr
        13370               13375               13380
Ser Ala Ala Asn Ala Tyr Leu Asp Ala Leu Ala Leu Trp Arg Arg
        13385               13390               13395
Glu Lys Pro Leu Ala Ala Leu Ser Ala Lys Trp Gly Pro Val Ser
        13400               13405               13410
Glu Val Gly Met Thr Ala Ala Ser Gly Ser Asp Ser Met Leu Glu
        13415               13420               13425
Ala Met Ala Leu Lys Ala Leu Ser Pro Ala Gln Val Gly Ser Ala
        13430               13435               13440
Met Arg Leu Leu Leu Thr Gln Gln Gly Ala Gly Val Asn Leu Arg
        13445               13450               13455
Ala Glu Leu Met Leu Ala Arg Val Asn Trp Ala Asp Phe Val Arg
        13460               13465               13470
Glu Val Gly Val Glu Ile Pro Gln Val Lys Glu Phe Gln Ser Gln
        13475               13480               13485
Glu Ala Leu Ala Val Thr Gly Lys Glu Ser Lys Ala Ser Ala Met
        13490               13495               13500
Ala Gly Met Thr Asp Asp Asp Arg Gln Ala Ala Val Leu Lys Ser
        13505               13510               13515
Ile Arg Ser Ala Ala Gln Gly Met Gly Leu Glu Met Asp Asp Glu
        13520               13525               13530
Thr Pro Leu Met Glu Ala Gly Ile Asp Ser Leu Ser Ala Val Glu
        13535               13540               13545
Phe Arg Asn Lys Val Ser Ser Glu Phe Arg Glu Val Arg Leu Pro
        13550               13555               13560
Ser Thr Leu Met Phe Asp Tyr Pro Thr Leu Thr Ala Leu Ala Gln
        13565               13570               13575
Tyr Val Ser Gly Gln Leu Ser Val Ala Ala Gly Gly Gln Ala Ala
        13580               13585               13590
Ser Ser Ala Ala Ala Ala Val Ala Leu Pro Ser Lys Pro Ala Ala
        13595               13600               13605
Ala Gly Gly Asn Ile Ala Val Leu Gly Gly Ala Cys His Leu Pro
        13610               13615               13620
Gly Asp Ser Trp Ser Leu Glu Ala Phe Ser His Thr Leu Val Lys
        13625               13630               13635
Gly Val Asp Cys Ile Val Glu Ile Pro Tyr Asp Arg Trp Asp Ala
        13640               13645               13650
Asp Glu Tyr Tyr Asp Pro Glu Ala Ser Thr Gly Leu Lys Met Tyr
        13655               13660               13665
Val Lys His Ala Gly Phe Ile Glu Gly Ala Glu Leu Phe Ala Ala
        13670               13675               13680
```

```
Ser Ser    Phe Asn Ile Val Lys    Ala Glu Ala Glu Thr    Met Asp Pro
    13685              13690                  13695

Gln Gln    Arg His Leu Leu Glu    Thr Ser Phe Glu Ala    Phe Val Val
    13700              13705                  13710

Gly Gly    Phe Thr Lys Gln Ser    Leu Met Gly Ser Phe    Thr Gly Val
    13715              13720                  13725

Phe Val    Gly Gln Asp Lys Cys    Asp Trp Asn Arg Met    Ile Ser Gly
    13730              13735                  13740

Ser Met    Gly Gly Pro Tyr Ala    Ala Thr Gly Gly Ser    Ser Ser Ile
    13745              13750                  13755

Ser Ala    Asn Arg Ile Ser Tyr    Ser Leu Gly Leu Lys    Gly Pro Ser
    13760              13765                  13770

Ala Thr    Met Asp Thr Ala Cys    Ser Ser Ser Leu Val    Ala Ala Asp
    13775              13780                  13785

Thr Ala    Ala Ala Thr Leu Arg    Arg Arg Arg Cys Asp    Ile Ala Thr
    13790              13795                  13800

Val Cys    Gly Val Asn Met Leu    Leu Leu Pro Gln Thr    Phe Ile Ala
    13805              13810                  13815

Cys Cys    Gln Ala His Met Leu    Ser Ala Phe Gly Arg    Cys Lys Thr
    13820              13825                  13830

Phe Asp    Glu Ser Ala Ser Gly    Tyr Val Arg Gly Glu    Gly Cys Gly
    13835              13840                  13845

Ala Gln    Thr Leu Met Gln Val    Ser Asp Lys Pro Ala    Tyr Ala Glu
    13850              13855                  13860

Met Ser    Gly Ser Ala Leu Asn    Gln Asp Gly Arg Ser    Ser Asn Leu
    13865              13870                  13875

Thr Ser    Pro Asn Gly Pro Ser    Gln Gln Ala Val Val    Leu Ala Ala
    13880              13885                  13890

Leu Ala    Glu Ala Gly Val Ala    Pro Ser Ala Leu Asp    Cys Leu Glu
    13895              13900                  13905

Thr His    Gly Thr Gly Thr Glu    Leu Gly Asp Pro Ile    Glu Val Gly
    13910              13915                  13920

Ala Leu    Gln Ala Ala Leu Gly    Gly Ala Ala Arg Gln    Lys Ala Leu
    13925              13930                  13935

Leu Leu    Gly Ala Val Lys Thr    Asn Ile Gly His Leu    Glu Gly Gly
    13940              13945                  13950

Ala Gly    Ile Ala Gly Leu Thr    Lys Leu Val Cys Met    Leu Asn Met
    13955              13960                  13965

Arg Thr    Met Val Pro Asn Leu    His Leu Arg Glu Ile    Asn Asp His
    13970              13975                  13980

Ile Asp    Glu Asp Leu Gln Ser    Phe Ala Val Arg Leu    Pro Thr Glu
    13985              13990                  13995

Ala Thr    Lys Leu Ala Ser Lys    Gly Ile Ile Thr Ser    Ser Val Ser
    14000              14005                  14010

Ser Phe    Gly Phe Gly Gly Thr    Asn Gly His Val Val    Leu Gln Thr
    14015              14020                  14025

Ala Ser    Lys Glu Met Pro Lys    Thr Ala Lys Pro Asn    Lys Asn Val
    14030              14035                  14040

Val Phe    Leu Phe Thr Gly Gln    Gly Ser Gln Tyr Ile    Gly Met Gly
    14045              14050                  14055

Arg Gly    Leu Tyr Asp Ser Gln    Pro Val Phe Lys Gln    Ala Leu Asp
    14060              14065                  14070
```

```
Lys Cys Ala Glu Val Leu Asp Lys Leu Leu Pro Thr     Pro Leu Met
    14075                 14080                 14085

Glu Val Leu Tyr Pro Ala Asp Glu Ser Lys Leu Ile     Asp Gln Thr
    14090                 14095                 14100

Gln Phe Ser Gln Pro Ala Ile Phe Ser Ile Glu Tyr     Ala Leu Ala
    14105                 14110                 14115

Thr Leu Trp Arg Ser Met Gly Val Glu Pro Val Ala     Val Leu Gly
    14120                 14125                 14130

His Ser Val Gly Glu Tyr Cys Ala Ala Val Val Ala     Gly Val Leu
    14135                 14140                 14145

Pro Leu Glu Asp Ala Leu Lys Leu Ile Ala Leu Arg     Gly Gln Cys
    14150                 14155                 14160

Ile Ala Glu Lys Cys Glu Ala Gly Ile Gly Ser Met     Ala Ala Val
    14165                 14170                 14175

Phe Ala Ser Glu Ala Asp Val Gln Lys Ala Ile Ala     Lys Val Gly
    14180                 14185                 14190

Ser Lys Asp Val Ser Val Ala Ala Val Asn Gly Pro     Lys Met Thr
    14195                 14200                 14205

Val Val Ser Gly Arg Ser Ala Asp Val Asp Lys Val     Val Ala Gln
    14210                 14215                 14220

Thr Gly Ala Thr Ser Arg Pro Leu Thr Val Ser His     Gly Phe His
    14225                 14230                 14235

Ser Pro Leu Met Lys Pro Ala Leu Glu Pro Phe Arg     Ala Gln Ala
    14240                 14245                 14250

Glu Thr Val Thr Phe Ser Arg Pro Ser Val Lys Phe     Phe Ser Thr
    14255                 14260                 14265

Leu Leu Gly Arg Glu Val Thr Asp Glu Leu Ala Gln     Pro Gln Tyr
    14270                 14275                 14280

Trp Val Asp His Ile Glu Asn Ala Val Lys Phe Met     Pro Ala Thr
    14285                 14290                 14295

Met Ala Leu Asp Glu Ala Leu Ser Pro Asp Leu Tyr     Leu Glu Ile
    14300                 14305                 14310

Gly Ala Ser Pro Val Leu Val Asn Met Ala Lys Arg     Phe Leu Ser
    14315                 14320                 14325

Arg Ser Val Glu Trp Met Pro Ser Leu Asp Asn Lys     Val Ser Asp
    14330                 14335                 14340

Gln Asp Ala Phe Lys Lys Ala Gln Gln Ala Leu Gly     Ala Ser Ala
    14345                 14350                 14355

Gly Arg Pro Lys Ala Asp Leu Lys Arg Thr Ala Phe     Pro Trp Arg
    14360                 14365                 14370

Glu Ala Gly His Pro Leu Leu Arg Ser Lys Lys Thr     Leu Pro Asp
    14375                 14380                 14385

Gly Thr Val Val Phe Gly Val His Phe Gly Gly His     Val Leu Glu
    14390                 14395                 14400

Leu Leu Ser His His Ile Val His Gly Glu Val Val     Val Pro Gly
    14405                 14410                 14415

Ala Cys Tyr Leu Glu Met Ile Val Ala Gly Cys Thr     Thr Phe Phe
    14420                 14425                 14430

Gly Arg Asp Gln Pro Trp Cys Val Glu Gln Leu Gly     Phe Ala Lys
    14435                 14440                 14445

Pro Leu Val Leu Arg Leu Ser Pro Glu Gly Lys Leu     Asp Glu Pro
    14450                 14455                 14460

Thr Glu Leu Arg Leu Val Ile Arg Pro Asp Met Arg     Ile Glu Val
```

```
           14465              14470              14475
Glu Ser  Glu Ile Gly Asp Asp  Pro Asp Asp Ser Ile  Val Ala Thr
         14480              14485              14490
His Val  Glu Ala Ile Leu Val  Lys Gln Thr Gly Thr  Trp Ala Ser
         14495              14500              14505
Asn Arg  Pro Glu Lys Asp Ala  Phe Ser Leu Asp Gln  Leu Lys Lys
         14510              14515              14520
Gln Cys  Ala Glu Pro Val Asp  Ile Asp Leu Met Tyr  Ser Phe Gly
         14525              14530              14535
Lys Asn  Ser Gly Leu Pro Leu  Gln Arg Arg Phe Arg  Thr Val Arg
         14540              14545              14550
His Val  Gln Lys Gly Asp Lys  Glu Ser Ile Gly Arg  Leu Glu Met
         14555              14560              14565
Glu Arg  Asp Gly Thr Gln Val  Gly Phe Trp Leu Gly  Pro Ser Leu
         14570              14575              14580
Ile Asp  Gly Ser Phe Gln Ala  Ser Met Ala Leu Ala  Asp Ala Asp
         14585              14590              14595
Val Gly  Ile Gly Thr Leu Lys  Ile Pro Leu Ser Ile  Arg Arg Leu
         14600              14605              14610
Gln Pro  Thr Gly Arg Ala Tyr  Asn Ile Ser Val Trp  Ser Tyr Phe
         14615              14620              14625
Gln Leu  Ile Asp Phe Thr Asp  Arg Ser Thr Val Phe  Arg Ser Trp
         14630              14635              14640
Leu Leu  Asn Asp Ala Gly Glu  Ala Leu Leu Tyr Phe  Asp His Val
         14645              14650              14655
His Leu  Gln Glu Val Arg Asp  Glu His Ile Gln Lys  Val Leu Gln
         14660              14665              14670
Ser Ser  Gly Arg Gln Gly Thr  Glu Gln Ser Asn Leu  Tyr Asp Val
         14675              14680              14685
Glu Trp  Arg Gln Leu Glu Leu  Ala Gly Lys Pro Ala  Ser Leu Pro
         14690              14695              14700
Asn Glu  Glu Phe Leu Val Val  Gly Gly Lys Ala Ala  Leu Glu Lys
         14705              14710              14715
Leu Asn  Leu Gly Lys Ser Pro  Gln Phe Ser Cys Met  Gln Ile Gly
         14720              14725              14730
Lys Asp  Ile Asp Ile Asn Asp  Asp Asp Ser Val Asn  Lys Ala Leu
         14735              14740              14745
Leu Gly  Lys Ala Trp Ala Gly  Ile Val Leu Ala Glu  Gly Leu Ala
         14750              14755              14760
Glu Lys  Val Gly Asp Val Asp  Val Val Thr Glu Ala  Met Ile Ile
         14765              14770              14775
Val Lys  Val Leu Thr Lys Ala  Gly Ser Lys Ala Pro  Pro Leu Trp
         14780              14785              14790
Leu Leu  Thr Ser Gly Ser Gln  Pro Leu Ala Ser Ala  Asp Ala Glu
         14795              14800              14805
Gln Arg  Lys Ala Gly Cys Ala  Thr His Ser Gly Leu  Trp Gly Phe
         14810              14815              14820
Ala Arg  Ala Val Arg Met Glu  Tyr Pro Gly Met Val  Arg Val Ser
         14825              14830              14835
Cys Leu  Asp Phe Asp Pro Thr  Ser Ser Lys Ser Thr  Gly Asp Glu
         14840              14845              14850
Leu Ser  Ala Arg Leu Ser Ser  Leu Thr Ala Asp Thr  Glu Asp Glu
         14855              14860              14865
```

-continued

Val Ala  Leu Arg Ser Asp Ser  Ala Ala Ser Ala Arg  Leu Val Arg
    14870            14875                14880

Ser Glu  Leu Gln Phe Val Gly  Pro Ser Arg Leu Asn  Met Ala Ala
    14885            14890                14895

Arg Gly  Ala Leu Ser Asn Leu  Arg Leu Val Ser Gln  Gly Lys Arg
    14900            14905                14910

Gln Thr  Pro Ile Pro Gly Phe  Val Gln Gln Arg Ile  Arg Ala Ile
    14915            14920                14925

Gly Leu  Asn Phe Arg Asp Val  Leu Asn Val Met Gly  Leu Tyr Pro
    14930            14935                14940

Gly Asp  Pro Gly Ala Pro Gly  Ala Asp Ser Ser Gly  Thr Ile Val
    14945            14950                14955

Glu Leu  Gly Asp Arg Val Asp  Thr Leu Lys Ile Ala  Asp Asp Val
    14960            14965                14970

Phe Gly  Glu Ser Pro Gly Cys  Leu Ser Thr Tyr Asn  Asn Gly Pro
    14975            14980                14985

Ala Ala  Leu Leu Ala Arg Lys  Pro Pro Ser Trp Ser  Tyr Glu Glu
    14990            14995                15000

Ala Cys  Ala Met Pro Val Ile  Phe Val Thr Val Glu  Glu Ala Leu
    15005            15010                15015

Gly Asp  Leu Ala Lys Leu Lys  Lys Gly Glu Thr Val  Leu Ile His
    15020            15025                15030

Ala Ala  Ala Gly Gly Val Gly  Leu Val Ala Ile Gln  Tyr Ala Gln
    15035            15040                15045

Trp Val  Gly Ala Lys Val Tyr  Ala Thr Ala Gly Ser  Glu Glu Lys
    15050            15055                15060

His Ala  Phe Leu Arg Lys Leu  Gly Val Asp Arg Ile  Thr Ser Thr
    15065            15070                15075

Arg Asp  Gly Ala Lys Phe Glu  Ala Glu Met Glu Lys  Met Leu Lys
    15080            15085                15090

Glu Asp  Lys Leu Glu Gly Val  Asp Val Val Leu Asn  Ser Leu Ser
    15095            15100                15105

His Asp  Asp Tyr Ile Pro Arg  Ser Leu Lys Val Leu  Lys Lys Gly
    15110            15115                15120

Gly Arg  Phe Met Glu Ile Gly  Lys Arg Gly Ile Trp  Ser His Glu
    15125            15130                15135

Glu Met  Phe Lys Ala Arg Pro  Asp Ile Met Tyr Glu  Lys Ile Ala
    15140            15145                15150

Ala Asp  Thr Met Met Glu Lys  Glu Cys Trp Arg Tyr  Asn Ala Tyr
    15155            15160                15165

Leu Asn  Arg Leu Leu Glu Arg  Ala Glu Thr Gly Gly  Leu Lys Pro
    15170            15175                15180

Ile Asn  Asp His Arg Phe Glu  Gly Leu Glu Lys Gly  Val Ala Ala
    15185            15190                15195

Leu Gln  Phe Leu Gln Arg Ala  Asn Asn Ile Gly Lys  Val Val Ile
    15200            15205                15210

Ser Glu  Pro Ser Arg Leu Gln  Cys Asn Pro Ala Asn  Ile Ser Val
    15215            15220                15225

Leu Ser  Gly Gly Met Gly Ala  Leu Gly Ile Val Thr  Ala Gln Phe
    15230            15235                15240

Leu Val  Glu Glu Gly Cys Lys  Lys Leu Ser Leu Leu  Ser Arg Ser
    15245            15250                15255

-continued

| | | | | | | | | | | |
|---|---|---|---|---|---|---|---|---|---|---|
| Gly | Thr 15260 | Pro | Ser | Ser | Asp Ala 15265 | Leu | Ala | Gln Phe Glu 15270 | Trp | Leu Lys |
| Ala | Ala 15275 | Ala | Ile | Glu | Val Gly 15280 | Val | Ser | Lys Cys Asp 15285 | Val | Ser Ser |
| Glu | Thr 15290 | Ser | Val | Lys | Ala Phe 15295 | Ala | Ser | Gly Leu Gln 15300 | Ser | Pro Ile |
| Asp | Cys 15305 | Leu | Met | His | Leu Ala 15310 | Gly | Val | Leu Ala Asp 15315 | Gly | Met Leu |
| Pro | Thr 15320 | Leu | Thr | Arg | Glu His 15325 | Phe | Glu | Lys Ser Tyr 15330 | Ala | Pro Lys |
| Val | His 15335 | Gly | Leu | Tyr | His Met 15340 | Val | Lys | His Trp Lys 15345 | Met | Ser Glu |
| Asp | Thr 15350 | Lys | Phe | Met | Leu Phe 15355 | Ser | Ser | Thr Ser Ala 15360 | Leu | Phe Gly |
| Ser | Pro 15365 | Gly | Gln | Ala | Asn Tyr 15370 | Ser | Ala | Ser Asn Ser 15375 | Val | Leu Asp |
| Ser | Leu 15380 | Ala | Pro | Ile | Trp Ser 15385 | Ala | Gln | Gly Arg Gln 15390 | Ser | Trp Thr |
| Val | Gln 15395 | Trp | Gly | Pro | Trp Ala 15400 | Glu | Val | Gly Met Ala 15405 | Val | Gln Lys |
| Asn | Thr 15410 | Leu | Ser | Arg | Ala Lys 15415 | Ala | Met | Gly Val Gly 15420 | Ala | Leu Ser |
| Thr | Ala 15425 | Val | Gly | Met | Ser Ile 15430 | Met | Gly | Ser Ile Leu 15435 | Gly | Ser Ala |
| Ser | His 15440 | Val | Val | Gly | Ala Val 15445 | Pro | Val | Arg Trp Ala 15450 | Lys | Tyr Leu |
| Arg | Ser 15455 | Ala | Tyr | Gln | Glu Thr 15460 | Pro | Met | Phe Leu Thr 15465 | Asp | Met Glu |
| Ala | Glu 15470 | Val | Arg | Arg | Ala Ala 15475 | Pro | Ala | Val Gly Glu 15480 | Gly | Gly Gly |
| Asn | Ser 15485 | Leu | Ala | Leu | Ala Asn 15490 | Leu | Ser | Ala Glu Glu 15495 | Arg | Leu Glu |
| Ala | Val 15500 | Arg | Glu | Ser | Leu Leu 15505 | Thr | Met | Ala Arg Glu 15510 | Val | Val Asp |
| Asn | Asp 15515 | Thr | Leu | Ser | Ala Glu 15520 | Asp | Ala | Leu Leu Glu 15525 | Ser | Gly Met |
| Asp | Ser 15530 | Leu | Ser | Gly | Val Glu 15535 | Phe | Arg | Asn Arg Leu 15540 | Val | Thr Glu |
| Phe | Glu 15545 | Gly | Val | Arg | Met Gly 15550 | Asn | Ser | Leu Ile Phe 15555 | Asp | His Pro |
| Thr | Val 15560 | Asn | Glu | Leu | Ala Ala 15565 | Phe | Ile | Ser Glu Glu 15570 | Leu | Gly Asn |
| Thr | Leu 15575 | Pro | Ala | Ala | Asp Ser 15580 | Ser | Ala | Ala Pro Ala 15585 | Ala | Leu Gln |
| Asn | Gly 15590 | Ala | Ser | His | Pro Val 15595 | Glu | Ala | Pro Glu Ser 15600 | Ser | Ala Ser |
| Phe | Val 15605 | Glu | Ser | Leu | Asn Ser 15610 | Arg | Ala | Ser Gly Thr 15615 | Pro | Ile Tyr |
| Phe | Val 15620 | Pro | Gly | Ala | Gly Met 15625 | Gln | Ala | Gly Gly Phe 15630 | Arg | Pro Leu |
| Ala | Gln 15635 | Ile | Leu | Pro | Val Pro 15640 | Ala | Tyr | Gly Leu Ser 15645 | Trp | Pro Lys |
| Gly | Ala | Val | Pro | Arg | Glu Glu | Trp | Pro | Thr Thr Ile | Asp | Gly Leu |

| | | | | | | | | | | |
|---|---|---|---|---|---|---|---|---|---|---|
| | 15650 | | | | 15655 | | | | 15660 | |
| Ala | Arg | Val | Phe | Leu | Thr | Glu | Val | Lys | Lys | Thr | Gln | Pro | Thr | Gly |
| | 15665 | | | | | 15670 | | | | 15675 | |
| Pro | Tyr | Arg | Phe | Ala | Gly | His | Ser | Phe | Gly | Ala | Ala | Val | Ala | Leu |
| | 15680 | | | | | 15685 | | | | 15690 | |
| Glu | Met | Ala | Lys | Ile | Ala | Gln | Ala | Gln | Gly | Leu | Glu | Val | Thr | Phe |
| | 15695 | | | | | 15700 | | | | 15705 | |
| Val | Ala | Leu | Leu | Asp | Pro | Arg | His | Met | Gly | Gly | Lys | Thr | Thr | Val |
| | 15710 | | | | | 15715 | | | | 15720 | |
| Asp | Val | Gly | Glu | Ala | Phe | Ser | Thr | Thr | Asp | Leu | Ala | Asp | Ser | Leu |
| | 15725 | | | | | 15730 | | | | 15735 | |
| Gly | Leu | Leu | Ala | Gln | Thr | Val | Pro | Asp | Gly | Ser | Lys | Tyr | Val | Gln |
| | 15740 | | | | | 15745 | | | | 15750 | |
| Ala | Leu | Glu | Glu | Ile | Val | Lys | Ser | Asp | Asp | Arg | Asp | Ala | Ala | Ala |
| | 15755 | | | | | 15760 | | | | 15765 | |
| Lys | Lys | Val | Leu | Ser | Pro | Ala | Val | Leu | Ala | Ser | Leu | Glu | His | Val |
| | 15770 | | | | | 15775 | | | | 15780 | |
| His | Glu | Thr | Thr | Lys | Trp | Tyr | Ser | Thr | Leu | Leu | Ala | Gly | Asp | Asn |
| | 15785 | | | | | 15790 | | | | 15795 | |
| Leu | Gln | Pro | Asp | Ala | Ser | Leu | Lys | Ala | Arg | Ile | Ala | Val | Leu | Arg |
| | 15800 | | | | | 15805 | | | | 15810 | |
| Ala | Pro | Glu | Thr | Trp | Leu | Ser | Pro | Gly | Asp | Asn | Glu | Thr | Ile | Ala |
| | 15815 | | | | | 15820 | | | | 15825 | |
| Asp | Lys | Met | Val | Arg | Glu | Phe | Gln | Ala | Lys | Thr | Phe | Gln | Gly | Asp |
| | 15830 | | | | | 15835 | | | | 15840 | |
| Asp | Glu | Val | Thr | Lys | Leu | Val | Asp | Glu | Trp | Cys | Gly | Val | Ala | Pro |
| | 15845 | | | | | 15850 | | | | 15855 | |
| Phe | Leu | Asn | Met | Lys | Val | Pro | Gly | Ser | His | Phe | Thr | Met | Leu | His |
| | 15860 | | | | | 15865 | | | | 15870 | |
| Glu | Pro | His | Val | Val | Ser | Leu | Ala | Met | Arg | Leu | Cys | Arg | Ala | Val |
| | 15875 | | | | | 15880 | | | | 15885 | |
| Asp | Glu | Ser | Glu | Gly | Glu | Leu | | | | | |
| | 15890 | | | | | 15895 | | | | | |

<210> SEQ ID NO 2
<211> LENGTH: 47688
<212> TYPE: DNA
<213> ORGANISM: Crypthecodinium cohnii

<400> SEQUENCE: 2

```
atgaggcgca gtggtgaaat gaaaggcgcc tctggaagtt ccggatcctc cggcccttcc      60
aagcgatccg gcttgaagag gtctggtgga aacactggat ctcagtccca attggcggac     120
atggtcgacc aactgtcggt caccaccagc acaggatcca tcaggatgct cgcacgagca     180
ggcctttgcc tctcgatggg catcgttcta gcgatgggac gacatacgcc gtggtggttg     240
atccccttcg gcgtcgtctt cgaaggagtt tccctagctt ggtttcacct catccaaaaa     300
gagtgtgaac agggcaagtt tttgccttct cccgagttga atagagtatt ggccgctctc     360
ctgcgatggg aggtgtgctc ggccttggtt atcgtgttgt tcttgtcggg agcctgggac     420
atctattcta tcttcaaata ctggctgctt cctctcttcg ttacccaagc caccttttcg     480
acatccagtg caacagagaa gccaaaatcc gagtctgcag aaggctcggg cagattgtcc     540
aagactccct caatgtcttc gttggatctg ctgtttcccg agttggaatc cgcagcaagc     600
caaatttcgg agttgttgga agcggcgcag catgcggacc agagcaacat gttcacacac     660
```

```
cacgttggcg ctgacgatgc cagcagtggc gatgactggc acttcggtgt cgctctgcat      720
cagatcccga tgtaccacct gcagtcactc tcccgaaatt tgaacaagga gctgaagcgc      780
gcgcgccctt ttgggtccag cgccaatttt a gcagctctca tgggtggggg cagccaagat    840
gctgaaccag gtggcgaaca ggacgaaggc ctccgacagc gacgctccaa accagctgcc      900
aggaagaagg aggagaaagg aaagaaagat gctgtgcagc aaactccttg ggcccaggtc      960
atgaacctca tcggctggcc agccaggtac ttgttcagag aaatgtggct ctggactgag     1020
aaggacctca ccctctatgc cgtcgtcgct attttcttgc tggaggtcta catcggaacg     1080
aagtactttt ctttcgcacc aatctgcctg ctctacccgc tgctgtcgag ttcctccgga     1140
gcccgaatgg cctctgaact gcaggaggag atcgttatgg tgatgggcct cgagcatcgc     1200
ttttggcgtc gcttgcacat cccggtggct ctgcaggtgt tggtgtgcca acacatggtt     1260
gtgtatttca ttttctctca aatcatcttt ggtggagtcg atccttacgt cggtgttgcc     1320
cccaagtggc aaacctttct ttttggcgtg tgctctacg ttttgtccat ggtcggcatg      1380
atcggaatga acttggtctg ggcctgcggt gccgtcgttt tggacctccc ccagaaagtc     1440
ttcctcatga tctgtgcctc taccgcgaac caaggcagca tcttccgatg gtgccgagat     1500
catcgtgccc accttatgaa caagggcacg gtggccgatc cttacgacta caaccgtggc     1560
gctaccttcg cctacatcgg ctggtttgtg cagcagaaga ctcgccgtgc gatcgaagcg     1620
tcaagatctg tcgacatgtc cgacctcctt gccgaccagg ttgtgatgtt ccaggctgat     1680
gtggacacct ggtggaattt gtcttggtgc catgccattc cggcattctt gaccttgatg     1740
tggggcgaag atttgttttt gggttgggtc atctgcggct gcttccgata tgtgctcgcc     1800
ttgcactcca acctcctcct tgtctaccat cagcatgcct ggggcccat ggaggtgaag      1860 gcccagccag tcttgacagg agaagtgact gccgccgcca ctggccgcag aactggtggc     1920
agccagatgt tgcgttctgc ctcgatcgca gagcagctgc aatctgtgcc cgaaacagaa     1980
gtcgccccca accgaccggc cccactggac actgctgctg caattgccca acaagcccga     2040
aacgccgagg acggcggtgt cttcgtcaag tacaaggtcg gccaggcctc cgctggcggc     2100
gagccctctt tggaggtccg tttggagccc ctctggagac gctccacgtt gatcgatttg     2160
gccaaggatg ctgtcgccga catcctgaag gtccagtcca gccaggtccg acccgaccgt     2220
cctttgatgg acttgggctt tgattcggcc agtgctctca ggctcaggga caagctcagc     2280
aggcgattga acgttgaatt gccacctacc ttgctgttcg atcacccaac gatcaatgac     2340
atggtcgaca acggcctgac caagtttgct cagcgcccga tgaccccctc cggcatcacc     2400
cccgatcaga aggctgctgc catgccagat ctggtggtga cttccactgc ctgcaacatg     2460
cccaaggcgg gctccctgg tgagctctgg aacatgcttg tgacgaagac cgatgcggtt     2520
gtggaggttc ctctcgcccg ttgggatcat tgcgagtact actctccaga gcctcaggag     2580
ggccagacct acgctcgaca cggaggcttc atcgacaacg ccgatctgtt cgatgtgcct     2640
ttcttcggtc ttaccgcggc agaggccaag gctacggatc cccagcagcg cctcatcctc     2700
acaacggcct acaactgctt ctatggagat ggatacgaca aggccgcttt ggcgggcgac     2760
aacattggtg tcttcgtcgg tttgagcaac ttggactggt accacctcag cctcagcaag     2820
ccagtgtctc acacaggcac cggtgtcgcc agtgctatcg cctcgaaccg aatttcttac     2880
gtcttcggac tcaagggacc cagcatgacc gtcgacacgg cttgctcttc ctccatttcg     2940
gccttgacct ccggtatcgc ctctatcaac aagtcccacg ctgtgcgcga ggcgttggtg     3000
```

```
gcgggtgccg agcttattca tggccccaac tctttcatcc ttcgatccgt ggcgggcatg   3060
ctgagcccg aggggcgctg taagaccttc aatgccaccg ccgatggcta cattcgagga    3120
gaaggtgccg cagcggctat cattaagttg gcctctgacg ccgaggaaaa gaggtgtgcc   3180
gtcgtggccg acgtgaagag cgccgtcatg aaccaggacg gaaagagtgc gaccctgacc   3240
gcgcccaacg gtccctccca ggaagaggtg ctggccaccg ccctcaggga ggccgccatg   3300
cagccgaacc aagtcaaggc catcgaatgc acggaacag gcactgcatt gggcgacccc     3360
atcgaggtca gcgccatcaa ggctgtcctc ggagccgaga gcaaggaggc cccgaagctg   3420
atgctctgcg ctggcaagtc gaaccatggt cacttggagg gatccgccgg cttcgccggc   3480
ctgatgaagg tcttcgggtg cctcacccaa agcgaagtgc ctccaaacat ccacttcgaa   3540
cgactgaacc cccacatgag cttggagggc tctagattga cagttgcgga ggcccagacc   3600
accatcccca agggcaacac agtgatgggc gtttcctcct tcggctttgg cggcaccaac   3660
gcgcatgcgc tgctcgccca ctccatccgc aagaagccca agaaattgtc cgagcaccgg   3720
gtcgccttcc ttttcactgg acagggctcc cagcgacagg ccatgggcaa gaggctctac   3780
aaggtcgatg aggccttcaa agtcgccctc gatgaggcag ctgtcatctg caaggacctc   3840
atcgaccagg acctcttgga cctcatgttc agcgaggacc gagagatgtt ggagaagttg   3900
aacaccacct actactccca gatcgccatc ttctccatcg agtacgccct cagcaagatg   3960
tgggccgcca agggcatcac gcccttcgca gtcttgggac acagcgtcgg cgagtacacg   4020
gccgctgtcg tggccggctc tctctccttg aaggacgcgc tgaaggctct ggctactcga   4080
ggtcgcttga tccaggagaa gtgcgaccct gccatcggca acatgtgctc catctttgcc   4140
tctgccgccg atgtggaatc tgccatccgc tccgtggacc ttcagggcga gactgtcaac   4200
atcgccgcta tcaacggccc ctctgccacg gtcgtctccg gccacaagaa ggcagtcgag   4260
aaggtgtgca gcaggtcaa tgctggcaac aaggagcttg ccatccagca cgccatgcac   4320
tccaagctca ccgagtgcat cttgcccgac ttgaagaagg tcttggacac ttgcgagttg   4380
aagaagccct ccagcgacat ccacttcgtc tccacgctca ccggtactga gatctccaac   4440
gagctcacaa aggccgccca ctgggtcggc cacgacgagg acaagccgat gctcttcctt   4500
cagggtatgg agactttgga gaagttgggc tgcaccgcct tcgtcgagtt gggaccacag   4560
ccagtgttga tgaagatggg acgtcgctgc gtccagacgg ccgccaccaa cttcgaatgg   4620
ctgtcttcct tgacgccagg ccgcgacgag gtcgagaaca ttctgttgat ctctcgtgcc   4680
ttgggcgctg cgtacgatcg tgtctccgaa ctgaagccca cgcccctccc ttggcgcgcg   4740
cctctcctcc accctctgtt gggcaagaag cagcaggacg cctccggcgc caccgtcttc   4800
gagtctggtg ccatcaagag tggcgccgcg atggaacttt cgagcagca ttgcgtcttc    4860
ggacaggtcg tgctgcctgg agcgagccac atccttcttg cagccgccgc ccagttggag   4920
agcgccacca cgcgcgtcgg tgctggagct gccgtggagc tcaacgatgc cgtcttcgag   4980
cgacccttcg tcgttcctga ggactccgac ctcaccgtcc gctgcagggc gactgtcgac   5040
accaccgaag tcgccagctc cactgacggg gccgcgcccg tggtccatgc tcgattcggc   5100
agtgctcgcg tcgtcggtgc tcccgccctg gctacccctg tccaggaacg tttgtcggcc   5160
ctcgagacac ctccctccgc agagggagtc aaggaccttt acaaggcctt cgaggacaag   5220
ggcttgggct acggaccgtc cttccagccc ctgcaggagt tcagcttcca gtcttccggt   5280
gctttggctc gcctgggcat caccttgaag acctgggagc agtctctcca gatgttgcac   5340
ccggccctct tggatggagc tcttcagctc ttggtcgaga gcgccacccg acgcgtcgag   5400
```

```
gaaaagtgca ccttcttgcc atttgcggtg aagaaggcca tcgtggcagc ccagtgccca   5460
accggcgagc tttgggccag cgtcaaggtt ctggacagca ccgccacctc tttgaatgcc   5520
gatgtggagg ttttcaatgc cgagggcaag ttggcgatcc gcctcgaggg cgccagctgc   5580
cgacgagttg aggagggtgc cgccgcagag aaggacaacg gagatcagtg cctctactcc   5640
atcagctggg tcggagcgga agaggacagc cgcggcatct tggtcactgg aaccaccctc   5700
gtcgttgccc ctgaatcaga gatccccgcg atcgccaagg ccatcggcgt ctcggagtcc   5760
cgctgcagcg ctgtcagcac agcagaagaa gctgtcaaga ctgctgccga ccgaccctgc   5820
aacaccatcg tgtaccaagc tgctggctca gagatcgatg ctctggaagt tgcgctcaag   5880
ctcacacagg gagttgcgaa gttcgatggc gatgtgcccc gaatcgtctt ggtcactact   5940 gccgccagc agccggactt gaaggacaag gaacacgacc ccaagcactc tggtctgtgg   6000
ggtttcgccc gcgctgcccg tttggagtac ccccacatgc aggtctcttg cgtggacttg   6060
gagggatctt ccgaagtcgc tgctcccaca ccttccgctg cgctttccgc agcagaggtc   6120
gaagtcagtg tgcgaaatgg tgcctctttg ggtgccaggc tcgcccgcag cagcatggcg   6180
ccgaagcgcc ccttgaggct caacatggcc cgtcgaggca gcctcatgaa cctccgaccc   6240
gtcccccaga ccaagcgcaa ggcccccgag gctggcgaga tcgaagtccg agttggcgcc   6300
attggtctca acttccgaga tgtcctcaac gtcatgggcc tctacccgg agaccccggt   6360 gagcctggta tggactgctc cggcactgtc gtgaacgtcg gcgagggctg ccccaaggag   6420
cttcgatgcg gggacgatgc tttcggtatc atctggggct gcctctgcac ctatggcaag   6480
accaagcacc agctcatggc ccccagaccc aacgactggg acgccgcctc ggccgcggcc   6540
ttgccgaccg tctacaccac cgtggacgtg gccttcgcag agctcgccaa gctgaagaag   6600
ggcgagaagg tcttgatcca cggcgccacc ggcggcgtcg gtctcatcgc agtgcagtac   6660
gctcagaagc tcggagccgt cgtctacgcg acagcaggca aggaggagaa gcagacgcac   6720
ttgcgcgacc tcggtgtcaa gttcatcacg agctcccgaa gcggcgacga attcgaggct   6780
gacatgaaga agttcttggg caaggagaag atcgatgttg tgctcaacag catgagccac   6840
gacgactaca tcccgaggtc tttgcgcctc ttggggaagg gtggccgatt cgtcgagatc   6900
ggcaagcgag atgcttggac ccctgagcag gtggcaaagg agttccccga cgtgcactac   6960 tacccctttgg ccattgacca cgtctgcgag ttcgagcccg acaggtacca gggtctgctc   7020
aagcgcttgg agggtgccat gcgcgagggc tggaagcctc tgccaatgaa gactttcgag   7080
ggcttggagc agggcgtcgc tgccttccag ttcttgcagc gagctcagca catcggaaag   7140
gtcgtcttga ctgttcctca gcgaatgggc ttgcagaagg acgcctccta catgctctcc   7200
ggaggcatgg gagctttggg tattgtgact gcacagacca tggtcgagga gggagccaag   7260
gagctcatcc tcctgtctcg aagcggcaag gtccctgccg aggtccagga gcagtgggcc   7320
tggctggaga actctgctgc tgaagtcatc tcctggaagt gcgacgttgg caagggcagc   7380
gacgacatcc tcaagaagct gaagggcaag aagggcaacg gcttgaaggg tctcttgcac   7440
ctggccggtg tcttggacga tgcatgatt ccggacttgg cccgctccaa cttcgagaat   7500
gcctatggac ccaaggtctt cggagcccac cacctcaggg aggctgccaa gaagaacggc   7560
tccaccttgg acttcttcgc cttgtactca tccactgcct cgcttttggg cgctgcaggt   7620
caggcgaact actgtgccgc caactctgcc ctcgatgcct tggccaacgc ctggcgatgc   7680
cagggcgaat ccgtccagag cgtgcagtgg ggcccttggc tctcggtcgg catggccgcc   7740
```

```
cagaacaact ccttcgctcg attgaagctc ggaggcatca gcaacgagtt gggtctctcc      7800
gtcctcagct ctgccatcac cagcggcgcc tgcgtcgtcg gctgcgccat cgtgcagtgg      7860
ccaggattcc tcaagcagtt ccccaagacg ccgctctacc tggagagctt caaggacacc      7920
gctgctggcg ccgcggtgc tggtcgggct ggcggcagcg agatggagat gacaccagaa       7980
ggcatcctcg cgtgggttag ctccgtcgca gccgacgtcg tcggcacaga ggtctccccc      8040
gatgagcctc tcatggctgc cggcatggac tcgctctcct cggttgagtt ccgaaatcgc      8100
ttgactgccg agtgcagctt cgccaagttc cccaacacct tgatgttcga ccacccgacc      8160
ctgcgagcgg tcacggagct tgtcacttct cagctctccc ccgagttggt cgcctctgcc      8220
accagcgctg tcgccaccgc cggccccgcc tccgacatcc aggtcgtggc tcgcggcttg      8280
ttctcccgct tccccagcgg cgatggcttg caggccaatt gggagaactg gcagaagaag      8340
atggactcca tcatcgaagt cccctttgct cgctgggatc tcctcgagtt ctggaatcct      8400
gacatggagg ccagcggcaa tgtgacctac tcccgtcatg gaagtttcat cgccgacgcc      8460
gaaatgttcg acccaggctt cttcggcatg tcggctgtgg aagcgaagac catcgatccc      8520
cagcagcgtc acctcttgga ggtctcctac gcagcctgcc accacgctgg catgtccaag      8580
gagaagctct tggccactga cactggcgtc ttcgtcggac agtgcaacaa cgattgggcc      8640
aagttctcca gcgaccgacc tgccaacccc tacactggac cgggcactca cgcctccatc      8700
agttccaacc gaatctccta caatttgggt ctccgaggcc ccagtgcttc catcgacacg      8760
gcttgctcct cgtccttggt cgctctggac atcgcctgca acaagctcaa gggctccctc      8820
atcggctccg ccattggtgc tgggtgccag ttgaacttga tcgccgagcc ctttgtcgcc      8880
ttcggaaagg cccgcatgtt ggcccccgat ggacgttgta agacattcga tgcctctgcc      8940
aacggctacg tgcgaggtga gggttgcgga gccgtttact tggtcggagc tgctgcatcg      9000
aagcaggacg agctcgcgat cttgcccggc atcgcagcca ccgcgacgaa ccaggatgga      9060
cgaagctcca ccttgacggc ccccaacggc ccctcccagc aggatgtgat caggaaggct      9120
ttggcccagg cgcaggtgct tgcctacgcc ctcggcttcg tcgaatgcca cggaactggc      9180
actgctttgg gagaccccat cgaggttggc gccttgaaag ctgtcctggc tccaaaccgc      9240
acaactcctc tgatcctggg aacagtcaag accaacattg gtcacttgga aggtgcagcg      9300
ggcattgccg gtatggtcaa ggccatgctg tctgtgcaga actccgaggt gcctcccaat      9360
ttgcacttca acaccctcaa ccccaacatc gatctggagg acttccccac cacaattccc      9420
acaagcattg agaacttgac tggagaccag cctacagccg gcctctcctc tttcggcttc      9480
ggcggcacga acgccatct caccttcagg gctgccccca accattgga gaacgcccag       9540 gattccgagg gtggtgccaa acgtcgagtg gcattcctct tcactggcca agggtctcag      9600
tacatcaaca tgggcaagca gctctacgag gccgagcctg tcttcaagtc tgtgctcgag      9660
aagtgcgccg agttgctcaa ccccttgctg gagcagccac tcttggaagt catcttcgat      9720
gcaggtggca agttcggtaa attgctggac cagactcaca tgtcccagcc agcgatcttc      9780
gccatcgagg tcgccttggc cagcatgtgg aaagcaaagg cttcgaaacc cgaggtcgtg      9840
atgggacaca gtgtcggcga gtacgccgct gcggtcacct gtggtgtcat gagcttggaa      9900
gatggctgca agatgattgc tgcccgtggc aagctcatcg cggacaagtg cgaggccgga      9960
gtgggcgcca tggtcgccac cttcgcccc gaggccgcca tcattgcggc aatcgacagc       10020
ttgagcgaca acgagaagaa ggaagtcgcc attgctggcg tcaatggacc gaagatgtgc      10080
gttgtctctg gtcgcaagga tgttgtggag aaggtcgttg ccgccaccgg cgctggcaac      10140
```

```
aaagccctga acgtctccca tgctttccac tcgcctctca tggccccaat gttggacagc   10200
ttccgacaga cggctcgggc cgccgacctt aagaccccaa gctctggccg ttttgtctcc   10260
accgtcactg gcaaggccgt cactaccgag ttgcaggatg ccgaatactg ggtgaagcat   10320
gtcgcccaga ctgtccgatt cgccgacgcc atgtctacct tggagaaaga aggtgttgat   10380
gccttcttgg agatcggtcc tgagccgacc cttgtgaaga tgggccgtcg ctgtgtctct   10440
ggcaccggct accagtggct cacctccatc gagggcaaag gagctcccgt aagcgaggtg   10500
gacgccgtga agcaggctgc tgccgtgatg cgaggaggac tgcctcctct gacctacaag   10560
aagcaggcct tccctggag ggatgccgga cctagaatgt tgaggaggcg cgccactacc   10620
gacaaggagg cccactttga cgtccccgtg cgcagcgatc tcttcgctgt ggccgccgag   10680
cacgtcgtct acggcgagat cgtcgtgcca ggtgtcatct tcgtggaaat ggccttggag   10740
tccgttcgcg ctcacctcgg cgagcatgtc cagctccgcg acgtgtccat ggtctggccc   10800
ctcgtcgtac ccaagaacgc cgactgcgag gagaagcagg tctggatgcg attggccatc   10860
attcagaaca agcgcttcga actccgatcc cagacgcccg gcgacgacaa gtggaccacg   10920
cactgcgagg gcaagttgga tttgaacgga ccggctgcac ccgtcgtcga ggagtccttc   10980
gacgagatcc gcgagcgctg ccccgaggat gtcgacgaga ccaagttgta tcctttggtg   11040
gacagcgtcg gcctgtggtt gggaccgaag ttccaggtgg tcagcgaaat gaagcgaagc   11100
aaggaggaaa tctcctgcaa gatgatgcta caccccgacg tcatcaacaa cggctacatc   11160
atccatcctt ccttgatgga cggaaccatc catgctgtct cgccaccat gctcgaccag   11220 gatcctcctt tcctcaagat tttcgccggc gtcggtcgaa tcgccatgca cgcgaaagct   11280
gccccgaaga acgtgaaggt caacctccac ctcaagatca gcgaactgtc cgaccagcag   11340
caaatcttcc agtgcgtcgt caccgacgac gacaagaaag ttctctgggt catggaggac   11400
gtcctcttca ggaaggtcct gcccgagcag atccagaagg ccctcgcggc cacgaaggag   11460
aaggatgcag tgaactactt cgaggcccag tggcagcctg ccactgtcga caacctctcc   11520
ggcggattca tcgagaaggg accgatgctg gtcatctgcg aggatgccga tgtcttggaa   11580
ggcatgcagg cagagctctc agaggagcac agcctcggca ccttcgccga gggctatccc   11640
gaggccctgg aagagttctc gcaggtgctc tgcgtcgcct cccctgttgc cggcccagtg   11700
gacttcctcg gcggagccct cgagctgctg cagaaggtca tcaagaagaa gatggatggc   11760
aaggacgtcc ccgaagtttg gttcgtcctc aactccacca cagcggtcaa tttgtcggaa   11820
ctcaagggaa aagctgtgcc caagcatgca ggcctttggg gtctctctcg ctgcctccga   11880
ctcgagcatc ctgacatcgc ctgcggcgtc atcgacctcg gctcgaaggt gcatgtcgac   11940
gatgcggccg gcattttgga aaggctcgcc tctgccaaga ctctccaaga cgatgccttc   12000
gaggccgaag tcttgatgga ggactcccag cagtacgtgg ctcgcttggt cgagacaact   12060
tcccaactcc agaaccttcc ctccgagcag tctttctcca aggacgcctc ctacgttgtc   12120
actggaggca ctggtggatt gggcctgctg ttcgcgcagt ggatggctga tcagggcgct   12180
ggccacttgg gcctgctctc ccgaactgga aaagcgccag ctggacctgc ctacaagaag   12240
ttggccagca ctccaggcgt cgaggtggct gttcgctctt gcgatgtcca ctccgaggag   12300
agtgtccgaa gcatcattgg cgaactcagc aagactgccg ccgttaaggg cgtgctgcac   12360
gctgccggcg tcttggaaga tcacttgatt gttgacctga agaaggaaca cttggaccca   12420
gtcttgcgac ctaagatcga cggaacttg aacttgcacg gtgctaccct cgacttggac   12480
```

| | |
|---|---|
| ttcttcgtca tgttctcgtc cattgctgcc atgcttggtt ctccgggcca ggctaactat | 12540 |
| tgctctggca acgccttcat ggacgccttc accttgcacc gacgagctca ggggcagtcc | 12600 |
| gcggtcagcg ttcagtgggg tccttgggct gaagtgggca tggccgctcg cgccggcacc | 12660 |
| tctgagacct cctaccagag gttggacccc acagcctcct tggcagccat gggcgccatc | 12720 |
| ttgggcgccg gtagcgaggc cgtcaccaac ggcatcgtgg gcgtcgcccg agtcaactgg | 12780 |
| agcaacttct tggccggctt ccctacgctg ccgccctact tgcagaactt caagaacttc | 12840 |
| aggagtgccg gagtcaagat gaccgacggc gtgtcgaaga ctgtggtgcg ggacaccatc | 12900 |
| gaagcagtgt tgtgcgacgt cctgggcgac cccgacttgg ccgacttctc tgttcctctc | 12960 |
| atggacatgg gtctcgactc cctctcggcc gtcgagttcc gaaatcgtgt tcaggcagcc | 13020 |
| ttcgagggct tgcacctcac tgcgacggtc atgttcgact accccactgt ggccgacctc | 13080 |
| acggacttcg tctgctcgca gttcagcgag ggcgaggagg aggaggccgc cggggcgct | 13140 |
| gcacgaggcg aggtcaatgc gcaggagcca ctcgccatgc tgggcgtggc cgccaggttc | 13200 |
| cctggatgca ggaccaacaa ccccgaggag tactggaaca tgctcttgct gggtcgcgac | 13260 |
| atgatccaag aagtcccgat cgagagatgg gatgtggact tgtactacga cgaggaccat | 13320 |
| tctgccccag gcaagatgta cgcccgaaac ggaggcttca ttttgggcct cgaaggtttc | 13380 |
| gatgcgaaaa tgttcggaat tgccgacagc gaagctcacg ccatggaccc ccatcaacga | 13440 |
| atcttgctgg aagttgccta cgagtccttc tggaacgctg gtttcaacaa ggacgacctc | 13500 |
| atgaacagcg acaccggctg cttcatcggc tgcgcgacgc tgggcggcat cagcgtcgag | 13560 |
| gacgacgaca tcgggccttt cacgaacatc ggctccttcc cctcggggaa ttctggacgt | 13620 |
| gtctctcacg ccctcggcct ccgaggtcct tgcttcaccc tcgacaccgc atgctccgcc | 13680 |
| accatcgtcg ccttggactg cgccgcccag gctatgcgcc tcaacaaggg cgagcgaagc | 13740 |
| tgcgtggcag gaagcaacct gcagctgcag gcgaacactt ggatcggttt ctgcaagatg | 13800 |
| ggagcactct ccgtggatgg acgctgtaag accttgacg ccagcgccaa tggcttcacc | 13860 |
| aggagcgaag gtgcaggctc gatgatcttg gagttgcaag atgcagccct gcgaaaggga | 13920 |
| cgaaccgaga tcgcgactgt cttgggcgcc tgcgtcaacc aggatggccg aagtgctacg | 13980 |
| atcaccgccc ccagtggacc tgcccagcag cgatgcatcc agtccgctct cgcggacggg | 14040 |
| tccgtcgacc ctctggacgt caccatgatc gaagtccacg gaacaggaac tgccttgggc | 14100 |
| gaccccatcg agatcggcgg cttgaagtcg accgtcggca agggacgaag tgccgacagc | 14160 |
| cccctgattt tgggagcagt caagtcaatc atcggtcacg aagagggagc cgccggcgtc | 14220 |
| gcaggcgtca tcaagatggt ctgcgaattc aagtaccgac agatccccaa gaacttgcac | 14280 |
| ctccacaagt tgaacccgaa catcgacctc agcgacttcg cctccgttgt catgccagac | 14340 |
| agcatcatcg attggaagtc tacttcgaca aagtctggca cttcgtcttt cggcttcagc | 14400 |
| ggtaccaact cccacgccat cttggaggcg gtcgacgggg acgagattgg aggcgtcgca | 14460 |
| ctgcagaact ccacgcccct caagtgggca agggtccctc accgcatgtc caccgagtgg | 14520 |
| tcctccggtc tctggtggtc cctggagtgg aaaaacacac ctttggcgac tggctcgctc | 14580 |
| gacgaccttc cttgcttgtt ggtgggtggc ggcgagattg ccaaggccgt tgcgaaggtc | 14640 |
| atctcggatg tcacagttgt ggacatcaag aacgctgcca aggccatcga ggagaaggaa | 14700 |
| tgggcaacga tcctcatcac cgagcccatc acctccaccg acgattgctt ggagggtgct | 14760 |
| gccatcatgc agctcatcga ggtcaccaag gcagttgtgg caagtggccg agccttgcgc | 14820 |
| ttcgtcgtcg ccaccgctgg tgcacagagt gccagcactg aggactcaaa gctgtcgcag | 14880 |

-continued

```
ggctgcctgg gcgccgccgc ttggggcctg atgaggacga tcatctggga ggctcctagc   14940
ctcaagttgc agaccatcga cctgccttcc caggcctccg ccgaggaaat ggccacgctc   15000
ttgaaggacg agctctccgc tgagggagat atcgagcccg agattgccta catgtctggc   15060
cagcgctctg tcccacgctt gagctccacc cggctccagc agacgtcgtg gtccctgaag   15120
aagcccgagg gcacgcagct cttgactggt ggcttcggtg gactcggctt gctgtgtgcg   15180
cagaccttgt tgcagttggg cagcaagagc atcttgttgg tttccaggaa gggaaagatc   15240
gccgatggcg acgacgtcat cgcagaccac atgaagaagt gcaggagac cgacgccgag   15300 atccacgcgt ggagctgcga cgtctccagc cgcaccaacg tcaagaagtt ggtcgaccgc   15360
gtgcagcagg agctgcccga gaacccctc agtggagtcg tgcatgccgc tggcatcttg   15420
gactacgccg aaattccctc ccagacctca gagaggctct cctctgtcta caaggccaag   15480
gtcgcaggcg cttggaacct tcattcggag tcccagaaca cagagctgga gaacttcatc   15540
gttttctcct ccgtatccgc cctcattgga ctcacaaggg gtgccagcta tcgtcttcc   15600 aacgcctacc tggatggttt ggtcctgtgg cgcagagctc gtggccttgc tgcatccagt   15660
cttcaatggg gacctgtggc ggaggtcgga atggccgcca aggacgattt ggccactgca   15720
gattcccctc tcaagtacct caaaccttcc caagtccagg ccgctttcaa gcagtcgatc   15780
ctgtctgcct cgcagccgtc gtcgttgctg ttcgccaagt gcgactggcc tcgctttgtg   15840
cagtccttgg gcaccgaggt gcctgtcttg aaggacttcg tgggtgccga ggaagaagtc   15900
tccagcggcg ccaagacagc cgtctcgtcg gcattccagg gcatgtccaa gtctgaagtc   15960
gagtcccgcg tcggtgacat ggtcttgagc gtggcctgta ctgtcctcgg catcgacgac   16020
ctttctccag aggccccatt gatggaatct ggcttggatt ctctgtcggc cgtggacttc   16080
cgcaaccaag tggccaagac tctcccagga ctgaagctcc ccagcactct gatgttcgac   16140
taccccacca cgtctgctat cgccaacttc gccgcctctc agctcgcccc agccgagagc   16200
tccaggcaag ctgtcgttgc cgcccctgct ggatcggctc ttgagaccac tgagcccatc   16260
gctctcaggg ccggtgccta ccgcttcccc atcgagggag agaaccttca gcagtactgg   16320
gatgctttgg tcaacaaggt taacggtgtc acagagattc ccctggaacg ctgggatgtg   16380
gatgcctact tcgatgccaa cccccgagacg ccaggcaaaa tgtacgtgcg acatggctct   16440
ttcgtcaaga acgccgacca gttcgactgc ggcttcttcg gcctgtcccc tgccgaatcc   16500
aaggttatgg atccccagca gcgcctgctc ctggaggtca tctaccgggg tttccacgag   16560
cacggcttgc gtcaggacac cctcaagggc atggacggct gcatcgcggt cggtcagtgc   16620
aacaacgatt ggggacacat gggattctct cccgacgaag ctgatgtgat tggcccatac   16680
acaggcttgg cggtctccac ctccatctcc tccaaccgag tctcctacat cttgggcttg   16740
aagggtccca gcttgactgt ggacacggcc tgctcgtctt ctttgacagc tgccgacatc   16800
gccatctcga acttgcgccg ccgaaggtgc gagatcagtg cagcggcagg cgtgaacttg   16860
aacctcatcc ctggaccgtt catcgcttgc tccaaggctc acatgctctc cgaggatggc   16920
ttctgcaaga ccttcgatgc gtctgccaac ggctacgtcc gaggcgaagg ctgcggcgtc   16980
gccattcttc agcgcttggc tgatctcggc acaggcaaga gcgccctcgt cgttgtgcac   17040
ggctctgccg tcaaccagga cggccgcagc tcctcgcaga cagcgcctca cggtccttcc   17100
cagcaggacg tcatcatgac cgcagtgaac gaggctggac ttctggcttc gaaggtcaac   17160
atcatcgagt gccatggaac cggcactgct ttgggtgacc ccatcgaggt tggagcattg   17220
```

| | |
|---|---|
| aagaacaccc tgggcgaggg acgcgaggag agcaaccctc ttgctttggc tgctgtgaag | 17280 |
| agcaacatcg gacacttgga gggcgccgct ggcgttgctg gactcttgaa ggtcgcctgc | 17340 |
| atgctgccca ggaagcaggt tccttccaac ttgcacttca aggagctgaa cccccacatc | 17400 |
| gacttggacg acttcccttc gacgatcccc acggacgtgg tcagcatcaa gcaggcagga | 17460 |
| gtgctgtctg ccggcctctc ctccttcggc ttcggaggca ccaacgctca catcgtctcc | 17520 |
| aagcagttcg aaggcgagcc cgagagccag ccccaggagc tcacctacac tcgacagagc | 17580 |
| ttcgcctggc agcagacgcg ccacacgctg ctcgccaagc gcttcaagac cgccgagaac | 17640 |
| gtgcaggtct tcagtgcgcc cttccaaggc cgactgctgc agttggtctc caccacatc | 17700 |
| atcttcggag agatcgtcgt gcccggcgca acctacctgg aaatggtttt ggcagctgga | 17760 |
| gagttccacc tgggtggcaa gggcaccgaa tggtacatca agaacgtcgg cttccaggcg | 17820 |
| cctttggtgc tgaagaccag cgacaccggc aagctgagcc gagagatcga cctctacttg | 17880 |
| gaagtcttcc cagacgggca ttgggccatg agcagctggg atgtcgccca gcagcgcaag | 17940 |
| gccgccaccc actccgaggg agaagtcgaa ttcaccggac gggccgttgc ggacaagcag | 18000 |
| accatcgaca tcgaggccgt caaagcgcgc tgcgacgagg acgtcgtgct ggagcgcctc | 18060 |
| tacctcccct tctccaagat cggactgcct ctgcagcctc gcttccgaac cgtccgccac | 18120 |
| atcttgcgcg gcgacgacga ggtcatctgc aaggtcgagg ccgagaacga cagcaccaac | 18180 |
| cagggcttcc tcttcaaccc ggccgtgctc gatggaacct tccagggaag catggcgctc | 18240 |
| atgctcgcgc gccgcgccac ggaggttgac gacttgacca gcttgaggat tcctctgttg | 18300 |
| tgccagaaga tcaccaacta ctctcagggc cactcgacaa gcatctgggt caaccactct | 18360 |
| ctgcgagaga tcaccgacaa ggaaaattgc gtcgacgcca agatctgcaa ggacgatgga | 18420 |
| actgtgctct tggccatgga cacccctcaaa ttccgagagg tccgccccga gcacatccag | 18480 |
| aagatgctcc agcaggccac cgaggacaac gagcaggacg tgctcgagca ggaatggacc | 18540 |
| actttggaag gcaagctggg cacagctggt cctctcagcg gcaaggtcat cttcgtgggc | 18600 |
| gcttcggcag ccatggagaa agctctccga gtcaagtact ccagcgcctc tttcgtgcga | 18660 |
| ggaggagagg acttgggaga ttgcgccaag gccaagatcg tctttgtcga ggccctctgc | 18720 |
| gaggaggctg gcgaaatgga aatcatccac cacgccatgc tgctggttca ggtcgtgatg | 18780 |
| aagatggccg acaaggactc cgacaccgcc cccgccctct ggtggatcac tcgaggcacc | 18840 |
| caggccgttg gagcatgcag cagctacgcc actgcaggac tttggggtat ggctcgcacc | 18900 |
| gccaggctcg aggagaggag cctcaagctg cgctgcttgg acttggacac cacccaaggc | 18960 |
| acagaggagg cggccgaggc tttgtccaca tggctgggca ctttgagcgg caacgccaat | 19020 |
| gttgatgctg aggctgaagt tgctctcagg atcgccgacg tgagaccaa ggcctacatc | 19080 |
| gcacgcctcg ccaggagcaa cactgaggtg aagaagccga tgcagctgaa gatgtcgtct | 19140 |
| cgcggctctt tggccaactt gcgacctgtc ccccagacca acaggcgtgc ccctggagcc | 19200 |
| ggagagtgcg agcttcgagt gcgagccatc ggtctcaact tccgagatgt cctcaacgtc | 19260 |
| atgggcatgt accccggcga ccctggaaac cccggcggcg attgtgccgg cactgtcact | 19320 |
| gccatcggcg agggtgtcga gcacttgcgc cctggcatga tgtcttcgg catcgcctgg | 19380 |
| ggcagcttgc agacgtacgt caccaccaac gcgctgctca tggtcgagaa gttcaaggac | 19440 |
| tggtctttcg agcagatggc cgcctggagc gtcactttcg cgaccaccga ggaggccttc | 19500 |
| caagagctgg ctcctctcgt gaaggcgag cgagtcttga tccacgctgc caccggcggc | 19560 |
| gtcggcctcg tggcggttca gttcgcgcag cgcgtcggtg ctaccatctt cgccacttgc | 19620 |

```
agtgcctcca aggtcgagca cctgaagggc atgggcgtga agtacatcac caccacccgc    19680
gacggcgccg cattcgaagc ggacatgcag aagttcctga aggaggatgg tgctgatggc    19740
atcgactgcg tcatgaacag cttgagccac gacgactaca tccctcgctc cttgaagcta    19800
ctgaagaagg gtggccgctt catggaaatc ggcaagcgtg gcatctggac tcatgagcag    19860
atggcccaag agcgacccga cgtcatgtac gagaagatcg ccatggactg ggtcatggag    19920
caccagccga agcgctacaa cagcttgatg aagcgattgg tcgagcagat cggcaagggc    19980
tggtgggcac caatgccaac aacgcccttc gtcggcttgg agaacggagt ggatgccctc    20040
aggtacctgc agcgcgccca gcagatcgga aaggtcgtgc tcactcagcc ctctcgcatg    20100
tcctgcgagc aggatggatg ctacctcttg tctggcggcg tcggcgccct cggattggtc    20160
actgctcaga ccatggccga ggagggagcg aagagcttgg tcctcatgtc tcgtcgcggc    20220
gccattcctt ccgacctgga agcacagtgg gccaagctgc agcagttcaa ggtggacttg    20280
cacttgaagt cctgcgacgt cgccaacatg gacagcgtgc agctcatgct caacggcctc    20340
aagaaggagc tccccacgaa gaccgtcatc cgcggtctct gcaccttgc cgccgtcctc    20400 gacgacgcca cgctgccgaa gctcacccga agccacttgg agaaagccta cggagcgaag    20460
gtctacggag ccaagcactt gcacaccgcc ctcgcctcag cgaagacgcc tctggacttc    20520
ttggtgctct tctcctccac tgcgggcctt ttgggctccc ccggccaggc aaactactcc    20580
gctgccaacg tcactttgga cgctgctgcg aactgctggc agggacgcgg agagaaggcc    20640
gtcgctgttc agtggggacc ttggcgtgaa gccggcatgg ctgcccagaa gggcaccgtg    20700
gagcgactca aagctcaggg cttgggaagc ttgggcaacg tcgtcggcat gtccgtcctc    20760 gccgaagct tgggcgccac cgcaggcgtc gtcgccgcct gccctgtcta ttggggagtc    20820
tacctcaagc agttcggctc ttccgtgccg aggttcttgt cccgattcca gaaggaggcc    20880
ggcgccggca gcagcggccc tcggcccatc acgggccagc aggatcgcgg cttgtccatc    20940
gcccctgcgg acgtcaagaa cttggtgcac accatcgccg tcgaggtgat gggcagcacc    21000
agcgtggacg acaccgaacc cctcatggag gctggcatgg actccttggc cgccgtggag    21060
ttccgaaacc gcctctcctc tcagttgcct ggcatcaagc tccccaacac gctcatcttc    21120
gactacccga cggtcaacgc catcggagac tacgctgccg cccaagtcgt tcccgttcct    21180
ggcggcgcgg agcctgcagg catctccttc agccgcagcg acgtcgagca gttggtgctc    21240
tccacggcca tcgaggtcat gggaagctcc accgtggacg tcagcgagcc cctcatggag    21300
gccggcatgg actccctcgc cgcagtcgag ctccgaaacc gactttcctc gcagttgcct    21360
ggtgtcaagc tgccgaacac gctcatcttc gaccacccaa ctgtctccgc catcaccgac    21420
ttcgctgcct ctcagatcgc cccttcggca ggctctcgag gcgcctctgc cgccctcggc    21480
ggagcgacgc aggagaagaa gcttctggac gtccgcggca tgtcttccat cttccccgga    21540
agccgtgacg cagcctactg gaaggacttt gtggacaaga aggacagtgt catcgagatc    21600
ccttacactc gctgggacgt ggatgcgtac ttcgacaagg accaggacgc acctggcaag    21660
atgtacacac gacatggagg cttcattgac ggcgccgaga tgttcgacgc aggcatgttc    21720
tcgctctctg cggccgaggc tgccatgatg gaccctcagc agaggttgat cttggaggtc    21780
accaacaccg ctttcaactt ggccggtcgg gacaaggcaa gcttgatggg cgccgacgtc    21840
ggcgttttca tcggtcagtg ccagtacgac tggttcgtga tgaagagcgc tggagaccac    21900
ttcaacacct acacaggcac cggcatctct gcctccatct cctccaaccg aacttcgtac    21960
```

```
atcttcggct tcaagggccc cagcctcacg tgcgacacgg cctgctcttc gtccttggtg   22020
gcgatggatg ccggctactc ctccatccag aggggcgtgt ccgagatggc cttgatcgga   22080
ggaaccaact tgatgttgca gccttctcct tacatctcct tcagcaaggc ccgcatgctc   22140
agcgaagacg gacgatgctt caccttcaac gccaccgcca acggctacgc ccgaggagaa   22200
ggcgtgggag gcatcgtcgt cggcgtcgcg ggcgacgcct cggccgatgt ttctgccatg   22260
ctgcgagcca ccgccgcgaa ccaggacggc cgcagcgcat ccctcacagc gcccaacgga   22320
ccttctcagc aagccgtcat cgctcgggcc ctcatggagg gatctatcgc tgccaaggat   22380
gtcaacgtcg tcgagtgtca cggaacaggc actgccttgg gtgacccat cgaggtggat   22440 gccctcaaga acaccctcaa cgtcgacagg agccagacgc tcatgctcac ctcggccaag   22500
accaacatcg cccacttgga gggttctgcc ggcatcgccg gcttcgtgaa ggccgcctac   22560
atgatgcgct atggccagtg ccccagcaac ttgcacttca aggaactcaa ccctcacatc   22620
gacttggagg acttcgactg cgagatcgcc accgaattga agcctttggc aggcaagcca   22680
gtggccggcc tctcctcctt cggcttcggc ggcaccaaca cgcacgtcgt cctcagctcc   22740
tccgagacac tcggcaccca ggccgcggaa gaggccccga agcagatcac cttcactcgc   22800
cagtccttcc cctggaagga tcgcatctac aggttgctgc caaagagact ccaagaaggt   22860
cgggacaccc acttcgaggt ggccatcaag accgatgtct tcaacatctg cgccgagcac   22920
gtcgtcttca acgagatcgt cgtgcctggt gtcgtctaca ctgagatggc catcgaggcc   22980
actcgcgtca tcatcggcaa ggaggctacc ctgaaggact tgaccatgac ttggcctctg   23040
gtcgtgccca agaacgctga cggacccaac gccaccacgg tctggctgcg cttcgcgcag   23100
atgggctccg agaagttcga ggttcgcagc cgccgcggcg acagcgacga gatgatcaca   23160
cattgcgaag gccgcatcgg ccgaagtttg tcggagcctg tgtcatgga catcgccggc   23220 ctgcagtctc gttgcgaccg caacgtcgac cccaaggacg tctacgcagc catccacaag   23280
ggaggtctgt acttgggacc aaagttccag gtctgccgcc acatgatcag gaacgacgac   23340
cacgtgctct gcaagctcgt ccactccgac gagtgcggac cgaaccaggg ctacttcatg   23400
caccctggca tgttggatgg aaccatccac actctcggat gcaccatggt cggctgggac   23460
gccccgctca aggtgttcgc cggcatcggc aagctcgtca tcaaggacca cacagacttc   23520
agcaggaacg agtcctactg gtgccacctg cacctcaaga ccttctccga gcaggaacag   23580
atcttcacgt ccaccgtcgc caacgaggag ggcaacatcc tcttcgtcgg cgaggacgtc   23640
tccttcagaa aggtcacgcc cgagcagatc cgaaaagcca tggagagcca ggccgccgag   23700
gacgaccaga agctctacga ggtcgagtgg acatctctgt ccacagcggc cagctccgag   23760
gaggacgagg acgccaagtg gttggtcatc gcagagaccg acagtgtcct ggcagatttg   23820
aagaaggagt tcggagaggc ccacacctac accaagttgg cgggcgcaga cctcggcgag   23880
atggagaact acagcaaggt cgtcagcgcc atcggcctcg agacctccgt gaattgcttg   23940
gacggcttgg accacgccct gcagctgatg aaggcgctgc ctaagtctgc cagcaccgca   24000
cccgagatgt ggttcctgac acaccaggct gtgcaggcag tgaagggaga catgaaggac   24060
gccgccatcc ctgtgcacgc aggtctctgg ggtctgtcga aggccttccg cgcagagttc   24120
cccgaactca aggtggcttg cttcgacctg gagggcggaa agatcacttc gctcaaggag   24180
aagttccagc aggccttgga tcaggccgcc gcctccttcg aacccgagct cgcgctccgc   24240
gctggctcgc tctacgcacc tcgccttggtg gactccacga ccaatttgga agcgaaagcc   24300
ctggacatct tcgacgccga cgcctcccac gtcatctccg gcggcaccgg cgccttgggc   24360
```

```
ttgctcaccg cgaagtggat ggccgagaag ggcgccaaga acttcgtcct cgcctcccga   24420
agcggcaagg tgcaggagga cgcccaggcc atgttcgacg aggtctcctc tgtcgccacc   24480
gtcaagaagc tcaacatgtc cagcttggac gacgtcaagc gcctcttcac ggaggtcgcg   24540
aagtcgatgc ctgccatcgg tggcatcacc cacgccgctg gtatcttgga cgatcacctc   24600
atcgccgact tgcagaggtc gcacttggag gcagtcttgg gcgccaaggt ggacggcaca   24660
ttgaacttgc acgagggctc gaaggacatg aagttgaagt acttcagcat gttctcctct   24720
ttggcttcct tgattggtac tgccggccag gccaactact gcgctgccaa cggcttcatg   24780
gacagcttcg cagcataccg aatcgactct ggaaagcccg ccgtcgccat tcagtgggga   24840
ccttgggctg acattggtat ggctgctcgc gctggcactt ccgagagcgt ggtcttgagg   24900
atcgacatcg aggagggtct ccgtgctatg gaggttatct tgagcaactc tggcgacttg   24960
atgaccggcg ccattggtgt ggcccgaatc aagtggaagt cttcttggc ccagatgcct   25020 gccctgccgc cattcctgga caacttcaag cagttcaaga aggacgctgg caagaagtcg   25080
gctgtcgctt tgggcgccgc accttccaag gacgtcgtcc gcggcggcat cgaaaacatc   25140
ctgaaggagg tcttgggaga cgacactttg gacgacttct cctcccctct catggatctg   25200
ggtctcgact ccctggctgc cgtcgagttc agaaacagag ttcagtccgc cttcgatgga   25260
gtccgactgg cctcgaccgt catgttcgac taccccacgg ttgccgacct caccgacttc   25320
atcctgtccc agttcgcccc cgaggaggac gaggtcgccg gtggaggctt gggagatccc   25380
gccgcgagcg ttcgggactc gatggccgtt atcggcgtct cgggccgcta cccaggcatg   25440
tctttcagca acgacttgga ggagtattgg acagccctct gcagtggaaa cgaccccatc   25500
caagagatcc ccatcgaacg cttcgacgtg gacgagatct acgacgaaga tcgctcggcc   25560
ccagggaaag tctacgtccg caacggcggc ttcatccagg gcgtccagga gttcgacaac   25620
ggcttcttcg gcatcgccga caccgaggcg aaggccatgg acgcgcatca gaggctgcag   25680
ttggaggtcg cctacgacag tttccacctg gctggcttca caaggagtc cctgagtggc   25740 atggaggttg gcgtctacgt cggctgctgc actttgacag gtatcgatgt ggagtctgac   25800
gacatcggac ctttcaccaa catcggtgcc ggcatcagtg gcctctccgg ccgcatctcg   25860
cacgccttgg gtctgcgcgg tccatgcttc gccatcgaca ccgcctgctc ctccacgctc   25920
gtggccttgg actgcgcggc gcaggccagc agattgggac gacaggaaat ggcttgcgtg   25980
gcaggaacga acctgcagtt gcgaacggac atgtggatcg gtttctgtaa gatgactggt   26040
ctggctgccg atggccgctg taagactttc gacgtctccg ccgacggctt cgcgcgatcc   26100
gagggctcag gctccatgat cctccgcatg cgcgcccacg ccgaggcgaa gggagaggcc   26160
tctgtgatga tggtccgagg cacgtgcgtg aaccaggacg gccgcagcgc caccatcacg   26220
gccccgagcg gtcctgcaca gcagcgagcc ttggccgcct ccttgaggga cggcgacttg   26280
aaggccctga agtctctttt gatcgaatgc cacggaaccg gtacctcctt gggcgacccc   26340
atcgaggtcg gagctcaaga gaagatctac ggcaaggagc gcatggagca ggacacgatc   26400
gtcttggcgg cggtgaagtc ttgcatcggc cacttggagg gcgccgccgg cgtcgctggc   26460
ctcgccaagc tcgtgaagat gatagagcac aagaaggtgc ctccgaactt gcacttgaag   26520
agcatgaacc ccaacatcga catctcgaac ttccctgtca acatcccgac cagcggcgcc   26580
atcgactgga gcaaccctgg cccagtcaag gctggtatca gttctttcgg cttcagcgga   26640
acgaactcgc acgtcaacac cgaggagccc tccaacgccg agggcgtcga gcctcccaag   26700
```

```
gtccagcctc tcgtctggca gcgccgggac ctctcctacc gcgactggac gaagggtctc   26760
ttcaccagca tcgagtggaa gcctgctgcc atcaaggcca ccggcaagat cgatgctgct   26820 gccacccttca tcattggcgg cggcgacatt gccaaggccc tggccgagat catccctggc   26880
tgcatcgtcg tcgcgccggg caaggcggcc aagacctcgg gcgacgtcta cagcatggac   26940
ttcaccaagg ccgaccaggt gtccgaggtt ctggacaaca aggagtggag caccgtcgtc   27000
ttcgccgaat ctttggtcgc cgacgaaccc accctggagg gccaggccgt cagcggtctc   27060
ctcctcactc tccaagccat gtcccagtgg aagcgctccg ccacgctcgt ggcattgacg   27120
gcaggtgctc agactgcgga agctggcgga aagatgggtg tcggagttgt gggagccgca   27180
gtgtggggct tcatgcgctc cgtgcgcctg gaggccgcga acgtggagcc tcgcgtcatc   27240
gacttcagcg ccgacgcgac cagcgatgcc tcggctttgg ctacggtcat cagcgaggag   27300
ctcgcggcca gcgacgctga gattgcgtac gtcaacggca accgctccac ccctcgcttg   27360
gtcgccacca acgtcaagaa cggcggcaag cccgagggca tcgaaggaac ctacctcatc   27420
accggcggct ttggcggcct cggcctcgtc atcgcacagc agttggtgga catgggagcc   27480
acctctgtgg ccttggtctc ccgaagtggc aagacgcccg ccggcgacga gaagttggcc   27540
gagatgctgc agcaggtcca gtcctcttcc gccaccgtcc acgcctgggc ctgcgacgtc   27600
tccgactcga agagagttgc agacttggtc aagaagtcga agaaggagct cagtgcggac   27660
catcccctca gcactgtggt gcacgccgct ggcatcatcg accactgcgc actgccgac    27720 ctcaccgtcg acagcattgc caacgtcttc aagcccaagg tcggcggcgc ctggcacctg   27780
cacagcgcca ccaaggacga cggcctcaaa gacttcgtgc tcttctcctc tgtcagcgcc   27840
ctcatcggcc tcagccgagg agtcacgtac tccacctcga acgccgccct cgatggtctc   27900
gcgctctggc gacgggccga gagcttggct gccacaagca tccagtgggg acccgtgtcc   27960
gaggtcggca tgtcgacgaa ggcggaccac gcggcctccg cagacttcgc cctcaagatg   28020 gtcacccca gcaggtcca ggccgccttc cagcgcctct tgtccgcgcc tccgaaagcc   28080
acatccgtgc tcttcgcccg cgccgactgg ggcaagtacc tcgaacagat gggcgtggac   28140
gtccctgtgc ttgcggacta cgcctccaca ggggcgcgg ctgcgggcgg cgccactgcc    28200
agcagcgctt tcagcggcat gagcatcgac gagatcgaga gcaaagtcac ggagatggtt   28260
gtggactgcg tccgaaccgt cctcggcgac gattccgtcg aagccgagtc ccctctcatg   28320
gagtccggcc tcgactcgct gtcggccgtg gacttcagga accaggtctc gaagcagctg   28380
ccgggcctca gttgccgaa cacccttgatg ttcgactacc ccactgcagg agccatcgcc   28440
ggctacgctg cctctcagct ggcaccggca acaagctcgg gaggagcagc tcgcgccacc   28500
actcagatcg tctctgcggc cgaagctcgc ggccctgtct ccatcttggg catggcctgc   28560
cagttccctg gagatgctga ctcctggac aacttctgga acgtggtcgt caacaaggtc    28620
gactgcgttg gcaacatccc gcccgagcga tgggatgccg acgagtactt ccaggagggc   28680
ggcggcgtcg gcaagatgta cgtcaagcag gccgccttcg tccgcgacgt cgagtccttc   28740
gacgccagcc tcttcgccat tcttctgcc gaggcctaca ccatggaccc ccagcagagg   28800 atgtctcttgg agaccgtgca cactgcttgg cagttgggca ctggcggaaa gaaggtctct   28860
ttggacgtcg gaagcttcgt cggagagtgc aacaacgatt ggggccatttt caagaatttg   28920 gaggtcgaaa agatgaaccc cttcagcgga accggtggat ccatgagcat ctctgccaat   28980
cgtctggcct acgtctttgg cttcaagggc ccgagcgtca cgtccgacac cgcatgctcc   29040
tcgtccttgg tggcggtgga tcaggccgtt tcgaacctct ggcgtggacg atgctccgcc   29100
```

```
tccgtcgcgg ccggcgtcaa cttgaacctc atcccaggac ccttcgtggc ctgctgccag    29160
gcccgcatgc tcgcagaaga tggccgatgt aagacgttcg acgccgcggc cgacggctac    29220
tctcgaggag aaggttgcgg cgctatcgcg atccgcggcc agagctccac tgagaacgcc    29280
gcgagcttcg tcgccgttgt gggaaccggt gtgaaccagg atggccgcag ctccagtctg    29340
actgcgccca acggcccctc acagcaggag gtcatcaaca tggcttggca ggaagccggc    29400
attgcaccca gcgccgccga cttcatcgag acccatggaa cgggcactgg cttgggcgat    29460
cctatcgaaa tcggagccct caacaacacc atggcagagg gacgaaccag cgaggtcgtc    29520
atcggagccg tcaagaccaa catcagccac ttggagggcg ccgccggcat cgctggcttg    29580
ctcaagggcg ccatggtgct cgagaactgc aaggtgcctc cgaacctgca cttgaagaag    29640
ctcaaccccc acctggacgt cgaggacttc gacgtctcct tccccaccga gttggtcgag    29700
aagtccagag agcagctcaa gagctctggt ctctcctcct tcggcttcgg cggtacgaac    29760
acgcactgcg tcaccacggc ccccacagag ggcaaggtcg atcagcagca ggaggctgtt    29820
gtcttcaaca gcagcgtttt cgcctggtct caggtcaagc ccctctctc ggtcgtcggc    29880 cgcaagggtg ccgaccccaa ccttactgtc ttcactgccc cgatccgagg aaaggtggtt    29940
cagctcctat ctcaccacat catctacggc gagattgtcg tgccgggcgc cacctatttg    30000
gaaatggtca tcgccaccac tgctttcagg ctcggcaagg acggcaccaa gttctccgtc    30060
gagggtgtcg gcttccagaa ccccctcgtg ttgaggactg ccaccccac cgagctggag    30120 cgaccgattg aactgaccct gcacatgtac gacaacggca aatggtccat gaacagctcc    30180
gaagccggcg aggtcctcgc cacgcacgcg gagggctccg tgagcttcgc gaacccgacg    30240
cctgagaaga aaatgctcga gctggaggag atcaagagcc gctgccctga ggttgtgcaa    30300
gacgagcgca tgtacgttcc cttcgccaac atcggtctgc ccctgcagcc ccgcttcagg    30360
actgtccgaa ccatcgaccg cagctccgac gagatcatcg cttgggtcgc agcagaagag    30420
gacggcacca atgccggctt catcttcggc cccgccgtca tcgatggatc cttccaggcc    30480
tcctgcgcct tccagaacct ggaggccctg cccagcttgc gaattccgct ctccatcgac    30540
aaggtcacga tctacggcca gggctacagc cagaaggtct gggtccacca caagctgctc    30600
gagaacaccg agaagaccat ggccacgaac gtgcagttgg cgcgcgacga caagacgatc    30660
atcttgacca tggaccgcat gcgcctgcgc gaagtcaggc ccgagcacat cgccaagatg    30720
ctggcccagg ccgcaggcga cgaggacgag gacctgttgg aggtcgagtg ggctgccatg    30780
gacaccaaga acgctaaggc cgtcgaattg ggaaagacct tggtcatcgg tgccaacgat    30840
gctctcaagg aagccctcag caaggagatc aagacagcca ccttcgcaga ctctgcagag    30900
gccctcgccg aggccacggg cgtcaaggag gtgctgttcg tcggggcgct cgtggacagc    30960
gcaccagaga tggaggtctt gcacaccgcg ctctccctcg cccaggaggc catcaagttc    31020
gccgccagca agaagaagga gagccctccc accgtctggt gggccaccaa gggcacccag    31080
gcggctggct tgggcgacag ctactaccat gcgggcttgt ggggtctggc caggaccttc    31140
cgcatggaag agcgttcggt gaacttgcga tgcttggact tggacatcag catgggctcg    31200
gccgaggccg ccgcggccgc cctcaaggaa tggctgcctc tgctctccgc cgccaacttg    31260
gtcggcgaga ccgaggtgac tttgaggccc aaggaagaca gcaaagagat ggcgccgctg    31320
gtgtctcgat tggcgaccag caccgccaag tcccagaagg ccggcatgct gatgatgtcc    31380
tctcgaggaa gcttgtccaa cttgcgaccc gtgctccagg agagtcgacc caagtgcgga    31440
```

```
cccaacgacg ccgaacttcg aattcgagcc gtcggtctca atttccgaga tgtgctcaac    31500
gtcatgggtc tctaccctgg cgaccctgga ccacctggcg ccgacacctc cggcaccgtc    31560
ctcaccgtgg gaggcgaagt cagtcacatc cgtcctggcg acgatgtgtt cggtgagtct    31620
cctggttgct tgaggaccta caacgccggc ccagccccgc tgctcacgca gaagcctcct    31680
acctggagct tcgaggatgc ctcaaccatg cccgtgatct tcgtcaccgt cgaggagtct    31740
ctcggagacc tggccaagct gaagaagggc gaaatcgtcc tcatccatgc tgctgcaggc    31800
ggcgtcggct tggtggccat ccagtacgct cagttcgtcg gtgcgactat catcggaact    31860
gccggatccg aggagaagca cgagttcctg cgcaacttgg gcgtgaagca catcaccagc    31920
acccgaaatg gccagaagtt cgaggacgac atgaagacca ttctcaagga gttgaaggtg    31980
gatggcatcg acgttgtctt gaacagtttg agccacgacg actacatccc gagatccctg    32040
gcattgctca agaagggcgg acgcttcatg gagatcggca agcgcggcat ctggagccac    32100
gaacagatgt tcgaggcccg acctgacgtc atgtacgaga agatcgccgc cgacaccatg    32160
atggacttgg aatcctggaa gtacaatgcc tacatgaaac gcctgctcac ccgagtggaa    32220
gaaggtggtc tcgtgcccat caacaagcac gtcttcacgg acatcgagaa gggagtcacc    32280
gccatgcagt tcttgcagcg agctcagaac atcggcaagg tcgtcatcgc actgcccagc    32340
cgaatggatt gcaagccaga ctccgagtac ctgctctctg gtggtatggg agcattggga    32400
atggtcaccg cccagtactt ggtcgaggaa ggtgcaaagc acatcacgct gctttctcga    32460
agcggcaagc catccaacga cgtgctcgac ctctgggagt ggctgcagaa gagcagcatc    32520
aacgtctctg cgaaggcttg cgacatcgcc cagatggaca cgtcaccga acttgcggtt    32580 accttgtcca aggacggcca gaagcgcagc cccaagactc atgtcggagg cgtcatccac    32640
ttggccgccg tcctcgacga cgccactctc cccaagctca ctcgaggcca cctcgagcgc    32700
tcgttcgcag ccaaggtttg gggcgccagg cacctccatt gcgcctacgc caaggagttg    32760
gacttcatgc tcctcttctc ctccacctcg gcgctcttgg gatcgcccgg ccaggccaac    32820
tactccgctt ccaactcctc tttggacgcc cacgcccgct actggcgcca gagtggcatg    32880
caggccacga gcgtgcagtg gggcccctgg agggaggtcg gcatggctgc gcagaagggt    32940
accgtcgagc gcttgcgcca gagcggtgtc ggctctctca ccaacgctgc aggcatggcc    33000
gccttggccg gtgccttgac cgccagctgc cccaccatcg tggctcagcc gatgaggtgg    33060
gccaactacc tgaagcagta ccccaagatc cccccttcc tgtcccgctt ctcggccgag    33120
ctcaagacga agaagccggc tgctcccgcc cgaccggccc agggcatgat gatgatgcag    33180
caggccgccc cctcggctcc tgccatcagc gtcaccgacc tcaagagcat gctccagcag    33240
atcgccagcg atgtcgccgg cggcggtgtt gtcgacgagg acagccctct catggaatct    33300
ggcatggact cgctctccgc cgtcgagttc cgcaaccgct tcacggccaa ggtccctcag    33360
atcaatttgc cgaacacgct catcttcgac taccccacga tctctgccat cgcggacttc    33420
gctgtcggcc agatgggccc cgccaccgcg gcccctgccg gctacgccat gcaggctgcc    33480
cctgcagcac ccggcatgac tgctgacgcg atcatggagt tgctgaaccg catcgccacc    33540
gacaccaccg gaggagctgt cgaggtcgac aagccattga tggagtctgg catggactcc    33600
ctgtctgctg tcgagttcag gaaccgcctc tcctctgagc tcccaagctt gcagttgccc    33660 aacacccctca tcttcgacta ccccacgatc tctgctgtcg cagactacgc ggtcgagcaa    33720
ttgggcgcca gcaccgtggc tgttcctact ggcggcgcaa tggtgccaat ggctgctgga    33780
gcctcttctg gggccttcga cgagcctttg gccatctcag gcaccgcctg ccacttccct    33840
```

```
gccggctcga cgggtccgaa cgtcttctac aagcagcttg cgcagggcgc cgacggcatc   33900
gtcgaagtgc ctttcacccg ctgggagctc gaggaggttt acgaccccaa ccccgacgct   33960
cctggaaaga tgtaccccg acacggagcc ttcattcagg gtgccgagca gttcgatgct    34020
tccttcttcg gaatctccgc acctgaagct cgcgccatgg atccccagca gaggctgttg   34080
ttggaggtgg cctacgactc gttggtcgac tctggcttca ccaagagctc tctgttgagt   34140
agcaacatcg ccgtcttggt cggacaggcg aacaacgact ggatccagat gcagagttgg   34200
gacctgaaga aggtgaaccc ctacactgcc actggcatgt ccgcttccat ctctgccgcc   34260
cgcatctcct actccttggg catgaagggc gcaagttaca tcatcgatac tgcctgctcc   34320
tctgccttgg tggccttgga tgctgccgcc gtgaccttgc gccgaaccag gtgcaccgct   34380
gccgtcaacg cggctgccaa cgtcatggtg agtccttcca cctacatcag cttcagcaag   34440
ccgcgcatgc tctccgagtc aggccgctgc ctcaccttcg accagagcgc gaacggctac   34500
gtccgaggag aaggaggcgg ctctgccgct ctcaggctcg tggccgatgc cggcgacttc   34560
gctcgctcca tcgttcgcgg cgtctcggtg aaccaggacg gacgaagctc cactttgacc   34620
gcccccaacg gacccagcca gcagatggtc atgatggccg ccctcaacga ggcgaagctc   34680
tcacctcaga gtgtcggcca cctggagtgc catggcactg gcacgccgct cggagacccc   34740
atcgagttgg gcgccttgca ggccgtcaac gcaggccgct cggagaacgt ccctctggtc   34800
ctcgctgcgg tcaagaccaa cgttggtcac ttggagggtg ccgcagcatc caccggattg   34860
atcaagatcg cctctgtgct ccagcatggg gcagccaagc caggcatcca cctcaagacc   34920
ctgaacccca acatcgccgc gctctccgcg ctgcctgccg tcttcgccag cgagtccctg   34980
cccctcccct cgggtggtgc ctacaggact agcggcctct cctccttcgg cttcggagga   35040
acgaacgcgc actccgtgac cagcgaggcc gaggtgcccg ccgagcccgt gcgaaccgtg   35100
atcccaggaa aggagtacaa gaggaaggcc ttcccttgga gggaggtcgg cttcagactg   35160
ctccgctcct cgccttccga caacgtcttc gaggtcgtga tgatctccga cgtctacgac   35220
gtcgtgagcc accacgtcgt cttcagctcg atcgtcgtgc ctggcgtggt ctacgtggag   35280
atggccttgg aggccactcg caagatcttc ggccacggtg cgaagctcac agacttcgga   35340
atggtcttcc ccttcgtgat cccttccgc accacgggcg tcgagcctgc cgccacgatg   35400
cgcttcgtgc tgcgcggcga gtcccgcttc gagatccaga gcacctcggc cacagggggcc  35460 gtgacggtcc acgccgaagg aggcatcgac agatcgccca tgaaagatcc ttccagggcg   35520
gagcctgtgc acttggacat ggtccgcaag cgagtcacag aagagattcc ggcaagcgtc   35580
gtctacgggg ccatcgacgg agtcggcttg tggctcggac ctatgttcca ggttgccaag   35640
cagctctggc gatatgagga gggagattcc atcgaagtgc tcggccgatt ggagttggac   35700
aagacgatcc ccaacgaagg ctacgttgtg cacccccgccc tcttggatgg aacgatccac   35760
accttgggaa ccgcctccat cggcaagaac gtgaacgact tgaagatctt tggaggtgtc   35820
ggtcgcgtca caatcgtcga ggagagcaat ttctcgaagg ccgacgagta ctggatttgg   35880
atggacatta aggagaagtt ggaggcctct gagaccttcg acgttcgcgt gatgaacagc   35940
tccggcaagg tcctcatgtt catggacgac gtcgtcttca ggaaggtctt gcccgagcag   36000
atccagatgg cgatcgccgc ccagagcgcc tccgaggacg ctcagaagct ctacgaagtg   36060
gattggactg ctgccgagga actggaggaa gtcgccgaag aggacgacgg acagtggctg   36120
gtcctcgctc ccgaggaggc cgctgcgaag gaactgaaga aggagcttgg cgacaagcac   36180
```

```
gactacaaga agctctcgga ggcccccacc gaaggcttgg agaaatactc caagatcgtc   36240
ttggccgcgg agagcgagcg aggcacccct gtcgatgtcc tcgacggtgc tctcaagctc   36300
ttccagtctt tggcccatgc tcaggagggc acgcccgaga cctggttctt gaccgccgcc   36360
actcaggccg ccgcctccaa cgaggacttg aagggcgctg cgatcccgac cactgctggc   36420
ttgtggggtc tctcgaaggc cttccgcaac gaacaccacg acgtcgagat gggcatcttg   36480
gatctggcct ccagcggcga tttgaagaaa cctttgaccg agaagttgac caatgcctcc   36540
gccctcatga aggccaagaa ggatgccgag gtcgccgcgc gagccgacgg cttgatggtg   36600
cctcgattgg tggagtgcac cagccgcatg ccggtccagg atgtcagctt ccccgaggat   36660
ggaactttcg tcatcagcgg tggtgtcggt gccttgggtc tcgtcttcgc cgaatggatg   36720
gccgccaacg gcgccaaaca tttcgcgctc atgtcgcgaa gcggcaagcc ccctgcagac   36780
cagaagagca cgctcaggaa gttgagctcg gtcgccactg tgaagaagtg cgacatcgcc   36840
tccaaggaca gcgtgcttgc tttgatgaag gaaatcgcta aggagatgcc ccctgtgaag   36900
ggcgccatcc acgctgcagg cactttggcc gacggactct tggtcgactt ggaccgcgag   36960
aagttggaag ccgtttgcgg cgcgaagatc gacggaaccc tgaacttgca cgaggccctc   37020
aagagcgctc cattggagca cttctggctc ttctcctccg tggccgccat gatcggctcg   37080
gtgggtcagg gcaactattg cgcagccaac gccttcatgg actcgttcgc tgcctaccga   37140
tcggcgcaag gcttgcctgc catcagcgtc cagtggggtc cttgggccga cgtcggtatg   37200
gccgctcggg ccggcaccag cgaaggcagc atcgccagga tcgagatcgc caagggcttg   37260
gaggccatgc agtccatctt gggagccagc tccaacttgc acggaggcgt cgtcggcgtc   37320
gcccgcatca agtggaagat gctcctcgga cagatgccaa aggtcccccc tctgctcacg   37380
aagttcagcg ccgaggccgg aggcaagaag gcctctgccg tctcgatggc tggcatcacg   37440
caggacgacg tgcagaactt ggtggttggc gtgttgaagg acgtcatgtc cggagacgac   37500
atggagctcg acctcagctc tcctttgatg gagatgggtc tggattcctt ggccggcgtc   37560
gagttccgaa accgcttgca ggcctccttc gaaggcctct cgctctcgtc gaccttgatg   37620
ttcgactacc ccacggtgcc cgatttggtg gacttcatct ggtcccaagt gggcccccgcc  37680
gaggacgagg aagttggtgg cgccgtcgct ggcggcgacg ctggcggcat gctttgcctg   37740
tccggctatg caggacgatt ccccggaagc cacaccaacg acatcgagga gtactggcac   37800
actctcagcc acggtttcga caccaccacc gagctgccgc ctgagcgatg ggacatcaac   37860
gcctacttcg actccgacat cgatgcgccg ggcaagacct acgtcaagct cggtcacttc   37920
atccctggta tcgaccactt cgatggtgag ttcttcggtg tttcggacgc cgaacagcga   37980
gccatggatc ctcaccagtg gttggcattg gaaatttcct acgaaggctt gtacgctgca   38040
ggcttgacca aggagaccat gtctggcatg gagtgcggcg tctacgtggg agcctgtaat   38100
ttgggtggaa acgacgtgga cttggaagca ctcggaccct tctccaacat cggtgccgcc   38160
tactctggct gctccggccg tgtctcgcac gtcctctctc ttcgtggtcc ttgcttcacc   38220
gtcgacaccg cttgctcctc caccatcgtt gccctggact ctggttgcca ggccgtccgc   38280
ttgggcaagt gcaagagcgc cctcgcctcg ggtgtcaacg tgcagattgc cgcttccatc   38340
tggatcggct tctctaagat gcgaggtttg gccatggacg gaaggtgtaa gactttcgat   38400
gcccgcgcag atggcttcgc ccgaggagaa ggtctcggcg ccgtctacat ccaggccgca   38460
gccaattgca ctgatgcgaa ccctgcgatc gccatgatca ccggctgctc gaccaaccac   38520
gacggccgcg ccgccaccat cactgcgccc aacggcaccg cccagcagcg cgtcctgcgc   38580
```

```
tccgccttgg cggagcgagg caccttggcc gaggacgtcg cctgcatcga gtgccacggt    38640
actggtaccg ccttgggaga tcctatcgag gtcggcgccc agaaggctgt ctacaacaag    38700
ggccgcagcg ccgctcgtcc gctcgtcttg gccgcaggca agtcggcgat gggtcacttg    38760
gagggctctg ccggcgtcgc cggtatctgc aaggtcatct gcaccttcaa gcactctgct    38820
attcctccga acttgatgct cgagaagctc aaccccaaca tcgacctctc tggcttcgac    38880
gtcttgatgc ctgactcctt ggtcgactgg aaggctgtgc ctcgcgcggg cgtctcctcc    38940
ttcggtttct ctggaaccaa cggccacgcc atcttggagg ccctcccac ccccggagac    39000
cagctgcccg agaggaagat tcagaagttc aaccgttccg tcaagccctg caccagtgg    39060
ctcgagaacg tcctctacga agaggcctgg aacacttgcg agttggtgcc cgtcaccgcc    39120
ttcgatgctt cttgcatcgt cgtcggcagc ggcagcatcg ccgaaaagat ccgaaagctg    39180
gccaaggcct ccacggtcgt ccctgcaggc acctccgcca aggacgtttc tgctgccatg    39240
gataaggcca atgctcaggt cgccatcttc gccacttccg cggacgagcc ggatggcgag    39300
atcccaggcg cccgattggt cgagctcctc tccttcttgc agggcgccca gagcgcctcg    39360
gagacaccca agatggtcgt cgttgtgacc aagggagccc aggatgccag ccgacccaaa    39420
ttcgatgctg gcgccactct ctggggtctt gtccgctccg cgcgcatcga gatgccccga    39480
accaccatca aggccatcga cgtcccccgtc gacgccgccg ccgacgccgc agcaaagatc    39540
gttgttgagg agttggccgc tgcagaggcc gaggtcgagg ttgctcacat tgcaggaaag    39600
ggacgatgcg tgcccgtcgt cacagaggcc cctcagacag ccaagagcct ccagaggcag    39660
gacgccatgc tggacaagaa gatcctcagc gaaggcttgc agatcgtcac tggcggtctc    39720
ggaggtctcg gactggtgtc tgccaggcag ttggctgagt tgggcgccac gacagtgatg    39780
ctcacgagcc gatctggcaa ggtgccagca ggacaaggat tggaagagca cctccgatgg    39840
ttggaggcca tccccaccac cgaagtcgtg atcaagaagt gcgatgtctc ctccagcagc    39900
tccgtctctg agctcatgaa ggaggcgacc gactccaagg gacctgtggc cggcatcatt    39960
cacgctgctg gagtcctcga caggtgcccc ttggccgaga tggcaaagga gaatttggac    40020
aaggtctgcg agcccaaggc cagcggcgcc tggtacctcc acagcagctc cgagcagagc    40080
gacttgaagc tcttcgtgct gttctcgtcc gtctctgcca ctgtcggctt ggccggtgga    40140
gcctcctact ctgcggccaa cgcgtacctc gatgccctcg ccctctggcg cagagagaag    40200
cccctcgcag ccctcagcgc caagtgggga cctgtctccg aagtcggcat gaccgcggcc    40260
tcgggcagcg actccatgtt ggaagcgatg gctctcaagg ccctctcgcc agcccaggtt    40320
ggctccgcca tgcgtttgtt gctcacgcaa cagggcgccg gtgtgaactt gcgagctgag    40380
ctgatgctcg cccgcgtgaa ctgggcggac ttcgtgcgcg aggtcggtgt cgagatccct    40440
caagtgaagg agttccagag ccaagaggcc ctcgccgtga caggcaagga gagcaaggcc    40500
agcgcgatgg ccggcatgac cgacgacgac cgccaggctg ccgtgctgaa gagcatccga    40560
agcgccgcgc aaggcatggg cttggaaatg gacgatgaga ctcctttgat ggaggccgga    40620
atcgactccc tgtctgccgt cgagttccgc aacaaggtct cctccgagtt ccgcgaggtt    40680
cgtctcccaa gcaccttgat gttcgactac cccacgctca ccgcgctcgc gcagtacgtc    40740
tcaggccagt tgagcgtcgc cgccggcggc caggctgcct ccagcgccgc tgctgctgtg    40800
gcccttcctt ccaagcctgc cgctgctgga ggaaacatcg ctgtcttggg tggcgcttgc    40860
cacttgcccg gagacagctg gtcattggaa gccttcagcc acaccttggt caaggagagtg   40920
```

```
gattgcatcg tggagattcc ttacgacagg tgggatgccg acgagtacta cgaccctgag   40980
gccagcaccg gattgaagat gtacgtcaag cacgccggtt tcatcgaagg cgccgagctc   41040
ttcgccgcct cgagcttcaa catcgtcaag gccgaggccg agaccatgga tccccagcag   41100
aggcacctct tggagacctc cttcgaggcc ttcgtcgtcg gtggcttcac caagcagtcc   41160
ttgatgggaa gcttcacagg agtcttcgtc ggtcaggaca agtgcgattg gaaccgcatg   41220
atcagcggaa gcatgggagg tccttacgct gccactggcg gctcttcgtc tatctcggcg   41280
aaccgcatct cctactcctt gggcttgaag ggcccgagtg cgacaatgga cacagcttgc   41340
tcttcctcgc tcgtcgctgc ggacaccgcc gctgccacgc tgcgaaggag gcgttgcgac   41400
atcgcgaccg tctgcggcgt caacatgctc ttgctgcctc agaccttcat cgcctgctgc   41460
caggcgcaca tgctcagcgc cttcggtcgc tgcaagacct tcgacgaaag tgcctctggc   41520
tacgttcgtg gagagggctg cggcgcgcag accttgatgc aggtctcgga caagcccgcc   41580
tacgcggaga tgtccggcag cgccctgaac caggatggac gaagttccaa cttgacctca   41640
cccaacggac cttcccagca ggccgtcgtg ttggctgcct tggccgaagc tggcgttgct   41700
ccctcggctt tggactgcct cgagacgcac ggcacgggca cggagctcgg agatccgatc   41760
gaggtcggcg ccctgcaggc cgccttgggc ggcgccgcga ggcagaaggc cctcttgctt   41820
ggcgctgtca agaccaacat cggtcacttg gagggcggtg ctggcatcgc tggcctcacg   41880
aagttggtgt gcatgctcaa catgaggacg atggtgccca acttgcactt gcgcgaaatc   41940
aacgaccaca tcgacgagga cctgcagagc ttcgccgttc gactgcctac cgaagcgacc   42000
aagctcgcat ccaagggcat catcacttcc agcgtctcct cgttcggctt cggcggaacc   42060
aacggacacg tcgtcttgca gaccgcttcc aaggaaatgc caaagacagc gaagcctaac   42120
aagaacgttg tcttcctctt cacaggtcaa ggatcgcagt acatcggtat gggccgtggc   42180
ttgtacgact cgcagcctgt cttcaagcag gccctggaca agtgcgccga ggttctggac   42240
aagttgctgc caacgccttt gatggaggtg ctctaccctg ccgacgagtc caaattgatc   42300
gaccagacgc agttctcgca gccggccatt ttctccatcg agtatgccct cgctacgctc   42360
tggcgctcca tgggagtcga gcccgttgcc gtcttgggtc acagcgtcgg cgagtattgc   42420
gccgccgtcg ttgctggagt gctgcctctc gaggacgccc tcaagctcat cgccctccgc   42480
ggccagtgca tcgccgagaa gtgcgaggct ggaatcggct ccatgccgc tgtcttcgca   42540
agcgaggcgg acgtgcagaa ggcgatcgcg aaggtcggaa gcaaggacgt ctctgtggct   42600
gctgtcaacg gacccaagat gacggtcgtc agtggccgca gcgccgacgt tgacaaggtg   42660
gttgcccaga ctggagctac cagccgacca ttgacggtct ctcacggctt ccactcgccg   42720
ctcatgaagc ctgctctgga gcccttccga gcacaggccg agaccgtgac tttctccaga   42780
ccatccgtca gttcttctc tacccctcttg gccgagaag tcacagacga gcttgctcag   42840
cctcagtact gggtcgacca catcgagaac gcggtcaagt tcatgcctgc caccatggcc   42900
ctggacgagg ctctcagccc cgatctctac ttggaaatcg tgcgtcccc cgtcttggtg   42960
aatatggcga agcgcttctt gtcgaggagc gtcgagtgga tgccttcttt ggacaacaag   43020
gtcagtgacc aggacgcctt caagaaggct cagcaggccc tggagcctc cgccggccg   43080
cctaaggccg acctcaagcg aactgccttc cctggagag aggcaggcca ccccttgctg   43140
cgctccaaga agaccctccc tgatggcacc gtcgtcttcg cgtccacttt cggaggacat   43200
gtgctcgagc ttctctccca ccacatcgtg cacgagagg tcgtcgtgcc tggcgcttgc   43260
tatctcgaga tgatcgttgc tggctgcacc accttcttcg gacgcgacca gccttggtgc   43320
```

```
gtcgaacagt tgggcttcgc caagcctttg gtcttgcgct tgagccctga aggaaagttg    43380
gacgagccga ccgaattgcg attggtcatc cgtccggata tgcgtatcga ggtcgagtcc    43440
gagatcggcg acgacccga cgacagcatc gtcgcgacgc acgtcgaggc catcttggtg    43500
aagcagaccg gcacttgggc aagcaaccga cccgagaagg atgcgttcag cttggatcag    43560
ttgaagaaac agtgtgccga gcctgtcgac atcgacctca tgtactcctt cggaaagaac    43620
agcggcttgc cactgcagcg ccgattccgc accgtgcgac acgtgcagaa gggtgacaag    43680
gagagtatcg gccgcttgga gatggagagg gacggcactc aagtcggatt ctggctgggt    43740
ccttccttga tcgacggctc cttccaggcc tccatggctc tcgcagatgc agatgttgga    43800
atcggcactc tgaagattcc tctctccatc cgacgcttgc agccaacagg ccgagcctac    43860
aacatctctg tctggtctta cttccagctc attgacttca ccgacaggag caccgtcttc    43920
cgctcgtggt tgctcaacga cgctggcgag gctttgttgt acttcgacca cgtccacttg    43980
caggaggtcc gagacgagca catccagaag gtcttgcagt cttcaggccg tcagggcacc    44040
gagcagtcca acttgtacga tgtcgaatgg cggcagttgg agcttgccgg aaagcctgcc    44100
tccctgccga acgaagagtt cctcgtcgtt ggtggcaagg ccgccctcga gaagctcaac    44160
ttgggcaaga gtcctcagtt ctcttgcatg cagatcggta aggacatcga catcaatgat    44220
gacgacagtg tgaacaaggc tctcttgggc aaggcctggg ccggcatcgt cttggccgaa    44280
ggtttggccg agaaggtcgg cgacgttgat gttgtcaccg aggccatgat catagttaag    44340
gtcctgacca aggcaggctc caaggcccct cctctctggc tcctcaccag tggctctcag    44400
cctctcgcct ccgcagacgc cgagcagcgc aaggccggtt gtgcaacaca ctccggtctc    44460
tggggtttcg cccgcgctgt gcgcatggag taccccggaa tggtgcgagt cagttgcttg    44520
gatttcgacc ccacaagttc gaagagcacc ggagacgagt tgtccgctcg cctgtctagc    44580
ttgaccgctg acactgagga cgaggtcgcc ctccgaagcg actccgccgc cagcgctcgc    44640
ttagtgcgtt ccgagctcca gttcgtgggt cccagccgct tgaacatggc cgcgcgcggc    44700
gccttgagca acttgaggct cgtgtcgcag ggcaagcgcc agaccccat ccctggcttc    44760
gtccagcaga ggatccgagc catcggcttg aacttccgtg acgtgctcaa tgtgatggga    44820
ctctaccctg gcgaccctgg agccccaggc gccgactcct ccggaaccat cgtcgagttg    44880
ggtgaccgcg tcgacaccct caagatcgcc gatgacgtct tcggagagtc tccaggctgc    44940
ctcagcacct acaacaatgg ccccgcggcc ctcttggcca ggaagccccc ctcttggtcg    45000
tacgaggagg cctgcgcaat gccggtcatc ttcgtcaccg tcgaggaggc gctcggagac    45060
ctggcgaagc tgaagaaggg tgagacggtc ttgatccacg ctgccgccgg cggtgtcggc    45120
ctcgtcgcca tccagtacgc ccagtgggtc ggtgccaagg tctatgccac tgctggatct    45180
gaggagaagc acgccttcct gcgcaagttg ggcgtcgatc gcatcaccag cacccgagac    45240
ggcgccaagt tcgaagcgga gatggagaag atgttgaagg aggacaagct cgagggcgtc    45300
gacgtcgtct tgaacagctt gagccacgac gactacatcc cacgctccct gaaggtcttg    45360
aagaagggtg gacgcttcat ggagatcggc aagcgaggca tctggagcca cgaggagatg    45420
ttcaaggcca ggcctgacat catgtacgag aagatcgccg ccgataccat gatggagaag    45480
gagtgctgga ggtacaacgc ctacctgaac cgactcttgg agcgcgccga gacaggcggc    45540
ttgaagccca tcaacgacca ccgattcgag ggtcttgaga agggagtcgc cgccctgcag    45600
ttcttgcagc gcgccaacaa catcggaaag gtcgtcatct ccgagcccag ccgactccag    45660
```

```
tgcaaccctg cgaacatctc cgtcctctca ggcggcatgg gcgccttggg catcgtcacc   45720
gcgcagttct tggttgaaga aggctgcaag aagctcagct tgctgtcccg aagcggcaca   45780
ccttcctcgg atgccttggc gcagttcgag tggctgaagg cagctgctat cgaagtcggc   45840
gtgagcaagt gcgatgtctc ttccgagact agcgtcaagg ccttcgccag tggcttgcag   45900
agccccatcg actgcctgat gcacctcgcc ggcgttctcg ccgacggcat gctgcctacc   45960
ttgacgaggg agcacttcga gaagtcgtac gcgccaaagg ttcacggtct gtaccacatg   46020
gtcaagcact ggaagatgag cgaggacacc aagttcatgc tcttctcttc cacctccgct   46080
ctcttcggat cgccgggcca ggccaactac tccgcatcca actctgtctt ggactccttg   46140
gctcctatct ggagtgccca gggacgacag tcttggacgg tgcagtgggg tccttgggcc   46200
gaagtcggaa tggccgtgca gaagaacacc ttgtcccgag ccaaggctat gggcgtgggt   46260
gccttgagca ctgccgtcgg tatgtccatc atgggaagca tcctcggctc tgcctcgcac   46320
gtcgtcggtg ctgtgcctgt caggtgggct aagtacctcc gaagtgccta ccaggagact   46380
cctatgttct tgactgacat ggaggccgag gtccgccgtg ccgccccagc cgttggtgag   46440
ggaggtggca attccttggc cttggccaac ctgtcggcag aggagcgctt ggaggccgtc   46500
cgcgagagcc tcctcaccat ggctcgcgag gtcgtcgaca cgacactct ctctgctgaa    46560
gacgcattgt tggagagcgg tatggactcc ctgtctggtg tcgagttccg aaaccgattg   46620
gtcaccgagt tcgaaggtgt ccgcatgggc aactccctca tcttcgacca ccccaccgtc   46680
aacgagctcg cggcgttcat ctcggaggag ttgggcaaca ccttgccagc ggccgactcg   46740
tctgctgccc cagcggcctt gcagaacggc gcctcccacc ctgtggaggc ccccgagtcc   46800
agcgccagct tcgtggagag cttgaactca cgcgccagcg gcactccgat ctacttcgtc   46860
cccgagccg gcatgcaggc cggaggcttc cgtccgttgg cccagatctt gccggtgcct    46920
gcctacggtc tttcttggcc gaagggcgcc gtgccgcgcg aggagtggcc taccaccatc   46980
gacggcctcg cacgagtctt cctcacagag gtcaagaaga cgcagcccac tggaccgtac   47040
cgcttcgctg gacactcctt cggagccgcg gtcgccctcg agatggccaa gatcgcacag   47100
gcccaaggtc tggaggttac tttcgtggcc ctccttggacc ccaggcacat gggtggaaag   47160
accaccgtcg acgtcggcga agccttctcc acgaccgacc tcgccgactc cttgggcctt   47220
ttggcccaaa ccgtgccaga cggctcgaag tacgtgcagg ccttggagga gatcgtcaag   47280
tccgacgacc gcgatgccgc tgctaagaag gtattgagcc cagccgtgtt ggcttctttg   47340
gagcatgttc acgagaccac gaagtggtac agcaccctgt tggcaggaga caacttgcag   47400
cctgacgcaa gcttgaaggc ccgaattgcg gtgctccgag ccctgagac ttggttgagc    47460
ccaggtgaca acgagacgat cgctgacaag atggtccggg aattccaggc caagacgttc   47520
cagggcgatg atgaggtcac caagctcgtg gacgagtggt gcggcgttgc ccccttcttg   47580
aacatgaagg ttcctggcag ccatttcacg atgttgcacg aacctcacgt ggtctcgctc   47640
gccatgcgct tgtgccgcgc agtcgacgag tccgagggtg aggagctc               47688
```

<210> SEQ ID NO 3
<211> LENGTH: 47866
<212> TYPE: DNA
<213> ORGANISM: Crypthecodinium cohnii

<400> SEQUENCE: 3

```
tggctcaagt cgttttgct caagatcgag catctcccat atttatatat tggcgctgtg       60
ccgaggtttt gttagtgtgc cgactttgaa agcacgatga ggcgcagtgg tgaaatgaaa     120
```

```
ggcgcctctg gaagttccgg atcctccggc ccttccaagc gatccggctt gaagaggtct    180
ggtggaaaca ctggatctca gtcccaattg gcggacatgg tcgaccaact gtcggtcacc    240
accagcacag gatccatcag gatgctcgca cgagcaggcc tttgcctctc gatgggcatc    300
gttctagcga tgggacgaca tacgccgtgg tggttgatcc ccttcggcgt cgtcttcgaa    360
ggagtttccc tagcttggtt tcacctcatc caaaaagagt gtgaacaggg caagttttg    420 ccttctcccg agttgaatag agtattggcc gctctcctgc gatgggaggt gtgctcggcc    480
ttggttatcg tgttgttctt gtcgggagcc tgggacatct attctatctt caaatactgg    540
ctgcttcctc ttctcgttac ccaagccacc ttttcgacat ccagtgcaac agagaagcca    600
aaatccgagt ctgcagaagg ctcgggcaga ttgtccaaga ctccctcaat gtcttcgttg    660
gatctgctgt ttcccgagtt ggaatccgca gcaagccaaa tttcggagtt gttggaagcg    720
gcgcagcatg cggaccagag caacatgttc acacaccacg ttggcgctga cgatgccagc    780
agtggcgatg actggcactt cggtgtcgct ctgcatcaga tcccgatgta ccacctgcag    840
tcactctccc gaaatttgaa caaggagctg aagcgcgcgc gccctttgg gtccagcgcc    900 aatttagcag ctctcatggg tggggcagc caagatgctg aaccaggtgg cgaacaggac    960
gaaggcctcc gacagcgacg ctccaaacca gctgccagga agaaggagga gaaaggaaag    1020
aaagatgctg tgcagcaaac tccttgggcc caggtcatga acctcatcgg ctggccagcc    1080
aggtacttgt tcagagaaat gtggctctgg actgagaagg acctcaccct ctatgccgtc    1140
gtcgctattt tcttgctgga ggtctacatc ggaacgaagt acttttcttt cgcaccaatc    1200
tgcctgctct acccgctgct gtcgagttcc tccggagccc gaatggcctc tgaactgcag    1260
gaggagatcg ttatggtgat gggcctcgag catcgctttt ggcgtcgctt gcacatcccg    1320
gtggctctgc aggtgttggt gtgccacaac atggttgtgt atttcatttt ctctcaaatc    1380
atctttggtg gagtcgatcc ttacgtcggt gttgccccca gtggcaaac cttcttttt    1440 ggcgtggtgc tctacgtttt gtccatggtc ggcatgatcg gaatgaactt ggtctgggcc    1500
tgcggtgccg tcgttttgga cctcccccag aaagtcttcc tcatgatctg tgcctctacc    1560
gcgaaccaag gcagcatctt ccgatggtgc cgagatcatc gtgcccacct tatgaacaag    1620
ggcacggtgg ccgatcctta cgactacaac cgtggcgcta ccttcgccta catcggctgg    1680
tttgtgcagc agaagactcg ccgtgcgatc gaagcgtcaa gatctgtcga catgtccgac    1740
ctccttgccg accaggttgt gatgttccag gctgatgtgg acacctggtg gaatttgtct    1800
tggtgccatg ccattccggc attcttgacc ttgatgtggg gcgaagattt gttttgggt    1860 tgggtcatct gcggctgctt ccgatatgtg ctcgccttgc actccaacct cctccttgtc    1920
taccatcagc atgcctgggg ccccatggag gtgaaggccc agccagtctt gacaggagaa    1980
gtgactgccg ccgccactgg ccgcagaact ggtggcagcc agatgttgcg ttctgcctcg    2040
atcgcagagc agctgcaatc tgtgcccgaa acagaagtcg ccccaaccg accggcccca    2100 ctggacactg ctgctgcaat tgcccaacaa gcccgaaacg ccgaggacgg cggtgtcttc    2160
gtcaagtaca aggtcggcca ggcctccgct ggcggcgagc cctctttgga ggtccgtttg    2220
gagcccctct ggagacgctc cacgttgatc gatttggcca aggatgctgt cgccgacatc    2280
ctgaaggtcc agtccagcca ggtccgaccc gaccgtcctt tgatggactt gggctttgat    2340
tcggccagtg ctctcaggct cagggacaag ctcagcaggc gattgaacgt tgaattgcca    2400
cctaccttgc tgttcgatca cccaacgatc aatgacatgg tcgacaacgg cctgaccaag    2460
```

```
tttgctcagc gcccgatgac cccctccggc atcaccccg atcagaaggc tgctgccatg    2520
ccagatctgg tggtgacttc cactgcctgc aacatgccca aggcgggctc ccctggtgag    2580
ctctggaaca tgcttgtgac gaagaccgat gcggttgtgg aggttcctct cgcccgttgg    2640
gatcattgcg agtactactc tccagagcct caggagggcc agacctacgc tcgacacgga    2700
ggcttcatcg acaacgccga tctgttcgat gtgcctttct tcggtcttac cgcggcagag    2760
gccaaggcta cggatcccca gcagcgcctc atcctcacaa cggcctacaa ctgcttctat    2820
ggagatggat acgacaaggc cgcttttggcg ggcgacaaca ttggtgtctt cgtcggtttg    2880
agcaacttgg actggtacca cctcagcctc agcaagccca gtgtctacac aggcaccggt    2940
gtcgccagtg ctatcgcctc gaaccgaatt tcttacgtct tcggactcaa gggacccagc    3000
atgaccgtcg acacggcttg ctcttcctcc atttcggcct tgacctccgg tatcgcctct    3060
atcaacaagt cccacgctgt gcgcgaggcg ttggtggcgg gtgccgagct tattcatggc    3120
cccaactctt tcatccttcg atccgtggcg ggcatgctga gccccgaggg gcgctgtaag    3180
accttcaatg ccaccgccga tggctacatt cgaggagaag gtgccgcagc ggctatcatt    3240
aagttggcct ctgacgccga ggaaaagagg tgtgccgtcg tggccgacgt gaagagcgcc    3300
gtcatgaacc aggacggaaa gagtgcgacc ctgaccgcgc ccaacggtcc ctcccaggaa    3360
gaggtgctgg ccaccgccct cagggaggcc gccatgcagc cgaaccaagt caaggccatc    3420
gaatgccacg aacaggcac tgcattgggc gaccccatcg aggtcagcgc catcaaggct    3480
gtcctcggag ccgagagcaa ggaggccccg aagctgatgc tctgcgctgg caagtcgaac    3540
catggtcact tggagggatc cgccggcttc gccggcctga tgaaggtctt cgggtgcctc    3600
acccaaagcg aagtgcctcc aaacatccac ttcgaacgac tgaaccccca catgagcttg    3660
gagggctcta gattgacagt tgcggaggcc cagaccacca tccccaaggg caacacagtg    3720
atgggcgttt cctccttcgg ctttggcggc accaacgcgc atgcgctgct cgcccactcc    3780
atccgcaaga agcccaagaa attgtccgag caccgggtcg ccttcctttt cactggacag    3840
ggctcccagc gacaggccat gggcaagagg ctctacaagg tcgatgaggc cttcaaagtc    3900
gccctcgatg aggcagctgt catctgcaag gacctcatcg accaggacct cttggacctc    3960
atgttcagcg aggaccgaga gatgttggag aagttgaaca ccacctacta ctcccagatc    4020
gccatcttct ccatcgagta cgccctcagc aagatgtggg ccgccaaggg catcacgccc    4080
ttcgcagtct tgggacacag cgtcggcgag tacacggccg ctgtcgtggc cggctctctc    4140
tccttgaagg acgcgctgaa ggctctggct actcgaggtc gcttgatcca ggagaagtgc    4200
gaccctgcca tcggcaacat gtgctccatc tttgcctctg ccgccgatgt ggaatctgcc    4260
atccgctccg tggaccttca gggcgagact gtcaacatcg ccgctatcaa cggcccctct    4320
gccacggtcg tctccggcca caagaaggca gtcgagaagg tgtgcaagca ggtcaatgct    4380
ggcaacaagg agcttgccat ccagcacgcc atgcactcca agctcaccga gtgcatcttg    4440
cccgacttga agaaggtctt ggacacttgc gagttgaaga agccctccag cgacatccac    4500
ttcgtctcca cgctcaccgg tactgagatc tccaacgagc tcacaaaggc cgcccactgg    4560
gtcgccacg acgaggacaa gccgatgctc ttccttcagg gtatggagac tttggagaag    4620
ttgggctgca ccgccttcgt cgagttggga ccacagccag tgttgatgaa gatgggacgt    4680
cgctgcgtcc agacggccgc caccaacttc gaatggctgt cttccttgac gccaggccgc    4740
gacgaggtcg agaacattct gttgatctct cgtgccttgg gcgctgcgta cgatcgtgtc    4800
tccgaactga agcccacgcc cctcccttgg cgcgcgcctc tcctccaccc tctgttgggc    4860
```

```
aagaagcagc aggacgcctc cggcgccacc gtcttcgagt ctggtgccat caagagtggc    4920
gccgcgatgg aacttttcga gcagcattgc gtcttcggac aggtcgtgct gcctggagcg    4980
agccacatcc ttcttgcagc cgccgcccag ttggagagcg ccaccacgcg cgtcggtgct    5040
ggagctgccg tggagctcaa cgatgctgtc ttcgagcgac ccttcgtcgt tcctgaggac    5100
tccgacctca ccgtccgctg cagggcgact gtcgacacca ccgaagtcgc cagctccact    5160
gacggggccg cgcccgtggt ccatgctcga ttcggcagtg ctcgcgtcgt cggtgctccc    5220
gccctggcta ccctgtcca ggaacgtttg tcggccctcg agacacctcc ctccgcagag    5280
ggagtcaagg acctttacaa ggccttcgag gacaagggct tgggctacgg accgtccttc    5340
cagcccctgc aggagttcag cttccagtct ccggtgctt tggctcgcct gggcatcacc    5400
ttgaagacct gggagcagtc tctccagatg ttgcacccgg ccctcttgga tggagctctt    5460
cagctcttgg tcgagagcgc cacccgacgc gtcgaggaaa agtgcacctt cttgccattt    5520
gcggtgaaga aggccatcgt ggcagccag tgcccaaccg gcgagctttg gccagcgtc     5580
aaggttctgg acagcaccgc cacctctttg aatgccgatg tggaggtttt caatgccgag    5640
ggcaagttgg cgatccgcct cgagggcgcc agctgccgac gagttgagga gggtgccgcc    5700
gcagagaagg acaacggaga tcagtgcctc tactccatca gctgggtcgg agcggaagag    5760
gacagccgcg gcatcttggt cactggaacc accctcgtcg ttgcccctga atcagagatc    5820
cccgcgatcg ccaaggccat cggcgtctcg gagtcccgct gcagcgctgt cagcacagca    5880
gaagaagctg tcaagactgc tgccgaccga ccctgcaaca ccatcgtgta ccaagctgct    5940
ggctcagaga tcgatgctct ggaagttgcg ctcaagctca cacagggagt tgcgaagttc    6000
gatggcgatg tgccccgaat cgtcttggtc actactgccg cccagcagcc ggacttgaag    6060
gacaaggaac acgacccaa gcactctggt ctgtggggtt tcgcccgcgc tgcccgtttg    6120
gagtaccccc acatgcaggt ctcttgcgtg gacttggagg gatcttccga agtcgctgct    6180
cccacacctt ccgctgcgct ttccgcagca gaggtcgaag tcagtgtgcg aaatggtgcc    6240
tctttgggtg ccaggctcgc ccgcagcagc atggcgccga agcgccctt gaggctcaac    6300
atggcccgtc gaggcagcct catgaacctc cgacccgtcc cccagaccaa gcgcaaggcc    6360
cccgaggctg gcgagatcga agtccgagtt ggcgccattg gtctcaactt ccgagatgtc    6420
ctcaacgtca tgggcctcta ccccggagac cccggtgagc ctggtatgga ctgctccggc    6480
actgtcgtga cgtcggcga gggctgcccc aaggagcttc gatgcgggga cgatgctttc    6540
ggtatcatct ggggctgcct ctgcacctat ggcaagacca agcaccagct catggccccc    6600
agacccaacg actgggacgc cgcctcggcc gcggccttgc cgaccgtcta caccaccgtg    6660
gacgtggcct tcgcagagct cgccaagctg aagaagggcg agaaggtctt gatccacggc    6720
gccaccggcg gcgtcggtct catcgcagtg cagtacgctc agaagctcgg agccgtcgtc    6780
tacgcgacag caggcaagga ggagaagcga cagcacttgc gcgacctcgg tgtcaagttc    6840
atcacgagct cccgaagcgg cgacgaattc gaggctgaca tgaagaagtt cttgggcaag    6900
gagaagatcg atgttgtgct caacagcatg agccacgacg actacatccc gaggtctttg    6960
cgcctcttgg ggaagggtgg ccgattcgtc gagatcggca agcgagatgc ttggaccccc    7020
gagcaggtgg caaaggagtt ccccgacgtg cactactacc ccttggccat tgaccacgtc    7080
tgcgagttcg agcccgacag gtaccagggt ctgctcaagc gcttggaggg tgccatgcgc    7140
gagggctgga agcctctgcc aatgaagact ttcgagggct tggagcaggg cgtcgctgcc    7200
```

```
ttccagttct tgcagcgagc tcagcacatc ggaaaggtcg tcttgactgt tcctcagcga    7260
atgggcttgc agaaggacgc ctcctacatg ctctccggag gcatgggagc tttgggtatt    7320
gtgactgcac agaccatggt cgaggaggga gccaaggagc tcatcctcct gtctcgaagc    7380
ggcaaggtcc ctgccgaggt ccaggagcag tgggcctggc tggagaactc tgctgctgaa    7440
gtcatctcct ggaagtgcga cgttggcaag ggcagcgacg acatcctcaa gaagctgaag    7500
ggcaagaagg gcaacggctt gaagggtctc ttgcacctgg ccggtgtctt ggacgatggc    7560
atgattccgg acttggcccg ctccaacttc gagaatgcct atggacccaa ggtcttcgga    7620
gcccaccacc tcagggaggc tgccaagaag aacggctcca ccttggactt cttcgccttg    7680
tactcatcca ctgcctcgct tttgggcgct gcaggtcagg cgaactactg tgccgccaac    7740
tctgccctcg atgccttggc caacgcctgg cgatgccagg gcgaatccgt ccagagcgtg    7800
cagtggggcc cttggctctc ggtcggcatg gccgcccaga acaactcctt cgctcgattg    7860
aagctcggag gcatcagcaa cgagttgggt ctctccgtcc tcagctctgc catcaccagc    7920
ggcgcctgcg tcgtcggctg cgccatcgtg cagtggccag gattcctcaa gcagttcccc    7980
aagacgccgc tctacctgga gagcttcaag gacaccgctg ctggcgccgg cggtgctggt    8040
cgggctggcg gcagcgagat ggagatgaca ccagaaggca tcctcgcgtg ggttagctcc    8100
gtcgcagccg acgtcgtcgg cacagaggtc tcccccgatg agcctctcat ggctgccggc    8160
atggactcgc tctcctcggt tgagttccga aatcgcttga ctgccgagtg cagcttcgcc    8220
aagttcccca cacccttgat gttcgaccac ccgaccctgc gagcggtcac ggagcttgtc    8280
acttctcagc tctcccccga gttggtcgcc tctgccacca cgctgtcgc caccgccggc    8340
cccgcctccg acatccaggt cgtggctcgc ggcttgttct cccgcttccc cagcggcgat    8400
ggcttgcagg ccaattggga gaactggcag aagaagatgg actccatcat cgaagtcccc    8460
tttgctcgct gggatctcct cgagttctgg aatcctgaca tggaggccag cggcaatgtg    8520
acctactccc gtcatggaag tttcatcgcc gacgccgaaa tgttcgaccc aggcttcttc    8580
ggcatgtcgg ctgtggaagc gaagaccatc gatccccagc agcgtcacct cttggaggtc    8640
tcctacgcag cctgccacca cgctggcatg tccaaggaga agctcttggc cactgacact    8700
ggcgtcttcg tcggacagtg caacaacgat tgggccaagt tctccagcga ccgacctgcc    8760
aaccccctaca ctggaccggg cactcacgcc tccatcagtt ccaaccgaat ctcctacaat    8820
ttgggtctcc gaggccccag tgcttccatc gacacggctt gctcctcgtc cttggtcgct    8880
ctggacatcg cctgcaacaa gctcaagggc tccctcatcg gctccgccat ggtgctgggg    8940
tgccagttga acttgatcgc cgagcccttt gtcgccttcg aaaggcccg catgttggcc    9000
cccgatggac gttgtaagac attcgatgcc tctgccaacg gctacgtgcg aggtgagggt    9060
tgcggagccg tttacttggt cggagctgct gcatcgaagc aggacgagct cgcgatcttg    9120
cccggcatcg cagccaccgc gacgaaccag gatggacgaa gctccacctt gacggccccc    9180
aacggcccct cccagcagga tgtgatcagg aaggctttgg cccagcgcca ggtgcttgcc    9240
tacgccctcg gcttcgtcga atgccacgga actggcactg cttttggaga cccctatcgag    9300
gttggcgcct tgaaagctgt cctggctcca aaccgcacaa ctcctctgat cctgggaaca    9360
gtcaagacca acattggtca cttggaaggt gcagcgggca ttgccggtat ggtcaaggcc    9420
atgctgtctg tgcagaactc cgaggtgcct cccaatttgc acttcaacac cctcaacccc    9480
aacatcgatc tggaggactt ccccaccaca attcccacaa gcattgagaa cttgactgga    9540
gaccagccta cagccggcct ctcctctttc ggcttcggcg gcacgaacgc ccatctcacc    9600
```

```
ttcagggctg cccccaaacc attggagaac gcccaggatt ccgagggtgg tgccaaacgt   9660
cgagtggcat tcctcttcac tggccaaggg tctcagtaca tcaacatggg caagcagctc   9720
tacgaggccg agcctgtctt caagtctgtg ctcgagaagt gcgccgagtt gctcaacccc   9780
ttgctggagc agccactctt ggaagtcatc ttcgatgcag gtggcaagtt cggtaaattg   9840
ctggaccaga ctcacatgtc ccagccagcg atcttcgcca tcgaggtcgc cttggccagc   9900
atgtggaaag caagggcttc gaacccgag gtcgtgatgg gacacagtgt cggcgagtac   9960
gccgctgcgg tcacctgtgg tgtcatgagc ttggaagatg gctgcaagat gattgctgcc  10020
cgtggcaagc tcatcgcgga caagtgcgag gccgagtgg gcgccatggt cgccaccttc  10080
gcccccgagg ccgccatcat tgcggcaatc gacagcttga gcgacaacga gaagaaggaa  10140
gtcgccattg ctggcgtcaa tggaccgaag atgtgcgttg tctctggtcg caaggatgtt  10200
gtggagaagg tcgttgccgc caccggcgct ggcaacaaag ccctgaacgt ctcccatgct  10260
ttccactcgc ctctcatggc cccaatgttg acagcttcc gacagacggc tcgggccgcc  10320
gaccttaaga ccccaagctc tggccgtttt gtctccaccg tcactggcaa ggccgtcact  10380
accgagttgc aggatgccga atactgggtg aagcatgtcg cccagactgt ccgattcgcc  10440
gacgccatgt ctaccttgga gaaagaaggt gttgatgcct tcttggagat cggtcctgag  10500
ccgacccttg tgaagatggg ccgtcgctgt gtctctggca ccggctacca gtggctcacc  10560
tccatcgagg gcaaaggagc tcccgtaagc gaggtggacg ccgtgaagca ggctgctgcc  10620
gtgatgcgag gaggactgcc tcctctgacc tacaagaagc aggccttccc ctggagggat  10680
gccggaccta gaatgttgag gaggcgcgcc actaccgaca aggaggccca cttttgacgtc  10740 cccgtgcgca gcgatctctt cgctgtggcc gccgagcacg tcgtctacgg cgagatcgtc  10800
gtgccaggtg tcatcttcgt ggaaatggcc ttggagtccg ttcgcgctca cctcggcgag  10860
catgtccagc tccgcgacgt gtccatggtc tggcccctcg tcgtacccaa gaacgccgac  10920
tgcgaggaga agcaggtctg gatgcgattg gccatcattc agaacaagcg cttcgaactc  10980
cgatcccaga cgcccggcga cgacaagtgg accacgcact gcgagggcaa gttggatttg  11040
aacggaccgg ctgcacccgt cgtcgaggag tccttcgacg agatccgcga gcgctgcccc  11100
gaggatgtcg acgagaccaa gttgtatcct ttggtggaca cgtcggcct gtggttggga  11160 ccgaagttcc aggtggtcag cgaaatgaag cgaagcaagg aggaaatctc ctgcaagatg  11220
atgctacacc ccgacgtcat caacaacggc tacatcatcc atccttcctt gatggacgga  11280
accatccatg ctgtctgcgc caccatgctc gaccaggatc ctcctttcct caagattttc  11340
gccggcgtcg gtcgaatcgc catgcacgcg aaagctgccc cgaagaacgt gaaggtcaac  11400
ctccacctca gatcagcga actgtccgac cagcagcaaa tcttccagtg cgtcgtcacc  11460
gacgacgaca agaaagttct ctgggtcatg gaggacgtcc tcttcaggaa ggtcctgccc  11520
gagcagatcc agaaggccct cgcggccacg aaggagaagg atgcagtgaa ctacttcgag  11580
gcccagtggc agcctgccac tgtcgacaac ctctccggcg gattcatcga aagggaccg  11640 atgctggtca tctgcgagga tgccgatgtc ttggaaggca tgcaggcaga gctctcagag  11700
gagcacagcc tcggcacctt cgccgagggc tatcccgagg ccctggaaga gttctcgcag  11760
gtgctctgcg tcgcctcccc tgttgccggc ccagtggact tcctcggcgg agccctcgag  11820
ctgctgcaga aggtcatcaa gaagaagatg atggcaagg acgtccccga agtttggttc  11880
gtcctcaact ccaccacagc ggtcaatttg tcggaactca agggaaaagc tgtgcccaag  11940
```

```
catgcaggcc tttggggtct ctctcgctgc ctccgactcg agcatcctga catcgcctgc   12000
ggcgtcatcg acctcggctc gaaggtgcat gtcgacgatg cggccggcat tttggaaagg   12060
ctcgcctctg ccaagactct ccaagacgat gccttcgagg ccgaagtctt gatggaggac   12120
tcccagcagt acgtggctcg cttggtcgag acaacttccc aactccagaa ccttccctcc   12180
gagcagtctt tctccaagga cgcctcctac gttgtcactg gaggcactgg tggattgggc   12240
ctgctgttcg cgcagtggat ggctgatcag ggcgctggcc acttgggcct gctctcccga   12300
actggaaaag cgccagctgg acctgcctac aagaagttgg ccagcactcc aggcgtcgag   12360
gtggctgttc gctcttgcga tgtccactcc gaggagagtg tccgaagcat cattggcgaa   12420
ctcagcaaga ctgccgccgt taagggcgtg ctgcacgctg ccggcgtctt ggaagatcac   12480
ttgattgttg acctgaagaa ggaacacttg acccagtctc tgcgacctaa gatcgacgga   12540
actttgaact tgcacggtgc tacctccgac ttggacttct tcgtcatgtt ctcgtccatt   12600
gctgccatgc ttggttctcc gggccaggct aactattgct ctggcaacgc cttcatggac   12660
gccttcacct tgcaccgacg agctcagggg cagtccgcgg tcagcgttca gtggggtcct   12720
tgggctgaag tgggcatggc cgctcgcgcc ggcacctctg agacctccta ccagaggttg   12780
gaccccacag cctccttggc agccatgggc gccatcttgg gcgccggtag cgaggccgtc   12840
accaacggca tcgtgggcgt cgcccgagtc aactggagca acttcttggc cggcttccct   12900
acgctgccgc cctacttgca gaacttcaag aacttcagga gtgccggagt caagatgacc   12960
gacggcgtgt cgaagactgt ggtgcgggac accatcgaag cagtgttgtg cgacgtcctg   13020
ggcgaccccg acttggccga cttctctgtt cctctcatgg acatgggtct cgactccctc   13080
tcggccgtcg agttccgaaa tcgtgttcag gcagccttcg agggcttgca cctcactgcg   13140
acggtcatgt tcgactaccc cactgtggcc gacctcacgg acttcgtctg ctcgcagttc   13200
agcgagggcg aggaggagga ggccgccggg ggcgctgcac gaggcgaggt caatgcgcag   13260
gagccactcg ccatgctggg cgtggccgcc aggttccctg gatgcaggac caacaacccc   13320
gaggagtact ggaacatgct cttgctgggt cgcgacatga tccaagaagt cccgatcgag   13380
agatgggatg tggacttgta ctacgacgag gaccattctg ccccaggcaa gatgtacgcc   13440
cgaaacggag gcttcatttt gggcctcgaa ggtttcgatg cgaaaatgtt cggaattgcc   13500
gacagcgaag ctcacgccat ggaccccat caacgaatct tgctggaagt tgcctacgag   13560
tccttctgga acgctggttt caacaaggac gacctcatga acagcgacac cggctgcttc   13620
atcggctgcg cgacgctggg cggcatcagc gtcgaggacg acgacatcgg gccttttcacg   13680
aacatcggct ccttcccctc ggggaattct ggacgtgtct ctcacgccct cggcctccga   13740
ggtccttgct tcaccctcga caccgcatgc tccgccacca tcgtcgcctt ggactgcgcc   13800
gcccaggcta tgcgcctcaa caagggcgag cgaagctgcg tggcaggaag caacctgcag   13860
ctgcaggcga acacttggat cggtttctgc aagatgggag cactctccgt ggatggacgc   13920
tgtaagacct tcgacgccag cgccaatggc ttcaccagga gcgaaggtgc aggctcgatg   13980
atcttggagt tgcaagatgc agccctgcga aagggacgaa ccgagatcgc gactgtcttg   14040
ggcgcctgcg tcaaccagga tggccgaagt gctacgatca ccgcccccag tggacctgcc   14100
cagcagcgat gcatccagtc cgctctcgcg gacgggtccg tcgaccctct ggacgtcacc   14160
atgatcgaag tccacggaac aggaactgcc ttgggcgacc ccatcgagat cggcggcttg   14220
aagtcgaccg tcggcaaggg acgaagtgcc gacagccccc tgattttggg agcagtcaag   14280
tcaatcatcg gtcacgaaga gggagccgcc ggcgtcgcag gcgtcatcaa gatggtctgc   14340
```

```
gaattcaagt accgacagat ccccaagaac ttgcacctcc acaagttgaa cccgaacatc    14400
gacctcagcg acttcgcctc cgttgtcatg ccagacagca tcatcgattg gaagtctact    14460
tcgacaaagt ctggcacttc gtctttcggc ttcagcggta ccaactccca cgccatcttg    14520
gaggcggtcg acggggacga gattggaggc gtcgcactgc agaactccac gcccctcaag    14580
tgggcaaggg tccctcaccg catgtccacc gagtggtcct ccggtctctg gtggtccctg    14640
gagtggaaaa acacacccttt ggcgactggc tcgctcgacg accttccttg cttgttggtg   14700
ggtggcggcg agattgccaa ggccgttgcg aaggtcatct cggatgtcac agttgtggac    14760
atcaagaacg ctgccaaggc catcgaggag aaggaatggg caacgatcct catcaccgag    14820
cccatcacct ccaccgacga ttgcttggag ggtgctgcca tcatgcagct catcgaggtc    14880
accaaggcag ttgtggcaag tggccgagcc ttgcgcttcg tcgtcgccac cgctggtgca    14940
cagagtgcca gcactgagga ctcaaagctg tcgcagggct gcctgggcgc cgccgcttgg    15000
ggcctgatga ggacgatcat ctgggaggct cctagcctca agttgcagac catcgacctg    15060
ccttcccagg cctccgccga ggaaatggcc acgctcttga aggacgagct ctccgctgag    15120
ggagatatcg agcccgagat tgcctacatg tctggccagc gctctgtccc acgcttgagc    15180
tccacccggc tccagcagac gtcgtggtcc ctgaagaagc ccgagggcac gcagctcttg    15240
actggtggct tcggtggact cggccttgctg tgtgcgcaga ccttggtgca gttgggcagc   15300
aagagcatct tgttggtttc caggaaggga aagatcgccg atggcgacga cgtcatcgca    15360
gaccacatga agaagttgca ggagaccgac gccgagatcc acgcgtggag ctgcgacgtc    15420
tccagccgca ccaacgtcaa gaagttggtc gaccgcgtgc agcaggagct gcccgagaac    15480
cccctcagtg gagtcgtgca tgccgctggc atcttggact acgccgaaat tccctcccag    15540
acctcagaga ggctctcctc tgtctacaag gccaaggtcg caggcgcttg gaaccttcat    15600
tcggagtccc agaacacaga gctggagaac ttcatcgttt tctcctccgt atccgccctc    15660
attggactca aagggggtgc cagctactcg tcttccaacg cctacctgga tggtttggtc    15720
ctgtggcgca gagctcgtgg ccttgctgca tccagtcttc aatggggacc tgtggcggag    15780
gtcggaatgg ccgccaagga cgatttggcc actgcagatt cccctctcaa gtacctcaaa    15840
ccttcccaag tccaggccgc tttcaagcag tcgatcctgt ctgcctcgca gccgtcgtcg    15900
ttgctgttcg ccaagtgcga ctggcctcgc tttgtgcagt ccttgggcac cgaggtgcct    15960
gtcttgaagg acttcgtggg tgccgaggaa gaagtctcca gcggcgccaa gacagccgtc    16020
tcgtcggcat tccagggcat gtccaagtct gaagtcgagt cccgcgtcgg tgacatggtc    16080
ttgagcgtgg cctgtactgt cctcggcatc gacgaccttt ctccagaggc cccattgatg    16140
gaatctggct tggattctct gtcggccgtg gacttccgca accaagtggc caagactctc    16200
ccaggactga agctccccag cactctgatg ttcgactacc ccaccacgtc tgctatcgcc    16260
aacttcgccg cctctcagct cgccccagcc gagagctcca ggcaagctgt cgttgccgcc    16320
cctgctggat cggctcttga ccactgag cccatcgctc tcagggccgg tgcctaccgc      16380
ttccccatcg agggagagaa ccttcagcag tactgggatg cttttggtcaa caaggttaac   16440 ggtgtcacag agattcccct ggaacgctgg gatgtggatc cctacttcga tgccaacccc    16500
gagacgccag gcaaaatgta cgtgcgacat ggctctttcg tcaagaacgc cgaccagttc    16560
gactgcggct tcttcggcct gtcccctgcc gaatccaagg ttatggatcc ccagcagcgc    16620
ctgctcctgg aggtcatcta ccggggtttc cacgagcacg gcttgcgtca ggacaccctc    16680
```

| | |
|---|---|
| aagggcatgg acggctgcat cgcggtcggt cagtgcaaca acgattgggg acacatggga | 16740 |
| ttctctcccg acgaagctga tgtgattggc ccatacacag gcttggcggt ctccacctcc | 16800 |
| atctcctcca accgagtctc ctacatcttg ggcttgaagg gtcccagctt gactgtggac | 16860 |
| acggcctgct cgtcttcttt gacagctgcc gacatcgcca tctcgaactt gcgccgccga | 16920 |
| aggtgcgaga tcagtgcagc ggcaggcgtg aacttgaacc tcatccctgg accgttcatc | 16980 |
| gcttgctcca aggctcacat gctctccgag gatggcttct gcaagacctt cgatgcgtct | 17040 |
| gccaacggct acgtccgagg cgaaggctgc ggcgtcgcca ttcttcagcg cttggctgat | 17100 |
| ctcggcacag gcaagagcgc cctcgtcgtt gtgcacggct ctgccgtcaa ccaggacggc | 17160 |
| cgcagctcct cgcagacagc gcctcacggt ccttcccagc aggacgtcat catgaccgca | 17220 |
| gtgaacgagg ctggacttct ggcttcgaag gtcaacatca tcgagtgcca tggaaccggc | 17280 |
| actgctttgg gtgaccccat cgaggttgga gcattgaaga acaccctggg cgagggacgc | 17340 |
| gaggagagca accctcttgc tttggctgct gtgaagagca acatcggaca cttggagggc | 17400 |
| gccgctggcg ttgctggact cttgaaggtc gcctgcatgc tgcccaggaa gcaggttcct | 17460 |
| tccaacttgc acttcaagga gctgaacccc cacatcgact tggacgactt cccttcgacg | 17520 |
| atccccacg acgtggtcag catcaagcag gcaggagtgc tgtctgccgg cctctcctcc | 17580 |
| ttcggcttcg gaggcaccaa cgctcacatc gtctccaagc agttcgaagg cgagcccgag | 17640 |
| agccagcccc aggagctcac ctacactcga cagagcttcg cctggcagca gacgcgccac | 17700 |
| acgctgctcg ccaagcgctt caagaccgcc gagaacgtgc aggtcttcag tgcgcccttc | 17760 |
| caaggccgac tgctgcagtt ggtctcccac cacatcatct tcggagagat cgtcgtgccc | 17820 |
| ggcgcaacct acctggaaat ggttttggca gctggagagt tccacctggg tggcaagggc | 17880 |
| accgaatggt acatcaagaa cgtcggcttc caggcgcctt tggtgctgaa gaccagcgac | 17940 |
| accggcaagc tgagccgaga gatcgacctc tacttggaag tcttcccaga cgggcattgg | 18000 |
| gccatgagca gctgggatgt cgcccagcag cgcaaggccg ccaccccactc cgagggagaa | 18060 |
| gtcgaattca ccggacgggc cgttgcggac aagcagacca tcgacatcga ggccgtcaaa | 18120 |
| gcgcgctgcg acgaggacgt cgtgctggag cgcctctacc tccccttctc caagatcgga | 18180 |
| ctgcctctgc agcctcgctt ccgaaccgtc cgccacatct tgcgcggcga cgacgaggtc | 18240 |
| atctgcaagg tcgaggccga gaacgacagc accaaccagg gcttcctctt caaccccggcc | 18300 |
| gtgctcgatg gaaccttcca gggaagcatg gcgctcatgc tcgcgcgccg cgccacggag | 18360 |
| gttgacgact tgaccagctt gaggattcct ctgttgtgcc agaagatcac caactactct | 18420 |
| cagggccact cgacaagcat ctgggtcaac cactctctgc gagagatcac cgacaaggaa | 18480 |
| aattgcgtcg acgccaagat ctgcaaggac gatggaactg tgctcttggc catggacacc | 18540 |
| ctcaaattcc gagaggtccg ccccgagcac atccagaaga tgctccagca ggccaccgag | 18600 |
| gacaacgagc aggacgtgct cgagcaggaa tggaccactt tggaaggcaa gctgggcaca | 18660 |
| gctggtcctc tcagcggcaa ggtcatcttc gtgggcgctt cggcagccat ggagaaagct | 18720 |
| ctccgagtca agtactccag cgcctctttc gtgcgaggag gagaggactt gggagattgc | 18780 |
| gccaaggcca agatcgtctt tgtcgaggcc ctctgcgagg aggctggcga atggaaaatc | 18840 |
| atccaccacg ccatgctgct ggttcaggtc gtgatgaaga tggccgacaa ggactccgac | 18900 |
| accgcccccg ccctctggtg gatcactcga ggcacccagg ccgttggagc atgcagcagc | 18960 |
| tacgccactg caggactttg gggtatggct cgcaccgcca ggctcgagga gaggagcctc | 19020 |
| aagctgcgct gcttggactt ggacaccacc caaggcacag aggaggcggc cgaggctttg | 19080 |

```
tccacatggc tgggcacttt gagcggcaac gccaatgttg atgctgaggc tgaagttgct   19140
ctcaggatcg ccgacggtga gaccaaggcc tacatcgcac gcctcgccag gagcaacact   19200
gaggtgaaga agccgatgca gctgaagatg tcgtctcgcg gctctttggc caacttgcga   19260
cctgtccccc agaccaacag gcgtgcccct ggagccggag agtgcgagct tcgagtgcga   19320
gccatcggtc tcaacttccg agatgtcctc aacgtcatgg gcatgtaccc cggcgaccct   19380
ggaaaccccg gcggcgattg tgccggcact gtcactgcca tcggcgaggg tgtcgagcac   19440
ttgcgccctg gcatggatgt cttcggcatc gcctgggca gcttgcagac gtacgtcacc   19500
accaacgcgc tgctcatggt cgagaagttc aaggactggt ctttcgagca gatggccgcc   19560
tggagcgtca ctttcgcgac caccgaggag gccttccaag agctggctcc tctcgtgaag   19620
ggcgagcgag tcttgatcca cgctgccacc ggcggcgtcg gcctcgtggc ggttcagttc   19680
gcgcagcgcg tcggtgctac catcttcgcc acttgcagtg cctccaaggt cgagcacctg   19740
aagggcatgg gcgtgaagta catcaccacc acccgcgacg gcgccgcatt cgaagcggac   19800
atgcagaagt tcctgaagga ggatggtgct gatggcatcg actgcgtcat gaacagcttg   19860
agccacgacg actacatccc tcgctccttg aagctactga agaagggtgg ccgcttcatg   19920
gaaatcggca agcgtggcat ctggactcat gagcagatgg cccaagagcg acccgacgtc   19980
atgtacgaga agatcgccat ggactgggtc atggagcacc agccggagcg ctacaacagc   20040
ttgatgaagc gattggtcga gcagatcggc aagggctggt gggcaccaat gccaacaacg   20100
cccttcgtcg gcttggagaa cggagtggat gccctcaggt acctgcagcg cgcccagcag   20160
atcggaaagg tcgtgctcac tcagccctct cgcatgtcct gcgagcagga tggatgctac   20220
ctcttgtctg gcggcgtcgg cgccctcgga ttggtcactg ctcagaccat ggccgaggag   20280
ggagcgaaga gcttggtcct catgtctcgt cgcggcgcca ttccttccga cctggaagca   20340
cagtgggcca agctgcagca gttcaaggtg gacttgcact tgaagtcctg cgacgtcgcc   20400
aacatggaca gcgtgcagct catgctcaac ggcctcaaga aggagctccc cacgaagacc   20460
gtcatccgcg gtctcttgca ccttgccgcc gtcctcgacg acgccacgct gccgaagctc   20520
acccgaagcc acttggagaa agcctacgga gcgaaggtct acggagccaa gcacttgcac   20580
accgccctcg cctcagcgaa gacgcctctg gacttcttgg tgctcttctc ctccactgcg   20640
ggccttttgg gctcccccgg ccaggcaaac tactccgctg ccaacgtcac tttgacgct   20700
gctgcgaact gctggcaggg acgcggagag aaggccgtcg ctgttcagtg gggaccttgg   20760
cgtgaagccg gcatggctgc ccagaagggc accgtggagc gactcaaagc tcagggcttg   20820
ggaagcttgg gcaacgtcgt cggcatgtcc gtcctcgccg gaagcttggg cgccaccgca   20880
ggcgtcgtcg ccgcctgccc tgtctattgg ggagtctacc tcaagcagtt cggctcttcc   20940
gtgccgaggt tcttgtcccg attccagaag gaggccggcg ccggcagcag cggccctcgg   21000
cccatcacgg gccagcagga tcgcggcttg tccatcgccc ctgcggacgt caagaacttg   21060
gtgcacacca tcgccgtcga ggtgatgggc agcaccagcg tggacgacac cgaacccctc   21120
atggaggctg gcatggactc cttggccgcc gtggagttcc gaaaccgcct ctcctctcag   21180
ttgcctggca tcaagctccc caacacgctc atcttcgact acccgacggt caacgccatc   21240
ggagactacg ctgccgccca agtcgttccc gtttctggcg gcgcggagcc tgcaggcatc   21300
tccttcagcc gcagcgacgt cgagcagttg gtgctctcca cggccatcga ggtcatggga   21360
agctccaccg tggacgtcag cgagcccctc atggaggcca gcatggactc cctcgccgca   21420
```

```
gtcgagctcc gaaaccgact ttcctcgcag ttgcctggtg tcaagctgcc gaacacgctc    21480
atcttcgacc acccaactgt ctccgccatc accgacttcg ctgcctctca gatcgcccct    21540
tcggcaggct ctcgaggcgc ctctgccgcc ctcggcggag cgacgcagga gaagaagctt    21600
ctggacgtcc gcggcatgtc ttccatcttc cccggaagcc gtgacgcagc ctactggaag    21660
gactttgtgg acaagaagga cagtgtcatc gagatccctt acactcgctg ggacgtggat    21720
gcgtacttcg acaaggacca ggacgcacct ggcaagatgt acacacgaca tggaggcttc    21780
attgacggcg ccgagatgtt cgacgcaggc atgttctcgc tctctgcggc cgaggctgcc    21840
atgatggacc ctcagcagag gttgatcttg gaggtcacca acaccgcttt caacttggcc    21900
ggtcgggaca aggcaagctt gatgggcgcc gacgtcggcg ttttcatcgg tcagtgccag    21960
tacgactggt tcgtgatgaa gagcgctgga gaccacttca acacctacac aggcaccggc    22020
atctctgcct ccatctcctc caaccgaact tcgtacatct tcggcttcaa gggccccagc    22080
ctcacgtgcg acacgccctg ctcttcgtcc ttggtggcga tggatgccgg ctactcctcc    22140
atccagaggg gcgtgtccga gatggccttg atcggaggaa ccaacttgat gttgcagcct    22200
tctccttaca tctccttcag caaggcccgc atgctcagcg aagacggacg atgcttcacc    22260
ttcaacgcca ccgccaacgg ctacgcccga ggagaaggcg tgggaggcat cgtcgtcggc    22320
gtcgcgggcg acgcctcggc cgatgtttct gccatgctgc gagccaccgc cgcgaaccag    22380 gacgccgca gcgcatccct cacagcgccc aacggaccttt ctcagcaagc cgtcatcgct    22440
cgggccctca tggagggatc tatcgctgcc aaggatgtca acgtcgtcga gtgtcacgga    22500
acaggcactg ccttgggtga ccccatcgag gtggatgccc tcaagaacac cctcaacgtc    22560
gacaggagcc agacgctcat gctcacctcg gccaagacca acatcgccca cttggagggt    22620
tctgccggca tcgccggctt cgtgaaggcc gcctacatga tgcgctatgg ccagtgcccc    22680
agcaacttgc acttcaagga actcaaccct cacatcgact tggaggactt cgactgcgag    22740
atcgccaccg aattgaagcc tttggcaggc aagccagtgg ccggcctctc ctccttcggc    22800
ttcggcggca ccaacacgca cgtcgtcctc agctcctccg agacactcgg cacccaggcc    22860
gcggaagagg ccccgaagca gatccacctt c actcgccagt ccttcccctg gaaggatcgc    22920
atctacaggt tgctgccaaa gagactccaa gaaggtcggg acacccactt cgaggtggcc    22980
atcaagaccg atgtcttcaa catctgcgcc gagcacgtcg tcttcaacga gatcgtcgtg    23040
cctggtgtcg tctacactga gatggccatc gaggccactc gcgtcatcat cggcaaggag    23100
gctaccctga aggacttgac catgacttgg cctctggtcg tgcccaagaa cgctgacgga    23160
cccaacgcca ccacggtctg gctgcgcttc gcgcagatgg gctccgagaa gttcgaggtt    23220
cgcagccgcc gcggcgacag cgacgagatg atcacacatt gcgaaggccg catcggccga    23280
agtttgtcgg agcctggtgt catggacatc gccggcctgc agtctcgttg cgaccgcaac    23340
gtcgacccca aggacgtcta cgcagccatc cacaagggag gtctgtactt gggaccaaag    23400
ttccaggtct gccgccacat gatcaggaac gacgaccacg tgctctgcaa gctcgtccac    23460
tccgacgagt gcggaccgaa ccagggctac ttcatgcacc ctggcatgtt ggatggaacc    23520
atccacactc tcggatgcac catggtcggc tgggacgccc cgctcaaggt gttcgccggc    23580
atcggcaagc tcgtcatcaa ggaccacaca gacttcagca ggaacgagtc ctactggtgc    23640
cacctgcacc tcaagacctt ctccgagcag gaacagatct tcacgtccac cgtcgccaac    23700
gaggagggca acatcctctt cgtcggcgag gacgtctcct tcagaaaggt cacgcccgag    23760
cagatccgaa aagccatgga gagccaggcc gccgaggacg accagaagct ctacgaggtc    23820
```

```
gagtggacat ctctgtccac agcggccagc tccgaggagg acgaggacgc caagtggttg    23880
gtcatcgcag agaccgacag tgtcctggca gatttgaaga aggagttcgg agaggccacc    23940
acctacacca agttggcggg cgcagacctc ggcgagatgg agaactacag caaggtcgtc    24000
agcgccatcg gcctcgagac ctccgtgaat tgcttggacg gcttggacca cgccctgcag    24060
ctgatgaagg cgctgcctaa gtctgccagc accgcacccg agatgtggtt cctgacacac    24120
caggctgtgc aggcagtgaa gggagacatg aaggacgccg ccatccctgt gcacgcaggt    24180
ctctggggtc tgtcgaaggc cttccgcgca gagttccccg aactcaaggt ggcttgcttc    24240
gacctggagg gcggaaagat cacttcgctc aaggagaagt tccagcaggc cttggatcag    24300
gccgccgcct ccttcgaacc cgagctcgcg ctccgcgctg gctcgctcta cgcacctcgc    24360
ttggtggact ccacgaccaa tttggaagcg aaagccctgg acatcttcga cgccgacgcc    24420
tcccacgtca tctccggcgg caccggcgcc ttgggcttgc tcaccgcgaa gtggatggcc    24480
gagaagggcg ccaagaactt cgtcctcgcc tcccgaagcg gcaaggtgca ggaggacgcc    24540
caggccatgt tcgacgaggt ctcctctgtc gccaccgtca agaagctcaa catgtccagc    24600
ttggacgacg tcaagcgcct cttcacggag gtcgcgaagt cgatgcctgc catcggtggc    24660
atcacccacg ccgctggtat cttggacgat cacctcatcg ccgacttgca gaggtcgcac    24720
ttggaggcag tcttgggcgc caaggtggac ggcacattga acttgcacga gggctcgaag    24780
gacatgaagt tgaagtactt cagcatgttc tcctctttgg cttccttgat tggtactgcc    24840
ggccaggcca actactgcgc tgccaacggc ttcatggaca gcttcgcagc ataccgaatc    24900
gactctggaa agcccgccgt cgccattcag tggggacctt gggctgacat tggtatggct    24960
gctcgcgctg gcacttccga gagcgtggtc ttgaggatcg acatcgagga gggtctccgt    25020
gctatggagg ttatcttgag caactctggc gacttgatga ccggcgccat tggtgtggcc    25080
cgaatcaagt ggaagtcttt cttggcccag atgcctgccc tgccgccatt cctggacaac    25140
ttcaagcagt tcaagaagga cgctggcaag aagtcggctg tcgctttggg cgccgcacct    25200
tccaaggacg tcgtccgcgg cggcatcgaa aacatcctga aggaggtctt gggagacgac    25260
actttggacg acttctcctc ccctctcatg gatctgggtc tcgactccct ggctgccgtc    25320
gagttcagaa acagagttca gtccgccttc gatggagtcc gactggcctc gaccgtcatg    25380
ttcgactacc ccacggttgc cgacctcacc gacttcatcc tgtcccagtt cgcccccgag    25440
gaggacgagg tcgccggtgg aggcttggga gatcccgccg cgagccttcg ggactcgatg    25500
gccgttatcg gcgtctcggg ccgctaccca ggcatgtctt tcagcaacga cttggaggag    25560
tattggacag ccctctgcag tggaaacgac cccatccaag agatccccat cgaacgcttc    25620
gacgtggacg agatctacga cgaagatcgc tcggccccag ggaaagtcta cgtccgcaac    25680
ggcggcttca tccagggcgt ccaggagttc gacaacggct tcttcggcat cgccgacacc    25740
gaggcgaagg ccatggacgc gcatcagagg ctgcagttgg aggtcgccta cgacagtttc    25800
cacctggctg gcttcaacaa ggagtccctg agtggcatgg aggttggcgt ctacgtcggc    25860
tgctgcactt tgacaggtat cgatgtggag tctgacgaca tcggacctttt caccaacatc    25920 ggtgccggca tcagtggcct ctccggccgc atctcgcacg ccttgggtct gcgcggtcca    25980
tgcttcgcca tcgacaccgc ctgctcctcc acgctcgtgg ccttggactg cgcggcgcag    26040
gccagcagat gggacgcaca ggaaatggct tgcgtggcag gaacgaacct gcagttcgca    26100
acggacatgt ggatcggttt ctgtaagatg actggtctgg ctgccgatgg ccgctgtaag    26160
```

| | |
|---|---|
| actttcgacg tctccgccga cggcttcgcg cgatccgagg gctcaggctc catgatcctc | 26220 |
| cgcatgcgcg cccacgccga ggcgaaggga gaggcctctg tgatgatggt ccgaggcacg | 26280 |
| tgcgtgaacc aggacggccg cagcgccacc atcacggccc cgagcggtcc tgcacagcag | 26340 |
| cgagccttgg ccgcctcctt gagggacggc gacttgaagg ccctggaagt ctctttgatc | 26400 |
| gaatgccacg gaaccggtac ctccttgggc gacccatcg aggtcggagc tcaagagaag | 26460 |
| atctacggca aggagcgcat ggagcaggac acgatcgtct tggcggcggt gaagtcttgc | 26520 |
| atcggccact tggagggcgc cgccggcgtc gctggcctcg ccaagctcgt gaagatgata | 26580 |
| gagcacaaga aggtgcctcc gaacttgcac ttgaagagca tgaacccaa catcgacatc | 26640 |
| tcgaacttcc ctgtcaacat cccgaccagc ggcgccatcg actggagcaa ccctggccca | 26700 |
| gtcaaggctg gtatcagttc tttcggcttc agcggaacga actcgcacgt caacaccgag | 26760 |
| gagccctcca acgccgaggg cgtcgagcct cccaaggtcc agcctctcgt ctggcagcgc | 26820 |
| cgggacctct cctaccgcga ctggacgaag ggtctcttca ccagcatcga gtggaagcct | 26880 |
| gctgccatca aggccaccgg caagatcgat gctgctgcca ccctcatcat ggcggcggc | 26940 |
| gacattgcca aggccctggc cgagatcatc cctggctgca tcgtcgtcgc gccgggcaag | 27000 |
| gcggccaaga cctcgggcga cgtctacagc atggacttca ccaaggccga ccaggtgtcc | 27060 |
| gaggttctgg acaacaagga gtggagcacc gtcgtcttcg ccgaatcttt ggtcgccgac | 27120 |
| gaacccaccc tggagggcca ggccgtcagc ggtctcctcc tcactctcca agccatgtcc | 27180 |
| cagtggaagc gctccgccac gctcgtggca ttgacggcag gtgctcagac tgcggaagct | 27240 |
| ggcggaaaga tgggtgtcgg agttgtggga gccgcagtgt ggggcttcat gcgctccgtg | 27300 |
| cgcctggagg ccgcgaacgt ggagcctcgc gtcatcgact tcagcgccga cgcgaccagc | 27360 |
| gatgcctcgg ctttggctac ggtcatcagc gaggagctcg cggccagcga cgctgagatt | 27420 |
| gcgtacgtca acggcaaccg ctccaccct cgcttggtcg ccaccaacgt caagaacggc | 27480 |
| ggcaagcccg agggcatcga aggaacctac ctcatcaccg gcggctttgg cggcctcggc | 27540 |
| ctcgtcatcg cacagcagtt ggtggacatg ggagccacct ctgtggcctt ggtctcccga | 27600 |
| agtggcaaga cgcccgccgg cgacgagaag ttggccgaga tgctggagca ggtccagtcc | 27660 |
| tcttccgcca ccgtccacgc ctgggcctgc gacgtctccg actcgaagag agttgcagac | 27720 |
| ttggtcaaga agtcgaagaa ggagctcagt gcggaccatc ccctcagcac tgtggtgcac | 27780 |
| gccgctggca tcatcgacca ctgcgcactg gccgacctca ccgtcgacag cattgccaac | 27840 |
| gtcttcaagc ccaaggtcgg cggcgcctgg cacctgcaca cgccaccaa ggacgacggc | 27900 |
| ctcaaagact tcgtgctctt ctcctctgtc agcgccctca tcggcctcag ccgaggagtc | 27960 |
| acgtactcca cctcgaacgc cgccctcgat ggtctcgcgc tctggcgacg ggccgagagc | 28020 |
| ttggctgcca caagcatcca gtggggaccc gtgtccgagg tcggcatgtc gacgaaggcg | 28080 |
| gaccacgcgg cctccgcaga cttcgccctc aagatggtca cccccaagca ggtccaggcc | 28140 |
| gccttccagc gcctcttgtc cgcgcctccg aaagccacat ccgtgctctt cgcccgcgcc | 28200 |
| gactggggca agtacctcga acagatgggc gtggacgtcc ctgtgcttgc ggactacgcc | 28260 |
| tccacagggg gcgcggctgc gggcggcgcc actgccagca gcgctttcag cggcatgagc | 28320 |
| atcgacgaga tcgagagcaa agtcacggag atggttgtgg actgcgtccg aaccgtcctc | 28380 |
| ggcgacgatt ccgtcgaagc cgagtcccct ctcatggagt ccggcctcga ctcgctgtcg | 28440 |
| gccgtggact tcaggaacca ggtctcgaag cagctgccgg gcctcaagtt gccgaacacc | 28500 |
| ttgatgttcg actaccccac tgcaggagcc atcgccggct acgctgcctc tcagctggca | 28560 |

```
ccggcaacaa gctcgggagg agcagctcgc gccaccactc agatcgtctc tgcggccgaa    28620
gctcgcggcc ctgtctccat cttgggcatg gcctgccagt tccctggaga tgctgactcc    28680
ctggacaact tctggaacgt ggtcgtcaac aaggtcgact gcgttggcaa catcccgccc    28740
gagcgatggg atgccgacga gtacttccag gagggcggcg gcgtcggcaa gatgtacgtc    28800
aagcaggccg ccttcgtccg cgacgtcgag tccttcgacg ccagcctctt cgccatctct    28860
tctgccgagg cctacaccat ggaccccag cagaggatgc tcttggagac cgtgcacact     28920
gcttggcagt tgggcactgg cggaaagaag gtctctttgg acgtcggaag cttcgtcgga    28980
gagtgcaaca cgattgggg ccatttcaag aatttggagg tcgaaaagat gaacccttc      29040 agcggaaccg gtggatccat gagcatctct gccaatcgtc tggcctacgt ctttggcttc    29100
aagggcccga gcgtcacgtc cgacaccgca tgctcctcgt ccttggtggc ggtggatcag    29160
gccgtttcga acctctggcg tggacgatgc tccgcctccg tcgcggccgg cgtcaacttg    29220
aacctcatcc caggacccTT cgtggcctgc tgccaggccc gcatgctcgc agaagatggc    29280
cgatgtaaga cgttcgacgc cgcggccgac ggctactctc gaggagaagg ttgcggcgct    29340
atcgcgatcc gcgccagag ctccactgag aacgccgcga gcttcgtcgc cgttgtggga    29400
accggtgtga accaggatgg ccgcagctcc agtctgactg cgcccaacgg cccctcacag    29460
caggaggtca tcaacatggc ttggcaggaa gccggcattg cacccagcgc cgccgacttc    29520
atcgagaccc atggaacggg cactggcttg ggcgatccta tcgaaatcgg agccctcaac    29580
aacaccatgg cagagggacg aaccagcgag gtcgtcatcg gagccgtcaa gaccaacatc    29640
agccacttgg agggcgccgc cggcatcgct ggcttgctca agggcgccat ggtgctcgag    29700
aactgcaagg tgcctccgaa cctgcacttg aagaagctca accccacct ggacgtcgag     29760 gacttcgacg tctccttccc caccgagttg gtcgagaagt ccagagagca gctcaagagc    29820
tctggtctct cctccttcgg cttcggcggt acgaacacgc actgcgtcac cacggccccc    29880
acagagggca aggtcgatca gcagcaggag gctgttgtct tcaacaagca gcgtttcgcc    29940
tggtctcagg tcaagcaccc tctctcggtc gtcggccgca agggtgccga ccccaacctt    30000
actgtcttca ctgccccgat ccgaggaaag gtggttcagc tcctatctca ccacatcatc    30060
tacggcgaga ttgtcgtgcc gggcgccacc tatttggaaa tggtcatcgc caccactgct    30120
ttcaggctcg gcaaggacgg caccaagttc tccgtcgagg tgtcggctt ccagaacccc     30180 ctcgtgttga ggactgccac ccccaccgag ctggagcgac cgattgaact gaccctgcac    30240
atgtacgaca acggcaaatg gtccatgaac agctccgaag ccggcgaggt cctcgccacg    30300
cacgcggagg gctccgtgag cttcgcgaac ccgacgcctg agaagaaaat gctcgagctg    30360
gaggagatca agagccgctg ccctgaggtt gtgcaagacg agcgcatgta cgttcccttc    30420
gccaacatcg gtctgcccct gcagccccgc ttcaggactg tccgaaccat cgaccgcagc    30480
tccgacgaga tcatcgcttg ggtcgcagca gaagaggacg gcaccaatgc cggcttcatc    30540
ttcggccccg ccgtcatcga tggatccttc caggcctcct gcgccttcca gaacctggag    30600
gccctgccca gcttgcgaat tccgctctcc atcgacaagg tcacgatcta cggccagggc    30660
tacagccaga aggtctgggt ccaccacaag ctgctcgaga acaccgagaa gaccatggcc    30720
acgaacgtgc agttggcgcg cgacgacaag acgatcatct tgaccatgga ccgcatgcgc    30780
ctgcgcgaag tcaggcccga gcacatcgcc aagatgctgg cccaggccgc aggcgacgag    30840
gacgaggacc tgttggaggt cgagtgggct gccatggaca ccaagaacgc taaggccgtc    30900
```

```
gaattgggaa agaccttggt catcggtgcc aacgatgctc tcaaggaagc cctcagcaag    30960
gagatcaaga cagccacctt cgcagactct gcagaggccc tcgccgaggc cacgggcgtc    31020
aaggaggtgc tgttcgtcgg ggcgctcgtg gacagcgcac cagagatgga ggtcttgcac    31080
accgcgctct ccctcgccca ggaggccatc aagttcgccg ccagcaagaa gaaggagagc    31140
cctcccaccg tctggtgggc caccaagggc acccaggcgg ctggcttggg cgacagctac    31200
taccatgcgg gcttgtgggg tctgccagg accttccgca tggaagagcg ttcggtgaac    31260
ttgcgatgct tggacttgga catcagcatg ggctcggccg aggccgccgc ggccgccctc    31320
aaggaatggc tgcctctgct ctccgccgcc aacttggtcg gcgagaccga ggtgactttg    31380
aggcccaagg aagacagcaa agagatggcg ccgctggtgt ctcgattggc gaccagcacc    31440
gccaagtccc agaaggccgg catgctgatg atgtcctctc gaggaagctt gtccaacttg    31500 cgaccgtgc tccaggagag tcgacccaag tgcggaccca acgacgccga acttcgaatt    31560
cgagccgtcg gtctcaattt ccgagatgtg ctcaacgtca tgggtctcta ccctggcgac    31620
cctggaccac ctggcgccga cacctccggc accgtcctca ccgtgggagg cgaagtcagt    31680
cacatccgtc ctggcgacga tgtgttcggt gagtctcctg gttgcttgag gacctacaac    31740
gccgccccag ccccgctgct cacgcagaag cctcctacct ggagcttcga ggatgcctca    31800
accatgcccg tgatcttcgt caccgtcgag gagtctctcg gagacctggc caagctgaag    31860
aagggcgaaa tcgtcctcat ccatgctgct gcaggcggcg tcggcttggt ggccatccag    31920
tacgctcagt tcgtcggtgc gactatcatc ggaactgccg gatccgagga gaagcacgag    31980
ttcctgcgca acttgggcgt gaagcacatc accagcaccc gaaatggcca gaagttcgag    32040
gacgacatga agaccattct caaggagttg aaggtggatg gcatcgacgt tgtcttgaac    32100
agtttgagcc acgacgacta catcccgaga tccctggcat tgctcaagaa gggcggacgc    32160
ttcatggaga tcggcaagcg cggcatctgg agccacgaac agatgttcga ggcccgacct    32220
gacgtcatgt acgagaagat cgccgccgac accatgatgg acttggaatc ctggaagtac    32280
aatgcctaca tgaaacgcct gctcacccga gtggaagaag gtggtctcgt gcccatcaac    32340
aagcacgtct tcacggacat cgagaaggga gtcaccgcca tgcagttctt gcagcgagct    32400
cagaacatcg gcaaggtcgt catcgcactg cccagccgaa tggattgcaa gccagactcc    32460
gagtacctgc tctctggtgg tatgggagca ttgggaatgg tcaccgccca gtacttggtc    32520
gaggaaggtg caaagcacat cacgctgctt tctcgaagcg gcaagccatc caacgacgtg    32580
ctcgacctct gggagtggct gcagaagagc agcatcaacg tctctgcgaa ggcttgcgac    32640
atcgcccaga tggacagcgt caccgaactt gcggttacct tgtccaagga cggccagaag    32700
cgcagcccca agactcatgt cggaggcgtc atccacttgg ccgccgtcct cgacgacgcc    32760
actctcccca agctcactcg aggccacctc gagcgctcgt tcgcagccaa ggtttgggc    32820 gccaggcacc tccattgcgc ctacgccaag gagttggact tcatgctcct cttctcctcc    32880
acctcggcgc tcttgggatc gcccggccag gccaactact ccgcttccaa ctcctctttg    32940
gacgcccacg cccgctactg gcgccagagt ggcatgcagg ccacgagcgt gcagtggggc    33000
ccctggaggg aggtcggcat ggctgcgcag aagggtaccg tcgagcgctt gcgccagagc    33060
ggtgtcggct ctctcaccaa cgctgcaggc atggccgcct tggccggtgc cttgaccgcc    33120
agctgcccca ccatcgtggc tcagccgatg aggtgggcca actacctgaa gcagtacccc    33180
aagatccccc ccttcctgtc ccgcttctcg gccgagctca agacgaagaa gccggctgct    33240
cccgcccgac cggcccaggg catgatgatg atgcagcagg ccgcccctc ggctcctgcc    33300
```

```
atcagcgtca ccgacctcaa gagcatgctc cagcagatcg ccagcgatgt cgccggcggc   33360
ggtgttgtcg acgaggacag ccctctcatg gaatctggca tggactcgct ctccgccgtc   33420
gagttccgca accgcttcac ggccaaggtc cctcagatca atttgccgaa cacgctcatc   33480
ttcgactacc ccacgatctc tgccatcgcg gacttcgctg tcggccagat gggcccgcc    33540 accgcggccc ctgccggcta cgccatgcag gctgcccctg cagcacccgg catgactgct   33600
gacgcgatca tggagttgct gaaccgcatc gccaccgaca ccaccggagg agctgtcgag   33660
gtcgacaagc cattgatgga gtctggcatg gactccctgt ctgctgtcga gttcaggaac   33720
cgcctctcct ctgagctccc aagcttgcag ttgcccaaca ccctcatctt cgactacccc   33780
acgatctctg ctgtcgcaga ctacgcggtc gagcaattgg gcgccagcac cgtggctgtt   33840
cctactggcg gcgcaatggt gccaatggct gctggagcct cttctggggc cttcgacgag   33900
cctttggcca tctcaggcac cgcctgccac ttccctgccg gctcgacggg tccgaacgtc   33960
ttctacaagc agcttgcgca gggcgccgac ggcatcgtcg aagtgccttt cacccgctgg   34020
gagctcgagg aggtttacga ccccaacccc gacgctcctg gaaagatgta cccccgacac   34080
ggagccttca ttcagggtgc cgagcagttc gatgcttcct tcttcggaat ctccgcacct   34140
gaagctcgcg ccatggatcc ccagcagagg ctgttgttgg aggtggccta cgactcgttg   34200
gtcgactctg gcttcaccaa gagctctctg ttgagtagca acatcgccgt cttggtcgga   34260
caggcgaaca acgactggat ccagatgcag agttgggacc tgaagaaggt gaacccctac   34320
actgccactg gcatgtccgc ttccatctct gccgcccgca tctcctactc cttgggcatg   34380
aagggcgcaa gttacatcat cgatactgcc tgctcctctg ccttggtggc cttggatgct   34440
gccgccgtga ccttgcgccg aaccaggtgc accgctgccg tcaacgcggc tgccaacgtc   34500
atggtgagtc cttccaccta catcagcttc agcaagccgc gcatgctctc cgagtcaggc   34560
cgctgcctca ccttcgacca gagcgcgaac ggctacgtcc gaggagaagg aggcggctct   34620
gccgctctca ggctcgtggc cgatgccggc gacttcgctc gctccatcgt tcgcggcgtc   34680
tcggtgaacc aggacggacg aagctccact ttgaccgccc ccaacggacc cagccagcag   34740
atggtcatga tggccgccct caacgaggcg aagctctcac ctcagagtgt cggccacctg   34800
gagtgccatg gcactggcac gccgctcgga gaccccatcg agttgggcgc cttgcaggcc   34860
gtcaacgcag gccgctcgga gaacgtccct ctggtcctcg ctgcggtcaa gaccaacgtt   34920
ggtcacttgg agggtgccgc agcatccacc ggattgatca agatcgcctc tgtgctccag   34980
catggggcag ccaagccagg catccacctc aagaccctga accccaacat cgccgcgctc   35040
tccgcgctgc ctgccgtctt cgccagcgag tccctgcccc tcccctcggg tggtgcctac   35100
aggactagcg gcctctcctc cttcggcttc ggaggaacga acgcgcactc cgtgaccagc   35160
gaggccgagg tgcccgccga gccgtgcga accgtgatcc caggaaagga gtacaagagg   35220
aaggccttcc cttggaggga ggtcggcttc agactgctcc gctcctcgcc ttccgacaac   35280
gtcttcgagg tcgtgatgat ctccgacgtc tacgacgtcg tgagccacca cgtcgtcttc   35340
agctcgatcg tcgtgcctgg cgtggtctac gtggagatgg ccttggaggc cactcgcaag   35400
atcttcggcc acggtgcgaa gctcacagac ttcggaatgg tcttccccctt cgtgatcccc   35460 ttccgcacca cgggcgtcga gcctgccgcc acgatgcgct tcgtgctgcg cggcgagtcc   35520
cgcttcgaga tccagagcac ctcggccaca ggggccgtga cggtccacgc cgaaggaggc   35580
atcgacagat cgcccatgaa agatccttcc agggcggagc ctgtggactt ggacatggtc   35640
```

```
cgcaagcgag tcacagaaga gattccggca agcgtcgtct acggggccat cgacggagtc    35700
ggcttgtggc tcggacctat gttccaggtt gccaagcagc tctggcgata tgaggaggga    35760
gattccatcg aagtgctcgg ccgattggag ttggacaaga cgatccccaa cgaaggctac    35820
gttgtgcacc ccgccctctt ggatggaacg atccacacct tgggaaccgc ctccatcggc    35880
aagaacgtga acgacttgaa gatctttgga ggtgtcggtc gcgtcacaat cgtcgaggag    35940
agcaatttct cgaaggccga cgagtactgg atttggatgg acattaagga gaagttggag    36000
gcctctgaga ccttcgacgt tcgcgtgatg aacagctccg gcaaggtcct catgttcatg    36060
gacgacgtcg tcttcaggaa ggtcttgccc gagcagatcc agatggcgat cgccgcccag    36120
agcgcctccg aggacgctca gaagctctac gaagtggatt ggactgctgc cgaggaactg    36180
gaggaagtcg ccgaagagga cgacggacag tggctggtcc tcgctcccga ggaggccgct    36240
gcgaaggaac tgaagaagga gcttggcgac aagcacgact acaagaagct ctcggaggcc    36300
cccaccgaag gcttggagaa atactccaag atcgtcttgg ccgcggagag cgagcgaggc    36360 accccctgtcg atgtcctcga cggtgctctc aagctcttcc agtctttggc ccatgctcag    36420
```

```
ggtgagttct tcggtgtttc ggacgccgaa cagcgagcca tggatcctca ccagtggttg   38100
gcattggaaa tttcctacga aggcttgtac gctgcaggct tgaccaagga gaccatgtct   38160
ggcatggagt gcggcgtcta cgtgggagcc tgtaatttgg gtggaaacga cgtggacttg   38220
gaagcactcg gacccttctc caacatcggt gccgcctact ctggctgctc cggccgtgtc   38280
tcgcacgtcc tctctcttcg tggtccttgc ttcaccgtcg acaccgcttg ctcctccacc   38340
atcgttgccc tggactctgg ttgccaggcc gtccgcttgg gcaagtgcaa gagcgccctc   38400
gcctcgggtg tcaacgtgca gattgccgct tccatctgga tcggcttctc taagatgcga   38460
ggtttggcca tggacggaag gtgtaagact ttcgatgccc gcgcagatgg cttcgcccga   38520
ggagaaggtc tcggcgccgt ctacatccag gccgcagcca attgcactga tgcgaaccct   38580
gcgatcgcca tgatcaccgg ctgctcgacc aaccacgacg gccgcgccgc caccatcact   38640
gcgcccaacg gcaccgccca gcagcgcgtc ctgcgctccg ccttggcgga gcgaggcacc   38700
ttggccgagg acgtcgcctg catcgagtgc acggtactgg gtaccgcctt gggagatcct   38760
atcgaggtcg gcgcccagaa ggctgtctac aacaagggcc gcagcgccgc tcgtccgctc   38820
gtcttggccg caggcaagtc ggcgatgggt cacttggagg gctctgccgg cgtcgccggt   38880
atctgcaagg tcatctgcac cttcaagcac tctgctattc ctccgaactt gatgctcgag   38940
aagctcaacc ccaacatcga cctctctggc ttcgacgtct tgatgcctga ctccttggtc   39000
gactggaagg ctgtgcctcg cgcgggcgtc tcctccttcg gtttctctgg aaccaacggc   39060
cacgccatct tggaggcccc tcccaccccc ggagaccagc tgcccgagag gaagattcag   39120
aagttcaacc gttccgtcaa gccctggcac cagtggctcg agaacgtcct ctacgaagag   39180
gcctggaaca cttgcgagtt ggtgcccgtc accgccttcg atgcttcttg catcgtcgtc   39240
ggcagcggca gcatcgccga aaagatccga aagctggcca aggcctccac ggtcgtccct   39300
gcaggcacct ccgccaagga cgtttctgct gccatggata aggccaatgc tcaggtcgcc   39360
atcttcgcca cttccgcgga cgagccggat ggcgagatcc caggcgcccg attggtcgag   39420
ctcctctcct tcttgcaggg cgcccagagc gcctcggaga cacccaagat ggtcgtcgtt   39480
gtgaccaagg gagcccagga tgccagccga cccaaattcg atgctggcgc cactctctgg   39540
ggtcttgtcc gctccgcgcg catcgagatg ccccgaacca ccatcaaggc catcgacgtc   39600
cccgtcgacg ccgccgccga cgccgcagca aagatcgttg ttgaggagtt ggccgctgca   39660
gaggccgagg tcgaggttgc tcacattgca ggaaagggac gatgcgtgcc cgtcgtcaca   39720
gaggcccctc agacagccaa gagcctccag aggcaggacg ccatgctgga caagaagatc   39780
ctcagcgaag gcttgcagat cgtcactggc ggtctcggag gtctcggact ggtgtctgcc   39840
aggcagttgg ctgagttggg cgccacgaca gtgatgctca cgagccgatc tggcaaggtg   39900
ccagcaggac aaggattgga agagcacctc cgatggttgg aggccatccc caccaccgaa   39960
gtcgtgatca agaagtgcga tgtctcctcc agcagctccg tctctgagct catgaaggag   40020
gcgaccgact ccaagggacc tgtggccggc atcattcacg ctgctggagt cctcgacagg   40080
tgccccttgg ccgagatggc aaaggagaat ttggacaagg tctgcgagcc caaggccagc   40140
ggcgcctggt acctccacag cagctccgag cagagcgact tgaagctctt cgtgctgttc   40200
tcgtccgtct ctgccactgt cggcttggcc ggtggagcct cctactctgc ggccaacgcg   40260
tacctcgatg ccctcgccct ctggcgcaga gagaagcccc tcgcagccct cagcgccaag   40320
tggggacctg tctccgaagt cggcatgacc gcggcctcgg gcagcgactc catgttggaa   40380
```

```
gcgatggctc tcaaggccct ctcgccagcc caggttggct ccgccatgcg tttgttgctc    40440
acgcaacagg gcgccggtgt gaacttgcga gctgagctga tgctcgcccg cgtgaactgg    40500
gcggacttcg tgcgcgaggt cggtgtcgag atccctcaag tgaaggagtt ccagagccaa    40560
gaggccctcg ccgtgacagg caaggagagc aaggccagcg cgatggccgg catgaccgac    40620
gacgaccgcc aggctgccgt gctgaagagc atccgaagcg ccgcgcaagg catgggcttg    40680
gaaatggacg atgagactcc tttgatggag gccggaatcg actccctgtc tgccgtcgag    40740
ttccgcaaca aggtctcctc cgagttccgc gaggttcgtc tcccaagcac cttgatgttc    40800
gactacccca cgctcaccgc gctcgcgcag tacgtctcag gccagttgag cgtcgccgcc    40860
ggcggccagg ctgcctccag cgccgctgct gctgtggccc ttccttccaa gcctgccgct    40920
gctggaggaa acatcgctgt cttgggtggc gcttgccact tgcccggaga cagctggtca    40980
ttggaagcct tcagccacac cttggtcaag ggagtggatt gcatcgtgga gattccttac    41040
gacaggtggg atgccgacga gtactacgac cctgaggcca gcaccggatt gaagatgtac    41100
gtcaagcacg ccggtttcat cgaaggcgcc gagctcttcg ccgcctcgag cttcaacatc    41160
gtcaaggccg aggccgagac catggatccc cagcagaggc acctcttgga gacctccttc    41220
gaggccttcg tcgtcggtgg cttcaccaag cagtccttga tgggaagctt cacaggagtc    41280
ttcgtcggtc aggacaagtg cgattggaac cgcatgatca gcggaagcat gggaggtcct    41340
tacgctgcca ctggcggctc ttcgtctatc tcggcgaacc gcatctccta ctccttgggc    41400
ttgaagggcc cgagtgcgac aatggacaca gcttgctctt cctcgctcgt cgctgcggac    41460
accgccgctc ccacgctgcg aaggaggcgt tgcgacatcg cgaccgtctg cggcgtcaac    41520
atgctcttgc tgcctcagac cttcatcgcc tgctgccagg cgcacatgct cagcgccttc    41580
ggtcgctgca agaccttcga cgaaagtgcc tctggctacg ttcgtggaga gggctgcggc    41640
gcgcagacct tgatgcaggt ctcggacaag cccgcctacg cggagatgtc cggcagcgcc    41700
ctgaaccagg atggacgaag ttccaacttg acctcaccca acggaccttc ccagcaggcc    41760
gtcgtgttgg ctgccttggc cgaagctggc gttgctccct cggctttgga ctgcctcgag    41820
acgcacggca cgggcacgga gctcggagat ccgatcgagg tcggcgccct gcaggccgcc    41880
ttgggcggcg ccgcgaggca gaaggccctc ttgcttggcg ctgtcaagac caacatcggt    41940
cacttggagg gcggtgctgg catcgctggc ctcacgaagt tggtgtgcat gctcaacatg    42000
aggacgatgg tgcccaactt gcacttgcgc gaaatcaacg accacatcga cgaggacctg    42060
cagagcttcg ccgttcgact gcctaccgaa gcgaccaagc tcgcatccaa gggcatcatc    42120
acttccagcg tctcctcgtt cggcttcggc ggaaccaacg gacacgtcgt cttgcagacc    42180
gcttccaagg aaatgccaaa gacagcgaag cctaacaaga acgttgtctt cctcttcaca    42240
ggtcaaggat cgcagtacat cggtatgggc cgtggcttgt acgactcgca gcctgtcttc    42300
aagcaggccc tggacaagtg cgccgaggtt ctggacaagt gctgccaac gcctttgatg    42360 gaggtgctct accctgccga cgagtccaaa ttgatcgacc agacgcagtt ctcgcagccg    42420
gccattttct ccatcgagta tgccctcgct acgctctggc gctccatggg agtcgagccc    42480
gttgccgtct gggtcacag cgtcggcgag tattgcgccg ccgtcgttgc tggagtgctg    42540
cctctcgagg acgccctcaa gctcatcgcc ctccgcggcc agtgcatcgc cgagaagtgc    42600
gaggctggaa tcggctccat ggccgctgtc ttcgcaagcg aggcggacgt gcagaaggcg    42660
atcgcgaagt tcggaagcaa ggacgtctct gtggctgctg tcaacggacc caagatgacg    42720
gtcgtcagtg gccgcagcgc cgacgttgac aaggtggttg cccagactgg agctaccagc    42780
```

```
cgaccattga cggtctctca cggcttccac tcgccgctca tgaagcctgc tctggagccc   42840
ttccgagcac aggccgagac cgtgactttc tccagaccat ccgtcaagtt cttctctacc   42900
ctcttgggcc gagaagtcac agacgagctt gctcagcctc agtactgggt cgaccacatc   42960
gagaacgcgg tcaagttcat gcctgccacc atggccctgg acgaggctct cagccccgat   43020
ctctacttgg aaatcggtgc gtcccccgtc ttggtgaata tggcgaagcg cttcttgtcg   43080
aggagcgtcg agtggatgcc ttctttggac aacaaggtca gtgaccagga cgccttcaag   43140
aaggctcagc aggccctggg agcctccgcc ggccgcccta aggccgacct caagcgaact   43200
gccttcccct ggagagaggc aggccacccc ttgctgcgct ccaagaagac cctccctgat   43260
ggcaccgtcg tcttcggcgt ccacttcgga ggacatgtgc tcgagcttct ctcccaccac   43320
atcgtgcacg gagaggtcgt cgtgcctggc gcttgctatc tcgagatgat cgttgctggc   43380
tgcaccacct tcttcggacg cgaccagcct tggtgcgtcg aacagttggg cttcgccaag   43440
cctttggtct tgcgcttgag ccctgaagga aagttggacg agccgaccga attgcgattg   43500
gtcatccgtc cggatatgcg tatcgaggtc gagtccgaga tcggcgacga ccccgacgac   43560
agcatcgtcg cgacgcacgt cgaggccatc ttggtgaagc agaccggcac ttgggcaagc   43620
aaccgacccg agaaggatgc gttcagcttg gatcagttga agaaacagtg tgccgagcct   43680
gtcgacatcg acctcatgta ctccttcgga aagaacagcg gcttgccact gcagcgccga   43740
ttccgcaccg tgcgacacgt gcagaagggt gacaaggaga gtatcggccg cttggagatg   43800
gagagggacg gcactcaagt cggattctgg ctgggtcctt ccttgatcga cggctccttc   43860
caggcctcca tggctctcgc agatgcagat gttggaatcg gcactctgaa gattcctctc   43920
tccatccgac gcttgcagcc aacaggccga gcctacaaca tctctgtctg gtcttacttc   43980
cagctcattg acttcaccga caggagcacc gtcttccgct cgtggttgct caacgacgct   44040
ggcgaggctt tgttgtactt cgaccacgtc cacttgcagg aggtccgaga cgagcacatc   44100
cagaaggtct tgcagtcttc aggccgtcag ggcaccgagc agtccaactt gtacgatgtc   44160
gaatggcggc agttggagct tgccggaaag cctgcctccc tgccgaacga agagttcctc   44220
gtcgttggtg gcaaggccgc cctcgagaag ctcaacttgg gcaagagtcc tcagttctct   44280
tgcatgcaga tcggtaagga catcgacatc aatgatgacg acagtgtgaa caaggctctc   44340
ttgggcaagg cctgggccgg catcgtcttg gccgaaggtt tggccgagaa ggtcggcgac   44400
gttgatgttg tcaccgaggc catgatcata gttaaggtcc tgaccaaggc aggctccaag   44460
gcccctcctc tctggctcct caccagtggc tctcagcctc tcgcctccgc agacgccgag   44520
cagcgcaagg ccggttgtgc aacacactcc ggtctctggg gtttcgcccg cgctgtgcgc   44580
atggagtacc ccggaatggt gcgagtcagt tgcttggatt tcgacccac aagttcgaag   44640 agcaccggag acgagttgtc cgctcgcctg tctagcttga ccgctgacac tgaggacgag   44700
gtcgccctcc gaagcgactc cgccgccagc gctcgcttag tgcgttccga gctccagttc   44760
gtgggtccca gccgcttgaa catggccgcg cgcggcgcct tgagcaactt gaggctcgtg   44820
tcgcagggca agcgccagac ccccatccct ggcttcgtcc agcagaggat ccgagccatc   44880
ggcttgaact tccgtgacgt gctcaatgtg atgggactct accctggcga ccctggagcc   44940
ccaggcgccg actcctccgg aaccatcgtc gagttgggtg accgcgtcga cccctcaag   45000 atcgccgatg acgtcttcgg agagtctcca ggctgcctca gcacctacaa caatggcccc   45060
gcggccctct tggccaggaa gccccctctc tggtcgtacg aggaggcctg cgcaatgccg   45120
```

```
gtcatcttcg tcaccgtcga ggaggcgctc ggagacctgg cgaagctgaa gaagggtgag    45180
acggtcttga tccacgctgc cgccggcggt gtcggcctcg tcgccatcca gtacgcccag    45240
tgggtcggtg ccaaggtcta tgccactgct ggatctgagg agaagcacgc cttcctgcgc    45300
aagttgggcg tcgatcgcat caccagcacc cgagacggcg ccaagttcga agcggagatg    45360
gagaagatgt tgaaggagga caagctcgag ggcgtcgacg tcgtcttgaa cagcttgagc    45420
cacgacgact acatcccacg ctccctgaag gtcttgaaga agggtggacg cttcatggag    45480
atcggcaagc gaggcatctg gagccacgag gagatgttca aggccaggcc tgacatcatg    45540
tacgagaaga tcgccgccga taccatgatg gagaaggagt gctggaggta caacgcctac    45600
ctgaaccgac tcttggagcg cgccgagaca ggcggcttga agcccatcaa cgaccaccga    45660
ttcgagggtc ttgagaaggg agtcgccgcc ctgcagttct gcagcgcgc caacaacatc    45720 ggaaaggtcg tcatctccga gcccagccga ctccagtgca accctgcgaa catctccgtc    45780
ctctcaggcg gcatgggcgc cttgggcatc gtcaccgcgc agttcttggt tgaagaaggc    45840
tgcaagaagc tcagcttgct gtcccgaagc ggcacacctt cctcggatgc cttggcgcag    45900
ttcgagtggc tgaaggcagc tgctatcgaa gtcggcgtga gcaagtgcga tgtctcttcc    45960
gagactagcg tcaaggcctt cgccagtggc ttgcagagcc ccatcgactg cctgatgcac    46020
ctcgccggcg ttctcgccga cggcatgctg cctaccttga cgagggagca cttcgagaag    46080
tcgtacgcgc caaaggttca cggtctgtac cacatggtca agcactggaa gatgagcgag    46140
gacaccaagt tcatgctctt ctcttccacc tccgctctct tcggatcgcc gggccaggcc    46200
aactactccg catccaactc tgtcttggac tccttggctc ctatctggag tgcccaggga    46260
cgacagtctt ggacggtgca gtgggtgcct tgggccgaag tcggaatggc cgtgcagaag    46320
aacaccttgt cccgagccaa ggctatgggc gtgggtgcct tgagcactgc cgtcggtatg    46380
tccatcatgg gaagcatcct cggctctgcc tcgcacgtcg tcggtgctgt gcctgtcagg    46440
tgggctaagt acctccgaag tgcctaccag gagactccta tgttcttgac tgacatggag    46500
gccgaggtcc gccgtgccgc cccagccgtt ggtgagggag gtggcaattc cttggccttg    46560
gccaacctgt cggcagagga gcgcttggag gccgtccgcg agagcctcct caccatggct    46620
cgcgaggtcg tcgacaacga cactctctct gctgaagacg cattgttgga gagcggtatg    46680
gactccctgt ctggtgtcga gttccgaaac cgattggtca ccgagttcga aggtgtccgc    46740
atgggcaact ccctcatctt cgaccacccc accgtcaacg agctcgcggc gttcatctcg    46800
gaggagttgg gcaacacctt gccagcggcc gactcgtctg ctgccccagc ggccttgcag    46860
aacggcgcct cccaccctgt ggaggccccc gagtccagcg ccagcttcgt ggagagcttg    46920
aactcacgcg ccagcggcac tccgatctac ttcgtccccg gagccggcat gcaggccgga    46980
ggcttccgtc cgttggccca gatcttgccg gtgcctgcct acggtctttc ttggccgaag    47040
ggcgccgtgc cgcgcgagga gtggcctacc accatcgacg gcctcgcacg agtcttcctc    47100
acagaggtca agaagacgca gcccactgga ccgtaccgct cgctggaca ctccttcgga    47160 gccgcggtcg ccctcgagat ggccaagatc gcacaggccc aaggtctgga ggttactttc    47220
gtggccctct ggaccccag gcacatgggg ggaaagacca ccgtcgacgt cggcgaagcc    47280
ttctccacga ccgacctcgc cgactccttg ggccttttgg cccaaaccgt gccagacggc    47340
tcgaagtacg tgcaggcctt ggaggagatc gtcaagtccg acgaccgcga tgccgctgct    47400
aagaaggtat tgagcccagc cgtgttggct tctttggagc atgttcacga gaccacgaag    47460
tggtacagca ccctgttggc aggagacaac ttgcagcctg acgcaagctt gaaggcccga    47520
```

-continued

```
attgcggtgc tccgagcccc tgagacttgg ttgagcccag gtgacaacga gacgatcgct    47580
gacaagatgg tccgggaatt ccaggccaag acgttccagg gcgatgatga ggtcaccaag    47640
ctcgtggacg agtggtgcgg cgttgccccc ttcttgaaca tgaaggttcc tggcagccat    47700
ttcacgatgt tgcacgaacc tcacgtggtc tcgctcgcca tgcgcttgtg ccgcgcagtc    47760
gacgagtccg agggtgagga gctctgaaga gtcttcctct agaagctcct cgatggttgt    47820
tgttccttcc ttctcgctct ctttttatgt gtgggattgc tattgc                  47866
```

<210> SEQ ID NO 4
<211> LENGTH: 91
<212> TYPE: PRT
<213> ORGANISM: Crypthecodinium cohnii

<400> SEQUENCE: 4

```
Val Val Leu Tyr Val Leu Ser Met Val Gly Met Ile Gly Met Asn Leu
1               5                   10                  15

Val Trp Ala Cys Gly Ala Val Val Leu Asp Leu Pro Gln Lys Val Phe
            20                  25                  30

Leu Met Ile Cys Ala Ser Thr Ala Asn Gln Gly Ser Ile Phe Arg Trp
        35                  40                  45

Cys Arg Asp His Arg Ala His Leu Met Asn Lys Gly Thr Val Ala Asp
    50                  55                  60

Pro Tyr Asp Tyr Asn Arg Gly Ala Thr Phe Ala Tyr Ile Gly Trp Phe
65                  70                  75                  80

Val Gln Gln Lys Thr Arg Arg Ala Ile Glu Ala
                85                  90
```

<210> SEQ ID NO 5
<211> LENGTH: 389
<212> TYPE: PRT
<213> ORGANISM: Crypthecodinium cohnii

<400> SEQUENCE: 5

```
Met Ala Gly Gln Gln Leu Gln Glu Val Ser Pro Ser Met Ala Ser Pro
1               5                   10                  15

Ser Ser Ser Ser Ser Tyr Cys Pro Gln Arg Leu Gln Ala Ser Ile Arg
            20                  25                  30

Ser Gly Arg Leu Arg Trp Ala Val Asn Ser Glu Asp Trp Ala Pro Ile
        35                  40                  45

Gly Ala Glu Lys Gly Pro Glu Phe Gln Phe Leu Leu Ser Leu Ile Gln
    50                  55                  60

Glu Thr Asp Asp Arg Gln Gln Val Thr Lys Tyr Met Arg Phe Gln Asp
65                  70                  75                  80

Gln Lys Arg Ala Leu Ile Ser Arg Leu Leu Val Arg His Ala Ser Ala
                85                  90                  95

Ser Val Leu Gly Leu Ser Ser Phe Arg Asp Val Glu Ile Ala Arg Thr
            100                 105                 110

Lys Gly Lys Lys Pro Phe Leu Arg Lys Pro Arg Pro Val Asp Ile Ala
        115                 120                 125

Ala Ala Ala Ala Thr Ala Ala Pro Asp Cys Ser Gly Glu Gly
    130                 135                 140

Thr Thr Arg Thr Thr Thr Ser Ser Ala Ser Ser Val Ala Ala Leu Ala
145                 150                 155                 160

Asn Phe Asn Phe Ser Val Ser His Glu Gly Asp Trp Val Val Leu Ala
                165                 170                 175
```

```
Ser Glu Pro Ile Cys Val Cys Gly Val Asp Val Ala Ala Pro Gln Glu
            180                 185                 190

Val Arg Pro Gly Gly Cys Ser Pro Ser Glu Ile Phe Arg Asp Leu Glu
        195                 200                 205

Asp Gln Leu Thr Glu Ala Glu Trp Glu Phe Val Arg Lys Gln Gly Ala
    210                 215                 220

Ser Ser Gly Gly Pro Glu Gly Glu Asp Pro Leu Tyr Ser Ala Phe Gln
225                 230                 235                 240

Arg His Trp Cys Leu Lys Glu Ala Tyr Val Lys Ala Arg Gly Asp Gly
                245                 250                 255

Leu Glu Phe Pro Phe Asn Arg Ile Glu Phe Gln Leu Arg Pro Ala Ser
            260                 265                 270

Leu Leu Asp Glu Glu Ala Ala Gly Arg Arg Leu Gly Phe Ala Gly
        275                 280                 285

Arg Val Asp Gly Val Asp Leu Asn Pro Arg Trp Arg Phe Tyr Gln Gln
    290                 295                 300

Arg Leu Pro Gly Asn His Trp Thr Ala Val Ala Arg Gly Pro Thr Thr
305                 310                 315                 320

Glu Val Ile Asp Ala Phe Gly Glu Phe Lys Arg Thr Phe Thr Arg Pro
                325                 330                 335

Thr Asp Gln Leu Pro Pro Ser Gly Val Thr Ala Glu Leu Glu Ala Glu
            340                 345                 350

Glu Pro Pro Phe Glu Ile Leu Pro Val Ala Phe Leu Val Pro Thr Asp
        355                 360                 365

His Ile Glu Gly Tyr Glu Ala Ala Gly Gly Gln Lys Trp Gln Ala Ile
    370                 375                 380

Asp Ala Ala Ala Ala
385

<210> SEQ ID NO 6
<211> LENGTH: 273
<212> TYPE: DNA
<213> ORGANISM: Crypthecodinium cohnii

<400> SEQUENCE: 6
gtggtgctct acgttttgtc catggtcggc atgatcggaa tgaacttggt ctgggcctgc        60
ggtgccgtcg ttttggacct cccccagaaa gtcttcctca tgatctgtgc ctctaccgcg       120
aaccaaggca gcatcttccg atggtgccga gatcatcgtg cccaccttat gaacaagggc       180
acggtggccg atccttacga ctacaaccgt ggcgctacct tcgcctacat cggctggttt       240
gtgcagcaga agactcgccg tgcgatcgaa gcg                                    273

<210> SEQ ID NO 7
<211> LENGTH: 12
<212> TYPE: PRT
<213> ORGANISM: Crypthecodinium cohnii

<400> SEQUENCE: 7

Thr Ala Val Ser Ser Ala Phe Gln Gly Met Ser Lys
1               5                   10

<210> SEQ ID NO 8
<211> LENGTH: 23
<212> TYPE: PRT
<213> ORGANISM: Crypthecodinium cohnii

<400> SEQUENCE: 8
```

```
Glu Leu Asn Pro His Ile Asp Leu Asp Asp Phe Pro Ser Thr Ile Pro
1               5                   10                  15

Thr Asp Val Val Ser Ile Lys
            20

<210> SEQ ID NO 9
<211> LENGTH: 11
<212> TYPE: PRT
<213> ORGANISM: Crypthecodinium cohnii

<400> SEQUENCE: 9

Asn Val Gly Phe Gln Ala Pro Leu Val Leu Lys
1               5                   10

<210> SEQ ID NO 10
<211> LENGTH: 14
<212> TYPE: PRT
<213> ORGANISM: Crypthecodinium cohnii

<400> SEQUENCE: 10

Gly Ala Ser Ala Ala Leu Gly Gly Ala Thr Gln Glu Lys Lys
1               5                   10

<210> SEQ ID NO 11
<211> LENGTH: 10
<212> TYPE: PRT
<213> ORGANISM: Crypthecodinium cohnii

<400> SEQUENCE: 11

Asp Ser Val Ile Glu Ile Pro Tyr Thr Arg
1               5                   10

<210> SEQ ID NO 12
<211> LENGTH: 14
<212> TYPE: PRT
<213> ORGANISM: Crypthecodinium cohnii

<400> SEQUENCE: 12

Arg Gly Asp Ser Asp Glu Met Ile Thr His Cys Glu Gly Arg
1               5                   10

<210> SEQ ID NO 13
<211> LENGTH: 18
<212> TYPE: PRT
<213> ORGANISM: Crypthecodinium cohnii

<400> SEQUENCE: 13

Gly Val Thr Tyr Ser Thr Ser Asn Ala Ala Leu Asp Gly Leu Ala Leu
1               5                   10                  15

Trp Arg

<210> SEQ ID NO 14
<211> LENGTH: 12
<212> TYPE: PRT
<213> ORGANISM: Crypthecodinium cohnii

<400> SEQUENCE: 14

Ala Thr Thr Gln Ile Val Ser Ala Ala Glu Ala Arg
1               5                   10

<210> SEQ ID NO 15
<211> LENGTH: 15
<212> TYPE: PRT
```

<213> ORGANISM: Crypthecodinium cohnii

<400> SEQUENCE: 15

Phe Ser Val Glu Gly Val Gly Phe Gln Asn Pro Leu Val Leu Arg
1               5                   10                  15

<210> SEQ ID NO 16
<211> LENGTH: 19
<212> TYPE: PRT
<213> ORGANISM: Crypthecodinium cohnii

<400> SEQUENCE: 16

Leu Val Glu Leu Leu Ser Phe Leu Gln Gly Ala Gln Ser Ala Ser Glu
1               5                   10                  15

Thr Pro Lys

<210> SEQ ID NO 17
<211> LENGTH: 13
<212> TYPE: PRT
<213> ORGANISM: Crypthecodinium cohnii

<400> SEQUENCE: 17

Glu Phe Gln Ser Gln Glu Ala Leu Ala Val Thr Gly Lys
1               5                   10

<210> SEQ ID NO 18
<211> LENGTH: 18
<212> TYPE: PRT
<213> ORGANISM: Crypthecodinium cohnii

<400> SEQUENCE: 18

Ala Ser Ala Met Ala Gly Met Thr Asp Asp Arg Gln Ala Ala Val
1               5                   10                  15

Leu Lys

<210> SEQ ID NO 19
<211> LENGTH: 13
<212> TYPE: PRT
<213> ORGANISM: Crypthecodinium cohnii

<400> SEQUENCE: 19

Ala Gln Gln Ala Leu Gly Ala Ser Ala Gly Arg Pro Lys
1               5                   10

<210> SEQ ID NO 20
<211> LENGTH: 22
<212> TYPE: PRT
<213> ORGANISM: Crypthecodinium cohnii

<400> SEQUENCE: 20

Ala Pro Pro Leu Trp Leu Leu Thr Ser Gly Ser Gln Pro Leu Ala Ser
1               5                   10                  15

Ala Asp Ala Glu Gln Arg
            20

<210> SEQ ID NO 21
<211> LENGTH: 12
<212> TYPE: PRT
<213> ORGANISM: Crypthecodinium cohnii

<400> SEQUENCE: 21

Ser Ala Asp Ser Pro Leu Ile Leu Gly Ala Val Lys
1               5                   10

```
<210> SEQ ID NO 22
<211> LENGTH: 15
<212> TYPE: PRT
<213> ORGANISM: Crypthecodinium cohnii

<400> SEQUENCE: 22

Met Tyr Val Pro Phe Ala Asn Ile Gly Leu Pro Leu Gln Pro Arg
1               5                   10                  15
```

US 10,793,837 B2

PRODUCTION OF POLYUNSATURATED FATTY ACIDS (PUFAS) USING A NOVEL MODULAR DOCOSAHEXAENOIC ACID (DHA) SYNTHASE

CROSS-REFERENCE TO RELATED APPLICATIONS

This application is a US National Stage of International Application No. PCT/US2016/035974 filed Jun. 6, 2016, which designated the US and claims the benefit of the filing date of U.S. Provisional Patent Application No. 62/172,049 filed Jun. 6, 2015, the entire contents of each of which are hereby incorporated herein by reference in their entireties.

FIELD OF THE INVENTION

The present invention is directed to isolated nucleic acid molecules and polypeptides of a docosahexaenoic acid (DHA) synthase involved in the production of PUFAs, especially DHA. The present invention is directed to vectors and host cells comprising the nucleic acid molecules, polypeptides encoded by the nucleic acid molecules, compositions comprising the nucleic acid molecules or polypeptides, and methods of making and uses thereof.

BACKGROUND OF THE INVENTION

Polyunsaturated fatty acids (PUFAs) are considered to be useful for nutritional applications, pharmaceutical applications, industrial applications, and other purposes. However, the current supply of PUFAs from natural sources and from chemical synthesis is not sufficient for long-term commercial needs. Efforts have been made to produce PUFAs in oil-seed crop plants or microalgae by expressing exogenous genes involved in PUFA synthesis pathways.

In the conventional, or standard, pathway for PUFA synthesis, medium chain-length saturated fatty acids (products of a fatty acid synthase (FAS) system) are modified by a series of elongation and desaturation reactions. The substrates for the elongation reactions are fatty acyl-CoAs (an activated form of the fatty acid chain to be elongated) and malonyl-CoA (the source of the two carbons added during each elongation reaction). The product of the elongase reaction is a fatty acyl-CoA that has two additional carbons in the linear chain. The desaturases create cis double bonds in the preexisting fatty acid chain by extraction of two hydrogens in an oxygen-dependent reaction.

An alternative pathway for PUFA synthesis has been described (Metz et al., Science, Vol. 293, no. 5528 (Jul. 13, 2001), pp. 290-293). This system carries out de novo synthesis of the fatty acids by multi-domain enzymes called PUFA synthases. These synthases contain domains that are most closely related to domains, or individual enzymes, found in Type I and Type II polyketide synthase (PKS) systems and Type II FAS systems. PUFA synthases are iterative Type I systems (see descriptions below). The domain content and organization of the PUFA synthases represented a novel system that did not fit with previously described FAS or PKS systems. The PUFA synthase pathway is a fundamentally different pathway from the elongase/desaturase pathway described above. It does not involve modification of pre-made shorter chain fatty acids and does not have a requirement for molecular oxygen. PUFA synthases are found in some marine bacteria and also in some Thraustochytrids.

Thraustochytrids are eukaryotic marine algae and presumably acquired the PUFA synthase system from the bacteria via lateral gene transfer. Several Thraustochytrids have been developed as commercial sources of oils that are highly enriched in PUFAs. The PUFAs in these oils (primarily docosahexaenoic acid (DHA, C22:6, n-3), docosapentaenoic acid (DPAn-6, C22:5, n-6) and eicosapentaenoic acid (EPA, C20:5, n-3)) are produced by the PUFA synthases present in these organisms.

Like the Thraustochytrids mentioned above, *C. cohnii* has been developed as a commercial source of oil that is highly enriched in PUFAs—specifically DHA. It was found that DHA is the only PUFA present in significant amounts in this oil and it can comprise over 50% of the total fatty acids present in the oil. Prior to this disclosure, the enzymatic pathway for synthesis of DHA in *C. cohnii* has not been described.

Research into the molecular genetics of fatty acid synthesis in dinoflagellates has only started. Efforts to assemble and analyze the genomes have been made recently (Shoguchi et al., Current Biology, Vol. 23, (2013), Issue 15 (Aug. 5, 2013), pp. 1399-1408). However, it has been predicted that the excessive sizes and peculiarities of dinoflagellate genomes will make the identification and characterization of biosynthesis pathways on the genetic level challenging at the very least (Kellmann et al., Mar. Drugs Vol. 8, no. 4 (Mar. 26, 2010), pp. 1011-1048).

Several studies on the biochemistry of *C. cohnii* fatty acid biosynthesis have been reported. It was found that *C. cohnii* is not capable of DHA synthesis by known desaturase-mediated and elongase-mediated paths (Beach et al., Biochim Biophys Acta Vol. 369 (Oct. 16, 1974), pp. 16-24). It was also found that *C. cohnii* is not capable of converting externally fed fatty acids (e.g., C16:0, C18:0, C18:1, C18:2 and C18:3) into DHA based on lack of detection of radiolabelled DHA when fed the radiolabelled potential precursors (Lippmeier, J. C., Ph.D. thesis entitled "Fatty Acid Metabolism of Marine Microalgae", University of Hull, (2007)).

There was also no indication in these reports of what the biochemical basis of DHA synthesis could be. No gene or protein associated with DHA synthesis has been identified prior to the present invention. Queries of EST libraries derived from *C. cohnii* mRNA with protein sequences from the standard elongase/desaturase pathway and from the PUFA synthase pathways were conducted but no unequivocal genetic evidence for a DHA synthesis system utilizing either pathway was observed (Lippmeier, J. C., Ph.D. thesis entitled "Fatty Acid Metabolism of Marine Microalgae", University of Hull, (2007), Ch. 5).

Here we describe the use of a combination of biochemical and bioinformatic approaches to identify a single very large protein that is associated with the synthesis of DHA in *C. cohnii*. Analysis of the enzymatic domains present in this protein revealed that it falls into the class of enzymes referred to as a modular Type I PKS.

Polyketides are a class of (primarily) secondary metabolites with a vast range of structures. The multi-domain enzymes that produce these compounds are referred to as polyketide synthases (PKSs). Although the products of PKS systems vary enormously, they are synthesized by a mechanism that is similar to fatty acid biosynthesis. In FASs, the elongation cycle is initiated by a decarboxylative condensation reaction between either a primer (an acetate unit), or a longer fatty acyl chain, that is esterified to the active site of a β-keto acyl-ACP synthase (KS) and a malonate unit linked to an acyl-carrier protein (ACP). This reaction yields an acyl chain, on the ACP, that has 2 carbons added (derived from the malonate unit) and has a keto group on the β carbon. In the standard elongation cycle sequential actions of a β-keto reductase (KR, to yield a β-alcohol group), a dehydratase (DH, to remove a water molecule and resulting in a double bond being inserted into the carbon chain) and finally an enoyl-reductase (ER) yield a fully reduced β-carbon. The differences between polyketide and fatty acid biosynthesis are in the number and type of acyl precursors used, the extent and position of keto-group reductions, and the subsequent (post-PKS) modifications.

PKS systems have been described in the literature as falling into one of several basic types, typically referred to as Type I (either modular or iterative), Type II, and Type III. The Type I PKS system is characterized by having large, multi-domain, proteins to carry out the enzymatic reactions required for the product synthesis. Domains of the enzyme, each performing a distinct type of enzymatic reaction, carry out the synthesis. If the system is a modular Type I PKS system, each enzymatic domain associated with the elongation cycles is used only once in the production of the end product. If the system is an iterative Type I PKS system, some of these elongation cycle domains are used multiple times to produce the end product. The Type II system is characterized by separable proteins, each of which carries out a distinct type of enzymatic reaction. The enzymes work in concert to produce the end product and each individual enzyme of the system typically participates several times in the production of the end product. The Type III systems belong to the plant chalcone synthase family of condensing enzymes. Type III PKSs utilize acyl-CoA substrates in iterative condensation reactions to produce the end product.

As indicated above, the *C. cohnii* DHA synthase described in this invention falls into the class of enzymes referred to as modular Type I PKSs. An interesting feature of these systems is that certain aspects of the structures of their products can often be predicted by the presence and arrangement of their domains. In modular Type I PKSs these domains are organized into modules—clusters of domains associated with a particular set of reactions. In many cases the modules are associated with the elongation reactions. These modules all contain the KS and ACP domains that carry out the condensation reaction and yield the elongated carbon chain with a keto group on the β-carbon. If the module also contains active KR, DH and ER domains the β-carbon will be fully reduced. If that module contains only the additional KR and DH domains a double bond will be retained in the carbon chain. If the module contains only an additional KR domain, then the β-keto group will only be reduced to a hydroxyl group. The elongated carbon chain, with its keto group, or hydroxyl group, or double bond, or fully reduced β-carbon is then passed on to the next module. Other domains are often present in the modular Type I PKS systems in addition to those associated with the elongation reactions. Acyl-transferase (AT) domains are required to load the ACPs with extension units (e.g., malonate) and to load the priming molecule (e.g., acetate). The final module often contains a thioesterase (TE) domain that can release the product as a free fatty acid. Additionally, domains associated with further modification of the product can be associated with the PKS system.

In the 'Detailed Description of the Invention' and the 'Examples' sections, the domain structure and organization of the PKS system responsible for production of DHA in *C. cohnii* and a rationale for the synthesis are described. It is proposed that ten elongation modules work sequentially to produce a fatty acid molecule that has 22 carbons in a linear chain. The domain structure indicates that three of the elongation modules will leave hydroxyl groups and three will leave trans double bonds at specific locations in that 22-carbon fatty acid chain. It is further proposed that a fatty acid with these hydroxyl groups and double bonds can be converted to DHA via a series of isomerization and dehydration reactions. A domain is present near the N-terminus of the synthase that is related to oxygen-dependent desaturase enzymes. The $O_2$-dependent desaturases represent a large class of enzymes that includes many examples that have been shown to carry out isomerase and dehydration reactions of the type we are proposing. We are calling this domain a 'Desaturase-related Isomerase and Dehydratase' (DrID) domain. This is the first time a domain of this type has been shown to be part of a modular Type I PKS system.

The products of PKS systems are typically associated with secondary metabolism and usually only minor amounts of the products are accumulated. It is therefore surprising that the modular DHA synthase from *C. cohnii* produces a molecule, DHA, which is normally associated with primary metabolism and that it accumulates to very high levels in that organism. In this sense it is similar to the PUFA synthase system in the Thraustochytrids. However the two systems are distinct in that the PUFA synthase is an iterative Type I system while the modular DHA synthase is clearly a modular Type I PKS system. Thus the system described in this report represents a novel system and is one that has certain advantages for production of DHA in heterologous organisms.

SUMMARY OF THE INVENTION

The present invention is based on the identification of a new modular docosahexaenoic acid (DHA) synthase from *C. Cohnii*. The new modular DHA synthase is expressed in a host organism, either alone or in combination with other accessory proteins, to add or improve the production of DHA or other PUFAs in the host organism.

Accordingly, the invention relates to:

An isolated nucleic acid molecule selected from the group consisting of:

(a) a nucleic acid molecule comprising a polynucleotide sequence encoding a protein having the amino acid sequence of SEQ ID NO:1;

(b) a nucleic acid molecule comprising a polynucleotide sequence encoding a protein having an amino acid sequence with substitution, deletion, insertion and/or addition of one or several amino acid residues in the amino acid sequence of SEQ ID NO:1, the protein having modular docosahexaenoic acid (DHA) synthase activity;

(c) a nucleic acid molecule comprising a polynucleotide sequence encoding a protein having at least 85% identity to the amino acid sequence of SEQ ID NO:1, the protein having modular docosahexaenoic acid (DHA) synthase activity;

(d) a nucleic acid molecule comprising the polynucleotide sequence of SEQ ID NO:2.

In some embodiments, the amino acid sequences encoded by the above-mentioned nucleic acid molecule are at least 70%, at least 80%, at least 90%, or at least 95% identical to the SEQ ID NO:1.

The invention also relates to an isolated nucleic acid molecule having a nucleic acid sequence of SEQ ID NO:6.

In an embodiment, the above-mentioned proteins have modular DHA synthase activity when co-expressed with a 4'-phosphopantetheinyl transferase (PPTase). In one embodiment, the PPTase has the amino acid sequence of SEQ ID NO:5.

The invention also relates to a recombinant nucleic acid molecule comprising the nucleic acid molecule(s) according to the above-mentioned isolated nucleic acid molecules, and is operatively linked to one or more expression control sequences.

The invention further relates to a recombinant host cell comprising the above recombinant nucleic acid molecules. In some embodiments, the host cell can be a microbial cell or a plant cell.

The invention also relates to a genetically modified organism, wherein the organism has been genetically modified to express the above-mentioned recombinant nucleic acid molecule(s). In some embodiments, the organism is selected from the group consisting of a plant, a microorganism, and an animal. For example, the microorganism can be a microalga, a bacterium, or a Thraustochytrid. The plant can be a soybean plant or a canola plant. In one embodiment, the genetically modified organism comprises DHA. In another embodiment, the genetically modified organism comprises at least one polyunsaturated fatty acid (PUFA) selected from the group consisting of: DPA (C22:5, n-6 or n-3), EPA (C20:5, n-3), ARA (C20:4, n-6), GLA (C18:3, n-6), ALA (C18:3, n-3), and SDA (C18:4, n-3), The invention also relates to a genetically modified organism, wherein the organism has been genetically modified to delete or inactivate the above-mentioned nucleic acid molecules.

The invention also relates to a method to produce at least one PUFA, comprising: expressing a modular DHA synthase gene in a host cell under conditions effective to produce PUFAs, wherein the modular DHA synthase gene comprises one or more of the above-mentioned nucleic acid molecules, and wherein at least one PUFA is produced. In some embodiments, the above-mentioned host cell is selected from the group consisting of a plant cell, an animal cell, and a microbial cell. At least one of the PUFAs produced is docosahexaenoic acid (DHA).

The invention also relates to a method to produce lipids enriched for DHA, comprising: expressing a modular DHA synthase gene in a host cell under conditions effective to produce lipids, wherein the modular DHA synthase gene comprises one or more of the above-mentioned nucleic acid molecules, and wherein lipids enriched with DHA are produced.

The invention also relates to a method of making a recombinant vector comprising inserting the one of the above-mentioned isolated nucleic acid molecules into a vector.

The invention also relates to a method of making a recombinant host cell comprising introducing the above-mentioned recombinant vector into a host cell. In some embodiments, the above-mentioned host cell is selected from the group consisting of a plant cell, an animal cell, and a microbial cell.

The invention also relates to a method of increasing DHA production in an organism having modular DHA synthase activity, comprising: expressing one or more of the above-mentioned isolated nucleic acid molecules in the organism under conditions effective to produce DHA, wherein the modular DHA synthase activity replaces an inactive or deleted activity, introduces a new activity, or enhances an existing activity in the organism, and wherein DHA production in the organism is increased.

The invention also relates to a process for transforming an organism to produce PUFAs, comprising transforming an organism with at least one of the above-mentioned isolated nucleic acid molecules.

The invention also relates to an oil obtained from one of the above-mentioned genetically modified organisms. In one embodiment, the oil produced contains DHA. The invention also relates to food product or feed product that contains the above-mentioned oil, or contains the above-mentioned genetically modified organisms. The invention also relates to a product that contains the above-mentioned oil.

The invention relates to a modular DHA synthase that catalyzes de novo synthesis of one or more linear fatty acids having at least 18 carbons and at least 3 carbon-carbon double bonds, wherein the synthesis reaction uses malonyl-CoA as the source of carbons for the extension reactions and does not require molecular oxygen, and the synthase comprises an amino acid sequence as set forth in SEQ ID NO:1 or a functional fragment, derivate, allele, homolog or isoenzyme thereof. In some embodiments, the above synthase may comprise an amino acid sequence encoded through a nucleotide sequence as set forth in SEQ ID NO:2 or a homologous nucleotide sequence which encodes an amino acid sequence that is at least about 85% identical to the amino acid sequence of SEQ ID NO:1. In some embodiments, the above nucleotide sequence may be part of a nucleic acid molecule. Thus, the invention also relates to a genetically modified organism, wherein the organism has been genetically modified to express such recombinant nucleic acid molecule. In some embodiments, the above genetically modified organism may be selected from a group consisting of a plant, a microorganism, and an animal. Such genetically modified organism according may have an altered or increased PUFA content. Such genetically modified organism may have its modular DHA synthase altered, characterized by an alteration in gene expression, catalytic activity and/or regulation of activity of the enzyme.

The invention relates to a process for the production of PUFAs, comprising growing the above-mentioned genetically modified organism under conditions whereby the above-mentioned modular DHA synthase is expressed. In one embodiment, PUFAs are produced by the above process.

The invention relates to the use of the modular DHA synthase described in this application or nucleic acid sequence encoding such modular DHA synthase in a cell or organism and cause an altered, preferably increased, PUFA content of this cell or organism.

The invention relates to an isolated nucleic acid molecule selected from the group consisting of:

(a) a nucleic acid molecule comprising a polynucleotide sequence encoding a protein having the amino acid sequence of SEQ ID NO:4;

(b) a nucleic acid molecule comprising a polynucleotide sequence encoding a protein having an amino acid sequence with substitution, deletion, insertion and/or addition of one or several amino acid residues in the amino acid sequence of SEQ ID NO:4, the protein having dehydratase and isomerase activities; and (c) a nucleic acid molecule comprising a polynucleotide sequence encoding a protein having at least 85%, at least 90%, at least 95% identity to the amino acid sequence of SEQ ID NO:4, the protein having dehydratase and isomerase activities.

The invention also relates to a recombinant nucleic acid molecule, comprising the above-mentioned isolated nucleic acid molecule, operatively linked to an expression control sequence.

The invention also relates to a genetically modified organism, wherein the organism has been genetically modified to express the above-mentioned isolated nucleic acid molecule. In some embodiments, the organism is selected from a group consisting of plant, microorganism, and animal. In some embodiments, the microorganism is a microalga, a bacterium, or a thraustochytrid. In some embodiments, the organism is a plant and the recombinant nucleic acid molecule encodes a protein that is targeted to the plastid of said plant. In some embodiments, the organism is a plant and said recombinant nucleic acid molecule encodes a protein that is expressed in the cytosol of said plant. In some embodiments, the plant is soybean or canola. In one embodiment, the genetically modified organism comprises DHA.

The invention also relates to a method to produce at least one PUFA, comprising:
expressing a dehydratase/isomerase gene in a host cell under conditions effective to produce PUFAs,
wherein the dehydratase/isomerase gene comprises the above-mentioned isolated nucleic acid molecule in the host cell, and
wherein at least one PUFA is produced.

In some embodiments, the above host cell is selected from a group consisting of a plant cell, an animal cell, and a microbial cell. In some embodiments, at least one PUFA comprises docosahexaenoic acid (DHA).

The invention also relates to a process for transforming an organism to produce PUFAs, comprising transforming an organism with at least one nucleic acid molecule polynucleotide sequence encoding a protein having at least 85%, at least 90%, at least 95% identity to the amino acid sequence of SEQ ID NO:4, and the protein having dehydratase and isomerase activities.

BRIEF DESCRIPTION OF THE DRAWINGS/FIGURES

FIG. 1 shows fatty acid synthesis in various fractions derived from the KO and KO-5 strains of *Crypthecodinium cohnii*.

LIST OF SEQ IDS

Figure 1A:
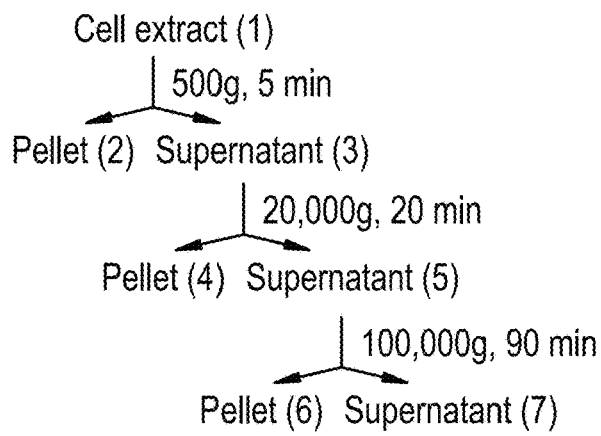
FIG. 1a shows cell homogenate fractionation scheme with reference numbering of the fractions.

SEQ ID NO:1—the amino acid sequence of the *C. cohnii* modular DHA synthase (15,896 amino acids)

SEQ ID NO:2—the nucleotide sequence of the open reading frame (ORF) of SEQ ID NO:3 (47,688 bases without the stop codon) encoding SEQ ID NO:1

SEQ ID NO:3—the full assembled cDNA sequence of 47,866 bases (the SEQ ID NO:2 ORF is embedded in this). It includes up and down stream non-coding sequences but does not include the A's of the poly A tail SEQ ID NO:4—the amino acid sequence of the 'DrID' domain of SEQ ID NO:1 (i.e. 91 amino acids—region 450 to 540 of that sequence)

SEQ ID NO:5—the amino acid sequence of the *C. cohnii* PPTase being used for heterologous expression SEQ ID NO:6—the nucleotide sequence encodes SEQ ID NO:4

SEQ ID NO:7—residues numbering 5306-531 refers to SEQ ID NO:1.

SEQ ID NO:8—residues numbering 5795-5817 refers to SEQ ID NO:1.

SEQ ID NO:9—residues numbering 5935-5965 refers to SEQ ID NO:1.

SEQ ID NO:10—residues numbering 7154-7168 refers to SEQ ID NO:1.

SEQ ID NO:11—residues numbering 7195-7204 refers to SEQ ID NO:1.

SEQ ID NO:12—residues numbering 7712-7725 refers to SEQ ID NO:1.

SEQ ID NO:13—residues numbering 9287-9304 refers to SEQ ID NO:1.

SEQ ID NO:14—residues numbering 9499-9510 refers to SEQ ID NO:1.

SEQ ID NO:15—residues numbering 10018-10032 refers to SEQ ID NO:1.

SEQ ID NO:16—residues numbering 13106-13124 refers to SEQ ID NO:1.

SEQ ID NO:17—residues numbering 13484-13496 refers to SEQ ID NO:1.

SEQ ID NO:18—residues numbering 13500-13517 refers to SEQ ID NO:1.

SEQ ID NO:19—residues numbering 14350-14362 refers to SEQ ID NO:1.

SEQ ID NO:20—residues numbering 14789-14810 refers to SEQ ID NO:1.

SEQ ID NO:21—residues numbering 4717-4728 refers to SEQ ID NO:1.

SEQ ID NO:22—residues numbering 10104-10118 refers to SEQ ID NO:1.

DETAILED DESCRIPTION OF THE INVENTION

The present invention generally relates to the provision of polypeptides and nucleic acid molecules encoding such polypeptides, for the improvement of the production of polyunsaturated fatty acids (PUFAs), particularly, docosahexaenoic acid (DHA), in a host organism that has been genetically modified to produce such PUFAs. The present invention also relates to the organisms that have been genetically modified to express certain of such polypeptides, and to methods of making and using such polypeptides and organisms. The present invention also relates to modification of such polypeptides such that molecules other than DHA are produced (e.g., other PUFAs or poly-hydroxy fatty acids).

*Crypthecodinium cohnii* can produce polyunsaturated fatty acids and particularly the nutritionally important polyunsaturated fatty acid DHA. *C. cohnii* can be grown in large-scale fermenters and has been used for commercial production of DHA enriched oil. However, little is known about the biochemistry and genetics of the synthesis of fatty acids in *C. cohnii*. The present inventors for the first time have identified a cDNA sequence encoding an enzyme that is involved in the production of DHA in *C. cohnii*. The identification of the cDNA sequence was accomplished using a combination of biochemical and bioinformatic methods. Biochemical methods were used to identify a single, very large, protein that was associated with in vitro DHA synthesis activity in extracts derived from cells of *C. cohnii*. The amino acid sequence of the candidate protein was deduced by MS-based sequencing of tryptic peptides generated from that protein with a cDNA sequence database as a reference. The cDNA utilized to generate that database was derived from RNA samples extracted from cells of *C. cohnii*. Features of the cDNA sequence indicate that it corresponds to the sequence of single mRNA species derived from a gene encoded in the nuclear genome. The inventors also used bioinformatic methods to determine the enzymatic domains present in the protein sequence and to deduce their biochemical functions. Strategies for expression of the enzyme in a heterologous host cell are also described.

As used herein, the term "modular DHA synthase" refers to a modular Type I PKS synthase that is involved in the de novo production of DHA. The term "*C. cohnii* modular DHA synthase" refers specifically to the modular Type I PKS synthase whose amino acid sequence is shown in SEQ ID NO:1. The amino acid sequence of SEQ ID NO:1 was deduced by translation of a single large open reading frame (ORF) present in the *C. cohnii* derived cDNA contig. The sequence of the ORF whose translation yields the amino acid sequence of SEQ ID NO:1 is shown in SEQ ID NO:2. The complete assembled cDNA sequence that contains the SEQ ID NO:2 ORF is shown as SEQ ID NO:3.

The data presented here describe a third distinct pathway for PUFA (specifically, DHA) synthesis and the second one involving de novo synthesis. This pathway was discovered by the present inventors in the unicellular, heterotrophic, dinoflagellate, *Crypthecodinium cohnii*.

The present invention is directed in part to a novel group of enzymes, and the nucleic acids encoding such enzymes, designated as modular DHA synthases. The modular DHA synthase catalyzes de novo production of PUFAs, using malonyl-CoA as the substrate for the extension reactions. Modular DHA synthases belong to a broad group of enzymes called modular Type I polyketide synthases. The novel features of the modular DHA synthase disclosed in the present invention include; its specific amino acid sequence, the particular organization of its enzymatic domains, its natural product (i.e., a PUFA, e.g., DHA) and one of its domains—specifically, the 'desaturase related isomerase and dehydratase' (DrID) domain.

In some embodiments, the subject modular DHA synthase catalyzes de novo synthesis of one or more linear fatty acids having at least 18 carbons and at least 3 carbon-carbon double bonds. The synthesis reactions use malonyl-CoA as the source of carbons for the extension reactions and do not require molecular oxygen. The synthase comprises an amino acid sequence as set forth in SEQ ID NO:1 or a functional fragment, derivate, allele, homolog or isoenzyme thereof. In some embodiments, synthase comprising an amino acid sequence encoded through a nucleotide sequence as set forth in SEQ ID NO:2 or a homologous nucleotide sequence which encodes an amino acid sequence that is at least 60%, at least 65%, at least 70%, at least 75%, at least 80%, at least 85%, at least 90%, or at least 95% identical to the amino acid sequence of SEQ ID NO:1.

The present invention is also directed to a nucleotide sequence that encodes the above *C. cohnii* modular DHA synthase (SEQ ID NO:2).

In some embodiments, the present invention is directed to an isolated nucleic acid molecule comprising a polynucleotide sequence encoding protein having an amino acid sequence with substitution, deletion, insertion and/or addition of one or several amino acid residues in the amino acid sequence of SEQ ID NO:1. In an embodiment, the above protein has modular docosahexaenoic acid (DHA) synthase activity.

In some embodiments, the present invention is directed to an isolated nucleic acid molecule comprising a polynucleotide sequence encoding protein having at least 60%; at least 65%; at least 70%; at least 75%; at least 80%; at least 81%; at least 82%; at least 83%; at least 84%; at least 85%; at least 86%; at least 87%; at least 88%; at least 89%; at least 90%; at least 91%; at least 92%; at least 93%; at least 94%; at least 95%; at least 96%; at least 97%; at least 98%; or at least 99% identity to an amino acid sequence of SEQ ID NO:1. In an embodiment, the above protein has modular docosahexaenoic acid (DHA) synthase activity.

The present invention is also directed in part to an enzymatic domain encoded by the region of amino acids from about 450 to about 540 of SEQ ID NO:1. This domain is called DrID domain, and is inferred to have trans-cis double bond isomerase activity and also dehydratase activity as described below. An exemplary sequence of this region is shown in SEQ ID NO:4. A nucleic acid sequence that encodes the DrID domain is shown in SEQ ID NO:6. Its activity is inferred from the reactions required to convert the predicted product of the elongation modules of the *C. cohnii* DHA synthase (shown in FIG. 6) to the structure of DHA (shown in FIG. 7), as well as, the established characteristics of the family of enzymes included in the $O_2$-dependent desaturases, as described below.

A sequential list of the domains detected in the *C. cohnii* modular DHA synthase is provided in Table 1. The data in Table 1 include: the enzymatic family detected (as defined by comparison to the Pfam database), an indication of the approximate boundaries of the region with homology to those enzymes, a motif associated with the domain and a reference location of one amino acid present in the listed motif. The first domain detected in the protein was the DrID domain described above. The DrID domain has homology to the $O_2$-dependent fatty acid desaturase family of enzymes and covers approximately amino acids 450 to 540 of SEQ ID NO:1. The $O_2$-dependent fatty acid desaturases rely on activation of molecular oxygen to facilitate the energetically demanding initial abstraction of hydrogen from a carbon chain. Three Histidine box motifs are associated with the binding of the oxygen required for this reaction. Alignment of the DrID domain sequence with examples of the $O_2$-dependent desaturases reveals that the DrID domain sequence lacks two of these Histidine box motifs completely and that the third motif (HxxHH) is represented by a partial sequence (HxxH). The location of this partial motif is indicated in Table 1. The absence of the complete set of Histidine box motifs indicates that the function of the DrID domain is not associated with $O_2$ dependent double bond formation. This is consistent with the observation that $O_2$ is not required for in vitro DHA synthesis (see Example 2). As described above, the $O_2$-dependent desaturase family of enzymes includes examples that, in addition to their desaturase activity, possess the ability to carry out carbon-carbon double bond isomerizations and also hydroxylation and dehydration reactions (Shanklin, et al., J. Biol. Chem., Vol. 284 (Jul. 10, 2009), pp. 18559-18563).

In the case of the modular DHA synthases, the $O_2$-dependent initial abstractions of hydrogens from saturated carbon chain is not required since it can be predicted that a fatty acid structure is produced that already contains hydroxyl groups and double bonds. We propose that the function of the DrID domain is to carry out trans-cis isomerizations of the preformed double bonds and to carry out the dehydration reactions (removal of an HOH) that insert additional cis-double bonds thus forming the DHA final product. These proposals are consistent with the anticipated products of the elongation cycles of the modular DHA synthase (see below) and with reactions that have been associated with this class of enzymes.

The present invention for the first time identified the DrID domain and its sequence and function as a component of a modular Type I PKS system.

The remaining 48 domains detected in SEQ ID NO:1, and listed in Table 1, are all related to enzyme classes typically found in modular Type I PKS's. As in the case of the DrID domain, the data in Table 1 indicate the approximations of the amino acid regions in SEQ ID NO:1 that show homology to other proteins known to be of those classes. Each of the listed enzyme classes (i.e., KS, KR, DH, ER, ACP, AT and TE) possesses a particular amino acid motif that can serve as an identifier for that type of domain and can be an indicator that it has the enzymatic activity, or function, associated with that domain. The following motifs have been associated with the domains listed in Table 1:

A key feature of modular Type I PKS systems is the assembly line aspect of the elongation reactions. In particular, the domains associated with each elongation cycle are clustered together in modules. These modules contain the KS and ACP domains to carry out the condensation reaction and may also have domains associated with further modification of the β-carbon. The elongation modules are utilized sequentially, progressing from the N-terminal towards the C-terminal regions of the protein. The first elongation module in the sequence catalyzes the condensation of a primer unit with an extender molecule. The product of that elongation module is then passed off to the next module. Table 2 shows a model for the domain organization of modules of the C. cohnii DHA synthase. The model is based on the sequential list of the domains shown in Table 1 and on comparison to other well-characterized modular Type I PKS proteins (e.g., Schwecke et al., Proc. Natl. Acad. Sci. USA, Vol. 92 (August, 1995), pp. 7839-7843).

Table 2 includes a designation for each module (M0, M1 through M10, and M-final), the domains that each module comprises, and a proposed function for the module. The first module, M0, is suggested to contain the DrID domain and an ACP domain while the last module, M-final, is proposed to consist of the TE domain alone. Each elongation module, M1 through M10, is proposed to end with an ACP domain. Alternative models for the domain content of the modules are possible (e.g., shifting the ACP to the beginning of the elongation modules), however, this would not alter the following discussion. There are two cases of tandem ACP domains (underlined in Table 2). The role of tandem ACP domains in PKS systems is a matter of ongoing debate. In many modular Type I PKS systems an AT domain is associated with each elongation module. There are also examples in which the AT enzyme associated with loading the extender unit on to ACP domains is encoded as a separate enzyme (Cheng, et al., Proc. Natl. Acad. Sci. USA, Vol. 100 (Mar. 18, 2003), pp. 3149-3154). In contrast, the C. cohnii DHA synthase does contains AT domains (italicized in Table 2) however, it has only three of them. Biochemical data

| Domain | Motif |
| --- | --- |
| KS (β-ketoacyl synthase - catalyses the condensation reaction between the starter unit, or an intermediate, with the extender unit leaving a keto group in the 'β' carbon of the acyl chain) | DxAC - the molecule to be extended is linked to the cysteine |
| KR (β-keto reductase - reduces the β-ketone group to a hydroxyl group) | LxSRxG (e.g., Choi et al., Microbiology, Vol. 153, pt 4 (April, 2007), pp. 1095-1102) |
| DH (dehydratase - reduces the β-hydroxyl group to an enoyl group, e.g., a carbon-carbon double bond in the 'trans' configuration) | HxxxGxxxxP, or HxxGxxxxS (in domain number 24 of Table 1) (Choi et al., Microbiology, Vol. 153, pt 4 (April, 2007), pp. 1095-1102) |
| ER (enoyl reductase - reduces an enoyl group to an alkyl group) | GGVGxxAxQxA (Choi et al., Microbiology, Vol. 153, pt 4 (April, 2007), pp. 1095-1102) |
| ACP (acyl carrier protein - holds the growing polyketide chain as a thiol ester. ACP domains require activation by attachment of a co-factor; phosphopantetheine. The activation is carried out by a phosphopantetheinyl transferase (PPTase) which can be a part of a Type I protein, or encoded separately) | GxDS - the serine is the site of attachment of the co-factor |
| AT (acyltransferase - loads the starter unit, extender units or other acyl intermediates onto domains in the protein) | GxSxG - the acyl group to be transferred is bound to the serine |
| TE (thioesterase - a type of acyltransferase that facilitates release of the final product of the synthase) | GxSxG | suggest that a separate AT protein is not required for DHA synthesis (see Example 3). These data suggest that one (or more) of the AT domains in the synthase is able to load the appropriate internal ACP domains with extender units. Ten modules, M1 through M10, are associated with carbon chain formation. With acetate as the primer (derived from either acetyl-CoA or via decarboxylation of malonate from malonyl-CoA) and 2-carbons per extension (derived via a decarboxylative reaction using malonyl-ACP) these elongation reactions would yield a 22-carbon fatty acid.

Figure 6:
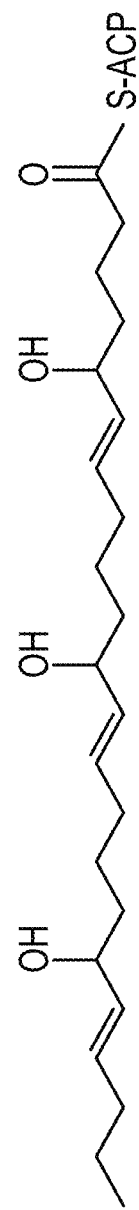
FIG. 6 shows the structure of a molecule that would be produced by the sequential actions of modules M1 through M10 of the *C. cohnii* modular DHA synthase.
Figure 7:
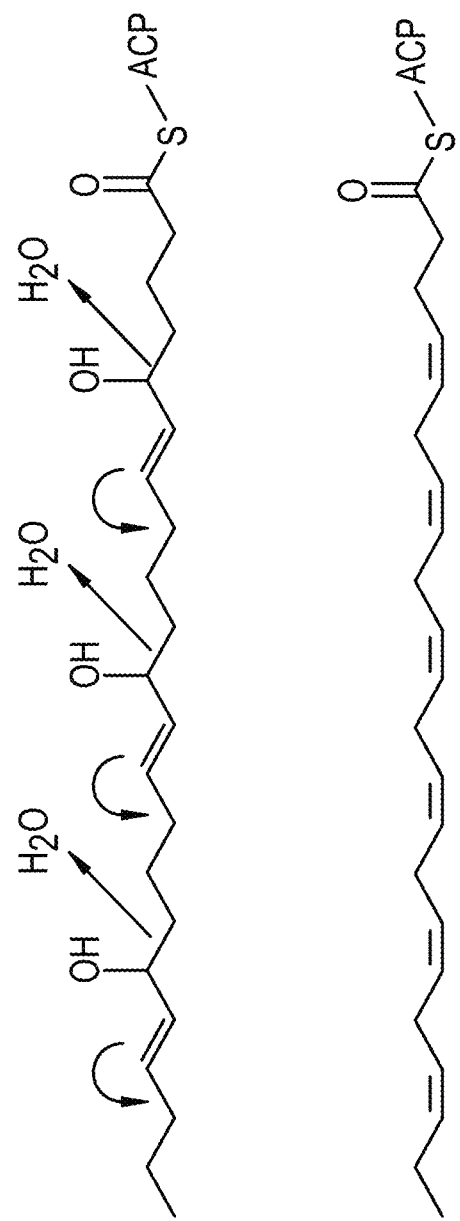
FIG. 7 shows a scheme for formation of DHA from the molecule in FIG. 6.

As shown in Table 2, the domain contents of the elongation modules indicate that the β-carbons resulting from the condensation reactions will be fully reduced in 4 cases, retain a hydroxyl group in 3 cases and be associated with a double bond in 3 cases. The structure of the fatty acid that would result from the sequential activities of the ten elongation modules is shown in FIG. 6. It is proposed that the activity of the DrID domain converts the hydroxyl groups and trans-double bonds created during the elongation cycles into the DHA molecule, with its six, methylene interrupted cis-double bonds, as diagrammed in FIG. 7. This conversion could take place during the fatty acid chain formation, or after completion of the elongation reactions. The final domain in the *C. cohnii* DHA synthase is the TE domain (module M-final). The TE domain is proposed to release the DHA product of the synthesis reactions by hydrolysis of the thioester bond that tethers it to an ACP domain.

TABLE 2

| Module Name | Domains | Function, or β-carbon status |
| --- | --- | --- |
| M0 | DrID, ACP | isomerization and dehydration reactions |
| M1 | KS, *AT*, DH, ER, KR, ACP | : full reduction |
| M2 | KS, *AT*, DH, KR, ACP | : double bond |
| M3 | KS, KR, ACP | : hydroxyl group |
| M4 | KS, DH, ER, KR, ACP-ACP | : full reduction |
| M5 | KS, DH, KR, ACP | : double bond |
| M6 | KS, KR, ACP | : hydroxyl group |
| M7 | KS, DH, ER, KR, ACP-ACP | : full reduction |
| M8 | KS, DH, KR, ACP | : double bond |
| M9 | KS, KR, ACP | : hydroxyl group |
| M10 | KS, *AT*, DH, ER, KR, ACP | : full reduction |
| M-final | TE | release of the end-product as a free fatty acid |

It is hypothesized that the *C. cohnii* modular DHA synthase, as well as homologous enzymes that may be discovered in other organisms, would be useful for modifying DHA accumulation in hosts expressing such an enzyme. For example, expressing the *C. cohnii* modular DHA synthase in a heterologous host cell that does not produce DHA may cause the cell to produce DHA. As another example, expressing the *C. cohnii* modular DHA synthase in a heterologous host cell that already produces DHA may cause an increase of DHA accumulation. Techniques for expression of proteins in heterologous hosts are known in the art but significant challenges remain in successfully expressing an extraordinarily large protein that is still functional. Some specific protocols that could be used for heterologous expression of the *C. cohnii* modular DHA synthase in heterologous hosts are given in the Examples section.

The present invention is also directed in part to a group of modified modular DHA synthases that may produce compounds other than DHA. Strategies for alteration of the DHA synthase such that it would produce other molecules could include (but not be limited to): removal, or addition, of specific elongation modules, inactivation of specific domains such as any of the ER, DH or KR domains, or inactivation of the DrID domain. In some embodiments, such alterations result in an enzyme that could produce PUFAs other than DHA (e.g., but not limited to, ARA (C20:4, n-6), DPA (C22:5, n-6 or n-3), EPA(C20:5, n-3), gamma-linolenic acid (GLA) (C18:3, n-6), alpha-linolenic acid (ALA) (C18:3, n-3), and/or stearidonic acid (SDA) (C18:4, n-3), or molecules containing hydroxyl groups and or trans double bonds. In one embodiment, such modified modular DHA synthases are modified *C. cohnii* modular DHA synthases.

Inventors of the present invention have also discovered and disclose for the first time herein a DrID domain in a modular Type I PKS synthase. Without being bound by theory, it is believed that the DrID domain converts the hydroxyl groups of the fatty acid chain to cis C=C bonds, and isomerize the trans double bonds to cis double bonds with migration towards methyl terminus, either during the elongation process or after the C22 backbone of the DHA molecule is fully formed by the catalysis of modules M1-M10. In other words, it is proposed that the DrID domain disclosed herein is responsible for the isomerization reactions and the dehydrations reaction in the DHA synthesis process.

The discovery of the DrID domain and its function suggest that it could be used independently of the modular DHA synthase. For example, the DrID domain could be cloned into a vector and transformed into a host cell that already produces a molecule (or molecules) that contain hydroxyl groups and/or trans-double bonds in the appropriate configurations such that they could serve as substrates and be converted to cis-double bonds.

Thus, the present invention is directed in part to a heterologously expressed polypeptide that comprises the DrID domain (SEQ ID NO:4), or one of its modified forms.

In some embodiments, the present invention is directed to an isolated nucleic acid molecule comprising a polynucleotide sequence encoding protein having an amino acid sequence with substitution, deletion, insertion and/or addition of one or several amino acid residues in the amino acid sequence of SEQ ID NO:4. In an embodiment, the above protein has dehydratase and isomerase activities.

In some embodiments, the present invention is directed to an isolated nucleic acid molecule comprising a polynucleotide sequence encoding a protein having at least 60%; at least 65%; at least 70%; at least 75%; at least 80%; at least 81%; at least 82%; at least 83%; at least 84%; at least 85%; at least 86%; at least 87%; at least 88%; at least 89%; at least 90%; at least 91%; at least 92%; at least 93%; at least 94%; at least 95%; at least 96%; at least 97%; at least 98%; or at least 99% identity to an amino acid sequence of SEQ ID NO:4. In an embodiment, the above protein has dehydratase and isomerase activities.

The *C. cohnii* modular DHA synthase contains multiple ACP domains. These domains require activation by covalent attachment of a phosphopantetheine co-factor to a conserved serine residue. This activation is achieved by post-translational modification by members of the phosphopantetheinyl transferase (PPTase) family of enzymes that transfer a 4'-phosphopantetheinyl moiety from coenzyme A to the ACP domains. In order to produce DHA in *C. cohnii*, a *C. cohnii* modular DHA synthase must work with a PPTase protein that activates its ACP domains. Structural and functional characteristics of PPTases have been described in detail (e.g., Lambalot et al., Chemistry & Biology, Vol. 3 (1996), pp. 923-936 and Beld et al., Natural Products Reports, Vol. 31 (2014), pp. 61-108).

PPTase domains have been found in some Type I FAS and Type I PKS proteins, however, no PPTase domain was detected in the protein sequence of the *C. cohnii* DHA synthase. This indicates that the PPTase(s) responsible for the activation of its ACP domains is encoded in a separate gene(s). Therefore, a *C. cohnii* modular DHA synthase system can be considered to include at least one separately encoded PPTase. The present inventors have identified a *C. cohnii* PPTase by querying the *C. cohnii* RNA derived cDNA sequence database (utilized for identification of the DHA synthase sequence) with several known PPTase sequences. The amino acid sequence of this protein is shown in SEQ ID NO:5. The sequence has motifs characteristic of PPTases and is identified as belonging to that enzyme family by comparison to the Pfam database. It is possible that this PPTases is responsible for the in vivo activation of the ACP domains of the *C. cohnii* modular DHA synthase.

When proteins having ACP domains are expressed in heterologous organisms it is possible that the endogenous PPTase(s) of that host will recognize the new ACP sequence and activate those domains. It is also possible that the endogenous PPTase(s) may not recognize the foreign ACP sequences. In that case a heterologous PPTase (one that does recognized those ACPs as substrates) will need to be provided. Accordingly, one embodiment of the invention relates to a genetically modified host cell or microorganism, wherein the host cell or microorganism has been genetically modified to express a modular DHA synthase as described herein, and also a PPTase as described herein. The PPTase may be expressed on the same or a different construct as one or more of the nucleic acid molecules encoding the PUFA synthase protein (or proteins). A suitable PPTase is described above (SEQ ID NO:5) and others that may serve this purpose are described in the art. In one embodiment, the PPTase is a native PPTase of *C. cohnii*. In another embodiment, the PPTase is one with a wide substrate range as described in the literature (e.g., Sfp from *Bacillus subtilis* or Svp from *Streptomyces verticillus*—see: Sanchez et al., Chemistry & Biology, Vol. 8, Issue 7 (July, 2001), pp. 725-738).

Thus, the present invention is directed in part to a heterologously expressed polypeptide that comprises PPTase (SEQ ID NO:5), or one of its modified forms.

In some embodiments, the present invention is directed to an isolated nucleic acid molecule comprising a polynucleotide sequence encoding protein having an amino acid sequence with substitution, deletion, insertion and/or addition of one or several amino acid residues in the amino acid sequence of SEQ ID NO:5. In an embodiment, the above protein has PPTase activities.

The invention includes the expression a modular DHA synthase as described herein together with a PPTase to produce DHA in a heterologous host. The invention also includes the expression of a modular DHA synthase as described herein together with a PPTase to increase DHA production and/or accumulation in a heterologous host.

Another aspect of the invention relates to a gene construct comprising the nucleic acid molecule of the present invention that is operably linked to another nucleic acid element.

The term operably linked means a serial organization, e.g., of a promoter, coding sequence, terminator and/or further regulatory elements whereby each element can fulfill its original function during expression of the nucleic acid molecule.

Further, a vector comprising of the nucleic acid molecule described herein is contemplated in the present invention. This includes also an expression vector as well as a vector further comprising a selectable marker gene and/or nucleotide sequences for the replication in a host cell and/or the integration into the genome of the host cell. Methods for making the above vectors are also contemplated in the present invention. Such methods comprise a step of inserting the subject nucleic acid molecule into a vector. In some embodiments, the methods further comprise a step of introducing the resulting recombinant vector into a host cell.

Further, the invention pertains to a host cell or organism containing above described nucleic acid molecules and/or a said gene construct and/or a said vector.

Methods for making the above host cell are also contemplated in the present invention. The methods comprise a step of introducing the above mentioned recombinant vector into a host cell.

The present invention further provides a method to produce at least one PUFA, comprising: expressing a PUFA synthase gene in a host cell under conditions effective to produce PUFAs, wherein the PUFA synthase gene comprises the above described nucleic acid molecules and/or a said gene construct and/or a said vector in the host cell, and wherein at least one PUFA is produced.

The present invention also provides a method to produce lipids enriched for DHA, comprising: expressing a modular DHA synthase gene in a host cell under conditions effective to produce lipids, wherein the modular DHA synthase gene comprises the above described nucleic acid molecule, and wherein lipids enriched with DHA are produced.

The present invention also provides a method of increasing DHA production in an organism having modular DHA synthase activity, comprising: expressing the above described nucleic acid molecule in the organism under conditions effective to produce DHA, wherein the modular DHA synthase activity replaces an inactive or deleted activity, introduces a new activity, or enhances an existing activity in the organism, and wherein DHA production in the organism is increased.

Additionally, the *C. cohnii* modular DHA synthase, or its modules disclosed herein, can be used to identify other modular DHA synthase homologs in nature. For example, the *C. cohnii* modular DHA synthase nucleic acid sequence disclosed herein can be used to isolate genes encoding homologous proteins. Isolation of homologous genes using sequence-dependent protocols is known in the art. Examples of sequence-dependent protocols include, for example and without limitation: methods of nucleic acid hybridization; methods of DNA and RNA amplification, as exemplified by various uses of nucleic acid amplification technologies (e.g., polymerase chain reaction (PCR), ligase chain reaction (LCR), and strand displacement amplification; and methods of library construction and screening by complementation. Also, the *C. cohnii* modular DHA synthase amino acid sequence can be used to query databases and to identify homologs with similar domain organizations and content. Additionally, the DrID domain amino acid sequence could be used to query databases and to identify other modular Type I PKS proteins that may possess regions with homology to that particular domain.

Genetically Modified Cells and Organisms

According to the present invention, an organism that has been genetically modified to express a modular DHA synthase, wherein the organism does not naturally (endogenously, without genetic modification) express such a system, can be referred to herein as a "heterologous" host organism with regard to the modification of the organism with the modular DHA synthase. Embodiments herein include host organisms (e.g., microorganisms, plants, and animals) that are genetically modified to express a modular DHA synthase. In some embodiments, an organism that has been genetically modified to express a heterologous *C. cohnii* modular DHA synthase, for example, a functional heterologous protein system comprising a modular DHA synthase and at least one accessory protein, e.g., a PPTase, thereof.

Accordingly, encompassed by the present invention are methods to make genetically modified organisms by: expressing one or more modular DHA synthase or its functional fragments, derivatives, alleles, homologs or isozymes described herein. In one embodiment, any of the exogenously introduced nucleic acid sequences can be optimized for codon usage or improved expression in the host. In one embodiment, any of the introduced nucleic acid sequences can be targeted to one or more organelles in the organism. Various embodiments of such sequences, methods to genetically modify an organism, specific modifications, and combinations thereof have been described in detail above and are encompassed here. Typically, the method is used to produce a particular genetically modified organism that produces a particular bioactive molecule or molecules.

Preferred genetically modified organisms include genetically modified microorganisms and genetically modified plants.

Preferably, a genetically modified organism of the invention produces one or more polyunsaturated fatty acids including, but not limited to, DHA (C22:6, n-3), DPA (C22:5, n-6 or n-3), EPA (C20:5, n-3), arachidonic acid (ARA) (C20:4, n-6), GLA (C18:3, n-6), ALA (C18:3, n-3), and/or SDA (C18:4, n-3), and more preferably, one or more longer chain PUFAs, including, but not limited to, DHA (C22:6, n-3), DPA (C22:5, n-6 or n-3), ARA (C20:4, n-6), or EPA (C20:5, n-3), or any combination thereof. In a particularly preferred embodiment, a genetically modified microorganism of the invention produces DHA (C22:6, n-3).

According to the present invention, a genetically modified organism includes an organism that has been modified using recombinant technology or by classical mutagenesis and screening techniques. As used herein, genetic modifications that result in a decrease in gene expression, in the function of the gene, or in the function of the gene product (i.e., the protein encoded by the gene) can be referred to as inactivation (complete or partial), deletion, interruption, blockage or down-regulation of a gene. For example, a genetic modification in a gene which results in a decrease in the function of the protein encoded by such gene, can be the result of a complete deletion of the gene (i.e., the gene does not exist, and therefore the protein does not exist), a mutation in the gene which results in incomplete or no translation of the protein (e.g., the protein is not expressed), or a mutation in the gene which decreases or abolishes the natural function of the protein (e.g., a protein is expressed which has decreased or no enzymatic activity or action). Genetic modifications that result in an increase in gene expression or function can be referred to as amplification, overproduction, overexpression, activation, enhancement, addition, or up-regulation of a gene.

Genetically Modified Microorganisms

As used herein, a genetically modified microorganism can include a genetically modified bacterium, protist, microalgae, algae, fungus, or other microbe. Such a genetically modified microorganism has a genome that is modified (i.e., mutated or changed) from its normal (i.e., wild-type or naturally occurring) form such that the desired result is achieved (i.e., decreased or modified modular DHA synthase activity and/or production and accumulation of a desired product using the modular DHA synthase system). Genetic modification of a microorganism can be accomplished using classical strain development and/or molecular genetic techniques. Such techniques known in the art and are generally disclosed for microorganisms, for example, in Sambrook et al., Molecular Cloning: A Laboratory Manual, Cold Spring Harbor Labs Press, 1989. A genetically modified microorganism can include a microorganism in which nucleic acid molecules have been inserted, deleted or modified (i.e., mutated; e.g., by insertion, deletion, substitution, and/or inversion of nucleotides), in such a manner that such modifications provide the desired effect within the microorganism.

Examples of suitable host microorganisms for genetic modification include, but are not limited to, yeast including *Saccharomyces cerevisiae, Saccharomyces carlsbergensis*, or other yeast such as *Candida, Kluyveromyces*, or other fungi, for example, filamentous fungi such as *Aspergillus, Neurospora, Penicillium*, etc. Bacterial cells also may be used as hosts. These include, but are not limited to, *Escherichia coli*, which can be useful in fermentation processes. Alternatively, and only by way of example, a host such as a *Lactobacillus* species or *Bacillus* species can be used as a host.

Other hosts for use in the present invention include microorganisms from a genus including, but not limited to: *Thraustochytrium, Japonochytrium, Aplanochytrium, Elina* and *Schizochytrium* within the Thraustochytriaceae, and *Labyrinthula, Labyrinthuloides*, and *Labyrinthomyxa* within the Labyrinthulaceae. Particularly preferred strains of Thraustochytriales include, but are not limited to: *Schizochytrium* sp. (S31)(ATCC 20888); *Schizochytrium* sp. (ATCC PTA-9695): *Schizochytrium* sp. (S8)(ATCC 20889); *Schizochytrium* sp. (LC-RM)(ATCC 18915); *Schizochytrium* sp. (PTA-10212); *Schizochytrium* sp. (PTA-10208); *Schizochytrium* sp. (SR21); *Schizochytrium* sp. N230D, *Schizochytrium aggregatum* (ATCC 28209); *Schizochytrium limacinum* (IFO 32693); *Thraustochytrium* sp. (23B)(ATCC 20891 or ATCC 20892); *Thraustochytrium striatum* (ATCC 24473); *Thraustochytrium aureum* (ATCC 34304); *Thraustochytrium roseum* (ATCC 28210); and *Japonochytrium* sp. (L1)(ATCC 28207).

Other preferred hosts include those microorganisms that are known to produce compounds used as pharmaceutical agents, flavoring agents, nutraceutical agents, functional food ingredients or cosmetically active agents or microorganisms that are genetically engineered to produce these compounds/agents.

In one embodiment of the present invention, the modular DHA synthase is exogenously introduced into a host microorganism that has an endogenous PUFA synthase system to increase the amount of PUFA produced. In another embodiment, the exogenous modular DHA synthase is introduced into a host microorganism that does not have any PUFA synthesis system to produce detectable amount of PUFAs. A heterologous sequence can also include a sequence encoding a modified functional domain (a homologue) of a natural *C. cohnii* modular DHA synthase. Other heterologous sequences that can be introduced into the host genome include PPTases.

Therefore, it is an object of the present invention to produce, via the genetic manipulation of microorganisms as described herein, PUFAs including DHA and, by extension, oils obtained from such microorganisms comprising these PUFAs. Examples of PUFAs that can be produced by the present invention include, but are not limited to, DHA, DPA (C22:5, n-6 or n-3), ARA, EPA, GLA, ALA, SDA, and any combinations thereof. The present invention allows for the production of commercially valuable lipids enriched in one or more desired (primary) PUFAs by the present inventors' development of genetically modified microorganisms through the use of the modular DHA synthase that produces DHA and modified modular DHA synthases that produce other PUFAs.

Genetically Modified Plants

Another embodiment of the present invention relates to a genetically modified plant or plant parts, wherein the plant has been genetically modified to recombinantly express a modular DHA synthase, including a PPTase, as described herein, for the improvement of the production and/or accumulation of PUFAs by the host. In another embodiment, the genetically modified plant has an endogenous PUFA production system or a previously introduced heterologous PUFA production system, and the modular DHA synthase or the modified modular DHA synthase as described herein are introduced into the plant to improve the production and/or accumulation of PUFAs, in particular, DHA.

As used herein, a genetically modified plant can include any genetically modified plant including higher plants and particularly, any consumable plants or plants useful for producing a desired bioactive molecule (e.g., PUFA) of the present invention. "Plant parts", as used herein, include any parts of a plant, including, but not limited to, seeds (including mature seeds and immature seeds), pollen, embryos, flowers, fruits, shoots, leaves, roots, stems, explants, etc. A genetically modified plant has a genome that is modified (i.e., mutated or changed) from its normal (i.e., wild-type or naturally occurring) form such that the desired result is achieved (i.e., increased or modified PUFA synthesis activity and/or production and/or accumulation of a desired product using the modular DHA synthase system). Genetic modification of a plant can be accomplished using classical strain development and/or molecular genetic techniques. Methods for producing a transgenic plant, wherein a recombinant nucleic acid molecule encoding a desired amino acid sequence is incorporated into the genome of the plant, are known in the art. A preferred plant to genetically modify according to the present invention is preferably a plant suitable for consumption by animals, including humans.

Preferred plants to genetically modify according to the present invention (i.e., plant host cells) include, but are not limited to any higher plants, including both dicotyledonous and monocotyledonous plants, and particularly consumable plants, including crop plants and especially plants used for their oils. Such plants can include, but are not limited to, for example: canola, soybean, rapeseed, linseed, corn, safflower, sunflower and tobacco. Thus, any plant species or plant cell may be selected. Particular cells used herein, and plants grown or derived therefrom, include, but are not limited to, cells obtainable from canola (e.g., *Brassica rapa* or *Brassica napus*); soybean (*Glycine max*); rapeseed (*Brassica* spp.); linseed/flax (*Linum usitatissimum*); maize (corn) (*Zea mays*); safflower (*Carthamus tinctorius*); sunflower (*Helianthus annuus*); tobacco (*Nicotiana tabacum*); *Arabidopsis thaliana*, Brazil nut (*Betholettia excelsa*); castor bean (*Riccinus communis*); coconut (*Cocus nucifera*); coriander (*Coriandrum sativum*); cotton (*Gossypium* spp.); groundnut (*Arachis hypogaea*); jojoba (*Simmondsia chinensis*); mustard (*Brassica* spp. and *Sinapis alba*); oil palm (*Elaeis guineeis*); olive (*Olea eurpaea*); rice (*Oryza sativa*); squash (*Cucurbita maxima*); barley (*Hordeum vulgare*); wheat (*Traeticum aestivum*); and duckweed (*Lemnaceae* sp.). It should be noted that in accordance herewith the genetic background within a plant species might vary.

Plant lines from these plants, optimized for a particularly desirable trait, e.g. disease resistance, ease of plant transformation, oil content or profile, etc., may be produced, selected or identified in accordance herewith. Preferred plant lines may be selected through plant breeding, or through methods such as marker assisted breeding and tilling. It should be noted that plant lines displaying modulated activity with respect to any of the herein mentioned accessory proteins, targeted inhibition of pathways, and/or the modular DHA synthase are particularly useful.

Some embodiments include the targeting of expression of the heterologous modular DHA synthase to one or more organelles of the host. For example, in some embodiments, expression of the heterologous modular DHA synthase is targeted to the plastid of a plant. Several plastid targeting sequences are known in the art and can be used in embodiments where the heterologous host is a plant or plant cell, and wherein targeting to the plastid is desired. In some embodiments, expression of the heterologous modular DHA synthase is in the cytosol. In some embodiments, expression of the heterologous modular DHA synthase is in the cytosol of a plant or is targeted to the plastid of the plant.

Other preferred plants include those plants that are known to produce compounds used as pharmaceutical agents, flavoring agents, nutraceutical agents, functional food ingredients or cosmetically active agents or plants that are genetically engineered to produce these compounds/agents.

The invention further includes any seeds produced by the plants described herein, as well as any oils produced by the plants or seeds described herein. The invention also includes any products produced using the plants, seed or oils described herein.

Therefore, it is an object of the present invention to produce, via the genetic manipulation of organisms as described herein, PUFAs including DHA and, by extension, oils obtained from such plants comprising these PUFAs. Examples of PUFAs that can be produced by the present invention include, but are not limited to, DHA, DPA (C22:5, n-6 or n-3), ARA, EPA, GLA, ALA, SDA, and any combinations thereof. The present invention allows for the production of commercially valuable lipids enriched in one or more desired (primary) PUFAs by the development of genetically modified plants through the use of the modular DHA synthase that produces DHA and modified modular DHA synthases that produce other PUFAs.

Uses for Genetically Modified Organisms of the Invention

One embodiment of the present invention is a method to produce desired bioactive molecules by growing a genetically modified organism of the present invention. Preferably, the bioactive molecule is a PUFA, and most preferably, DHA. Preferably, the genetically modified organism is a genetically modified microorganism. Such a method includes, for example, the step of culturing in a fermentation medium a microorganism as described previously herein and in accordance with the present invention. Preferred host cells and microorganisms for genetic modification related to the modular DHA synthase of the invention are described above.

One embodiment of the present invention is a method to produce desired PUFAs by culturing a genetically modified microorganism of the present invention. Such a method includes the step of culturing in a fermentation medium and under conditions effective to produce the PUFA(s) in a microorganism that has a genetic modification as described previously herein and in accordance with the present invention. An appropriate, or effective, medium refers to any medium in which a genetically modified microorganism of the present invention, when cultured, is capable of producing the desired PUFA product(s). Such a medium is typically an aqueous medium comprising assimilable carbon, nitrogen and phosphate sources. Such a medium can also include appropriate salts, minerals, metals and other nutrients. Any microorganisms of the present invention can be cultured in conventional fermentation bioreactors. The microorganisms can be cultured by any fermentation process which includes, but is not limited to, batch, fed-batch, cell recycle, and continuous fermentation.

The invention further includes any microorganisms or plants described herein as well as any oils produced by the microorganisms or plants described herein. In some embodiments, the oil produced is DHA. In some embodiments, the oil produced is a mixture of PUFAs selected from a group consisting of DPA, EPA, ARA, GLA, ALA, SDA, and DHA. The invention also includes any products produced using the microorganisms or plants, or oils described herein.

One embodiment of the present invention relates to a method to modify a product containing at least one fatty acid, comprising adding to the product a microorganism, plant, or oil produced by a genetically modified microorganism or plant according to the invention and as described herein (e.g., a microorganism or plant that has been genetically modified with a modular DHA synthase, makes use of any of the strategies for improvement of production and/or accumulation of PUFAs described herein, and has a fatty acid profile described herein). Any products produced by this method or generally containing any microorganisms or plants, or oils from the microorganisms or plants described herein are also encompassed by the invention.

Preferably, the product is selected from the group consisting of a food, a dietary supplement, a pharmaceutical formulation, a feedstuff, a humanized animal milk, and an infant formula. Suitable pharmaceutical formulations include, but are not limited to, an anti-inflammatory formulation, a chemotherapeutic agent, an active excipient, an osteoporosis drug, an anti-depressant, an anticonvulsant, an anti-*Heliobacter pylori* drug, a drug for treatment of neurodegenerative disease, a drug for treatment of degenerative liver disease, an antibiotic, and a cholesterol lowering formulation. In one embodiment, the product is used to treat a condition selected from the group consisting of: chronic inflammation, acute inflammation, gastrointestinal disorder, cancer, cachexia, cardiac restenosis, neurodegenerative disorder, degenerative disorder of the liver, blood lipid disorder, osteoporosis, osteoarthritis, autoimmune disease, preeclampsia, preterm birth, age related maculopathy, pulmonary disorder, and peroxisomal disorder.

In some embodiments of the invention, the PUFAs produced by the genetically modified organisms or the methods disclosed in the present invention can be incorporated into a component of food or feed (e.g., a food supplement). Types of food products into which the PUFAs can be incorporated according to the present invention are not particularly limited, and include food products such as fine bakery wares, bread and rolls, breakfast cereals, processed and unprocessed cheese, condiments (ketchup, mayonnaise, etc.), dairy products (milk, yogurt), puddings and gelatin desserts, carbonated drinks, teas, powdered beverage mixes, processed fish products, fruit-based drinks, chewing gum, hard confectionery, frozen dairy products, processed meat products, nut and nut-based spreads, pasta, processed poultry products, gravies and sauces, potato chips and other chips or crisps, chocolate and other confectionery, soups and soup mixes, soya based products (milks, drinks, creams, whiteners), vegetable oil-based spreads, and vegetable-based drinks.

Examples of feedstuffs into which the PUFAs produced in accordance with the present invention may be incorporated include, for instance, pet foods such as cat foods, dog foods and the like, feeds for aquarium fish, cultured fish or crustaceans, etc., feed for farm-raised animals (including livestock and further including fish or crustaceans raised in aquaculture). The PUFA containing genetically modified organisms produced in accordance with the present invention, such as the genetically modified microorganisms or plants, may be incorporated directly into feed products.

The following examples are provided to illustrate certain particular features and/or embodiments. The examples should not be construed to limit the disclosure to the particular features or embodiments exemplified.

EXAMPLES

The following examples describe a biochemical approach that was used to identify a single, very large, protein that is associated with the synthesis of DHA in *C. cohnii*. The amino acid sequence of the entire protein was determined using molecular biology and bioinformatic techniques. Furthermore, the enzymatic domains present in that protein are characterized and a rationale for the synthesis of the DHA molecule is presented. The identification of the protein was accomplished by: 1), demonstrating in vitro DHA synthesis in cell free extracts derived from selected strains of *C. cohnii*, 2), enrichment of the synthesis activity using fractionation methods, and 3), identification of a protein candidate by correlation of DHA synthesis activity in various fractions with proteins present in those same fractions. MS based sequencing of tryptic peptides derived from the purified candidate protein was used to obtain initial protein sequence data. The peptide sequencing was facilitated by use of a virtual protein database obtained by high through put sequencing of cDNA derived from a total RNA sample isolated from cells of *C. cohnii*. The sequence of a cDNA contig encoding the protein associated with the DHA synthesis activity was obtained by bioinformatic methods using data from an additional round of cDNA sequencing. The protein has the characteristics of a modular Type I PKS and is referred to here as a modular DHA synthase. Methods appropriate for production of DHA and other PUFAs in heterologous organisms via expression of the modular DHA synthase and accessory proteins are also provided.

Example 1

The following example describes the development of an in vitro assay demonstrating de novo synthesis of DHA from malonyl-CoA in cell free extracts derived from selected strains of *Crypthecodinium cohnii*.

Two strains derived from the *C. cohnii* ATCC stock culture (ATCC No. 30340) were used for the development of an in vitro DHA synthesis activity assay. Some heterogeneity was observed in single cell colonies derived from the ATCC sample. The first strain used in this study, designated "KO", was selected from a single "wet-looking" colony after streaking out cells from the ATCC sample on plates containing 2% agar in "50:6 medium" [50 g/L glucose and 6 g/L Tastone™ 154 yeast extract (Sensient Flavors, Indianapolis, Ind.) in 100% reconstituted Instant Ocean™ salt mixture (Aquarium Systems, Mentor, Ohio)]. The second strain was derived from the "KO" strain after random mutagenesis induced by ultraviolet radiation. This second strain, designated "KO-5", was capable of growth only when supplied with medium chain length saturated fatty acids, suggesting that a mutation in this strain had reduced its ability to synthesize those fatty acids.

Cells of both strains were grown in 2.8 L flat bottom Fernbach flasks containing 1 L of 50:6 medium. For cultivation of the "KO-5" strain, 0.5 mM of C14:0 fatty acid (NuCheckPrep, Elysian, Minn.) complexed with randomly methylated cyclodextrin was added to the medium. The 1 L of medium was inoculated with 10 mL of a 3-day culture and incubated for 4 days at 25° C., at 135 rpm, prior to collection of the cells.

The samples tested in the initial assays were prepared using the following protocol. Cells in the 1 L of culture were spun down at 3,000×g for 15 minutes at 4° C. The resulting cell pellet was washed twice in 250 mL of 50 mM Tris buffer (pH 8.0) and then with 250 mL of 50 mM Tris (pH 8.0) containing 10% glycerol before being resuspended in ice-cold Buffer A [50 mM Tris (pH 8.0), 10% glycerol, 2 mM DTT, 1 mM EDTA] containing 100 mM KCl to form a slurry and 10 mL aliquots were transferred to 50 mL Falcon tubes. Acid washed 0.5 mm glass beads were added to each tube up to the 32.5 mL volume mark. The cells were disrupted by vigorously shaking by hand for 2 minutes followed by placing the samples on ice for 2 minutes. This was repeated 10 times. The resulting homogenates were separated from the beads by decanting and the beads rinsed with an additional 10 mL of buffer. The volume of the combined material from each sample was adjusted to 32.5 mL with Buffer A containing 100 mM KCl and then fractionated by centrifugation at 4° C. First, the samples were centrifuged at 500×g for 5 min. The resulting cell free supernatants (adjusted to 32.5 mL with Buffer A containing 100 mM KCl) were then centrifuged at 20,000×g for 20 minutes. The resulting supernatants (adjusted to 32.5 mL with Buffer A containing 100 mM KCl) were further centrifuged at 100,000×g for 90 minutes. The resulting supernatant volumes were again adjusted to 32.5 mL with Buffer A containing 100 mM KCl. All of the pellet fractions were also resuspended and adjusted to 32.5 mL with Buffer A containing 100 mM KCl.

The synthesis of fatty acids in the various fractions was then evaluated using $[1-^{14}C]$-malonyl-CoA as a substrate. The initial assay cocktail components and conditions were based on those often utilized for assays of Fatty Acid Synthases (FASs), polyketide synthases (PKSs) and for the PUFA synthases that are found in some marine bacteria and in some Thraustochytrids. Once in vitro synthesis of DHA was demonstrated the assay cocktail was simplified and optimized for production of that DHA.

For the initial assays the following protocol was typically followed. A 100 portion of each sample was mixed with 100 μL of a cocktail containing 2.4 mM NADH, 2.4 mM NADPH, 4 mM DTT, 120 μM acetyl-CoA, 120 μM $[1-^{14}C]$-malonyl-CoA, 5 mM ATP and 10 mM $MgCl_2$. The mixtures were incubated for 1 hr at 25° C. The reactions were stopped and the fatty acids present in the sample were converted to FAMEs using the methanolic boron trifluoride (BF3) method originally described by Morrison and Smith (Morrison and Smith, J. Lipid Research, Vol. 5 (October, 1964), pp. 600-608). Typically, 300 μL of fresh toluene/BHT and 800 μL of NaOH/methanol were added to the samples which were then incubated at 100° C. for 5 min. One mL of BF3/methanol was then added and the samples were incubated at 100° C. for 30 min. Samples were then briefly placed on ice before the lipids were extracted with 2 mL of hexane. The extracted lipids were then fractionated using silver ion chromatography following guidelines described by Nikolova-Damyanova (Nikolova-Damyanova, B. "Silver ion chromatography and lipids." In: *Advances in Lipid Methodology*—One. (Ed. W. W. Christie, Oily Press, Ayr, 1992) pp. 181-237). The hexane extracts were loaded onto Ag-Ion SPE cartridges (Sigma-Aldrich) and the FAMEs bound to the cartridges were separated into two classes by elution with two different solvents. Solvent A, consisting of 97% acetone and 3% acetonitrile, was used to elute FAMEs having medium chain length saturated fatty acids and those with up to 3 double-bonds in the fatty acid chain. Solvent B, consisting of 60% acetone and 40% acetonitrile, was used to elute FAMEs containing the longer chain fatty acids with 4 or more double bonds, such as DHA. The volumes of the eluted fractions were equalized and the radioactivity in each sample was measured by liquid scintillation counting (LSC) of a portion of the sample. The fractionation scheme (and reference numbers) for samples derived from the KO and KO-5 strains is shown in FIG. 1a. The radioactivity associated with lipids (after separation into two fractions on the Ag-Ion SPE cartridges) produced during the in vitro assays of the various samples derived from both strains is shown in the bar graph of FIG. 1b. FIG. 1c shows the results of analyses by reverse phase TLC of some representative Ag-Ion SPE cartridge fractions. The radioactivity present on the plate was detected and evaluated with a radioanalytical scanner.

Figure 1B:
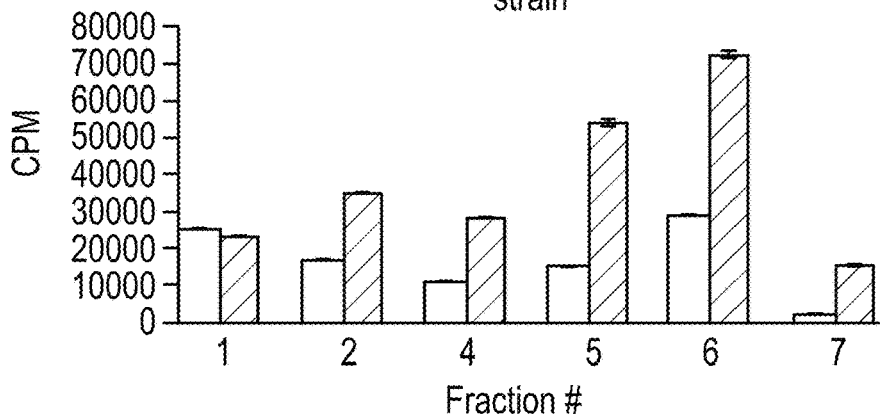
FIG. 1b shows in vitro synthesis of hexane extractable lipids that have incorporated label from $[1-^{14}C]$-malonyl-CoA in the various fractions indicated in FIG. 1a (represented as counts per minute (CPM)) from the KO and KO-5 strain following separation on Ag-Ion SPE cartridges with solvents A and B (shown as buffer A and B in the figure).
Figure 1B:
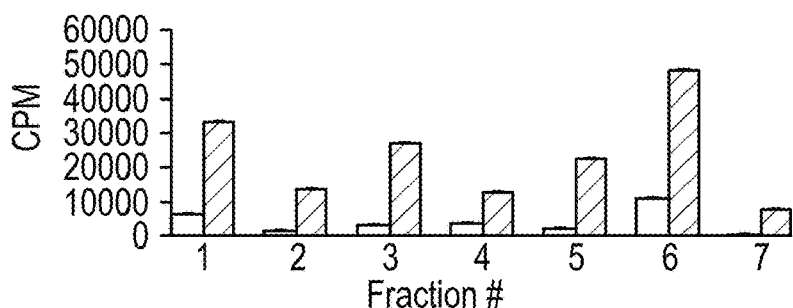
Figure 1C:
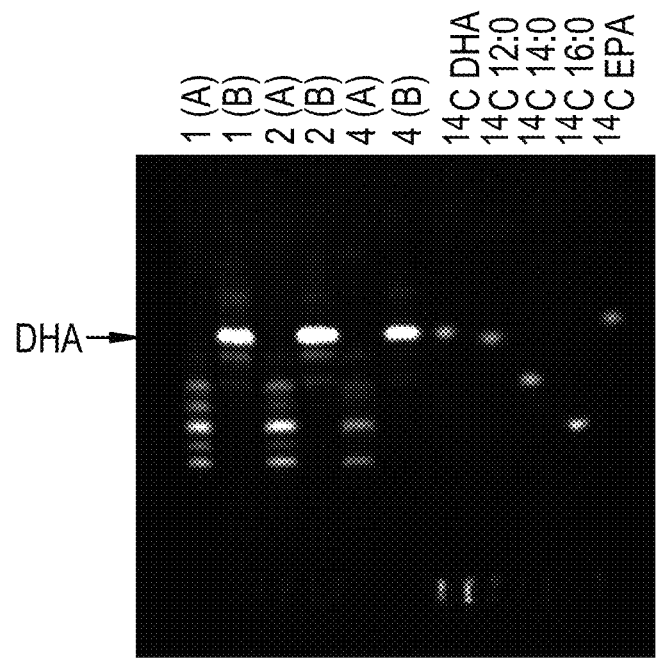
FIG. 1c shows the radioactivity detected in selected fractions from the KO strain after separation using reverse phase TLC (the numbers in FIG. 1c refer to those in FIG. 1a, A and B indicate lipids eluted from the Ag-Ion SPE cartridge by solvents A or B, respectively). Several radiolabeled FAME standards are present on the left portion of the TLC plate.

The data presented in FIG. 1b indicate that during the in vitro incubations radioactivity from $[1-^{14}C]$-malonyl-CoA is incorporated into materials that can be extracted by hexane and shows the distribution of that activity in the various fractions assayed. For each assay the products were separated into 2 fractions by use of the Ag-Ion SPE cartridge. The data in FIG. 1c shows analysis of the radiolabelled lipids present in representative samples using reverse phase TLC. The radioactivity present in the samples is separated into distinct bands on the TLC plate and most of those bands co-migrated with one of the radiolabelled FAME standards run on the same plate. Furthermore, it is clear that the material eluted from the Ag-Ion SPE cartridge by solvent A includes compounds that co-migrate with the C16:0 and C14:0 FAME standards. It is likely that the fatty acid components of these FAMEs are derived from the products of a FAS system. In contrast, the major radiolabelled band in the material eluted by solvent B co-migrated with the DHA-FAME standard. This was taken as evidence of de novo synthesis of DHA from radiolabelled malonyl-CoA occurring in these cell-free extracts. The appearance of radioactivity incorporated into the putative DHA-FAME was noted in most of the fractions shown in the scheme outlined in FIG. 1a, including some activity in the 100,000×g supernatant fractions. These observations provided encouragement to proceed with attempts to enrich the activity using various methods. The incorporation of radioactivity from $[1-^{14}C]$-malonyl-CoA into shorter chain fatty acids was greatly reduced in extracts from the KO-5 strain when compared to extracts from the KO strain. It was therefore decided to use extracts derived from the KO-5 strain for further attempts to enrich the DHA synthesis activity. For optimization assays the DHA synthesis activity was followed by appearance of radioactivity in the material eluted from Ag-Ion SPE cartridges by solvent B (following the protocol described above).

Example 2

The following example describes characterization and initial optimization of the in vitro *C. cohnii* DHA synthesis activity.

Figure 2:
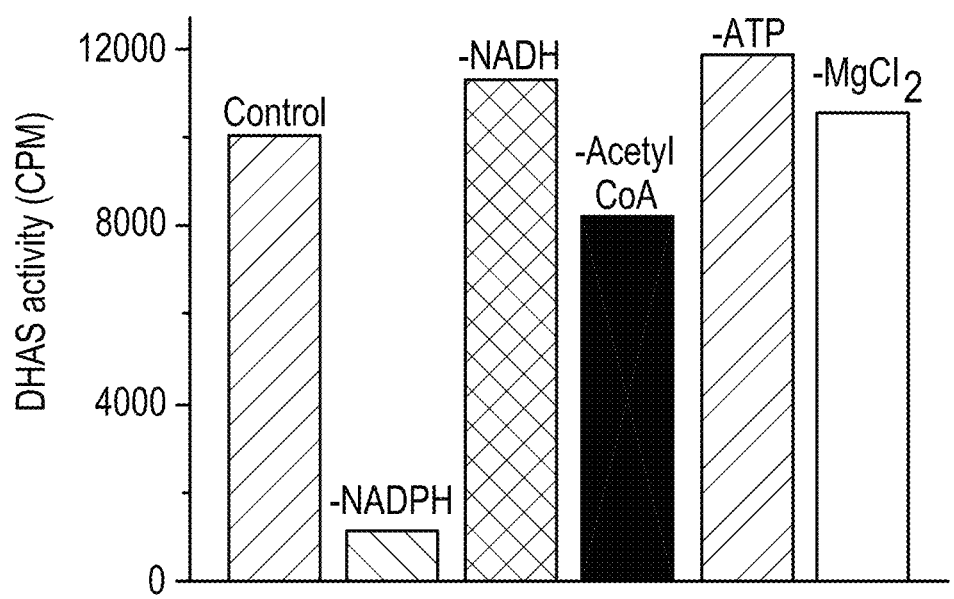
FIG. 2 shows the reaction cocktail component requirements for in vitro assays of *C. cohnii* DHA synthesis activity.

As indicated in Example 1, extracts derived from the *C. cohnii* KO-5 strain were chosen for further characterization of the DHA synthesis activity. For the data shown in FIG. 2, fraction 6 from the scheme outlined in FIG. 1*a* (the resuspended 100,000×g pellet fraction) was utilized. After some additional tests, the assay cocktail was adjusted so that the final concentrations of its components in the reaction mixtures were as follows; 1.2 mM NADPH, 1.2 mM NADH, 2 mM DTT, 60 μM acetyl-CoA, 25 μM ATP, 0.5 mM MgCl2 and 15 μM [1-$^{14}$C]-malonyl-CoA. The reactions were typically run for 50 min at 25° C. The reactions were stopped, fatty acids were converted to FAMEs, lipids present in the samples extracted into hexane, applied to Ag-Ion SPE cartridges and eluted using solvents A and B as described above. The radioactivity eluted by solvent B was determined by LSC. The bar graph in FIG. 2 shows the radioactivity present in the fraction eluted by solvent B under various assay conditions. The first bar in FIG. 2 shows the radioactivity from the assay that contained all of the indicated reaction components (Control). For each of the other assays, one of the components of the assay cocktail was omitted (indicated at the top of the appropriate bar in FIG. 2).

The data shown in FIG. 2 indicated: 1), NADPH is the preferred reductant for in vitro DHA synthesis—NADH is not required; 2), removal of ATP or MgCl$_2$ did not reduce the activity; 3), removal of acetyl-CoA resulted in a decrease in activity. Based on these results; ATP, MgCl$_2$ and NADH were excluded from the reaction cocktail in subsequent experiments while NADPH and acetyl-CoA were retained.

As a prelude to efforts to use chromatographic techniques to enrich the DHA synthesis activity, several other exploratory tests were performed. For example, fraction 7 shown in FIG. 1*a* of the KO-5 extracts was used to obtain an indication of the pH optimum for DHA synthesis activity. Briefly, buffers at several different pH values were tested (ranging from pH 6.0 to pH 9.4). In each case, the buffer in a portion of fraction 7 was exchanged with buffer having the desired pH using desalting spin columns (Pierce, Inc.). The enzyme activity assay was then carried out as described above in the presence of NADPH, acetyl-CoA and [1-$^{14}$C]-malonyl-CoA. The optimal pH for the in vitro modular DHA synthase activity was determined to be between pH 7.5 and 8.5. Subsequent assays utilized a solution buffered with 50 mM Tris-HCl at pH 8.0. Also, the effects of the inclusion of various levels of KCl on the DHA synthesis activity were tested. As for the pH test, fraction 7 was utilized to test this effect. It was determined that modest levels (e.g., 100 mM) of KCl could significantly inhibit the incorporation of radioactivity into the material eluted from the Ag-Ion SPE cartridge by solvent B and this inhibition increased with increasing KCl concentrations. The DHA synthesis activity could be fully recovered by subsequent removal of the KCl. Typically, desalting spin columns (Pierce, Inc.) were used to accomplish the KCl removal. Based on these data, any chromatographic fraction that could contain high levels of KCl was desalted prior to performing the DHA synthesis in vitro assay.

It is well established that the introduction of double bonds into preformed fatty acid chains is a reaction that has a requirement for molecular oxygen (O$_2$). To determine if such reactions were involved in the synthesis of DHA in the in vitro reactions being monitored here an assay, utilizing fraction 6 derived from the KO-5 described above, was performed in the absence of O$_2$. The biological sample and the cocktail mixture were flushed with argon prior to being combined and also during the full time of the reaction. It was determined that this procedure had no effect on the incorporation of radioactivity into DHA FAME in the assay. This indicated that O$_2$ dependent desaturases are not involved in the *C. cohnii* DHA synthase reaction.

Example 3

The following example describes methods used to identify a protein associated with the in vitro *C. cohnii* DHA synthesis activity.

Once in vitro *C. cohnii* DHA synthesis activity had been established in cell free extracts and some of the basic enzymatic characteristics determined, efforts to identify the protein, or proteins, associated with that activity were initiated. Several buffering solution components were tested in efforts to increase the proportion of the activity that remained in the 100,000×g supernatant fraction that would serve as the starting material for chromatographic separations. Additionally, a diverse set of chromatographic media and separation procedures were explored. Two of these separation methods, utilizing anion exchange and size exclusion chromatography, were found to be particularly useful and were incorporated into the enrichment procedures.

The following is a description of a protocol utilized to enrich the DHA synthesis activity and to identify a candidate protein for association with that activity.

Several liters of the *C. cohnii* KO-5 strain were grown for 4 days at 25° C. in the 50:6 medium supplemented with 0.5 mM C14:0 as described above. The cells were collected by centrifugation (3,000×g for 15 min at 4° C.) in 1 L bottles. The resulting pellets were washed twice in 250 mL ice-cold 50 mM Tris (pH 8.0) and the centrifugation step repeated. The resulting pellets were resuspended in 250 mL ice-cold 50 mM Tris (pH 8.0) containing 10% glycerol and centrifuged again. The resulting pellets were each resuspended in 25 mL of ice-cold Buffer A [50 mM Tris (pH 8.0), 10% glycerol, 2 mM DTT, 1 mM EDTA] and transferred to 50 mL Falcon tubes on ice. Acid washed 0.5 mm glass beads were added to the tubes up to the 32.5 mL volume mark and the samples were shaken by hand 10 times for 2 minutes with 2 minutes sitting on ice in between. The cell homogenates were decanted into new tubes. The glass beads were rinsed with 25 mL of Buffer A, the liquid added to the first portions of the cell extracts and then centrifuged at 10,000×g for 10 minutes at 4° C. The resulting supernatants were transferred to 12.5 mL quick-seal tubes for ultracentrifugation at 100,000×g for 30 minutes at 4° C. The resulting supernatants were passed through a 0.22 μm filter, aliquoted and frozen at −80° C. until further use. Those samples were called the S2 fraction.

Figure 3:
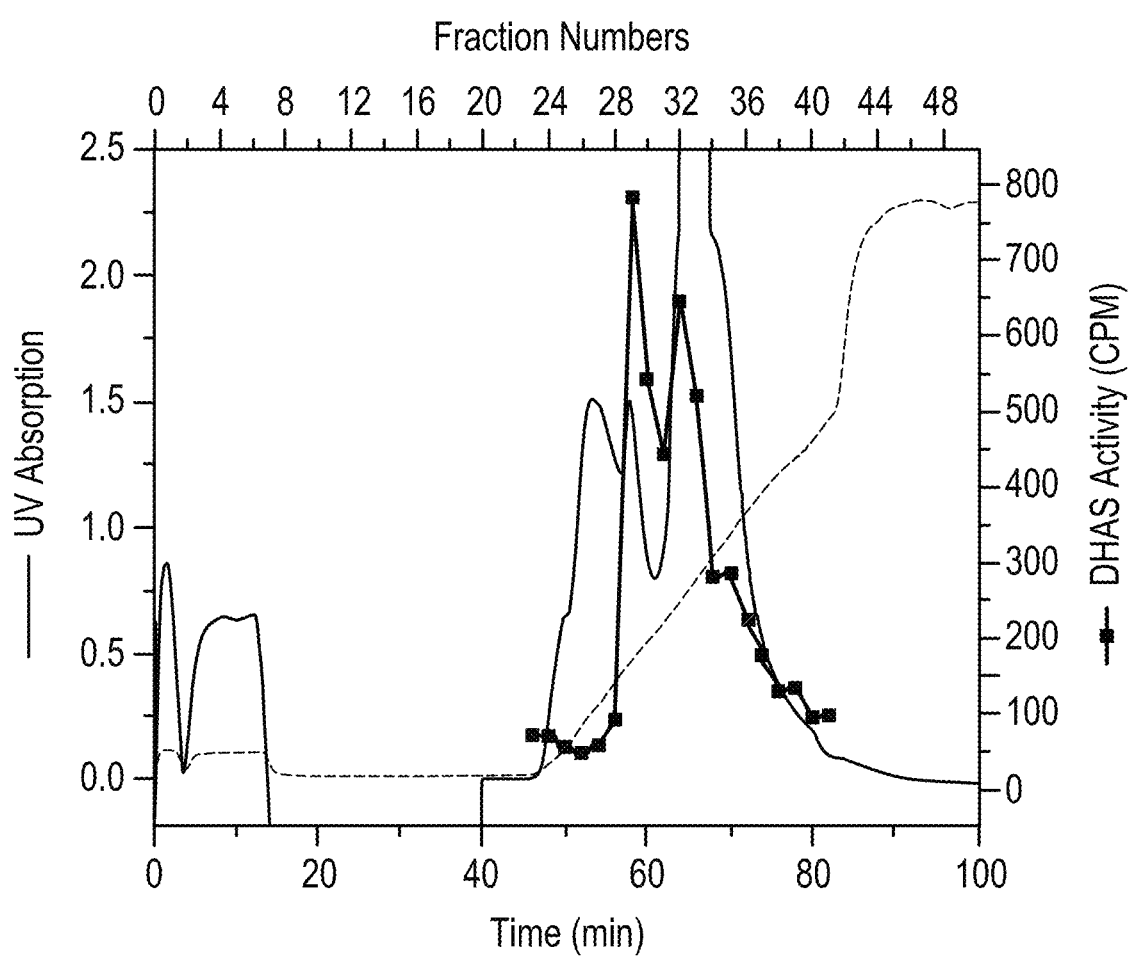
FIG. 3 shows the chromatographic fractionation of a sample enriched in DHA synthesis activity on an UNO1 anion exchange column.

Two chromatographic methods were then utilized to enrich the DHA synthesis activity. First, approximately 10 mL of the S2 fraction were loaded onto a UNO1 column (Bio-Rad Laboratories, Inc.) that had been pre-equilibrated with Buffer A [50 mM Tris (pH 8.0), 10% glycerol, 2 mM DTT, 1 mM EDTA]. The column was washed with equilibration buffer and then a linear salt gradient, 0 to 1 M KCl in Buffer A, was applied, followed by several mL of Buffer A containing 2 M KCl. Fractions were collected and those spanning the linear KCl gradient were assayed for DHA synthesis activity after removal of the KCl. A chromatogram of this column separation is shown in FIG. 3. The traces on the chromatogram represent: the absorbance at 280 nm (scale on the right), the readings from a conductivity meter (scale not shown) and the results of in vitro DHA synthesis activity assays [indicated to the left as radioactivity (CPM) in hexane soluble material] of selected fractions. Numbering of the collected fractions is indicated at the top of the figure and the chromatography time (measured from injection of the sample) is indicated at the bottom. The DHA synthesis activity was eluted in the middle portion of the applied KCl gradient. In the example shown here, fractions 29 through 33 were pooled for the next chromatographic step.

Figure 4:
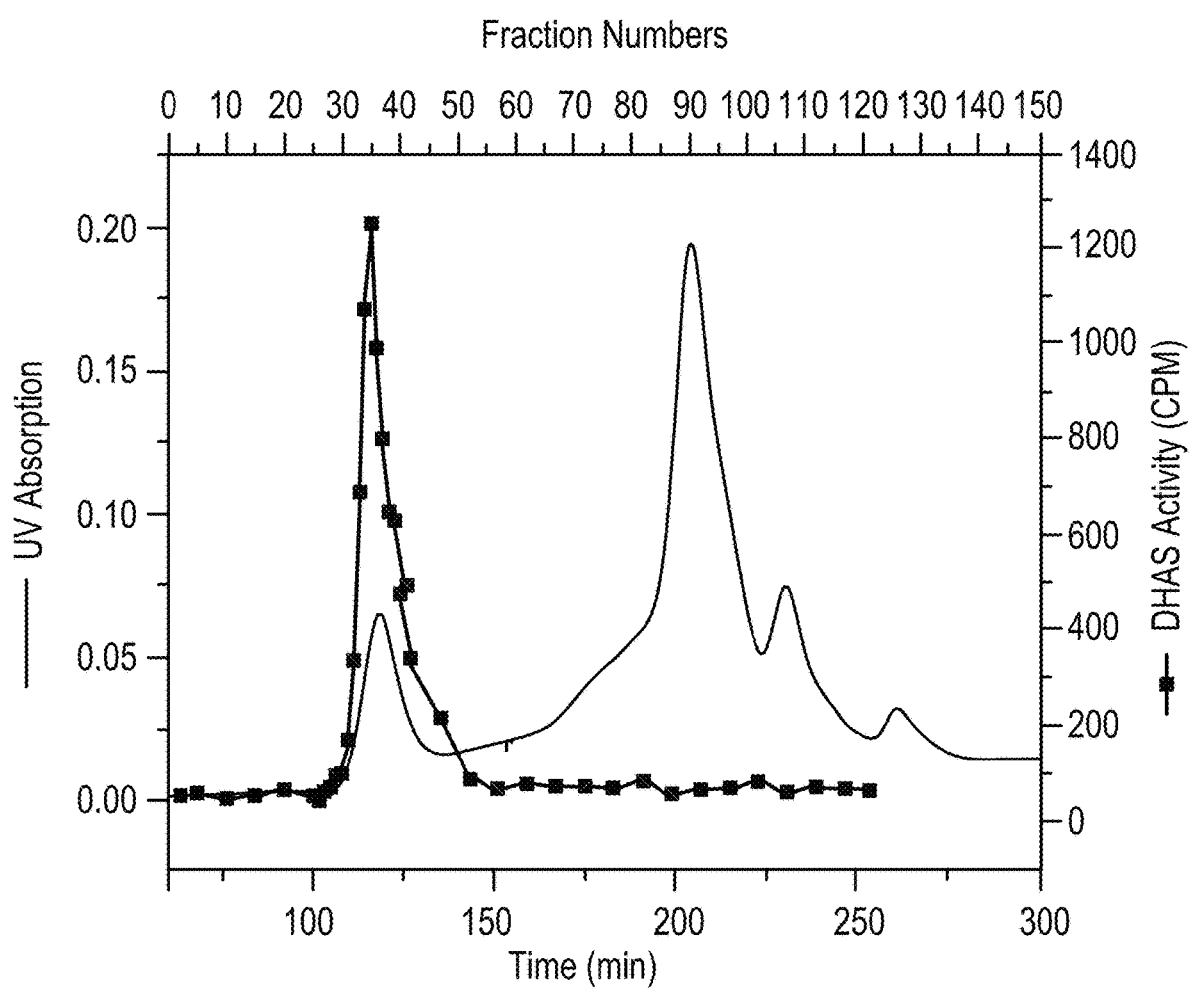
FIG. 4 shows the chromatographic fractionation of a sample enriched in DHA synthesis activity derived from the *C. cohnii* KO-5 strain on a Tricorn column pre-packed with Superose 6B.

The pooled fractions from the UNO1 column were concentrated and the KCl level reduced via ultrafiltration using a Centriprep YM-50 filtration device. The concentrated sample (~0.5 mL) was loaded onto a Tricorn column pre-packed with Superose 6B (GE Healthcare Life Sciences, Inc.) that had been equilibrated with Buffer A [50 mM Tris (pH 8.0), 10% (w/v) glycerol, 2 mM DTT, 1 mM EDTA] containing 50 mM KCl and eluted with the same buffer. Fractions were collected and the appropriate fractions were assayed for DHA synthesis activity. The DHA synthesis activity was retained by the column matrix under these conditions. FIG. 4 shows chromatographic information from this particular column run. The flow rate for the column was 0.5 mL per minute and 1.0 mL fractions were collected. A portion of selected fractions was assayed for DHA synthesis activity and the results are indicated in the figure. Numbering of the collected fractions is indicated at the top of FIG. 4 and the chromatography time (measured from injection of the sample) is indicated at the bottom. The DHA synthesis activity appeared as a symmetrical peak early in the profile. The molecular mass of the activity peak was estimated to be ~1.8 million daltons by comparison to a curve generated by plotting the elution volumes of protein standards of known molecular masses.

The data from these experiments indicated that the *C. cohnii* DHA synthesis activity was associated with a soluble protein, or protein complex, (as defined by retention in the 100,000×g supernatant fraction), that it could be bound to and eluted from an anion exchange matrix and that the native 'enzyme' was retained on the Superose 6 column (exclusion limit of ~5×10$^6$ daltons) but had a large apparent molecular mass (~1.8 mega Da).

Figure 5:
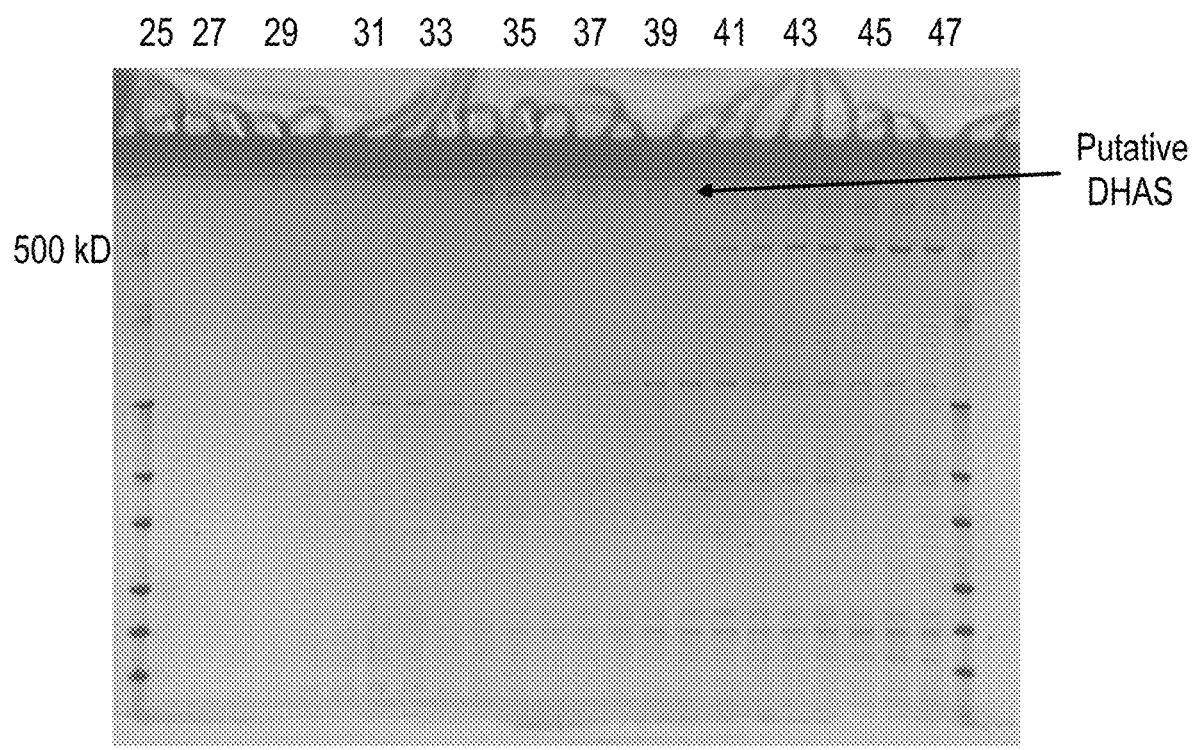
FIG. 5 shows the SDS-PAGE analysis of fractions selected from the chromatographic separation shown in FIG. 4.

Analysis of the protein composition of selected fractions from the Superose 6B column separation shown in FIG. 4 was carried out using SDS polyacrylamide gel electrophoresis (SDS-PAGE). Briefly, 100 µL of each fraction was concentrated with a Microcon YM-30 centrifugal filtration device (EMD-Millipore) and the final volume of the retentate adjusted to 10 µL. The samples were prepared for SDS-PAGE on denaturing 3-8% acrylamide, Tris-Acetate gels (prepared using the solutions and procedures recommended in the NuPage Technical guide, Invitrogen/Life Technologies). After separation, protein bands in the gel were revealed by staining with Coomassie Brilliant Blue. The stained gel containing the samples from the Superose 6B column described above is shown in FIG. 5. Reference column fraction numbers are indicated at the top of the figure. Proteins standards were included on either side of the gel. The molecular mass of the largest standard (500 KDa) is indicated on the left side of the figure. As indicated in the figure, a single band—the candidate DHA synthase—was identified whose staining intensity in the various lanes appeared to correlate with the level of DHA synthesis activity detected in those same fractions. The mobility of the candidate protein band was significantly slower than that of the largest molecular mass standard run on the gel, indicating that it is a very large polypeptide.

Example 4

The following example describes methods used to obtain the sequence of a cDNA contig encoding the protein associated with the *C. cohnii* DHA synthesis—i.e., the candidate DHA synthase.

Once a candidate DHA synthase protein had been identified, its full amino acid sequence was determined using a combination of peptide sequencing and molecular biology and bio-informatic methods. A chromatographic fraction enriched in the candidate protein was prepared, concentrated and subjected to SDS-PAGE on three separate gels using the methods described in the prior example. The gels were stained with Coomassie Brilliant Blue and submitted to the Lerner Research Institute's Mass Spectroscopy Laboratory for Protein Sequencing, at the Cleveland Clinic Foundation. At the Laboratory, the bands of interest (i.e., those associated with the candidate protein) were cut from the gel, digested with trypsin and the fragments subjected to sequencing via mass spectroscopic methods. Interpretation of the mass spectra data using the Mascot program with publically available protein databases did not yield significant peptide sequence data. To facilitate the interpretation of the spectral information a database derived from *C. cohnii* itself was prepared. This database was based on synthesis of cDNA from a total RNA sample isolated from *C. cohnii* and sequencing using 454 technology. Briefly, cells of the *C. cohnii* KO strain were grown on 50:6 medium as described in Example 1. Total RNA was extracted from frozen 1 ml cell pellets using a commercially available kit (the PureZol kit, Bio-Rad Laboratories, Hercules, Calif.) and following their recommended protocols. The total RNA sample was sent to an outside vender (Eurofins MWG Operon) where it was checked for quality, cDNA prepared, sequences associated with ribosomal RNA (rRNA) content reduced and sequencing of the remaining cDNA carried out. Over 6 million individual sequencing reads were obtained and overlapping regions (contigs) were assembled. The database of contigs and single reads derived from this effort was provided to the Lerner Research Institute and the spectral data obtained from the DHA synthase candidate protein were reanalyzed. With the new database as a reference, a total of 71 significant peptide sequences were identified. These peptides were associated with 13 unique nucleotide contigs. Analyses of the contig sequences, using the BLASTX program, indicated that most of them contained open reading frames (ORFs) that encoded proteins with homology to known polyketide and fatty acid synthases. Based on these encouraging results, an additional total RNA sample was prepared and submitted to another outside vender (SeqWright Genomic Services). The sample was checked for quality, the rRNA content reduced and cDNA synthesized. Sequencing of the cDNA library in this case was performed using Illumina technology. Both assembled contigs and the raw sequence data were used for the next step.

Using the 454 sequencing data and the tentative DHA synthase contigs, all 454 reads matching the candidate DHA synthase contigs were extracted from the complete 454 data set using the mirabait utility from the MIRA package. The reads were then assembled using the MIRA software. The resulting contigs were then loaded into the open source finishing tool GAP4 from the Staden package. The contigs were manually extended to a maximum using low quality clipped parts of reads. Manual contig joining in low quality areas was performed. The operation was repeated until the results were left unchanged. The data from the second round of RNA derived sequencing (performed using Illumina 250 bp MiSeq and 100 bp HiSeq methods) was then utilized. All of the MiSeq and 454 reads matching the previous contigs were extracted (using mirabait) from the complete MiSeq and 454 dataset. The reads were assembled with MIRA again and resulted in one "master contig" which was manually checked (GAP4) to contain all previously known tentative contigs. The operation was repeated again until the "master contig" did not grow. Using a subset of the available HiSeq plus all MiSeq and 454 reads, all reads matching the "master contig" or previous "tentative DHA contigs" were extracted using mirabait. The reads were assembled with MIRA and resulted again in one contig that was checked (GAP4) to be identical to the previous "master contig". The MiSeq and 454 "master contig" having been assured to be valid, subsets of the HiSeq data matching the "master contig" were mapped to the master contig using MIRA and no differences were found. The "master contig" was declared to be final. A translation in all 6 frames revealed one long, continuous ORF in one of the frames, further ascertaining that no frameshift was present in the "master contig". The sequence of the "master contig" is shown in SEQ ID NO:3. Although a string of adenine bases was detected at the 3' end of this sequence (i.e., a poly-A tail), those nucleotides were not included in the sequence shown in SEQ ID NO:3 since it is difficult to accurately determine the number of nucleotides in the repetitive region. The sequence of the long continuous ORF is shown separately as SEQ ID NO:2.

Example 5

In this example the characteristics of the "master contig" associated with the mRNA encoding the candidate DHA synthase protein are described.

As indicated in Example 4, a single large contig, SEQ ID NO:3, was assembled by analysis of high through-put sequencing of cDNA derived from RNA samples isolated from *C. cohnii*. The assembly relied on initial identification of contigs based on sequencing of peptides from the candidate DHA synthase protein. The full-length contig was assembled using bioinformatic techniques. The data suggests that the nucleotide sequence shown in SEQ ID NO:3 represents the coding strand of cDNA derived from a single large mRNA that encodes the candidate DHA synthase protein identified in Example 3. The sequence shown in SEQ ID NO:3 contains 47,866 bases. As indicated in Example 4, SEQ ID NO:3 does not include a string of 'A's that was detected in the contig (i.e., a Poly A tail), but whose length was not precisely determined. Embedded in the mRNA sequence is an open reading frame (ORF) extending from an ATG (methionine) codon (the A occurs at position 97 in SEQ ID NO:3) all the way to a TGA stop codon (the T occurs at position 47,785 in SEQ ID NO:3). The ORF therefore consists of 47,688 bases (excluding the stop codon), representing 15,896 codons (shown separately as SEQ ID NO:2).

Several species of dinoflagellates have been shown to modify nuclear-encoded mRNAs by splicing of a leader to the 5' end of the RNA (Zhang et al., Proc. Natl. Acad. Sci., Vol. 104, no. 11 (Mar. 13, 2007), pp. 4618-4623). This trans-spliced leader is typically ~22 nucleotides in length and has a characteristic (conserved) sequence. The 5' end of the SEQ ID 1 shows homology to the spliced leader sequences found in other dinoflagellates. The presence of the spliced leader sequence and the detection of a Poly A tail associated with the contig indicates that gene from which the mRNA was derived is encoded in the nuclear DNA of *C. cohnii*, as opposed to being encoded in organellar DNA. Additionally, although dinoflagellate genomes often contain multiple tandem copies of genes, the data from the bioinformatic process suggested that only one copy of this gene is present in the *C. cohnii* genome.

Example 6

In this example the characteristics of the candidate DHA synthase protein are described. The protein is shown to be a modular Type I polyketide synthase possessing a number of distinct enzymatic domains. The enzymatic classes of the specific domains and their linear organization in the protein are used to provide a rationale for the production of DHA as a final product. The data are consistent with the protein being described as a modular DHA synthase.

As indicated above, SEQ ID NO:3 contains a 47,688 nucleotide ORF (excluding the stop codon) listed as SEQ ID NO:2. The translation of that ORF is shown in SEQ ID NO:1. The deduced protein contains 15,896 amino acids with a predicted molecular mass of 1,698,964.9 daltons (~1.7 mega Da). The predicted size of the protein is consistent with the mobility of the candidate band observed during denaturing SDS-PAGE. Although the mass of the native enzyme estimated by gel filtration was close to this number (i.e., ~1.8 mega Da), the uncertainties associated this method are significant, especially for very large enzymes. The possibility that the native enzyme has more than one polypeptide chain (e.g., a homo-dimer) cannot be excluded. No signal or organelle targeting signal sequences were detected in the N-terminal portion of the protein. It is presumed that the enzyme occurs in the cytosol.

With the complete amino acid sequence of the candidate DHA synthase protein in hand, analyses to determine if its structure could be linked to its proposed function were initiated. Comparisons to the Pfam database were used to determine the potential enzymatic functions of regions of the protein. Due to the protein's large size, sequential portions of the sequence were used as queries (e.g., ~1,500 amino acids at time). The analysis revealed the presence of 49 distinct domains, 48 of which were those typically associated with Type I PKS systems. Additionally, the domains were organized in the manner of a modular Type I PKS system. Modular Type I PKS systems were originally detected in bacteria and have large proteins containing multiple biosynthetic modules. A key feature of these systems is that the chemical structures of the intermediate products of the synthase reactions can often be predicted based on the enzymatically active components of the individual modules and the sequential order of those modules. Seven distinct classes of PKS related domains were detected in the candidate DHA synthase protein. These enzyme classes, along with the type of reaction they catalyse and conserved motifs that may be present in the sequence were described in the 'Detailed Description of the Invention' section.

A sequential list of the domains detected in the candidate modular DHA synthase protein is shown in Table 1. The data in Table 1 include: the enzymatic family detected by comparison to the Pfam database, an indication of the approximate boundaries of the region with homology to those enzymes, the motif associated with domain (if present) including a reference amino acid location. The first ~430 amino acids of SEQ ID NO:1 did not match any enzymatic class in the Pfam database and did not have any significant matches revealed by a blastp search of publically available databases. The first domain detected in the protein was in the region from ~450 to 540 amino acids and had homology to the oxygen-dependent desaturase family of enzymes. The features of this 'DrID' domain and its implications in a proposed DHA synthesis mechanism were described in the 'Detailed Description of the Invention' section. The following 48 domains were related to those typically found in PKS systems as described above.

By analogy to other modular Type I PKS systems (e.g., the classic 6-deoxyerythronolide B synthase; Schwecke et al., Proc. Natl. Acad. Sci., Vol. 92, no. 17 (Aug. 15, 1995), pp. 7839-7843), a model for the organization of the candidate DHA synthase system was devised and is shown in Table 2. The model contains a total of 12 modules. Ten of these modules (designated M1 thru M10) are associated with carbon chain extensions and modification of the newly added unit. The first module (designated M0) contains the DrID domain and an ACP domain. The final module (M-final) contains a TE domain. In this model, the ACP domains are placed at the right side of the extension modules. This organization is similar the module organization proposed for the 6-deoxyerythronolide B synthase. Other models are possible (e.g., placing the ACP domains at the left side of the extension modules) however this would not alter the predictions concerning structure of the product of the synthase.

A total of 12 ACP domains were detected in the SEQ ID NO:1 protein including two tandem sets (underlined in Table 2). Only three AT domains (italicized in Table 2) were detected in the protein. AT reactions are typically associated with loading of the starter unit (e.g., either from acetyl-CoA or malonyl-CoA) and the extension unit (e.g., from malonyl-CoA) onto the ACPs. In some modular Type I PKS systems, an AT domain is associated with each extension module. Other cases have been characterized in which a separately encoded AT is recruited to carry out these activities (Cheng et al., Proc. Natl. Acad. Sci., Vol. 100, no. 6 (Mar. 18, 2003), pp. 3149-3154). DHA synthesis activity was detected in material that had been subjected to chromatography on anion exchange and size exclusion columns indicating that the required AT activities are associated with the candidate protein. This implies that one or more of the AT domains listed above will have access to the internal ACP domains of the protein. The final domain identified in SEQ ID NO:1 has homology to thioesterases. This suggests the product of the synthase will be released as a free fatty acid. No PPTase domain was detected in the protein. This indicates that a PPTase encoded in a separate gene carries out activation of the ACP domains of the *C. cohnii* modular DHA synthase.

As described in the 'Detailed Description of the Invention' section, the domains associated with modules M1 thru M10, along with the in vitro synthesis data (indicating the carbons are derived from malonyl-CoA), can be used to predict the status of the β carbon of each extension unit. The predicted structure of the molecule that the reactions of modules M1 through M10 would produce is shown in FIG. 6.

The identification of the protein whose sequence is shown in SEQ ID NO:1 was based on in vitro synthesis of DHA, not the molecule shown in FIG. 6. However, the characteristics of the initial domain detected in that protein, i.e., the DrID domain, provides a rationale for production of DHA from that molecule. The oxygen-dependent desaturases belong to a large family of enzymes that carry out a diverse set of reactions. Included in this family are enzymes capable of trans-cis double bond isomerizations and hydroxylation/dehydration reactions (e.g., Broadwater et al., J. Biol. Chem., Vol. 277, no. 18 (May 3, 2002), pp. 15613-15620 and Shanklin, et al., J. Biol. Chem., Vol. 284 (Jul. 10, 2009), pp. 18559-18563). For all of these enzymes, the initial reaction step involves the abstraction of hydrogen from an internal, saturated, portion of a fatty acid carbon chain. This reaction is energetically demanding and is accomplished by activation of molecular oxygen bound at a diiron active site. A conserved motif containing eight histidine residues, arranged in three clusters, has been identified that is associated with that activity. Alignment of the desaturase-related domain of SEQ ID NO:1 (i.e., the DrID domain listed as SEQ ID NO:4) with sequences of established desaturases reveals that only 2 of the 8 histidines are present. It was established that in vitro synthesis of DHA in extracts from *C. cohnii* can occur under anaerobic conditions (Example 2). Additionally, the proposed product of modules M1 through M10, already contains hydroxyl groups and double bonds that have been introduced during the extension cycles (FIG. 6). A scheme showing conversion of the molecule shown in FIG. 6 into DHA is presented in FIG. 7. The scheme includes the isomerization and dehydration reactions that can plausibly be associated with the 'DrID' domain as described above.

Example 7

This example describes the expression of the modular DHA synthases in heterologous organisms.

The data presented in the previous examples indicates that modular DHA synthases produce DHA de novo using malonate (from malonyl-CoA) for the extension reactions, possibly using acetate (from acetyl-CoA) as the priming molecule and using NADPH as a reductant. This suggests that expression of an active modular DHA synthase in any heterologous system that is capable of fatty acid synthesis could result in the production of DHA (or other products of the synthase) by that introduced system.

The enzymatic domains of the *C. cohnii* modular DHA synthase are all contained on one very large protein (in contrast to the 3 or 4 subunits of the PUFA synthases). It is likely that some resynthesis of the coding region will be required to achieve expression of that large protein in the heterologous hosts. If the endogenous PPTase(s) of the new host cells are not capable of activating the ACP domains of the modular DHA synthase, it will be necessary to co-express an appropriate PPTase. Suitable PPTases could be sfp (from *B. subtilis*) or svp (from *Streptomyces verticillus*). These PPTases have been shown to recognize a wide range of ACP substrates. Another approach could be to utilize a PPTase from *C. cohnii* itself, i.e., the endogenous PPTase that activates the *C. cohnii* modular DHA synthase ACP domains.

Queries of the *C. cohnii* derived cDNA databases (described in Example 4) with known PPTase sequences were used to identify a contig encoding a protein with homology to those enzymes. The amino acid sequence of the *C. cohnii* PPTase identified by this search is shown in SEQ ID NO:5. In vitro assays using the methods described in (Jiang et al., J. Am. Chem. Soc., Vol. 130, no. 20 (Apr. 29, 2008), pp. 6336-6337) indicate that this enzyme is capable of pantetheinylating ACP domains of the *C. cohnii* modular DHA synthase and that it would therefore be suitable for this application.

Depending on the intended use, other accessory enzymes could also be of use to facilitate increased accumulation of DHA (or other products of the synthase) in the heterologous hosts. For example, the data indicate that the product of the *C. cohnii* modular DHA synthase is released as a free fatty acid. If it is desired to have those products enter into the phospholipids or neutral lipid synthesis pathways in the new host, the co-expression of appropriate enzyme(s) to convert the free fatty acid to an acyl-CoA (i.e., acyl-CoA synthetases) could be included so that it could enter those pathways. Also, the addition of various acyl-transferases that could recognize the DHA-CoA (or other product CoAs), such as DGATs or LPAATs, could lead to increased accumulation of the products in the phospholipid and neutral lipids of the heterologous host (see for e.g., Metz et al., U.S. Pat. No. 7,759,548 (Jul. 20, 2010)).

One of suitable heterologous hosts for the modular DHA synthase is *Schizochytrium*. An example of expression of the *C. cohnii* modular DHA synthase in this organism is described in the following paragraphs.

In this experiment, the coding region of the *C. cohnii* modular DHA synthase was resynthesized so that the codon usage more closely matches the codon usage of *Schizochytrium*. The incorporation of the *C. cohnii* modular DHA synthase in *Schizochytrium* relies on the homologous recombination that has been shown to occur in this organism (see U.S. patent application Ser. No. 10/124,807, supra). The loci of the *Schizochytrium* PUFA synthase genes (pfa1, pfa2 and pfa3) have been extensively characterized. It is known that disruption of the pfa3 gene, for example, will lead to an inability to synthesize DHA, rendering the strain auxotrophic for PUFAs (Apt et al., U.S. Pat. No. 8,940,884 (Jan. 27, 2015)). This site was used as the target location to insert the *C. cohnii* DHA synthase transgene in between the promoter and terminator of the pfa3 gene.

Due to the large size of the sequence (47,688 bases), the *C. cohnii* modular DHA synthase gene was incorporated in appropriate vectors for serial transformation as 3 codon-optimized fragments of roughly the same size.

The first fragment (F1) included the first part of the coding sequence up to the end of module 3 (M3) as described in Table 2 (and SEQ ID NO:2). It was cloned into vector 1 containing the immediate upstream region of the pfa3 gene (1901 bp), the SV40 terminator, the tubulin promoter (derived from pMON50000, see examples in Apt et al., U.S. Pat. No. 8,940,884 (Jan. 27, 2015)) followed by the neomycin phosphotransferase (npt) gene (described in that same patent) and the immediate downstream region of the pfa3 gene (1979 bp). F1 was inserted in vector 1 with a V5 tag at the 3'-end, following standard molecular engineering procedures, in-between the 3'-end of the upstream region of the pfa3 gene and 5'-end of the SV40 terminator.

The second fragment (F2) included the middle part of the coding sequence of the DHA synthase from the beginning of module 4 (M4) to the end of module 7 (M7) (Table 2 and SEQ ID NO:2). It was cloned into vector 2 containing the 3'-end of F1 (1998 bp), the SV40 terminator, the tubulin promoter followed by the Zeocin™ resistance gene (described in Apt et al., U.S. Pat. No. 8,940,884 (Jan. 27, 2015)) and the immediate downstream region of the pfa3 gene (1979 bp). F2 was inserted in vector 2 with a polyhistidine tag at the 3'-end in-between the 3'-end of F1 and 5'-end of the SV40 terminator.

The third fragment (F3) included the end of the DHA synthase coding sequence from the beginning of module 8 (M8) to the end of the coding sequence described in Table 2 and SEQ ID NO:2. It was cloned into vector 3 containing the 3'-end of F2 (1998 bp), the SV40 terminator, the tubulin promoter followed by the neomycin phosphotransferase (npt) gene and the immediate downstream region of the pfa3 gene (1979 bp). F3 was inserted in vector 3 with or without a V5 tag at the 3'-end, following standard molecular engineering procedures, in-between the 3'-end F2 and 5'-end of the SV40 terminator.

The three final constructs were linearized and used for the serial transformation of *Schizochytrium* cells via particle bombardment. Cells from transgenic *Schizochytrium* expressing the PPTase of *C. cohnii* (SEQ ID NO:5), or another PPTase of interest such as Het1 or Sfp, integrated at the carotene synthase locus (described in Weaver et al., U.S. Pat. No. 7,585,659), were used. Cells bombarded with the first construct containing the first part (F1) of the *C. cohnii* modular DHA synthase were spread on plates containing both paromomycin and a supply of PUFAs. Colonies that grew on these plates were then streaked onto paromomycin plates that are not supplemented with PUFAs. A few of the colonies that were resistant to paromomycin and required PUFA supplementation were characterized further by PCR to confirm the presence of the transgene.

Expression of the first part of the enzyme (F1) was also characterized by immunoblot using an antibody that recognized the V5 epitope tag located at the 3'-end of F1. The cells of a transgenic strain containing the first part of the *C. cohnii* modular DHA synthase were then bombarded with the second construct containing the second part (F2) of the *C. cohnii* modular DHA synthase. Proper integration of the construct resulted in the removal of F1 V5 tag and stop codon. Similarly as above, the cells were then spread on plates containing both Zeocin and a supply of PUFAs. Colonies that grew on these plates were then streaked onto Zeocin plates that were not supplemented with PUFAs and paromomycin plates that were supplemented with PUFAs. A few of the colonies that were resistant to zeocin, sensitive to paromomycin, and required PUFA supplementation were characterized further by PCR to confirm the presence of the second part of the DHA synthase gene.

Expression of the modular DHA synthase up to the end of module 7 (i.e. F1+F2) could also be characterized by immunoblot using an antibody that recognize the polyhistidine-tag located at the 3'-end of F2. The cells of a transgenic strain containing both F1 and F2 of the *C. cohnii* modular DHA synthase sequence were then bombarded with the third construct containing the third fragment (F3) of the *C. cohnii* modular DHA synthase sequence. Similarly as above, the cells were then spread on plates containing both paromomycin and a supply of PUFAs. Colonies that grew on these plates were then streaked on paromomycin plates that were not supplemented with PUFAs and zeocin plates that were supplemented with PUFAs. A few of the colonies that were resistant to paromomycin and sensitive to zeocin were characterized further by PCR and sequencing to confirm the integration of the full modular DHA synthase sequence in the right configuration.

Expression of the full-length protein can be characterized by immunoblot analysis using an antibody that recognizes the V5 epitope tag located at the 3'-end of the full sequence, if used. The identity of the protein can also be confirmed by peptide sequence analysis by capillary column Liquid Chromatography-tandem Mass Spectrometry (Table 3).

TABLE 3

Example of peptides identified in liquid-chromatography-mass spectrometry analysis of Coomassie blue stained gel bands obtained from a partially purified protein extract from transgenic *Schizochytrium* expressing the *C. cohnii* modular DHA synthase and separated by SDS-PAGE. Residues numbering refers to SEQ ID NO: 1.

| Residues | Sequence |
|---|---|
| 4717-4728 | SADSPLILGAVK (SEQ ID NO: 21) |
| 5306-531 | TAVSSAFQGMSK (SEQ ID NO: 7) |
| 5795-5817 | ELNPHIDLDDFPSTIPTDVVSIK (SEQ ID NO: 8) |
| 5935-5965 | NVGFQAPLVLK (SEQ ID NO: 9) |
| 7154-7168 | GASAALGGATQEKK (SEQ ID NO: 10) |

TABLE 3-continued

Example of peptides identified in liquid-chromatography-mass spectrometry analysis of Coomassie blue stained gel bands obtained from a partially purified protein extract from transgenic *Schizochytrium* expressing the *C. cohnii* modular DHA synthase and separated by SDS-PAGE. Residues numbering refers to SEQ ID NO: 1.

| Residues | Sequence |
| --- | --- |
| 7195-7204 | DSVIEIPYTR (SEQ ID NO: 11) |
| 7712-7725 | RGDSDEMITHCEGR (SEQ ID NO: 12) |
| 9287-9304 | GVTYSTSNAALDGLALWR (SEQ ID NO: 13) |
| 9499-9510 | ATTQIVSAAEAR (SEQ ID NO: 14) |
| 10018-10032 | FSVEGVGFQNPLVLR (SEQ ID NO: 15) |
| 10104-10118 | MYVPFANIGLPLQPR (SEQ ID NO: 22) |
| 13106-13124 | LVELLSFLQGAQSASETPK (SEQ ID NO: 16) |
| 13484-13496 | EFQSQEALAVTGK (SEQ ID NO: 17) |
| 13500-13517 | ASAMAGMTDDDRQAAVLK (SEQ ID NO: 18) |
| 14350-14362 | AQQALGASAGRPK (SEQ ID NO: 19) |
| 14789-14810 | APPLWLLTSGSQPLASADAEQR (SEQ ID NO: 20) |

The cells expressing the full length *C. cohnii* modular DHA synthase along with the PPTase of choice are not necessarily expected to grow without PUFAs during the standard selection procedure following transformation. Growth conditions are then adjusted to promote production of DHA, which is then detected by FAME analysis as described above. In vivo DHA synthesis by the *C. cohnii* modular DHA synthase can also be characterized by pulse labeling with universally-labeled $C^{14}$-acetate.

What is claimed is:

1. A recombinant nucleic acid molecule selected from the group consisting of: (a) a nucleic acid molecule comprising a polynucleotide sequence encoding a protein having the amino acid sequence of SEQ ID NO: 1; (b) a nucleic acid molecule comprising a polynucleotide sequence encoding a protein with modular docosahexaenoic acid (DHA) synthase activity and having at least 95% amino acid sequence identity to the amino acid sequence of SEQ ID NO: 1; and (c) a nucleic acid molecule comprising the polynucleotide sequence of SEQ ID NO: 2 encoding the protein of SEQ ID NO: 1, wherein said recombinant nucleic acid molecule is operably linked to a transcription control sequence, and wherein said polynucleotide sequence is heterologous to said transcription control sequence.

2. The recombinant nucleic acid molecule of claim 1, wherein said protein has modular docosahexaenoic acid (DHA) synthase activity when coexpressed with a 4'-phosphopantetheinyl transferase (PPTase) in a host cell.

3. The recombinant nucleic acid molecule of claim 2, wherein said 4'-phosphopantetheinyl transferase (PPTase) has the amino acid sequence of SEQ ID NO: 5.

4. A recombinant host cell comprising the recombinant nucleic acid molecule of claim 3.

5. The recombinant host cell of claim 4, wherein the recombinant host cell is a microbial cell or a plant cell.

6. A genetically modified organism transformed with a recombinant vector comprising the recombinant nucleic acid molecule of claim 1 to express said protein with modular docosahexaenoic acid (DHA) synthase activity, wherein expression of said recombinant nucleic acid molecule encoding said protein increases docosahexaenoic acid (DHA) content in said genetically modified organism as compared to a control organism of the same species, and wherein the genetically modified organism is a plant or a microorganism.

7. The genetically modified organism of claim 6, wherein the microorganism is a microalga.

8. The genetically modified organism of claim 6, wherein the microorganism is a bacterium.

9. The genetically modified organism of claim 7, wherein the microalga is a Thraustochytrid species.

10. The genetically modified organism of claim 6, wherein said genetically modified organism is a plant.

11. The genetically modified organism of claim 10, wherein the plant is soybean or canola.

12. The genetically modified organism of claim 7, wherein the genetically modified organism further comprises at least one polyunsaturated fatty acid (PUFA) selected from the group consisting of: DPA (C22:5, n-6 or n-3), EPA (C20:5, n-3), ARA (C20:4, n-6), GLA (C18:3, n-6), ALA (C18:3, n-3), and SDA (C18:4, n-3).

13. A method of producing docosahexaenoic acid (DHA) content in an organism, comprising: transforming an organism with a recombinant vector comprising the recombinant nucleic acid molecule of claim 1, expressing said recombinant nucleic acid molecule in said transformed organism, wherein expression of said recombinant nucleic acid molecule encoding said protein increases docosahexaenoic acid (DHA) content in said transformed organism as compared to a control organism of the same species lacking said recombinant nucleic acid molecule, and wherein the transformed organism is a plant or a microorganism.

14. A method of making a recombinant vector comprising inserting the recombinant nucleic acid molecule of claim 1 into a vector.

15. A method of making a recombinant host cell comprising introducing a recombinant vector comprising the recombinant nucleic acid molecule of claim 1 into a host cell, and wherein the recombinant host cell is a microbial cell or a plant cell.

* * * * *